(12) United States Patent
Holzer et al.

(10) Patent No.: US 10,905,799 B2
(45) Date of Patent: Feb. 2, 2021

(54) XENOTRANSPLANTATION PRODUCTS AND METHODS

(71) Applicants: XENOTHERAPEUTICS, INC., Boston, MA (US); XENOTHERAPEUTICS CORPORATION, Enfield, NH (US)

(72) Inventors: Paul W. Holzer, Enfield, NH (US); Jon Adkins, Londonderry, NH (US); Rodney L. Monroy, North Fort Myers, FL (US); Elizabeth J. Chang, Pittsford, NY (US)

(73) Assignees: Xenotherapeutics Corporation, Enfield, NH (US); Xenotherapeutics, Inc., Boston, MA (US)

( * ) Notice: Subject to any disclaimer, the term of this patent is extended or adjusted under 35 U.S.C. 154(b) by 0 days.

(21) Appl. No.: 17/016,937

(22) Filed: Sep. 10, 2020

(65) Prior Publication Data

US 2020/0405910 A1    Dec. 31, 2020

Related U.S. Application Data

(62) Division of application No. 16/593,785, filed on Oct. 4, 2019, now Pat. No. 10,799,614.

(60) Provisional application No. 62/742,188, filed on Oct. 5, 2018, provisional application No. 62/756,925, filed on Nov. 7, 2018, provisional application No. 62/756,955, filed on Nov. 7, 2018, provisional application No. 62/756,977, filed on Nov. 7, 2018, provisional application No. 62/756,993, filed on Nov. 7, 2018, provisional application No. 62/792,282, filed on Jan. 14, 2019, provisional application No. 62/795,527, filed on Jan. 22, 2019, provisional application No. 62/823,455, filed on Mar. 25, 2019, provisional application No. 62/848,272, filed on May 15, 2019.

(51) Int. Cl.
*A61L 27/36*    (2006.01)

(52) U.S. Cl.
CPC ......... *A61L 27/362* (2013.01); *A61L 27/3604* (2013.01); *A61L 27/3687* (2013.01); *A61L 27/3691* (2013.01)

(58) Field of Classification Search
None
See application file for complete search history.

(56) References Cited

U.S. PATENT DOCUMENTS

| | | | |
|---|---|---|---|
| 5,964,096 A | 10/1999 | Watson et al. | |
| 6,242,482 B1 | 6/2001 | Shorr et al. | |
| 6,413,769 B1 | 7/2002 | Gustafsson et al. | |
| 6,469,229 B1 | 10/2002 | Sachs et al. | |
| 6,521,212 B1 | 2/2003 | Cloutier et al. | |
| 6,558,663 B1 | 5/2003 | Seebach et al. | |
| 6,610,288 B1 | 8/2003 | Edge et al. | |
| 6,756,033 B2 | 6/2004 | Cloutier et al. | |
| 6,867,347 B2 | 3/2005 | Patience | |
| 7,128,719 B2 | 10/2006 | Rosenberg | |
| 7,141,716 B2 | 11/2006 | Sachs et al. | |
| 7,547,522 B2 | 6/2009 | Hawley | |
| 7,547,816 B2 | 6/2009 | Day et al. | |
| 7,794,709 B2 | 9/2010 | Rosenberg | |
| 7,795,493 B2 | 9/2010 | Phelps et al. | |
| 7,816,560 B1 | 10/2010 | Zitzmann et al. | |
| 8,088,969 B2 | 1/2012 | Elliott et al. | |
| 8,106,251 B2 | 1/2012 | Ayares et al. | |
| 8,119,124 B2 | 2/2012 | Gorecki et al. | |
| 8,540,983 B2 | 9/2013 | Gorecki et al. | |
| 8,624,077 B2 | 1/2014 | Rosenberg | |
| 9,089,515 B2 | 7/2015 | Zitzmann et al. | |
| 9,326,992 B2 | 5/2016 | Kole et al. | |
| 9,339,519 B2 | 5/2016 | Ayares | |
| 9,420,770 B2 | 8/2016 | Tector, III | |
| 9,585,374 B2 | 3/2017 | Wells et al. | |
| 9,713,599 B2 | 7/2017 | Wade | |
| 9,833,468 B2 | 12/2017 | Kole et al. | |
| 9,834,791 B2 | 12/2017 | Zhang et al. | |
| 9,883,939 B2 | 2/2018 | Yamada et al. | |
| 9,888,673 B2 | 2/2018 | Hering et al. | |
| 9,888,674 B2 | 2/2018 | Tector et al. | |
| 10,016,463 B2 | 6/2018 | Jeffs | |

(Continued)

FOREIGN PATENT DOCUMENTS

| WO | 98053850 | 12/1998 |
|---|---|---|
| WO | 2006006167 | 1/2006 |
| WO | 2018195402 A1 | 10/2018 |

OTHER PUBLICATIONS

Asako Ando et al., "Genomic sequence analysis of the 238-kb swine segment with a cluster of TRIM and olfactory receptor genes located, but with no class I genes, at the distal end of the SLA class I region", Immunogenetics, (2005) 57: 864-873.

(Continued)

*Primary Examiner* — Scott Long
*Assistant Examiner* — Evelyn Y Pyla
(74) *Attorney, Agent, or Firm* — Rothwell, Figg, Ernst & Manbeck, P C.

(57) ABSTRACT

A biological product for clinical xenotransplantation into a human and a method of preparing biological product for clinical xenotransplantation into a human involving producing a non-wild type, biologically engineered swine having a biologically engineered genome such that the swine does not express one or more extracellular surface glycan epitopes, is free of certain pathogens, is reared according to a bioburden-reducing procedure in a closed designated pathogen free herd, wherein the biological product is harvested following the swine being euthanized and the product is aseptically removed from the swine, the biological product is processed involving sterilization and storing the product in a sterile container, and the product does not contain one or more extracellular surface glycans, is free of certain designated pathogens, is biologically active and comprises live cells and tissues capable of vascularizing after xenotransplantation.

19 Claims, 33 Drawing Sheets

(56) References Cited

U.S. PATENT DOCUMENTS

| | | | |
|---|---|---|---|
| 10,071,123 B2 | 9/2018 | Jeffs et al. |
| 10,076,505 B2 | 9/2018 | Wade |
| 10,080,730 B2 | 9/2018 | Jeffs et al. |
| 10,130,737 B2 | 11/2018 | Ayares et al. |
| 10,149,461 B2 | 12/2018 | Ayares et al. |
| 10,278,372 B2 | 5/2019 | Hering et al. |
| 10,300,112 B2 | 5/2019 | Ayares et al. |
| 2001/0046965 A1 | 11/2001 | Ayares |
| 2001/0049827 A1 | 12/2001 | Hunter et al. |
| 2002/0012660 A1 | 1/2002 | Colman |
| 2003/0024002 A1 | 1/2003 | Colman |
| 2003/0053958 A1 | 3/2003 | Cloutier |
| 2003/0109480 A1 | 6/2003 | Corden |
| 2003/0192066 A1 | 10/2003 | Zhang |
| 2004/0208846 A1 | 10/2004 | Zhang |
| 2005/0260176 A1 | 11/2005 | Ayares et al. |
| 2005/0266561 A1 | 12/2005 | Wells et al. |
| 2006/0130157 A1 | 6/2006 | Wells |
| 2006/0147432 A1 | 7/2006 | Moore |
| 2008/0131398 A1 | 6/2008 | Jeffs |
| 2008/0250517 A1 | 10/2008 | Colman |
| 2009/0010910 A1 | 1/2009 | Toren et al. |
| 2009/0049562 A1 | 2/2009 | Koike |
| 2009/0124697 A1 | 5/2009 | Cloutier |
| 2009/0186097 A1 | 7/2009 | Ayares |
| 2010/0077494 A1 | 3/2010 | Wells |
| 2010/0137365 A1 | 6/2010 | Zitmann |
| 2011/0038841 A1 | 2/2011 | Ayares |
| 2011/0184019 A1 | 7/2011 | Zitmann |
| 2012/0090039 A1 | 4/2012 | Ayares |
| 2012/0255047 A1 | 10/2012 | Phelps |
| 2012/0282226 A1 | 11/2012 | Ayares |
| 2013/0024961 A1 | 1/2013 | Burlak |
| 2013/0083042 A1 | 4/2013 | Sagall |
| 2013/0195798 A1 | 8/2013 | Jeffs |
| 2013/0202569 A1 | 8/2013 | Ayares |
| 2014/0017215 A1 | 1/2014 | Ayares |
| 2014/0024698 A1 | 1/2014 | Kole |
| 2014/0115728 A1 | 4/2014 | Tector |
| 2014/0193379 A1 | 7/2014 | Jeffs |
| 2015/0106959 A1 | 4/2015 | Phelps |
| 2015/0135344 A1 | 5/2015 | Tector |
| 2015/0164834 A1 | 6/2015 | Wade |
| 2015/0182664 A1 | 7/2015 | Ayares |
| 2015/0216909 A1 | 8/2015 | Jeffs |
| 2015/0246078 A1 | 9/2015 | Jeffs |
| 2015/0264900 A1 | 9/2015 | Tector |
| 2016/0165861 A1 | 6/2016 | Hering et al. |
| 2016/0227750 A1 | 8/2016 | Harada et al. |
| 2016/0278349 A1 | 9/2016 | Ayares |
| 2016/0278350 A1 | 9/2016 | Ayares |
| 2016/0346498 A1 | 12/2016 | Tector |
| 2017/0183685 A1 | 6/2017 | Wells |
| 2017/0216358 A1 | 8/2017 | Gregory et al. |
| 2017/0251646 A1 | 9/2017 | Tector |
| 2017/0311579 A1 | 11/2017 | Tector |
| 2018/0042876 A1 | 2/2018 | Wade |
| 2018/0110807 A1 | 4/2018 | Ilagan |
| 2018/0153146 A1 | 6/2018 | Tector |
| 2018/0184630 A1 | 7/2018 | Tector, III |
| 2018/0228144 A1 | 8/2018 | Bonvillain |
| 2018/0249688 A1 | 9/2018 | Ayares |
| 2018/0332832 A1 | 11/2018 | Phelps et al. |
| 2019/0008904 A1 | 1/2019 | Jeffs |
| 2019/0111180 A1 | 4/2019 | Ayares |
| 2019/0004063 A1 | 7/2019 | Tector |

OTHER PUBLICATIONS

G. Bentley et al., "High-resolution, high-throughput HLA genotyping by next-generation sequencing", Tissue Antigens, 74, 393-403.

Caixia Gao et al., "Characterization of swine leukocyte antigen (SLA) polymorphismby sequence-based and PCR-SSP methods in Chinese Bama miniature pigs", Developmental and Comparative Immunology, 45 (2014) 87-96.

John K. Lunney et al., "Molecular genetics of the swine major histocompatibility complex, the SLA complex", Developmental and Comparative Immunology, 33 (2009) 362-374.

Atsuko Shigenari et al., "Nucleotide sequencing analysis of the swine 433-kb genomic segment located between the non-classical and classical SLA class I gene clusters", Immunogenetics, (2004) 55:695-705.

Kelton, Reprogramming MHC specificity by CRISPR-Cas9-assisted cassette exchange, Apr. 2017, Scientific Reports.

Sachs article (Jul. 2010), https://apps.dtic.mil/dtic/tr/fulltext/u2/a535275.pdf.

Tucker article (2002, Xenotransplantation 9: 191-202), https://www.ncbi.nlm.nih.gov/pubmed/11983017.

Zhu et al. Frontiers in Surgery, Mar. 2014, vol. 1, Art. 7, 1-8.

Stone et al., Advancements in Regenerative Strategies Through the Continuum of Burn Care, Frontiers in Pharm., Jul. 2018, vol. 9, Art. 62, pp. 1-33.

Klymiuk N, Aigner B, Brem G, Wolf E. Genetic modification of pigs as organ donors for xenotransplantation. Mol Reprod Dev. 2010;77:209-221.

Hryhorowicz M, Zeyland J, Stomski R, Lipiński D. Genetically mod-ified pigs as organ donors for xenotransplantation. Mol. Biotechnol. 2017;59:435-444.

Yang L, Guell M, Niu D, et al. Genome-wide inactivation of porcine endogenous retroviruses (PERVs). Science. 2015;350:1101-1104.

Sachs DH, Galli C. Genetic manipulation in pigs. Curr Opin Organ Transplant. 2009;14:148-153.

Phelps CJ, Koike C, Vaught TD, et al. Production of alpha 1,3-galactosyltransferase-deficient pigs. Science. 2003;299:411-414.

Fishman JA. Xenosis and xenotransplantation: addressing the infectious risks posed by an emerging technology. Kidney Int—Suppl. 1997;58:S41-S45.

Fishman J, Patience C. Xenotransplantation: infectious risk revisited. Am J Transplantation. 2004;4:1383-1390.

Fishman JA. Infection in xenotransplantation. J Card Surg. 2001;16:363-373.

Fishman JA. Infection and xenotransplantation. Developing strategies to minimize risk. Ann NY Acad Sci. 1998;862:52-66.

Fishman JA. The risk of infection in xenotransplantation. Introduction. Ann N Y Acad Sci. 1998;862:45-51.

Moraes et al., Prediction of early kidney transplant rejection by a crossmatch with donor skin. Dec. 1989;48(6):951-2.

Ravi Starzl et al., Review of the Early Diagnoses and Assessment of Rejection in Vascularized Composite Allotransplantation. Hindawi Publishing Corporation Clinical and Developmental Immunology vol. 2013, Article ID 402980, 9 pages.

Shackman R, Castro JE. Prelusive skin grafts in live-donor kidney transplantation. Lancet. Sep. 20, 1975;2(7934)521-4.

Kelly et al, How many patients do we need for a clinical trial Demystifying sample size calculations Sample size estimation in nephrology. Nephrology, vol. 15, Issue 8, Dec. 2010, pp. 725-731.

Villiger, et al., Getting Real About Valuations in Biotech, Nature Biotechnology, vol. 23, Issue 4, Apr. 2005, pp. 423-428.

Booth et al., In defense of life sciences venture investing. Nature Biotechnology, vol. 29, 2011, pp. 579-583.

K. Paradis, Search for Cross-Species Transmission of Porcine Endogenous Retrovirus in Patients Treated with Living Pig Tissue, Science, vol. 285, Issue 5431, pp. 1236-1241.

Fishman, Infectious disease risks in xenotransplantation. American Journal of Transplantation, Aug. 2008, vol. 18, Issue 8, pp. 1857-1864.

Nellore et al., Donor-derived infections and infectious risk in xenotransplantation and allotransplantation, Xenotransplantation, 2018, vol. 25, Issue 4, pp. e12423.

Fishman et al., Absence of interaction between porcine endogenous retrovirus and porcine cytomegalovirus in pig-to-baboon renal xenotransplantation in vivo. Xenotransplantation, Sep. 2018, vol. 25, Issue 5, pp. e12395.

(56) References Cited

OTHER PUBLICATIONS

Schuurman, The International Xenotransplantation Association consensus statement on conditions for undertaking clinical trials of porcine islet products in type 1 diabetes—chapter 2: Source pigs. Xenotransplantation, Jul.-Aug. 2009, vol. 16, Issue 4, pp. 215-222.
Denner et al., The International Xenotransplantation Association consensus statement on conditions for undertaking clinical trials of porcine islet products in type 1 diabetes—chapter 5: Strategies to prevent transmission of porcine endogenous retroviruses. Xenotransplantation, Jul.-Aug. 2009. vol. 16, Issue 4, pp. 239-248.
Paradis et al., Search for cross-species transmission of porcine endogenous retrovirus in patients treated with living pig tissue. The XEN 111 Study Group. Science (New York, N.Y.), Aug. 20, 1999. vol. 285, Issue 5431, pp. 1236-1241.
Spizzo et al., First update of the International Xenotransplantation Association consensus statement on conditions for undertaking clinical trials of porcine islet products in type 1 diabetes—Chapter 2a source pigs—preventing xenozoonoses. Xenotransplantation, 2016, vol. 23, Issue 1, pp. 25-31.
Cooper et al., Joint FDA-IXA Symposium, Sep. 20, 2017, Xenotransplantation, Nov. 2017, vol. 24, Issue 6.
Fishman et al., Innovation in organ transplantation A meeting report. American Journal of Transplantation, 2018, vol. 18, Issue 8, pp. 1875-1878.
Fishman et al., Pneumocystis jiroveci in Solid Organ Transplantation—Guidelines from the American Society of Transplantation Infectious Diseases Community of Practice. Clinical Transplantation, May 11, 2019, pp. e13587.
Fishman, *Mycobacterium tuberculosis* in transplantation Immunity sufficient to perpetuate disease American Journal of Transplantation, 2019, vol. 19, Issue 5, pp. 1262-1263.
Hartline, Xenotransplantation panel for the detection of infectious agents in pigs, Xenotransplantation, 2018, vol. 25, Issue 4, pp. e12427.
Estrada, Evaluation of human and non-human primate antibody binding to pig cells lacking GGTA1CMAHβ4GaINT2 genes, Xenotransplantation, May 2015, vol. 22, Issue3, pp. 194-202.
Adams e al., Xenoantigen Deletion and Chemical Immunosuppression Can Prolong Renal Xenograft Survival. Annals of Surgery, Oct. 2018, vol. 268, Issue 4, pp. 564-573.
Ladowski et al., The desirable donor pig to eliminate all xenoreactive antigens. Xenotransplantation, 2016, pp. e12504.
Ladowski et al, Swine Leukocyte Antigen Class II Is a Xenoantigen. Transplantation, Feb. 2008, vol. 102, Issue 2, pp. 249-254.
Kim et al., Long-term survival of pig-to-rhesus macaque renal xenografts is dependent on CD4 T cell depletion. American Journal of Transplantation, 2019, vol. 19, Issue 8, pp. 2174-2185.
Martens et al., Humoral Reactivity of Renal Transplant-Waitlisted Patients to Cells From GGTA1CMAHB4GaINT2, and SLA Class I Knockout Pigs. Transplantation, Apr. 2017, vol. 101, Issue 4.
Ladowski et al., Examining the Biosynthesis and Xenoantigenicity of Class II Swine Leukocyte Antigen Proteins. Journal of Immunology (Baltimore, Md. 1950), Apr. 15, 2018, vol. 200, Issue 8, pp. 2957-2964.
Wang et al., Eliminating Xenoantigen Expression on Swine RBC. Transplantation, Mar. 2017, vol. 101, Issue 3, pp. 517-523.
Butler et al., Efficient generation of targeted and controlled mutational events in porcine cells using nuclease-directed homologous recombination. Journal of Surgical Research, May 2017, vol. 212, pp. 238-245.
Yamamoto et al., Data on B cell phenotypes in baboons with pig artery patch grafts receiving conventional immunosuppressive therapy. Sep. 13, 2018, vol. 20, pp. 1965-1974.
Nunes Dos Santos, CRISPRCas and recombinase-based human-to-pig orthotopic gene exchange for xenotransplantation. The Journal of Surgical Research, Sep. 2018, vol. 229, pp. 28-40.
Weiss, "Xenografts and Retroviruses" Perspective Biomedicine. Aug. 20, 1999, vol. 285, Issue 5431, pp. 1221-1222.
Lawrence et al., "HIV Transmission and Skin Grafts" The Lancet. Apr. 25, 1987, p. 983.

Hansmann, "The Economics and Ethics of Markets for Human Organs" Journal of Health Politics, Policy and Law. 1989, vol. 14 No. 1, pp. 57-85.
Fansa et al., "Stimulation of Schwann cell proliferation and axonal regeneration by FK 506" Restorative Neurology and Neuroscience. 2000, vol. 16, pp. 77-86.
Fansa et al., "Cryopreservation of Peripheral Nerve Grafts" Muscle Nerve. 2000, vol. 23, pp. 1227-1233.
Diaz-Siso et al., "Vascularized Composite Tissue Allotransplantation-State of the Art" Clinical Transplantation. May 2013, vol. 27, Issue 3, pp. 330-337.
Cooper et al., "Progress in pig-to-non-human primate transplantation models (1998-2013): a comprehensive review of the literature" Xenotransplantation. Sep. 2014, vol. 21, Issue 5, pp. 397-419.
Choukairi et al., "Letter to the Editor" Burns. Sep. 2008, vol. 34, Issue 6, p. 896.
Chiarini et al., "In vitro and in vivo characteristics of frozen/thawed neonatal pig split-skin strips: A novel biologically active dressing for areas of severe, acute or chronic skin loss" International Journal of Molecular Medicine. Feb. 1, 2007, vol. 19 pp. 245-255.
Cetrulo et al., "Penis Transplantation: First US Experience" Annals of Surgery. May 2018, vol. 267, Issue 5, pp. 983-988.
Boneva et al., "Xenotransplantation and risks of zoonotic infections" Annals of Medicine. Jan. 2004, vol. 36, Issue 7, pp. 504-517.
Kealey et al., "Cadaver skin allografts and transmission of human cytomegalovirus to burn patients." Journal of the American College of Surgeons. Mar. 1996, vol. 182, Issue 3, pp. 201-205.
Klein et al., "A reliable and cost-effective in vitro assay of skin viability for skin banks and burn centers" The Journal of Burn Care & Rehabilitation. Nov.-Dec. 1996, vol. 17, Issue 6 Pt 1, pp. 565-570.
Pegg, "Viability assays for preserved cells, tissues, and organs" Cryobiology. Jun. 1989, vol. 26, Issue 3, pp. 212-231.
Robson et al., "Factors in xenograft rejection." Annals of the New York Academy of Sciences. Jun. 18, 1999, vol. 875, pp. 261-276.
Merrell et al., "An in vivo test of viability for cryopreserved human skin" Current Surgery. Jul.-Aug. 1986, vol. 43, Issue 4, pp. 296-300.
Farley et al., "Cells, tissues, organs and systems" Nursing Standard, Aug. 29-Sep. 4, 2012, vol. 26, Issue 52, pp. 40-45.
Ezzelarab et al., "Reducing Gal expression on the pig organ—a retrospective review" Xenotransplantation. Jul. 2005, vol. 12, Issue 4, pp. 278-285.
Scudiero et al., "Evaluation of a soluble tetrazolium/formazan assay for cell growth and drug sensitivity in culture using human and other tumor cell lines" Cancer Research. Sep. 1, 1988, vol. 48, Issue 17, pp. 4827-4833.
Marshall, "A critical assessment of the use of microculture tetrazolium assays to measure cell growth and function." Growth Regulation. Jun. 1995, vol. 5, Issue 2, pp. 69-84.
May et al., "Recent developments in skin banking and the clinical uses of cryopreserved skin" Journal of the Medical Association of Georgia. Apr. 1984, vol. 73, Issue 4, pp. 233-236, 57.
Vloemans et al., "Commentary on: "The effect of moist and moist exposed dressings on healing and barrier function restoration of partial thickness wounds" by Atiyeh et al." European Journal of Plastic Surgery. Apr. 1, 2003, vol. 26, Issue 1, pp. 12-12.
Vloemans et al., "The use of glycerol-preserved allografts in the Beverwijk Burn Centre: a retrospective study" Burns. Oct. 1, 2002, vol. 28, pp. 2-9.
Clavien et al., "Preservation and reperfusion injuries in liver allografts. An overview and synthesis of current studies" Transplantation. May 1992, vol. 53, Issue 5, pp. 957-978.
Koyama et al., "The role of oxygen free radicals in mediating the reperfusion injury of cold-preserved ischemic kidneys" Transplantation. Dec. 1985, vol. 40, Issue 6, pp. 590-595.
Riss et al., "Cell Viability Assays" Assay Guidance Manual. May 1, 2013, 31pgs.
Lee et al., "High-resolution donor-recipient HLA matching contributes to the success of unrelated donor marrow transplantation" www.bloodjournal.org, Dec. 15, 2007, vol. 110, Issue 13, 28 pgs.
Fishman, "Screening of source animals and clinical monitoring for xenotransplantation" Xenotransplantation. Jul. 2007, vol. 14, Issue 4, pp. 349-352.

(56) References Cited

OTHER PUBLICATIONS

Murray, "Organ Transplantation (Skin, Kidney, Heart) and the Plastic Surgeon" Plastic and Reconstructive Surgery. May 1971, vol. 47, Issue 5, p. 425.
Kawai et al., "Tolerance—One Transplant for Life" Transplantation. Jul. 27, 2014, vol. 98, Issue 2, pp. 117-121.
Barth et al., "Vascularized Bone Marrow-Based Immunosuppression Inhibits Rejection of Vascularized Composite Allografts in Nonhuman Primates" American Journal of Transplantation. Jul. 1, 2011, vol. 11, Issue 7, pp. 1407-1416.
Wachtel et al., "Viability of frozen allografts" American Journal of Surgery. Dec. 1979, vol. 138, Issue 6, pp. 783-787.
Sokolic et al., "The use of heterograft skin as a biological dressing" Surgical Forum. 1960, vol. 10, pp. 847-849.
May et al. "Skin Banking.: Part III. Cadaveric Allograft Skin Viability" Journal of Burn Care & Research. May 1, 1981, vol. 2.
Levi et al., "Liver allotransplantation after extracorporeal hepatic support with transgenic (hCD55/hCD59) porcine livers: clinical results and lack of pig-to-human transmission of the porcine endogenous retrovirus" Transplantation. Jan. 27, 2000, vol. 69, Issue 2, pp. 272-280.
Ersek et al., "Porcine xenografts in the treatment of pressure ulcers." Annals of Plastic Surgery, Dec. 1980, vol. 5, Issue 6, pp. 464-470.
Ravindra et al., "The need for inducing tolerance in vascularized composite allotransplantation" Clinical and Developmental Immunology. vol. 2012, 11 pgs.
Morozov et al., "No PERV transmission during a clinical trial of pig islet cell transplantation" Virus Research. Jan. 2017, vol. 227, pp. 34-40.
Dheda et al., "Validation of housekeeping genes for normalizing RNA expression in real-time PCR" BioTechniques. Jul. 2004, vol. 37, Issue 1, pp. 112-114, 116, 118-119.
Shi et al., "Inhibition of porcine endogenous retrovirus (PERV) replication by HIV-1 gene expression inhibitors" Antiviral Research. Aug. 2009, vol. 83, Issue 2, pp. 201-204.
Teh, "Why do skin grafts fail?" Plastic and Reconstructive Surgery Mar. 1979, vol. 63, Issue3, pp. 323-332.
Cooper et al., "The role of genetically engineered pigs in xenotransplantation research: Genetically engineered pigs in xenotransplantation" The Journal of Pathology. Jan. 2016, vol. 238, Issue 2, pp. 288-299.
Denner, "Why was PERV not transmitted during preclinical and clinical xenotransplantation trials and after inoculation of animals?" Retrovirology. Dec. 2018, vol. 15, Issue, 1 p. 28.
Denner et al., "Is it currently possible to evaluate the risk posed by PERVs for clinical xenotransplantation?" Xenotransplantation. 2018, vol. 25, Issue 4, pp. e12403.
Yamamoto et al., "Skin xenotransplantation: Historical review and clinical potential" Burns: Journal of the International Society for Burn Injuries. Nov. 2018, vol. 44, Issue 7, pp. 1738-1749.
Irgang, "Porcine endogenous retroviruses: no infection in patients treated with a bioreactor based on porcine liver cells" Journal of Clinical Virology. Oct. 2003, vol. 28, Issue 2, pp. 141-154.
Di Nicuolo et al., "Long-term absence of porcine endogenous retrovirus infection in chronically immunosuppressed patients after treatment with the porcine cell-based Academic Medical Center bioartificial liver: Absence of PERV after BAL treatment" Xenotransplantation. Nov. 2010, vol. 17, Issue 6, pp. 431-439.
Zych et al., "Application of Genome Editing Techniques in Immunology" Archivum Immunologiae et Therapiae Experimentalis. Aug. 2018, vol. 66, Issue 4, pp. 289-298.
Issa et al., "Absence of Replication of Porcine Endogenous Retrovirus and Porcine Lymphotropic Herpesvirus Type 1 with Prolonged Pig Cell Microchimerism after Pig-to-Baboon Xenotransplantation" Journal of Virology. Dec. 12, 2008, vol. 82, Issue 24, pp. 12441-12448.
Holmes et al., "Anti-pig antibody levels in naive baboons and cynomolgus monkeys" Xenotransplantation. Mar. 2002, vol. 9, Issue 2, pp. 135-147.

Zhang et al., "Lamellar Keratoplasty Treatment of Fungal Corneal Ulcers With Acellular Porcine Corneal Stroma: Acellular Porcine Cornea in Keratoplasty" American Journal of Transplantation. Apr. 2015, vol. 15, Issue 4, pp. 1068-1075.
Turhan-Haktanir et al., "Evaluation of amniotic fluid as a skin graft storage media compared with RPMI and saline" Burns. Jun. 1, 2011, vol. 37, Issue 4, pp. 652-655.
Valdez-Gonzalez et al., "no. evidence of porcine endogenous retrovirus in patients with type 1 diabetes after long-term porcine islet xenotransplantation" Journal of Medical Virology. 2010, vol. 82, Issue 2, pp. 331-334.
Vadori et al., "Immunological Challenges and Therapies in Xenotransplantation" Cold Spring Harbor Preservatives in Medicine. Apr. 2014, vol. 4, Issue 4.
Chardon et al., "Sequence of the swine major histocompatibility complex region containing all non-classical class I genes" Tissue Antigens. Jan. 2001, vol. 57, Issue 1, pp. 55-65.
Byrne et al., "Recent investigations into pig antigen and anti-pig antibody expression" International Journal of Surgery. Nov. 2015, vol. 23, pp. 223-228.
Buhler et al., "An investigation of the specificity of induced anti-pig antibodies in baboons" Xenotransplantation. Jan. 2003, vol. 10, Issue 1, pp. 88-93.
Floss et al., "Insights into IL-23 biology: From structure to function" Cytokine & Growth Factor Reviews, Oct. 1, 2015, vol. 26, Issue 5, pp. 569-578.
Patience et al., "No evidence of pig DNA or retroviral infection in patients with short-term extracorporeal connection to pig kidneys" The Lancet. Aug. 1998, vol. 352, Issue 9129, pp. 699-701.
Zhu et al., "Anti-N-glycolylneuraminic acid antibodies identified in healthy human serum" Xenotransplantation. Nov. 2002, vol. 9, Issue 6, pp. 376-381.
Morozov et al., "Islet cell transplantation from Göttingen minipigs to cynomolgus monkeys: analysis of virus safety" Xenotransplantation. Jul. 2016, vol. 23, Issue 4, pp. 320-327.
Choi et al., "Long-term safety from transmission of porcine endogenous retrovirus after pig-to-non-human primate corneal transplantation" Xenotransplantation. Jul. 2017, vol. 24, Issue 4, 13 pgs.
Heneine et al., "No evidence of infection with porcine endogenous retrovirus in recipients of porcine islet-cell xenografts" The Lancet. Aug. 1998, vol. 352, Issue 9129, pp. 695-699.
Lin et al., "The role of antibodies in acute vascular rejection of pig-to-baboon cardiac transplants." Journal of Clinical Investigation. Apr. 15, 1998, vol. 101, Issue 8, pp. 1745-1756.
Varki, "Loss of N-glycolylneuraminic acid in humans: Mechanisms, consequences, and implications for hominid evolution" American Journal of Physical Anthropology. 2001, vol. Suppl 33, pp. 54-69.
Vimr et al., "Diversity of microbial sialic acid metabolism" Microbiology and Molecular Biology Reviews. Mar. 2004, vol. 68, Issue 1, pp. 132-153.
Diswall et al., "Structural characterization of alpha1,3-galactosyltransferase knockout pig heart and kidney glycolipids and their reactivity with human and baboon antibodies" Xenotransplantation. Jan.-Feb. 2010, vol. 17, Issue 1, pp. 48-60.
Brochner et al., "Pathophysiology of the systemic inflammatory response after major accidental trauma" Scandinavian Journal of Trama, Resusitation and Emergency Medicine. Sep. 15, 2009, vol. 17, p. 43.
Kravitz, "Immune consequences of burn injury" AACN Clinical Issues in Critical Care Nursing. May 1993, vol. 4, Issue 2, pp. 399-413.
Pavoni et al., "Outcome predictors and quality of life of severe burn patients admitted to intensive care unit" Scandinavian Journal of Trauma, Resuscitation and Emergency Medicine. Apr. 27, 2010, vol. 18, Issue 24, 8 pgs.
Mailer et al., "Pig kidney transplantation in baboons: anti-Gal(alpha)1-3Gal IgM alone is associated with acute humoral xenograft rejection and disseminated intravascular coagulation" Transplantation. Dec. 15, 2001, vol. 72, Issue 11, pp. 1743-1752.
Cendales et al., "The Banff 2007 Working Classification of Skin-Containing Composite Tissue Allograft Pathology: Banff CTA Allograft Pathology Classification" American Journal of Transplantation. Jul. 2008, vol. 8, Issue 7, pp. 1396-1400.

(56) References Cited

OTHER PUBLICATIONS

Levy et al., "Liver allotransplantation after extracorporeal hepatic support with transgenic (hCD55/hCD59) porcine livers: clinical results and lack of pig-to-human transmission of the porcine endogenous retrovirus" Transplantation. Jan 27, 2000, vol. 69, Issue 2, pp. 272-280.
Sharp, "Splicing of Messenger RNA Precursors" Science. 1987, vol. 235, Issue 4790, pp. 766-771.
Buermann et al., "Pigs expressing the human inhibitory ligand PD-L1 (CD 274) provide a new source of xenogeneic cells and tissues with low immunogenic properties" Xenotransplantation. Sep. 2018, vol. 25, Issue 5, pp. E12387.
Butler et al., "Recent advances in genome editing and creation of genetically modified pigs" International Journal of Surgery. Nov. 2015, vol. 23, pp. 217-222.
Hara et al., "Human dominant-negative class II transactivator transgenic pigs—effect on the human anti-pig T-cell immune response and immune status" Immunology, Sep. 2013, vol. 140, Issue 1, pp. 39-46.
Wang et al., "IL-36 promotes anti-viral immunity by boosting sensitivity to IFN-α/β in IRF1 dependent and independent manners" Nature Communications. Oct. 16, 2019, vol. 10, Issue 1, pp. 1-17.
Ohara, "From transcriptome analysis to immunogenomics: Current status and future direction" FEBS Letters, vol. 583, Issue 11, pp. 1662-1667.
Forte et al., "HLA-E Expression on Porcine Cells: Protection from Human NK Cytotoxicity Depends on Peptide Loading" American Journal of Transplantation. 2005, vol. 5, Issue 9, pp. 2085-2093.
Gupta et al., "Immunogenomics: recent discoveries" International Journal of Genetics. Dec. 30, 2009, vol. 1, Issue 2, pp. 1-5.
Greiff et al., "Learning the High-Dimensional Immunogenomic Features That Predict Public and Private Antibody Repertoires" The Journal of Immunology. Oct. 15, 2017, vol. 199, Issue 8, pp. 2985-2997.
Miretti et al., "Immunogenomics: Molecular hide and seek" Human Genomics. Jan. 1, 2006, vol. 2, Issue 4, pp. 244-251.
Holt, "Immunogenomics: a foundation for intelligent immune design" Genome Medicine. Nov. 19, 2015, vol. 7, Issue 116, pp. 1-3.
Kralovic et al., "Position-Dependent Repression and Promotion of DQB1 Intron 3 Splicing by GGGG Motifs" The Journal of Immunology. Feb. 15, 2006, vol. 176, Issue 4, pp. 2381-2388.
Simmonds et al., "Structural and Functional Implications of the Intron/Exon Organization of the Human Endothelial Cell Protein C/Activated Protein C Receptor (EPCR) Gene: Comparison With the Structure of CD1/Major Histocompatibility Complex □1 and □2 Domains" Blood. Jul. 15, 1999, vol. 94, Issue 2, pp. 632-641.
Hughes, "Evolution of introns and exons of class II major histocompatibility complex genes of vertebrates" Immunogenetics. 2000, vol. 51, Issue 6, pp. 473-486.
Mach et al., "Regulations of MHC Class II Genes: Lessons from a Disease" Annual Review of Immunology. vol. 14, pp. 301-331.
Reith et al., "Regulation of MHC class II gene expression by the class II transactivator" Nature Reviews Immunology. Oct. 2005, vol. 5, Issue 10, pp. 793-806.
Zachary et al., "HLA Mismatching Strategies for Solid Organ Transplantation—A Balancing Act" Frontiers in Immunology.
Figueiredo et al., "Immunoengineering of the Vascular Endothelium to Silence MHC Expression During Normothermic Ex Vivo Perfusion" Human Gene Therapy. Apr. 2019, vol. 30, Issue 4, pp. 485-496.
Deuse et al., "Hypoimmunogenic derivatives of induced pluripotent stem cells evade immune rejection in fully immunocompetent allogeneic recipients" Nature Biotechnology. Mar. 2019, vol. 37, pp. 252-258.
Harara et al., "Generation of a Novel HLA Class I Transgenic Mouse Model Carrying a Knock-in Mutation at the β $_2$-Microglobulin Locus" The Journal of Immunology. Jan. 1, 2017, vol. 198, Issue 1, pp. 516-527.
Lanza et al., "Engineering universal cells that evade immune detection" Nature Reviews Immunology. Aug. 15, 2019, pp. 1-11.

Taneja et al., "HLA transgenic mice as humanized mouse models of disease and immunity." Journal of Clinical Investigation. Mar. 1, 1998, vol. 101, Issue 5, pp. 921-926.
Wolf et al., "Genetically modified pigs as donors of cells, tissues, and organs for xenotransplantation" Animal Frontiers. Jun. 25, 2019, vol. 9, Issue 3, pp. 13-20.
Gadola et al., "TAP deficiency syndrome" Clinical and Experimental Immunology. Aug. 2008, vol. 121, Issue 2, pp. 173-178.
Shimizu et al., "Thrombotic microangiopathy associated with humoral rejection of cardiac xenografts from alpha,3-galactosyltransferase gene-knockout pigs in baboons" The American Journal of Pathology. Jun. 2008, vol. 172, Issue 6, pp. 1471-1481.
Laird et al., "Transgenic expression of human leukocyte antigen-E attenuates GalKO.hCD46 porcine lung xenograft injury" Xenotransplantation. Mar. 2017, vol. 24, Issue 2.
Esmaeili et al., "Frequencies of HLA-A, B and DRB1 alleles in a large normal population living in the city of Mashhad, Northeastern Iran" Iranian Journal of Basic Medical Sciences. Aug. 2017, vol. 20, Issue 8, pp. 940-943.
Aminikhah et al., "HLA Class I and Class II Genes Distribution of the Sistanis in Iran" Iranian Journal of Immunology. Jun. 2018, vol. 15, Issue 2, pp. 97-111.
Alter et al., "HLA class I haplotype diversity is consistent with selection for frequent existing haplotypes" PLOS Computational Biology Aug. 28, 2017, vol. 13, Issue 8, pp. e1005693.
Kirijas et al., "HLA profile of the donors in the Macedonian Bone Marrow Donor Registry" International Journal of Immunogenetics. Dec. 2018, vol. 45, Issue 6, pp. 337-346.
Jawdat et al., "HLA-A, B, C, DRB1 and DQB1 allele and haplotype frequencies in volunteer bone marrow donors from Eastern Region of Saudi Arabia" HLA. Jul. 2019, vol. 94, Issue 1, pp. 49-56.
Tshabalala et al., "HLA-A, B, C, DRB1 and DQB1 allele and haplotype frequencies in volunteer bone marrow donors from Eastern Region of Saudi Arabia" Journal of Immunology Research. 2018, vol. 2018, pp. 2031571.
Briata et al., "Alternative Splicing of HLA-DQB Transcripts and Secretion of HLA-DQ β-Chain Proteins: Allelic Polymorphism in Splicing and Polyadenylylation Sites" National Academy of Sciences. 1989, vol. 86, Issue 3, pp. 1003-1007.
Samandary et al., "Associations of HLA-A, HLA-B and HLA-C Alleles Frequency with Prevalence of Herpes Simplex Virus Infections and Diseases Across Global Populations: Implication for the Development of an Universal CD8+ T-Cell Epitope-Based Vaccine" Human Immunology. Aug. 2014, vol. 75, Issue 8, pp. 715-729.
Gornalusse et al., "HLA-E-expressing pluripotent stem cells escape allogeneic responses and lysis by NK cells" Nature Biotechnology. Aug. 2017, vol. 35, Issue 8, pp. 765-772.
Takahashi et al., "Exhaustive Characterization of TCR-pMHC Binding Energy Estimated by the String Model and Miyazawa-Jernigan Matrix" General Medicine. 2014, vol. 2, Issue 1.
Taxman et al., "Identification of Class II Transcriptional Activator-Induced Genes by Representational Difference Analysis: Discoordinate Regulation of the DNα/DOβ Heterodimer" The Journal of Immunology. Aug. 1, 2000, vol. 165, Issue 3, pp. 1410-1416.
Ouederni et al., "Major histocompatibility complex class II expression deficiency caused by a RFXANK founder mutation: a survey of 35 patients" Blood. Nov. 10, 2011, vol. 118, Issue 19, pp. 5108-5118.
Hanna et al., "MHC class I and II deficiencies" Journal of Allergy and Clinical Immunology. Aug. 1, 2014, vol. 134, Issue 2, pp. 269-275.
Takeda et al., "MHC class II molecules are not required for survival of newly generated CD4+ T cells, but affect their long-term life span" Immunity. Sep. 1996, vol. 5, Issue 3, pp. 217-228.
Grusby et al., "Mice lacking major histocompatibility complex class I and class II molecules" Proceedings of the National Academy of Sciences of the United States of America. May 1, 1993, vol. 90, Issue 9, pp. 3913-3917.
Cosgrove et. al., "Mice lacking MHC class II molecules." Cell. Sep. 6, 1991, vol. 66, Issue 5, pp. 1051-1066.
Reith et al., "The Bare Lymphocyte Syndrome and the Regulation of MHC Expression" Annual Review of Immunology. 2001, vol. 19, Issue 1, pp. 331-373.

(56) References Cited

OTHER PUBLICATIONS

International Search Report issued for PCT/US2019/054833, dated Jan. 17, 2020. 16 pgs.
World Health Organization, First WHO Global Consultation on Regulatory Requirements for Xenotransplantation Clinical Trials. Changsha, China. Nov. 2008.
Holzer et al., "352 Cryopreserved Gal-Knockout Xenografts Provide Efficacious Temporary Coverage of Full-Thickness Wounds: Good Laboratory Practice-Compliant Studies in Non-Human Primates." Journal of Burn Care and Research. 2019, vol. 40, Issue 1, 2 pgs.
Kemter et al., "Will Genetic Engineering Carry Xenotransplantation of Pig Islets to the Clinic?" Current Diabetes Reports. 2018, vol. 18, Issue 103, pp. 1-12.
Groenen, "A Decade of Pig Genome Sequencing: A Window on Pig Domestication and Evolution" Genetics, Selection, Evolution:GSE. Mar. 29, 2016, vol. 48, pp. 1-9.
Matczynska et al., "Analysis of swine leukocyte antigen class I gene profiles and porcine endogenous retrovirus viremia level in a transgenic porcine herd inbred for xenotransplantation research" Journal of Veterinary Science. 2018, vol. 19, Issue 3, pp. 384-392. 1-7.
Tanaka-Matsuda et al., "Difference in number of loci of swine leukocyte antigen classical class I genes among haplotypes" Genomics. Mar. 1, 2009, vol. 93, Issue 3, pp. 261-273.
Dadi et al., "Genetic Diversity and mRNA Expression of Porcine MHC Class I Chain-Related 2 (SLA-MIC2) Gene and Development of a High-Resolution Typing Method" PLOS ONE. Aug. 25, 2015, vol. 10, Issue 8 pp. e0135922.
Warr et al., "Identification of Low-Confidence Regions in the Pig Reference Genome (Sscrofa10.2)" Frontiers in Genetics. 2015, vol. 6, pp. 1-8.
Yang et al., "Swine Leukocyte Antigen-DQA Gene Variation and Its Association with Piglet Diarrhea in Large White, Landrace and Duroc" Asian-Australasian Journal of Animal Sciences. Aug. 2013, vol. 26, Issue 8, pp. 1065-1071.
Le et al., "β2-microglobulin gene duplication in cetartiodactyla remains intact only in pigs and possibly confers selective advantage to the species" PLoS ONE. 2017, vol. 12, Issue 8, pp. e0182322.
Reinoso-Barbero et al., "Anatomical comparison of sciatic nerves between adults and newborns: clinical implications for ultrasound guided block" Journal of Anatomy. Feb. 2014, vol. 224, Issue 2, pp. 108-112.
Sinis et al., "Bioartificial reconstruction of peripheral nerves using the rat median nerve model" Annals of Anatomy—Anatomischer Anzeiger. Jul. 2011, vol. 193, Issue 4, pp. 341-346.
Kelly et al., "End-to-side nerve coaptation: a qualitative and quantitative assessment in the primate" Journal of Plastic, Reconstructive & Aesthetic Surgery. Jan. 1, 2007, vol. 60, Issue 1, pp. 1-12.
Gao et al., "Nerve autografts and tissue-engineered materials for the repair of peripheral nerve injuries: a 5-year bibliometric analysis" Neural Regeneration Research. Jun. 2015, vol. 10, Issue 6, pp. 1003-1008.
Kornfeld et al., "Nerve grafting for peripheral nerve injuries with extended defect sizes" Wiener Medizinische Wochenschrift (1946). Nov. 21, 2018, vol. 169, Issue 9-10, pp. 240-251.
Kowalska et al., "Normal and sonographic anatomy of selected peripheral nerves. Part III: Peripheral nerves of the lower limb" Journal of Ultrasonography. Jun. 2012, vol. 12, Issue 49, pp. 48-163.
Kouyoumdjian et al., "Peripheral nerve injuries: A retrospective survey of 1124 cases" Neurology India. May 9, 2017. vol. 65, Issue 3, pp. 551-555.
Matsumoto et al., "Peripheral nerve regeneration across an 80-mm gap bridged by a polyglycolic acid (PGA)-collagen tube filled with laminin-coated collagen fibers: a histological and electrophysiological evaluation of regenerated nerves" Brain Research. Jun. 2013, vol. 868, Issue 2, pp. 315-328.
Stenberg et al., "Regeneration of long-distance peripheral nerve defects after delayed reconstruction in healthy and diabetic rats is supported by immunomodulatory chitosan nerve guides" BMC Neuroscience. Jul. 18, 2017, vol. 18.
Alshami et al., "Reliability and size of the measurement error when determining the cross-sectional area of the tibial nerve at the tarsal tunnel with ultrasonography" Ultrasound in Medicine & Biology. Jul. 2009, vol. 35, Issue 7, pp. 1098-1102.
Campana, "Schwann Cells: Activated Peripheral Glia and Their Role in Neuropathic Pain" Brain, behavior, and immunity. Jul. 2007, vol. 21, Issue 5, pp. 522-527.
Liu et al., "Specific Marker Expression and Cell State of Schwann Cells during Culture In Vitro" PLOS ONE. Apr. 10, 2015, vol. 10, Issue 4, pp. e0123278.
Koller et al., "The influence of the graft length on the functional and morphological result after nerve grafting: an experimental study in rabbits" British Journal of Plastic Surgery. Dec. 1, 1997, vol. 50, Issue 8, pp. 609-614.
Gaudet et al., "Wallerian degeneration: gaining perspective on inflammatory events after peripheral nerve injury" Journal of Neuroinflammation. Aug. 2011, vol. 8, pp. 1-13.
Fishman et al., Xenotransplantation, 2020, 27: e12595, pp. 1-6 (Year: 2020).
Guell et al., Xenotransplantation, 2017;24:e12366 (Year: 2017).
Council of Europe, Report on the State of the Art in the field of Xenotransplantation, 2003, 99 pages. (Year: 2003).
Davis et al., Frontiers in Microbiology, vol. 4, Article 123, pp. 1-4, published May 15, 2013 (Year: 2013).
Foley et al., Curr. Derm Rep (2013) vol. 2, pp. 101-112 (Year: 2013).
International Atomic Energy Agency, Decontamination of Animal Feeds by Irradiation, 1979, 167 pages (Year: 1979).
Kotton et al., Clinical Infectious Diseases 2007; 44:857-66 (Year: 2007).
Mendes et al., Medicine (2016) vol. 95:46(e5271) (Year: 2016).
Morgan et al., Journal of Antimicrobial Chemotherapy (2008), vol. 62, 1181-1187 (Year: 2008).
Swindle et al J Invest Surg. Jul.-Aug. 1996; 9(4):267-71 (Year: 1996).
U.S. Department of Health and Human Services, Source Animal, Product, Preclinical, and Clinical Issues Concerning the Use of Xenotransplantation Products in Humans, Guidance for Industry, Apr. 2003, 64 pages (Year: 2003).
Wang et al., Xenotransplantation—New Insights, Chapter 5, 2017 (Year: 2017).
Carey et al., "Factors affecting HLA expression: A review" International Journal of Immunogenetics. 2019, 14 pgs.
Carey et al., "Frequency of off-targeting in genome edited pigs produced via direct injection of the CRISPR/Cas9 system into developing embryos" BMC Biotechnology. 2019, 8pgs.
Chen et al., "Conserved Nature of the Antigen-Presenting of Bony Fishes Provides Insights into the the Structure of the MHC Class I Molecule System" Journal of Immunology. Oct. 20, 2017, 12 pgs.
Cole et al., "Modification of MHC Anchor Residues Generates Heteroclitic Peptides That Alter TCR Binding and T Cell Recognition" Journal of Immunology. Jul. 16, 2010, 12 pgs.
Cooper et al., "Perspectives on the Optimal Genetically Engineered Pig in 2018 for Initial Clinical Trials of Kidney or Heart Xenotransplantation" Transplantation. Dec. 2018, vol. 102, No. 12, 9 pgs.
Cooper et al., "Justification of specific genetic modifications in pigs for clinical organ xenotransplantation" Xenotransplantation. 2019, 12 pgs.
Guo et al., "Sequencing of the MHC region defines HLA-DQA1 as the major genetic risk for seropositive rheumatoid arthritis in Han Chinese population" Epidemiological Science. Ann Rheum Dis, 2019, vol. 78, 8 pgs.
Henneke et al., "T Cell Receptor—MHC Interactions up Close" Cell, vol. 104, Jan. 12, 2001, 4 pgs.
Iwase et al., "Regulation of Human Platelet Aggregation by Genetically Modified Pig Endothelial Cells and Thrombin Inhibition" Xenotransplantation. Jan. 2014, 21 pgs.
Jo et al., "Introns: the Functional Benefits of Introns in Genomes" Genomics and Informatics. 2015, vol. 13, Issue 4, 7 pgs.

(56) References Cited

OTHER PUBLICATIONS

Li et al., "Strict major histocompatibility complex molecule class-specific binding by co-receptors enforces MHC-restricted ab TCR recognition during T lineage subset commitment" Frontiers in Immunology. Nov. 22, 2013, 8 pgs.
Ogawa et al., "Next-generation sequencing identifies contribution of both class I and II HLA genes on susceptibility of multiple sclerosis in Japanese" Journal of Neuroinflammation. 2019, 9 pgs.
Van den Elsen, P.J. "Expression regulation of major histocompatibility complex class I and class II encoding genes" Frontiers in Immunology. Oct. 4, 2011, 9 pgs.
Reche et al., "Sequence Variability Analysis of Human Class I and Class II MHC Molecules: Functional and Structural Correlates of Amino Acid Polymorphisms" Journal of Molecular Biology, vol. 331, Issue 3, Aug. 15, 2003, pp. 623-641.
Renard et al., "Sequence of the pig major histocompatibility region containing the classical class I genes" Immunogenetics, 2001, 11 pgs.
Renard et al., "The genomic sequence and analysis of the swine major histocompatibility complex" Genomics. 1998, vol. 88, 12 pgs.
Sasazuki et al., "Effects of Matching of Class I HLA Alleles on Clinical Outcome after Transplantation of Hematopoietic Stem Cells from an Unrelated Donor" The New England Journal of Medicine. Oct. 22, 1998, 17 pgs.
Shen et al., "The Utility of Supertype Clustering in Prediction for Class II MHC-Peptide Binding" Molecules. Nov. 20, 2018, 18 pgs.
Song et al., "Expression and Regulation Profile of Mature MicroRNA in the Pig: Relevance to Xenotransplantation" BioMed Research International. Mar. 21, 2018, 9 pgs.
Southwood et al., "Several Common HLA-DR Types Share Largely Overlapping Peptide Binding Repertoires" Journal of Immunology. 1998, 12 pgs.
Van Chanh Li et al., "Analysis of peptide-SLA binding by establishing immortalized porcine alveolar macrophage cells with dierent SLA class II haplotypes" Veterinary Research, 2018, 10 pgs.
Whyte "Genetic Modifications of Pigs for Medicine and Agriculture" Molecular Reproduction & Development. 2011, 13 pgs.
Zavala-Ruiz "A Polymorphic Pocket at the P10 Position Contributes to Peptide Binding Specificity in Class II MHC Proteins" Chemistry & Biology. vol. 11, Oct. 2004, 8 pgs.
Gussow et al, "The human beta 2-microglobulin gene. Primary structure and definition of the transcriptional unit." Journal of Immunology. 1987, 8pgs.
Glimcher et al., "Sequences and Factors: A Guide to MHC Class-II Transcription" Annu. Rev. Immunol. 1992, 37 pgs.
Quatrini et al., "Endogenous glucocorticoids control host resistance to viral infection through the tissue-specific regulation of PD-1 expression on NK cells" Nature Immunology, vol. 19, Sep. 2018, 14 pgs.
Hull, "Genollle C,oinposition, Organization, and Expression" Plant Virology. 2014, 1 pg.
Sharp, "Splicing of Messenger RNA Precursors" Science, New Edition. Vo. 235, No. 4790, Feb. 13, 1987, 7 pgs.
Shiina et al., "The HLA genomic loci map: expression, interaction, diversity and disease" Journal of Human Genetics. 2009, vol. 54, 25 pgs.
Castelli et al., "Transcriptional and Posttranscriptional Regulations of the HLA-G Gene" Journal of Immunology Research. 2014, 15 pgs.
Dib et al., "Polymorphic sites preferentially avoid coevolving residues inMHC class I proteins" PLOS Computational Biology. May 21, 2018, 19 pgs.
Artyomov et al., "CD4 and CD8 binding to MHC molecules primarily acts to enhance Lck delivery" PNAS. Sep. 28, 2010, vol. 107, No. 39, 6 pgs.
Ting et al., "Genetic Control of MHC Class II Expression" Cell, vol. 109, Apr. 2002, 13 pgs.
Yamaguchi et al., "Major Histocompatibility Complex (MHC) Genes and Disease Resistance in Fish" Cells. 2019, 31 pgs.

Fisher et al., "Viable pigs after simultaneous inactivation of porcine MHC class I and three xenoreactive antigen genes GGTA1, CMAH and B4GALNT2" Xenotransplantation. 2019, 11 pgs.
Rosales et al., "Systematic pathological component scores for skin-containing vascularized composite allografts" Vascularized Composite Allotransplantation. 2017, 13 pgs.
Joly et al., "The orthology of HLA-E and H2-Qa1 is hidden by their concerted evolution with other MHC class I molecules" Biology Direct. Jan. 31, 2006, 18 pgs.
Reith et al., "Cloning of the Major Histocompatability Complex Class II Promoter Binding Protein Affected in a Hereditary defect in Class II Gene Regulation" Proc. Natl. Acad. Sci. USA. 1989, 5 pgs.
Chen et al., "Distribution Characteristics of Alleles of Classical SLA-I and II Genes and Bioinformatic Analysis of Novel Alleles in Guizhou Miniature Pigs" Pakistan J. Zool. 2014, vol. 46(3), 8 pgs.
Nakamura et al., "Liver Allograft Rejection in Sensitized Recipients Observations in a Clinically Relevant Small Animal Model" American Journal of Pathology. May 1993, vol. 142, No. 5.
Nariai et al., "HLA-VBSeq: accurate HLA typing at full resolution from whole-genome sequencing data" BMC Genomics. 2015, 6 pgs.
Shuurman, "Regulatory aspects of clinical xenotransplantation" International Journal of Surgery. 2015, 10 pgs.
Tector et al., "Rejection of Pig Liver Xenografts in Patients With Liver Failure: Implications for Xenotransplantation" Liver Transplantation, Feb. 2001, vol. 7, No. 2, 8 pgs.
Xie et al., "Fast and accurate HLA typing from short-read next-generation sequence data with xHLA" PNAS. Jul. 25, 2017, vol. 114, No. 30, 6 pgs.
Demetris et al., "Antibody Mediated Rejection of Human Liver Allografts: Transplantation Across ABO Blood Group Barriers" Transplant Proc. Feb. 1989, 8 pgs.
Dilthey et al., "High-Accuracy HLA Type Inference from Whole-Genome Sequencing Data Using Population Reference Graphs" PLOS Computational Biology. Oct. 28, 2016, 16 pgs.
Erlich et al., "Next-generation sequencing for HLA typing of class I loci" BMC Genomics. 2011, 13 pgs.
Furuya et al., "Preformed Lymphocytotoxic Antibodies: The Effects of Class, Titer and Specificity on Liver vs. Heart Allografts" Hepatology. Dec. 1992, 16 pgs.
Mezrich et al., "Histocompatible Miniature Swine: An Inbred Largeanimal Model1" Transplantation. Mar. 27, 2003, vol. 75, No. 6, 4 pgs.
Galili et al., Man, Apes, and Old World Monkeys Differ from Other Mammals in the Expression of a-Galactosyl Epitopes on Nucleated Cells* The Journal of Biological Chemistry. 1988, vol. 263, No. 33, 8 pgs.
Sachs et al., "Transplantation in Miniature Swine" Transplantation, 1976, vol. 22 No. 6, 9 pgs.
Tsururi et al., "Exhaustive Characterization of TCR-pMHC Binding Energy Estimated by the String Model and Miyazawa-Jernigan Matrix" General Medicine. 2013, 7 pgs.
Varela et al., "Cross-Reactivity between Swine Leukocyte Antigen and Human Anti-HLA-Specific Antibodies in Sensitized Patients Awaiting Renal Transplantation" Journal of the American Society of Nephrology. 2003, 7 pgs.
Ali et al., "Could Sentinel Skin Transplants Have Some Utility in Solid Organ Transplantation?" Elsevier. 2016, 6 pgs.
Cooper et al., "Genetically Engineered Pigs" The Lancet. Sep. 11, 1993, 2pgs.
Achauer et al., Long-Term Skin Allograft Survival After Short-Term Cyclosporin Treatment ina Patient with Massive Burns. The Lancet, Jan. 1986, vol. 327, Issue 8471, pp. 14-15.
Albritton et al., Lack of Cross-Sensitization Between α-1,3-Galactosyltransferase Knockout Porcine and Allogeneic Skin Grafts Permits Serial Grafting. Transplantation, 62014, vol. 97, Issue 12, pp. 1209-1215.
Ardehali, 1. While millions and millions of lives have been saved, organ transplantation still faces massive problems after 50years; organ preservation is a big part of the solution. Cryobiology, Aug. 2015, vol. 71 Issue 1, pp. 164-165.

(56) References Cited

OTHER PUBLICATIONS

Argaw et al., Susceptibility of porcine endogenous retrovirus to anti-retroviral inhibitors. Xenotransplantation, Mar. 2016, vol. 23, Issue 2, pp. 151-158.
Atiyeh et al., Military and Civilian Burn Injuries During Armed Conflicts. Annals of Burns and Fire Disasters, Dec. 31, 2007, vol. 20, Issue 4, pp. 203-215.
Banner et al., Effect of Heart Transplantation on Survival in Ambulatory and Decompensated Heart Failure:, Transplantation, Dec. 2008, vol. 86, Issue 11, pp. 1515-1522.
Barker et al., Historical overview of transplantation. Cold Spring Harbor Perspectives in Medicine, Apr. 1, 2013, vol. 3, Issue 4, pp. a014977.
Barone et al., Genetically modified porcine split-thickness skin grafts as an alternative to allograft for provision of temporary wound coverage: preliminary characterization. Burns, May 2015, vol. 41, Issue 3, pp. 565-574.
Barret et al., Cost-Efficacy of Cultured Epidermal Autografts in Massive Pediatric Burns:, Annals of Surgery, Jun. 2000, vol. 231, Issue 6, pp. 869-876.
Becker, Thomas Schlich, The Origins of Organ Transplantation: Surgery and Laboratory Science 1880-1930, Social History of Medicine, May 1, 2012, vol. 25, Issue 2, pp. 549-550.
Belzer et al., Principles of solid-organ preservation by cold storage. Transplantation, Apr. 1988,vol. 45, Issue 4, pp. 673-676.
Ben-Bassat et al., How long can cryopreserved skin be stored to maintain adequate graft performance. Burns, Aug. 2001, vol. 27, Issue 5, pp. 425-431.
Bender et al., Evaluation of demineralized bone matrix paste and putty in periodontal intraosseous defects. Journal of Periodontology, May 2005, vol. 76, Issue 5, pp. 768-777.
Benichou et al., Immune recognition and rejection of allogeneic skin grafts. Immunotherapy, Jun. 2011, vol. 3, Issue 6, pp. 757-770.
Benson et al., Burns. BJM, 2006, vol. 332, Issue 7542, pp. 649-652.
Beziat et al., NK cell responses to cytomegalovirus infection lead to stable imprints in the human KIR repertoire and involve activating KIRs. Blood, Apr. 4, 2013, vol. 121, Issue 14, pp. 2678-2688.
Boas, Where do human organs come from? Trends of generalized and restricted altruism in organ donations—ScienceDirect. Soc Sci Med, Nov. 2011, vol. 73, Issue 9, pp. 1378-1385.
Bramhall, Presumed consent for organ donation: a case against. Annals of the Royal College of Surgeons of England, May 2011, vol. 93, Issue 4, pp. 270-272.
Branski et al., Fibrin sealant improves graft adherence in a porcine full-thickness burn wound model. Burns, Dec. 2011, vol. 37, Issue 8, 1360-1366.
Braud, et al., HLA-E binds to natural killer cell receptors CD94/NKG2A, B and C. Nature, Feb. 1998, vol. 391, Issue 6669, pp. 795-799.
Bravo et al., Effect of storage and preservation methods on viability in transplantable human skin allografts. Burns, 2000, vol. 26, pp. 367-378.
Burd et al., Allogenic skin in the treatment of burns. Clinics in Dermatology, Jul. 2005, vol. 23, Issue 4, pp. 376-387.
Burke et al., Immunosuppression and temporary skin transplantation in the treatment of massive third degree burns. Annals of Surgery, Sep. 1975, vol. 182, Issue 3, pp. 183-197.
Burlak et al., N-linked glycan profiling of GGTA1/CMAH knockout pigs identifies new potential carbohydrate xenoantigens. Xenotransplantation, Sep.-Oct. 2013, vol. 20, Issue 5 pp. 277-291.
Burlak et al., Reduced binding of human antibodies to cells from GGTA1/CMAH knockout pigs. American Journal of Transplantation, Aug. 2014, vol. 14, Issue 8, pp. 1895-1900.
Butler et al., Silencing porcine CMAH and GGTA1 genes significantly reduces xenogeneic consumption of human platelets by porcine livers. Transplantation, Mar. 2016, vol. 100, Issue 3, pp. 571-576.
Butler et al., Silencing porcine genes significantly reduces human-anti-pig cytotoxicity profiles: an alternative to direct complement regulation. Transgenic Research, Oct. 2016, vol. 25, Issue 5, pp. 751-759.
Byrne et al., B4GALNT2 and xenotransplantation: A newly appreciated xenogeneic antigen, Xenotransplantation, Sep. 2018, vol. 25, Issue 5, pp. e12394.
Byrne et al., Cloning and expression of porcine β1,4 N-acetylgalactosaminyl transferase encoding a new xenoreactive antigen. Xenotransplantation, Nov. 2014, vol. 21, Issue 6, pp. 543-554.
Castagnoli et al., Evaluation of donor skin viability: fresh and cryopreserved skin using tetrazolioum salt assay. Burns, Dec. 2003, vol. 29, Issue 8, pp. 759-767.
Cetrulo et al., Vascularized Composite Allograft Transplant Survival in Miniature Swine: Is MGC Tolerance Sufficient for Acceptance of Epidermis? Transplantation, Dec. 15, 2013, vol. 96, Issue 11, 966-974.
Chambers et al., A band of surgeons, a long healing line: development of craniofacial surgery in response to armed conflict. The Journal of craniofacial surgery, 2010, vol. 21, Issue 4, pp. 991-997.
Chambers et al., Achieving Growth and Excellence in Medicine the Case History of Armed Conflict and Modem Reconstructive Surgery. Annals of plastic surgery, Nov. 1, 2009, vol. 63, pp. 473-478.
Chihara et al., Fibronectin from alpha 1,3-galactosyltransferase knockout pigs is a xenoantigen. Journal of Surgical Research, Oct. 2013, vol. 184, Issue 2, pp. 1123-1133.
Chiu et al., "Xenograft" dressing in the treatment of burns. Clinics in Dermatology, Jul. 2005, vol. 23, Issue 4, pp. 419-423.
Christiansen et al., Veterinarians' role in clients' decision-making regarding seriously ill companion animal patients. Acta Veterinaria Scandinavica, May 25, 2016, vol. 58, Issue 1, p. 30.
Church et al., Burn Wound Infections. Clinical Microbiology Reviews, Apr. 2006, vol. 19, Issue 2, pp. 403-434.
Cleland et al., Clinical application and viability of cryopreserved cadaveric skin allografts in severe burn: A retrospective analysis. Burns, Feb. 2014, vol. 40, Issue 1, pp. 61-66.
Cooper et al., A brief history of clinical xenotransplantation. International Journal of Surgery, Nov. 2015, vol. 23, pp. 205-210.
Cooper et al., Immunobiological barriers to xenotransplantation. International Journal of Surgery (London, England), Nov. 2015, vol. 23, Issue Pt B, pp. 211-216.
Cooper et al., Pig Liver Xenotransplantation: A Review of Progress Toward the Clinic. Transplantation, Oct. 2016, vol. 100, Issue 10, pp. 2039-2047.
Cooper et al., Xenotransplantation—the current status and prospects. British Medical Bulletin, Mar. 1, 2018, vol. 125, Issue 1, pp. 5-14.
Cooper, A Brief History of Cross-Species Organ Transplantation. Baylor University Medical Center Proceedings, Jan. 2012, vol. 25, Issue 1, pp. 49-57.
Cowan et al., The Resurgence of Xenotransplantation. American Journal of Transplantation, Oct. 2017, vol. 17, Issue 10, pp. 2531-2536.
Dalal, Philosophy of organ donation: Review of ethical facets. World Journal of Transplantation, Jun. 24, 2015, vol. 5, Issue 2, pp. 44-51.
Demange et al., Porcine endogenous retrovirus-A/C: biochemical properties of its integrase and susceptibility to raltegravir. Journal of General Virology, 2015, vol. 96, Issue 10, pp. 3124-3130.
Denner et al., Infection Barriers to Successful Xenotransplantation Focusing on Porcine Endogenous Retroviruses. Clinical Microbiology Reviews, Apr. 2012, vol. 25, Issue 2, pp. 318-343.
Denner et al., Preventing transfer of infectious agents. Nov. 2015, vol. 23, pp. 306-311.
Denner, Can Antiretroviral Drugs Be Used to Treat Porcine Endogenous Retrovirus (PERV) Infection after Xenotransplantation? Viruses, Aug. 8, 2017, vol. 9, Issue 8.
Denner, Paving the Path toward Porcine Organs for Transplantation. New England Journal of Medicine, Nov. 9, 2017, vol. 377, Issue 19, pp. 1891-1893.

(56) References Cited

OTHER PUBLICATIONS

Denner, Reduction of the survival time of pig xenotransplants by porcine cytomegalovirus. Virology Journal, 2018, vol. 15, Issue 1, p. 171.

Denner, Xenotransplantation-Progress and Problems: A Review. Journal of Transplantation Technologies & Research. 2014, vol. 4, Issue 2.

Deschamps et al., History of xenotransplantation. Xenotransplantation, Mar. 2005, vol. 12, Issue 2, pp. 91-109.

Dickens, Morals and legal markets in transplantable organs. Health Law Journal, 1994, vol. 2, pp. 121-134.

Dor et al., ??1,3-Galactosyltransferase Gene-Knockout Miniature Swine Produce Natural Cytotoxic Anti-Gal Antibodies:, Transplantation, Jul. 2004, vol. 78, Issue 1, pp. 15-20.

Duncan et al., Transplant-related Immunosuppression. Proceedings of the American Thoracic Society. Dec. 2005, vol. 2, Issue 5, pp. 449-455.

Durand et al., How is organ transplantation depicted in internal medicine and transplantation journals. BMC Medical Ethics, Oct. 2, 2013, vol. 14, pp. 39.

Ekser et al., Current status of pig liver xenotransplantation. International Journal of Surgery, Nov. 2015, vol. 23, pp. 240-246.

Ekser et al., et al., The Need for Xenotransplantation as a Source of Organs and Cells for Clinical Transplantation. International journal of surgery (London, England), Nov. 2015, vol. 23, Issue 0 0, pp. 199-204.

Ekser et al., Pig Liver Xenotransplantation as a Bridge to Allotranspantation: Which Patients Might Benefit? Transplantation, Nov. 15, 2009, vol. 88, Issue 9, pp. 1041-1049.

Ekser et al., Progress toward clinical xenotransplantation. International Journal of Surgery (London, England), Nov. 2015, vol. 23, Issue Pt B, pp. 197-198.

Ekser, et al., A Novel Approach in Combined Liver and Kidney Transplantation With Long-term Outcomes. Annals of Surgery, May 2017, vol. 265, Issue 5, pp. 1000-1008.

Ericsson et al., Identification of receptors for pig endogenous retrovirus. Proceedings of the National Academy of Sciences, May 27, 2003, vol. 100, Issue 11, pp. 6759-6764.

Favier, et al., Functions of HLA-G in the immune system. Tissue Antigens, Apr. 2007, vol. 69, pp. 150-152.

Fishman et al., Transmission of Infection with Human Allografts: Essential Considerations in Donor Screening. Clinical Infectious Diseases, Sep. 1, 2012, vol. 55, Issue 5, pp. 720-727.

Fishman et al., Xenotransplantation-associated infectious risk: a WHO consultation: Xenotransplantation-associated infectious risk. Xenotransplantation, Mar. 2012, vol. 19, Issue 2, pp. 72-81.

Food and Drug Administration, Source Animal, Product, Preclinical, and Clinical Issues Concerning the Use of Xenotransplantation Products in Humans; Guidance for Industry. Zotero, Dec. 2016.

Gala et al., HIV-1 detection by nested PCR and viral culture in fresh or cryopreserved postmortem skin: potential implications for skin handling and allografting. Journal of Clinical Pathology, Jun. 1, 1997, vol. 50, Issue 6, pp. 481-484.

Gao et al., Production of α1,3-galactosyltransferase and cytidine monophosphate-N-acetylneuraminic acid hydroxylase gene double-deficient pigs by CRISPR/Cas9 and handmade cloning. Journal of Reproduction and Development, 2017, vol. 63, Issue 1, pp. 17-26.

Ge et al., The viability change of pigskin in vitro. Burns, Jun. 2010, vol. 36, Issue 4, pp. 533-538.

Godehardt et al., Review on porcine endogenous retrovirus detection assays-impact on quality and safety of xenotransplants. Xenotransplantation, Mar. 2015, vol. 22, Issue 2, pp. 95-101.

Goodier et al., NKG2C+ NK Cells Are Enriched in AIDS Patients with Advanced-Stage Kaposi's Sarcoma. Journal of Virology, Jan. 2007, vol. 81, Issue 1, pp. 430-433.

Gore et al., Deceased donor skin allograft banking: Response and utilization. Indian Journal of Plastic Surgery: Official Publication of the Association of Plastic Surgeons of India, Sep. 2010, vol. 43, Issue Suppl, pp. S114-S120.

Greenwood et al., Real-Time Demonstration of Split Skin Graft Inosculation and Integra Dermal Matrix Neovascularization Using Confocal Laser Scanning Microscopy. Eplasty, Aug. 20, 2009, vol. 9, pp. 309-318.

Hawley, Genetic modification of pigs by nuclear transfer. Xenotransplantation, May 2002, vol. 9, Issue 3, pp. 159-160.

Hector et al., Pre-screening of miniature swine may reduce the risk of transmitting human tropic recombinant porcine endogenous retroviruses. Xenotransplantation, May 2007, vol. 14, Issue 3, pp. 222-226.

Heneine et al., Evidence of Porcine Endogenous Retroviruses in Porcine Factor VIII and Evaluation of Transmission to Recipients with Hemophilia. The Journal of Infectious Diseases, Feb. 15, 2001, vol. 183, Issue 4, pp. 648-652.

Hermans, Porcine xenografts vs. (cryopreserved) allografts in the management of partial thickness burns: Is there a clinical difference. Burns, May 2014, vol. 40, Issue 3, pp. 408-415.

Hermans, Results of an Internet Survey on the Treatment of Partial Thickness Burns, Full Thickness Burns, and Donor Sites. Journal of Burn Care & Research, Nov. 2007, vol. 28, Issue 6, pp. 835-847.

Higginbotham et al., Pre-transplant antibody screening and anti-CD154 costimulation blockade promote long-term xenograft survival in a pig-to-primate kidney transplant model. Xenotransplantation, 2015, vol. 2, Issue 3, pp. 221-230.

Holzer et al., A Comparative Examination of the Clinical Outcome and Histological Appearance of Cryopreserved and Fresh Split-Thickness Skin Grafts. Journal of Burn Care & Research: Official Publication of the American Burn Association, Jan.-Feb. 2017, vol. 38, Issue 1, pp. e55-e61.

Hosseini et al., Xenoderm dressing in the treatment of second degree burns. Burns, Sep. 2007, vol. 33, Issue 6, pp. 776-781.

Huang et al., Mechanochemical studies of enzymatic degradation of insoluble collagen fibers. Journal of Biomedical Materials Research, Jan. 1977, vol. 11, Issue 1, pp. 137-154.

Hunt et al., HLA-G and immune tolerance in pregnancy. The FASEB Journal, May 2005, vol. 19, Issue 7, pp. 681-693.

Hunter, One organ at a time: Research has been making much progress to create in vitro human tissues for transplantation but laboratory-grown complex organs still remain decades away. EMBO reports, Mar. 1, 2014, vol. 15, Issue 3, pp. 227-230.

Iop et al., Xenotransplantation: The Way beyond and Ahead toward Clinical Application. 2018, vol. 2018, pp. 6191359.

Jo et al., The Unreliability of MTT Assay in the Cytotoxic Test of Primary Cultured Glioblastoma Cells. Experimental Neurobiology, 2015, vol. 24, Issue 3, p. 235.

Johnson et al., Partial-thickness burns: identification and management. Advances in Skin & Wound Care, 2003, vol. 16, Issue 4, pp. 178-187; quiz 188-189.

Jones et al., Skin grafting for venous leg ulcers. The Cochrane Database of Systematic Reviews, Jan. 31, 2013, Issue 1, pp. CD001737.

Jonsen, The Ethics of Organ Transplantation: A Brief History. AMA Journal of Ethics, Mar. 1, 2012, vol. 14, Issue 3, pp. 264-268.

Kallinen et al., Multiple Organ Failure as a Cause of Death in Patients With Severe Burns. Journal of Burn Care & Research, Mar. 1, 2012, vol. 33, Issue 2, pp. 206-211.

Kararoudi et al., Clustered Regularly Interspaced Short Palindromic Repeats/Cas9 Gene Editing Technique in Xenotransplantation. Frontiers in Immunology, Sep. 5, 2018, vol. 9.

Kaserman, "Should we sell human organs?" Correction of a faulty analysis. Int J of Social Economics, Oct. 1, 2005, vol. 32, Issue 10, pp. 893-898.

King et al., Evidence for the expression of HLA-C class I mRNA and protein by human first trimester trophoblast. Journal of Reproductive Immunology, Oct. 1996, vol. 31, Issue 3, pp. 232-233.

King et al., Uterine NK Cells and Trophoblast HLA Class I Molecules. American Journal of Reproductive Immunology, Jun. 1997, vol. 37, Issue 6, pp. 459-462.

King, French doctors on trial for manslaughter. The Lancet, Feb. 23, 2008, vol. 371, Issue 9613, p. 637.

Kirkeby et al., Binding of <i>Griffonia simplicifolia</i> 1 isolectin B4 (GS1 B4) to α-galactose antigens. Immunology and Cell Biology, Apr. 2001, vol. 79, Issue 2, pp. 121-127.

(56) References Cited

OTHER PUBLICATIONS

Kitala et al., Allogeneic vs. Autologous Skin Grafts in the Therapy of Patients with Burn Injuries: A Restrospective, Open-label Clinical Study with Pair Matching. Advances in Clinical and Experimental Medicine, 2016, vol. 25, Issue 5, pp. 923-929.

Kobayashi et al., Cadaveric Skin Allograft-Associated Cytomegalovirus Transmission in a Mouse Model of Thermal Injury. Clinical Immunology, Aug. 1999, vol. 92, Issue 2, pp. 181-187.

Kolber-Simonds et al., Production of -1,3-galactosyltransferase null pigs by means of nuclear transfer with fibroblasts bearing loss of heterozygosity mutations. Proceedings of the National Academy of Sciences, May 11, 2004, vol. 101, Issue 19, pp. 7335-7340.

Kubal et al., Prospective Monitoring of Donor-specific Anti-HLA Antibodies After Intestine/Multivisceral Transplantation: Significance of De Novo Antibodies. Transplantation, Aug. 2015, vol. 99, Issue 8, pp. e49-e56.

Lai et al., Production of α-1,3-Galactosyltransferase Knockout Pigs by Nuclear Transfer Cloning. Science, New Series, 2002, vol. 295, Issue 5557, pp. 1089-1092.

Lee et al., Expression of NeuGc on Pig Corneas and Its Potential Significance in Pig Corneal Xenotransplantation. Cornea, Jan. 2016, vol. 35, Issue 1, pp. 105-113.

Lee et al., HLA-E is a major ligand for the natural killer inhibitory receptor CD94/NKG2A. Proceedings of the National Academy of Sciences, Apr. 28, 1998, vol. 95, Issue 9, pp. 5199-5204.

Lee et al., The physicochemical basis for thermal and non-thermal 'burn' injuries. Burns, 1996, vol. 22, Issue 7, pp. 509-519.

Leidig-Bruckner et al., Frequency and predictors of osteoporotic fractures after cardiac or liver transplantation: a follow-up study. The Lancet, Feb. 2001, vol. 357, Issue 9253, pp. 342-347.

Leonard et al., Skin grafts from genetically modified α-1,3-galactosyltransferase knockout miniature swine: A functional equivalent to allografts. Burns: Journal of the International Society for Burn Injuries. Dec. 2017, vol. 43, Issue 8, pp. 1717-1724.

Li et al., Efficient generation of genetically distinct pigs in a single pregnancy using multiplexed single-guide RNA and carbohydrate selection. Xenotransplantation, Jan. 2015, vol. 22, Issue 1, pp. 20-31.

Lutz et al., Double knockout pigs deficient in N-glycolylneuraminic acid and Galactose α-1,3-Galactose reduce the humoral barrier to xenotransplantation. Xenotransplantation, Jan. 2013, vol. 20, Issue 1, pp. 27-35.

Manara et al., Donation after circulatory death. British Journal of Anaesthesia, Jan. 1, 2012, vol. 108, pp. 108-121.

Martin et al., Genomic presence of recombinant porcine endogenous retrovirus in transmitting miniature swine. Virology Journal, 2006, p. 6.

McGregor et al., PERVading strategies and infectious risk for clinical xenotransplantation. Xenotransplantation, Jul. 2018, vol. 25, Issue 4, pp. e12402.

McGregor et al., The angiosome—an in vim study by fluorescein angiography. British Journal of Plastic Surgery, Apr. 1992, vol. 45, Issue 3, pp. 219-221.

McLafferty et al., The integumentary system: anatomy, physiology and function of skin. Nursing Standard (Royal College of Nursing (Great Britain): 1987), Sep. 19-25, 2012, vol. 27, Issue 3, pp. 35-42.

Mulder et al., Johann "Hans" Ehrenhaft (1915-2009): (The Ultimate) Renaissance Mentor. The Annals of Thoracic Surgery, vol. 89, Issue 4, pp. 1337-1338.

Nakajima et al., A New Concept of Vascular Supply to the Skin and Classification of Skin Flaps According to Their Vascularization. Annals of Plastic Surgery, Jan. 1986, vol. 16, Issue 1, pp. 1-19.

Nathan et al., Organ donation in the United States. American Journal of Transplantation, Apr. 2003, vol. 3, Issue S4, pp. 20-40.

Nekrep et al., When the Lymphocyte Loses Its Clothes. Immunity, Apr. 2003, vol. 18, Issue 4, pp. 453-457.

Office of Regulatory Affairs, Expiration Dating and Stability Testing for Human Drug Products. FDA, Nov. 3, 2018.

Padler-Karavani et al., Potential impact of the non-human sialic acid N-glycolylneuraniinic acid on transplant rejection risk: Invited Commentary. Xenotransplantation, Jan. 2011, vol. 18, Issue 1, pp. 1-5.

Petitdemange et al., Unconventional Repertoire Profile Is Imprinted during Acute Chikungunya Infection for Natural Killer Cells Polarization toward Cytotoxicity. PLoS Pathogens, Sep. 22, 2011, vol. 7, Issue 9. pp. e1002268.

Petrini, Ethical and legal considerations regarding the ownership and commercial use of human biological materials and their derivatives. Journal of Blood Medicine, Aug. 7, 2012, vol. 3, pp. 87-96.

Petruzzo et al., Outcomes After Bilateral Hand Allotransplantation: A Risk/Benefit Ratio Analysis. Ann Surg, 2014.

Pfeiffer et al., Hyperacute lung rejection in the pig-to-human model. III. platelet receptor inhibitors synergistically modulate complement activation and lung injury:. Transplantation, Apr. 2003, pp. 953-959.

Pirnay et al., Beware of the commercialization of human cells and tissues: situation in the European Union. Cell and Tissue Banking, Aug. 2012, vol. 13, Issue 3, pp. 487-498.

Pirnay et al., HIV transmission by transplantation of allograft skin: a review of the literature. Burns: Journal of the International Society for Burn Injuries, Feb. 1997, vol. 23, Issue 1, pp. 1-5.

Platt et al., The Future Promises of Xenotransplantation a,b. Annals of the New York Academy of Sciences, Dec. 1998, vol. 862, Issue 1, pp. 5-18.

Powell et al., Creating effective biocontainment facilities and maintenance protocols for raising specific pathogen-free, severe combined immunodeficient (SCID) pigs. Laboratory Animals, Aug. 2018, vol. 52, Issue 4, pp. 402-412.

Rappaport et al., Early use of xenografts as a biologic dressing in burn trauma. The American Journal of Surgery, Aug. 1970, vol. 120, Issue 2, pp. 144-148.

Reyes et al., Characterization of swine leucocyte antigen alleles in a crossbred pig to be used in xenotransplant studies. Tissue Antigens, 2014, vol. 84, Issue 5, pp. 484-488.

Reyes et al., Creating Class I MHC-Null Pigs Using Guide RNA and the Cas9 Endonuclease. The Journal of Immunology, Dec. 1, 2014, vol. 193, Issue 11, pp. 5751-5757.

Rheinwald et al., Serial Cultivation of Strains of Human Epidermal Keratinocytes: the Formation of Keratinizing Colonies from Single Cells. Cell, Nov. 1975, vol. 6, pp. 331-344.

Rithalia et al., Impact of presumed consent for organ donation on donation rates: a systematic review. BMJ, Jan. 15, 2009, vol. 338, pp. a3162.

Rubin, Impact of cytomegalovirus infection on organ transplant recipients. Reviews of Infectious Diseases, Sep. Oct. 1990, vol. 12 Suppl 7, pp. S754-S766.

Sachs et al., Induction of Tolerance through Mixed Chimerism. Cold Spring Harbor Perspectives in Medicine, Jan. 1, 2014, vol. 4, Issue 1, pp. a015529-a015529.

Sachs, The lure of transplantation. Clinical Transplants 2008 edition, 2008, pp. 287-305.

Saidi et al., Challenges of Organ Shortage for Transplantation: Solutions and Opportunities. International Journal of Organ Transplantation Medicine, 2014, vol. 5, Issue 3, pp. 87-96.

Schook et al., Unraveling the swine genome: implications for human health. Annual Review of Animal Biosciences, 2015, vol. 3, pp. 219-244.

Schulz, Necrotizing Fasciitis: Background, Pathophysiology, Etiology. eMedicine, Feb. 2, 2019, https://emedicine.medscape.com/article/2051157-overview.

Scobie et al., Long-Term IgG Response to Porcine Neu5Gc Antigens without Transmission of PERV in Burn Patients Treated with Porcine Skin Xenografts. The Journal of Immunology, Sep. 15, 2013, vol. 191, Issue 6, pp. 2907-2915.

Shafran et al., Organ Shortage: The Greatest Challenge Facing Transplant Medicine. World Journal of Surgery, Jul. 2014, vol. 38, Issue 7, pp. 1650-1657.

Shaw et al., Kidney Xenotransplantation: Steps toward Clinical Application. Clinical Journal of the American Society of Nephrology, Apr. 5, 2019, vol. 14, Issue 4, pp. 620-622.

Sheridan e al., Skin Substitutes in Burns, Burns, 1999, vol. 25, pp. 97-103.

(56) References Cited

OTHER PUBLICATIONS

Sheridan, Closure of the Excised Burn Wound: Autografts, Semi-permanent Skin Substitutes, and Permanent Skin Substitutes. Clinics in Plastic Surgery, Oct. 2009, vol. 36, Issue 4, pp. 643-651.

Shlobin et al., Persistent cytomegalovirus-specific memory responses in the lung allograft and blood following primary infection in lung transplant recipients. Journal of Immunology (Baltimore, Md.: 1950), Feb. 15, 2006, vol. 176, Issue 4, pp. 2625-2634.

Siemionow et al., Nerve Allograft Transplantation—A Review. Journal of Reconstructive Microsurgery, Nov. 2007, vol. 23, Issue 8, pp. 511-520.

Snyderman et al., Prolonged Skin Homograft and Heterograft Survival in Patients with Neoplastic Disease. Plastic and Reconstructive Surgery, Oct. 1960, vol. 26, Issue 4, p. 373.

Spurgeon, French doctors are tried for treating children with infected growth hormone. British Medical Journal, Feb. 16, 2008, vol. 336, Issue 7640, pp. 348-349.

Stewart, The fire at Cocoanut Grove. Journal of Burn Care & Research: Official Publication of the American Burn Association, Jan.-Feb. 2015, vol. 36, Issue 1, pp. 232-235.

Takefman et al., Detection and Characterization of Porcine Endogenous Retrovirus in Porcine Plasma and Porcine Factor VIII. Journal of Virology, May 15, 2001, vol. 75, Issue 10, pp. 4551-4557.

Takeo et al., Wound Healing and Skin Regeneration. Cold Spring Harbor Perspectives in Medicine, Jan. 1, 2015, vol. 5, Issue 1, pp. a023267-a023267.

Taniguchi et al., Clinical xenotransplantation: past, present and future. Annals of the Royal College of Surgeons of England. Jan. 1997, vol. 79, Issue 1, pp. 13-19.

Tavis et al., Graft Adherence to De-epithelialized Surfaces: A Comparative Study. Annals of Surgery, Nov. 1976, vol. 184, Issue 5, pp. 594-600.

Tector, New Hope for Liver Xenotransplantation. Annals of Surgery, Jun. 2016, vol. 263, Issue 6, pp. 1072.

Thornton et al., Skin Grafts and Skin Substitutes and Principles of Flaps. Selected Readings in Plastic Surgery, 2004, vol. 10, Issue 1, pp. 16-19.

Trohler, Emil Theodor Kocher (1841-1917). Journal of the Royal Society of Medicine, Sep. 2014, vol. 107, Issue 9, pp. 376-377.

US Department of Health & Human Services FDA, Guidance for Industry, Current Good Tissue Practice (CGTP) and Additional Requirements for Manufacturers of Human Cells, Tissues, and Cellular and Tissue-Based Products (HCT/Ps). Zotero, Dec. 2011, p. 67.

Wadman, FDA 'fails to keep track of transplant patients'. Nature, Jan. 1998, vol. 391, Issue 5, p. 315.

Wang et al., Erythrocytes from GGTA1/CMAH knockout pigs: implications for xenotransfusion and testing in non-human primates. Xenotransplantation, Jul.-Aug. 2014, vol. 21, Issue 4, pp. 376-384.

Wang et al., Immunogenicity of Renal Microvascular Endothelial Cells From Genetically Modified Pigs. Transplantation, Jan. 30, 2016, vol. 100, Issue 3, pp. 533-537.

Warnecke et al., Normothermic perfusion of donor lungs for preservation and assessment with the Organ Care System Lung before bilateral transplantation: a pilot study of 12 patients. The Lancet, Nov. 2012, vol. 380, Issue 9856, pp. 1851-1858.

Watson et al., Organ transplantation: historical perspective and current practice. British Journal of Anaesthesia, Jan. 2012, vol. 108, pp. i29-i42.

Weathers et al., Full-Thickness Skin Grafting in Nasal Reconstruction. Seminars in Plastic Surgery, Aug. 14, 2013, vol. 27, Issue 2, pp. 090-095.

Weiner et al., Prolonged survival of GalT-KO swine skin on baboons. Xenotransplantation, Mar. 2010, vol. 17, Issue 2, pp. 147-152.

Wendler et al., The Consent Process for Cadaveric Organ Procurement: How Does It Work? How Can It Be Improved? JAMA, Jan. 17, 2001, vol. 285, Issue 3, pp. 329-333.

Wilhelm et al., Susceptibility of recombinant porcine endogenous retrovirus reverse transcriptase to nucleoside and non-nucleoside inhibitors. Cellular and Molecular Life Sciences (CMLS), Dec. 1, 2002, vol. 59, Issue 12, pp. 2184-2190.

Wojda et al., Keys to successful organ procurement: An experience-based review of clinical practices at a high-performing health-care organization. International Journal of Critical Illness and Injury Science, 2017, vol. 7, Issue 2, pp. 91-100.

Wolf et al., Comparison between civilian burns and combat burns from Operation Iraqi Freedom and Operation Enduring Freedom. Ann Surg, 2006, vol. 243, pp. 786.

Wood et al., The use of cultured epithelial autograft in the treatment of major burn injuries: A critical review of the literature. Burns, Jun. 2006, vol. 32, Issue 4, pp. 395-401.

Wood et al., The use of pigskin in the treatment of thermal burns. The American Journal of Surgery, Dec. 1972, vol. 124, Issue 6, pp. 720-723.

Wynyard et al., Microbiological safety of the first clinical pig islet xenotransplantation trial in New Zealand. Xenotransplantation,, Jul. 2014, vol. 21, Issue 4, pp. 309-323.

Yannas et al., Correlation of in vivo collagen degradation rate within vitro measurements. Journal of Biomedical Materials Research, Nov. 1975, vol. 9, Issue 6, pp. 623-628.

Yue et al., A study on the susceptibility of allogeneic human hepatocytes to porcine endogenous retrovirus. European review for medical and pharmacological sciences, Sep. 2015, vol. 19, Issue 18, pp. 3486-3491.

Zuo et al., Observation of viable alloskin vs xenoskin grafted onto subcutaneous tissue wounds after tangential excision in massive burns. Burns & Trauma, Dec. 2016, vol. 4, Issue 1.

| PROCESS RESOURCE | PROCESS STEP | PROCESS DESCRIPTION | PROCESS DURATION |
|---|---|---|---|
| CRYOVIAL | PRE-LABELING CRYOVIAL | PRE-LABELING OF THE CRYOVIALS REDUCES PROCESSING TIME AND UNNECESSARY MATERIAL EXPOSURE TO DMSO PRIOR TO CRYOPRESERVATION | N/A |
| DRUG SUBSTANCE & ANTIMICROBIAL SOLUTION | DRUG SUBSTANCE STERILIZATION | UNDER ISO 5 HOOD, REMOVE XENOTRANSPLANTATION SKIN PRODUCT FROM RPMI BATH & PLACE INTO ANTIMICROBIAL SOLUTION | NOT LESS THAN 30 MINUTES |
| DRUG SUBSTANCE & PACKAGING COMPONENT | PLACEMENT OF NYLON MESH PACKAGING COMPONENT | UNDER ISO 5 HOOD, PLACEMENT OF XENOTRANSPLANTATION SKIN PRODUCT FROM THE ANTIMICROBIAL SOLUTION ONTO NYLON MESH PACKAGING COMPONENT USING STERILE TECHNIQUE | 1 MINUTE EACH |
| CRYOVIAL | PACKAGING INTO PRIMARY CONTAINER CLOSURE SYSTEM | UNDER ISO 5 HOOD, OPERATOR WILL THEN TIGHTLY ROLL THE DRUG SUBSTANCE AND NYLON MESH PACKAGING COMPONENT AND PLACE THE COMBINATION WITHIN THE PRIMARY CONTAINER CLOSURE SYSTEM | 1 MINUTE EACH |
| CRYOSTOR CS5 | ADDITION OF CRYOPROTECTANT MEDIA | UNDER ISO 5 HOOD, EACH CRYOVIAL IS FILLED WITH 5-7ml OF CRYOSTOR CS5 UNTIL THE XENOTRANSPLANTATION SKIN PRODUCT IS FULLY IMMERSED AND THEN THE PRIMARY CONTAINMENT CLOSURE SYSTEM IS SEALED | 1 MINUTE EACH |
| CONTROL RATE FREEZER | CRYOPRESERVATION | DRUG PRODUCT IS PLACED IN CERTIFIED, Q-A CONTROL RATE-FREEZER PER SOP | 40 MINUTES PER BATCH TIME ELAPSE FROM ROOM TEMP TO -80 °C |
| -80 °C FREEZER | STORAGE | TRANSFER DRUG PRODUCT TO A Q/A CERTIFIED, -80 °C FREEZER UNTIL USE | 1 MINUTE |

FIG. 2

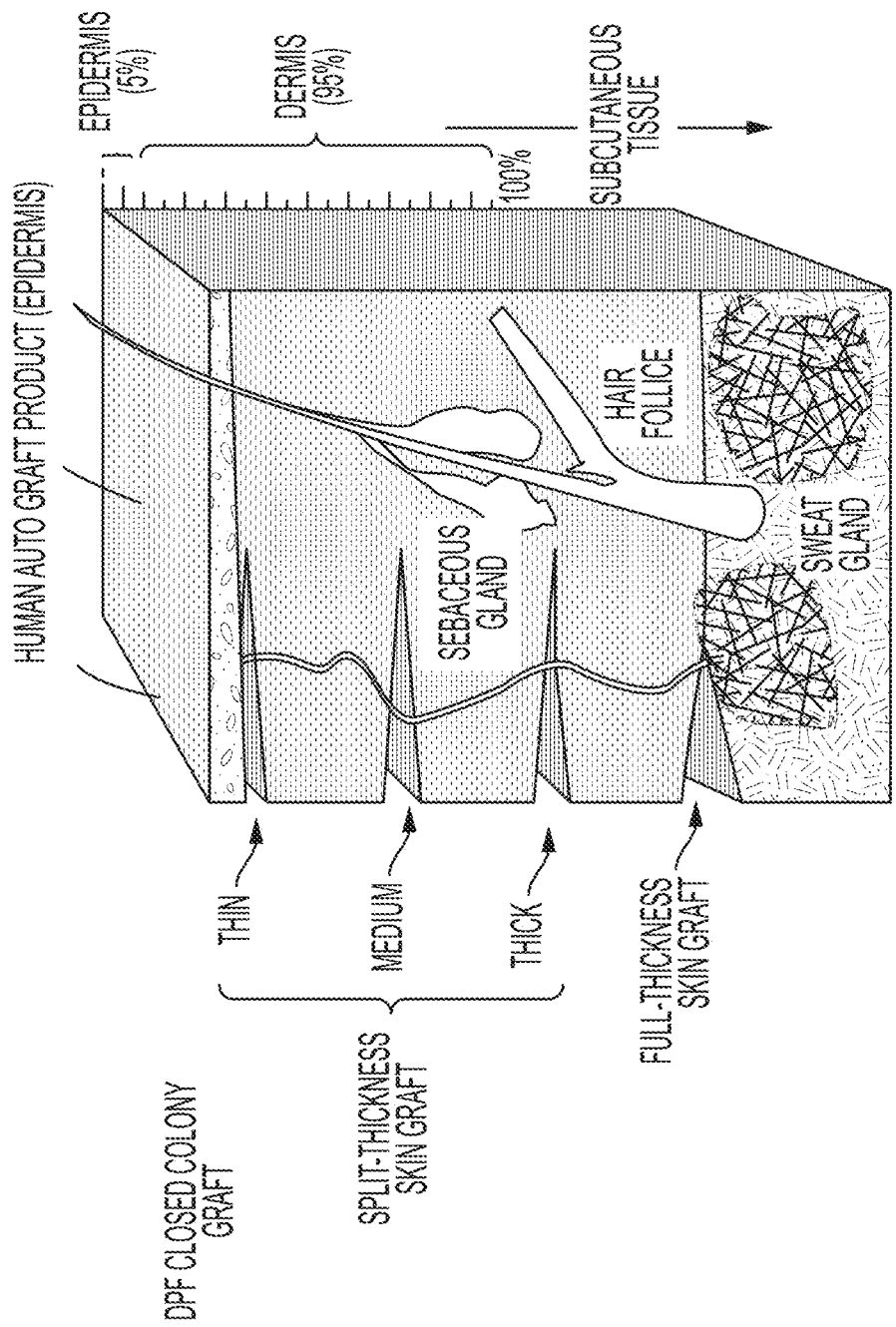

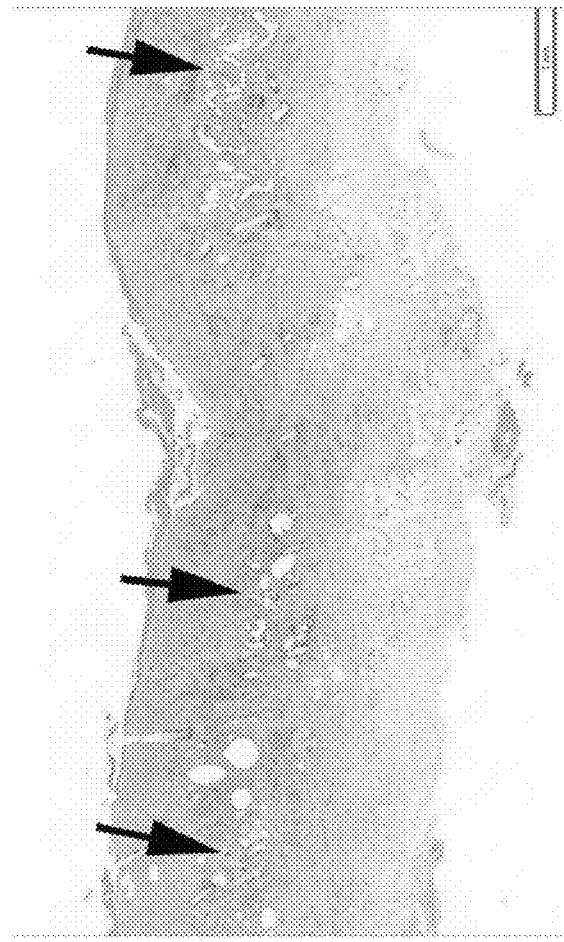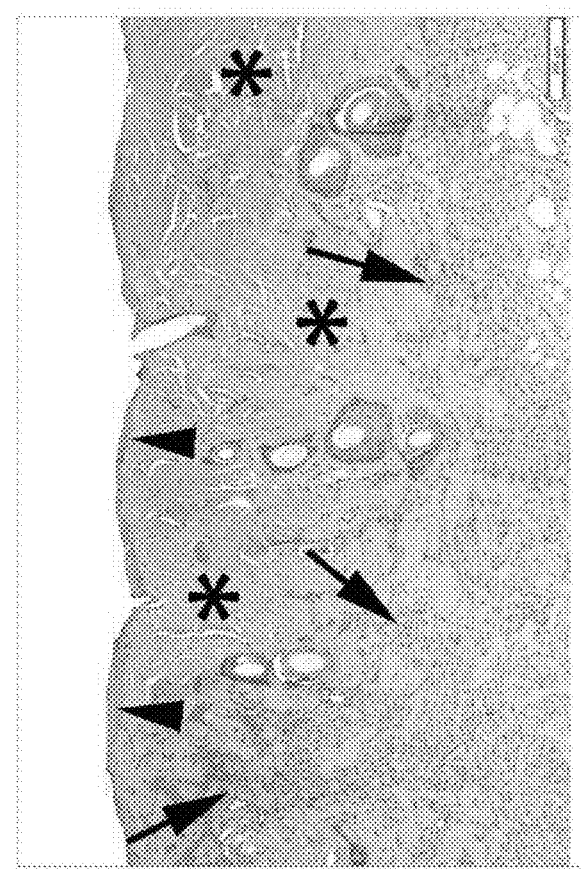
FIG. 9A
FIG. 9B

HLA: The Most Polymorphic (Diverse) Genes in the Human Genome

TABLE 1. Target of anti-HLA Antibodies

| HLA Gene | Serological antigens[a] | Proteins | Alleles[b] |
|---|---|---|---|
| Class I | | | |
| A | 28 | 2703 | 3830 |
| B | 62 | 3408 | 4647 |
| C | 10 | 2391 | 3382 |
| Class II | | | |
| DRA | 24 | 2 | 7 |
| DRB1 | 24 | 1465 | 2011 |
| DQA1 | 9 | 34 | 77 |
| DQB1 | 9 | 727 | 1054 |
| DPA1 | Undefined | 22 | 44 |
| DPB1 | Undefined | 615 | 740 |

[a]Serological antigens according to the World Health Organization.
[b]Not including null alleles.
Data from {Robinson:2015ca}.

Modified from Krandorf. Evan P., et al. "HLA Population Genetics in Solid Organ Transplantation" Transplantation 101.9 (2017); 1971-1976, http://journals.lww.com/transplantjournal/Abstract/2017/09000/HLA_Population_Genetics_in_Solid_Organ.II.asPX

FIG. 15

Figure 25-50 Molecular Biology of the Cell 5/e (© Garland Science 2008)

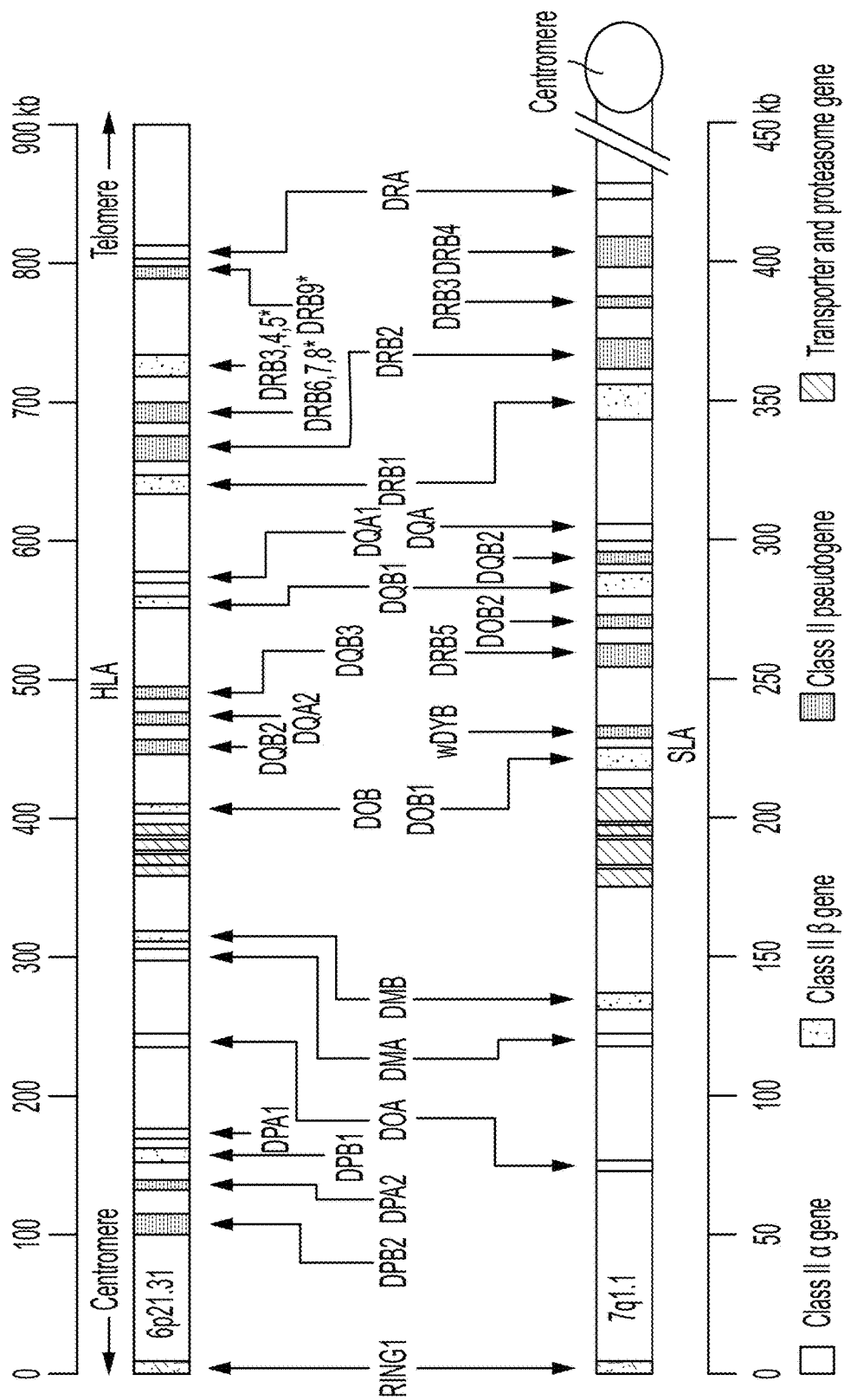

Fig. 2. Comparative genomic organization of the human and swine major histocompatibility complex (MHC) class II region. The human leukocyte antigen (HLA) class II map is adapted from Ref. [17] and the swine leukocyte antigen (SLA) class II map is based only on one fully sequenced haplotype (H01) [4]. Note that not all the genes are shown here and the scale is approximate. *The number and location of expressed HLA-DRB genes and pseudogenes may vary between haplotypes.

FIG. 24

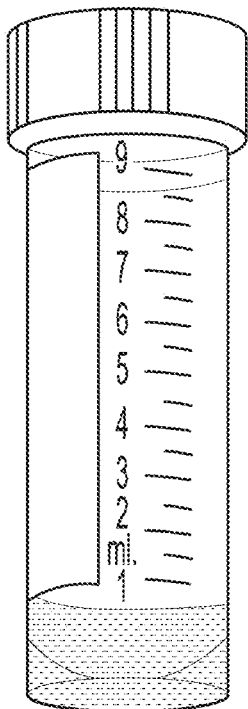

Cryovial

Vertical ribs facilitate cap removal

Silicone washer

Both cap and tube are made of same polypropylene material, therefore same coefficient of expansion ensures secure seal at all temperatures Super fast 1¼ turn thread design Thick wall makes vial almost unbreakable Large white marking area Excellent clarity makes sample easy to see Round bottom / Very easy to empty contents completely

FIG. 30

| Grade | Graft dislocation | Grade | Graft adherence | Grade | Granulation tissue | Grade | Hyber granulation | Grade | Hematoma | Grade | Fibrin deposition |
|---|---|---|---|---|---|---|---|---|---|---|---|
| 0 | None | 0 | Full graft loss | 0 | None, full depth thickness | 0 | None | 0 | None | 0 | None |
| 1 | 5-10%, tissue still fully viable | 1 | Graft 20% adherent, 50% graft loss | 1 | Low level of granulation tissue | 1 | 10% | 1 | Up to 10% wound size | 1 | Small patches, up to 10% wound size |
| 2 | 10-25%, one or two spots, 10% tissue not viable | 2 | Graft 50% adherent, 30% graft loss | 2 | Granulation tissue level at half of initial wound depth | 2 | 20% | 2 | Up to 20% wound size | 2 | Thicker, confluent patches, up to 20% wound size |
| 3 | 25-50%, more than 20% tissue not viable | 3 | Graft 75% adherent, 20% graft loss | 3 | Granulation tissue level just below surrounding tissue | 3 | 40% | 3 | Up to 40% wound size | 3 | Confluent patches, up to 40% wound size |
| 4 | 50-80%, more than 50% tissue not viable | 4 | Graft 90% adherent | 4 | Granulation at level with surrounding tissue | 4 | 65% | 4 | Up to 60% wound size, partial graft loss | 4 | Confluent patches, up to 60% wound size |
| 5 | Graft completely dislocated, full tissue loss | 5 | Full graft adherence | 5 | Fully granulated wound, exceeds level of surrounding tissue | 5 | 100% | 5 | Up to 100% total graft loss | 5 | Wound fully covered with fibrin and graft skin totally macerated |
| NA | Not applicable* | NA | Not applicable* | NA | Not applicable* | NA | Not applicable* | NA | Not applicable* | NA | Not applicable* |

*It is expected that some characteristics, particularly granulation and fibrin deposition, may not be assessable at all stages of the grafting process, therefore the investigator may record "NA" for the grade as necessary, along with a brief explanation in the source notes.

FIG. 32

XENOTRANSPLANTATION PRODUCTS AND METHODS

CROSS-REFERENCE TO RELATED APPLICATIONS

This application is a divisional of U.S. Ser. No. 16/593,785 filed Oct. 4, 2019, which claims priority benefit of U.S. provisional application No. 62/742,188, filed Oct. 5, 2018; 62/756,925, filed Nov. 7, 2018; U.S. 62/756,955 filed Nov. 7, 2018; U.S. 62/756,977, filed Nov. 7, 2018; U.S. 62/756,993, filed Nov. 7, 2018; U.S. 62/792,282, filed Jan. 14, 2019; U.S. 62/795,527, filed Jan. 22, 2019; U.S. 62/823,455, filed Mar. 25, 2019; and U.S. 62/848,272, filed May 15, 2019, the disclosures of all of which are incorporated herein by reference in their entireties.

FIELD OF THE INVENTION

The subject matter disclosed herein relates to biological products derived from genetically engineered organisms, and related methods, for use in xenotransplantation.

BACKGROUND OF THE INVENTION

According to the United Network for Organ Sharing ("UNOS"), every ten minutes, someone is added to the national transplant waiting list, and 20 people die each day waiting for a transplant. As of August 2019, there were about 114,000 people in need of a lifesaving organ transplant in the United States, with only about 10,000 donors identified and about 36,000 transplants performed in 2018 (data from the United Network for Organ Sharing (UNOS)). The need for specific organs in the United States is as follows (as of Aug. 12, 2019):

| Organ | Candidates |
|---|---|
| Kidney | 102,927 |
| Liver | 13,354 |
| Pancreas | 846 |
| Kidney/Pancreas | 1,703 |
| Heart | 3,795 |
| Lung | 1,443 |
| Heart/Lung | 43 |
| Intestine | 231 |
| Total | 124,363 |

More than 7,000 candidates died in 2016 while on the waiting list, or within 30 days of leaving the list for personal or medical reasons, without receiving an organ transplant. Sadly, each day, 30 people either die or are removed from the waiting list (because they are too sick for the requisite surgery) due to this inadequate supply of organs. While the rate of divergence between available donors and unmet need of recipients has been improved marginally, this disparity has continued to present day and remains considerable; the supply remains disastrously inadequate. For these patients, and the millions not included in these statistics who also would benefit significantly from tissue transplants such as cornea or pancreatic islet cells, "allotransplantation will never prove to be a sufficient source." Ekser B, Cooper D K C, Tector A J (2015) The Need for Xenotransplantation as a Source of Organs and Cells for Clinical Transplantation. International journal of surgery (London, England), 23(0 0): 199-204.

Beyond the shortage of organs, other significant issues related to allotransplantation exist and present a multifaceted problem, involving safety, logistical, ethical, legal, institutional, and cultural complications. Logistically, numerous factors must be considered prior to a successful organ donation and transplant procedure. Blood type and other medical factors must be evaluated for every donated organ, but further, each organ type presents unique characteristics that also must be weighed, such as post-mortem ischemia, immunological compatibility, patient location, and institutional capabilities. Allogeneic tissues from human donors carry significant infectious disease risks. Denner reports in 2018 that "[human] CMV is the single most important infectious agent affecting recipients of organ transplants, with at least two-thirds of these patients having CMV infection after transplantation." Denner J (2018) Reduction of the survival time of pig xenotransplants by porcine cytomegalovirus. Virology Journal, 15(1): 171; Rubin R H (1990) Impact of cytomegalovirus infection on organ transplant recipients. Reviews of Infectious Diseases, 12 Suppl 7:S754-766.

Regulations regarding tissue transplants include criteria for donor screening and testing for adventitious agents, as well as strict regulations that govern the processing and distribution of tissue grafts. The transmission of viruses has occurred as a result of allotransplantation. Exogenous retroviruses (Human T-cell leukemia virus type 1 (HTLV-1), Human T-cell leukemia virus type 2 (HTLV-2), and Human immunodeficiency virus (HIV) have been transmitted by human tissues during organ and cell transplantation, as have viruses such as human cytomegalovirus, and even rabies. Due to technical and timing constraints surrounding organ viability and post-mortem screening, absolute testing is hindered, and this risk cannot be eliminated. Immunological disparities between recipient and donor prevent graft-survival for extended durations, without immunosuppressive regimens that pose their own set of complications and additional risks. When a patient receives an organ from a (non-self) donor (living or deceased), the recipient's immune system will recognize the transplant as foreign. This recognition will cause their immune system to mobilize and "reject" the organ unless concomitant medications that suppress the immune system's natural processes are utilized. Benichou, et al., describes the response to an allogeneic skin graft as a "potent" immune response involving engagement of both the innate and adaptive immune systems Abbas A K, Lichtman A H H, Pillai S (2017) Cellular and Molecular Immunology can blunt the natural immunological processes; unfortunately, these medications are often a lifelong requirement after organ transplantation and increase recipient susceptibility to otherwise routine pathogens. While these drugs allow transplant recipients to tolerate the presence of foreign organs, they also increase the risk of infectious disease and symptoms associated with a compromised immune system, as a "broad array of organisms may be transmitted with human allografts." Fishman J A, Greenwald M A, Grossi P A (2012) Transmission of infection With Human Allografts: Essential Considerations in Donor Screening. Clinical Infectious Diseases, 55(5):720-727.

One, often overlooked logistical constraint involves the intricate and timely preservation methods of donated organs necessary to maintain viability between the time of procurement and transplantation. This is a critical logistical and scientific underpinning of transplantation as a field of medicine and as a promising, clinical adjunct therapy. Limitations on organ preservation are considerable and directly impact surgical capacity. Examples of common, maximum organ preservation times include: kidney, 24-36 hours; pancreas, 12-18 hours; liver, 8-12 hours; heart or lung, 4-6 hours. The fundamental reason for these restrictive, limiting timeframes is due to the inability to preserve the fundamental vital capacity of the numerous and diverse cells comprising the larger tissue or organ. Interruption or complete termination of necessary and highly complex, interdependent cellular activity thereby erodes the potential clinical utility of the transplant.

Despite these drawbacks, organ transplantation is unquestionably the preferred therapy for most patients with end stage organ failure, in large part due to a lack of viable alternatives. However, the advent of organ transplantation as a successful life-saving therapeutic intervention, juxtaposed against the paucity of organs available to transplant, unfortunately places medical professionals in an ideologically vexing position of having to decide who lives and who dies. Ultimately, alternative and adjunct treatment options that would minimize the severe shortcomings of allotransplant materials while providing the same mechanism of action that makes them so effective would be of enormous benefit to patients worldwide.

With regard to the organ of skin, patients with severe and extensive, deep partial and full thickness burn wounds are in immediate need of temporary treatment options to bridge them prior to more permanent treatments. During this critical period, patients with severe burns are at risk of deteriorating clinical condition due to infection from opportunistic pathogens, disrupted skin barrier, and impairment of immune response, as well as hypovolemia through fluid loss at the burn site. This is frequently followed by electrolyte, temperature and pH imbalances that contribute to organ failure, and possibly death. While it would be ideal to utilize autograft to treat such injuries, the supply of the patient's own skin is often limited during the acute phase of burn care (within 96 hours of injury) especially in cases where burns cover 20% or more of total body surface area. More importantly, autologous graft harvest is often clinically contraindicated as it results in further insult to the patient's already compromised homeostasis and worsens morbidity. See, e.g., Johnson, "*Partial-thickness burns: identification and management*," Adv Skin. Wound Care. 2003; 16(4):178-87. Thus, in instances where autograft is not available and/or contraindicated, the current method is to utilize human cadaveric allograft ("HCA") to provide temporary wound coverage until autograft is available and/or indicated. Unfortunately, given the inherent logistical and supply constraints, as well as infectious agent concerns, the availability of HCA is severely limited.

To address the unmet clinical need due to limited availability of autograft and allograft solutions, other "stop-gap" temporary coverage materials are commonly used. These include various synthetic or other tissue-based products comprised of terminally sterilized, non-viable cells used primarily to attempt to treat superficial burns and provide a barrier for infection. Examples of such products include Biobrane®, Transcyte®, cultured epidermal allogeneic keratinocytes, Dermagraft, Apligraf®, and hydrocolloid dressings such as Aquacel®. Other wound closure products include non-genetically altered porcine xenografts (Gal+), and tissue-engineered delivery systems. Many of these wound cover and closure products have limited indications and other limitations as described in the literature. See, e.g., Thornton J F and Gosman A A, "Skin Grafts and Skin Substitutes and Principles of Flaps," *Baylor University Medical Center*, 2004 10(1): 2-78. Such products do not vascularize and are not intended for treatment of severe and extensive, deep partial and full thickness burn wounds and allow for vascularization of the wound bed. Prior to the present invention, no skin substitute is able to approximate the biologic properties of viable human skin and there is no satisfactory replacement for human allograft skin. Thus, with regard to skin in particular, there remains a need for a high quality, temporary method of coverage for severe and extensive, deep partial and full thickness burn wounds to provide a barrier function (equivalent to or better than allograft) and vascularize in the wound bed.

The urgent need for organs and other transplantation tissue generally, including for temporary therapies while more permanent organs or other tissue are located and utilized, has led to investigation into utilization of organs, cells and tissue from non-human sources, including other animals for temporary and/or permanent xenotransplantation.

Pigs have long been considered a potential non-human source of organs, tissue and/or cells for use in human xenotransplantation given that their size and physiology are compatible with humans. Xenotransplantation from swine to humans, however, has significant roadblocks, not the least of which is hyperacute rejection where natural human antibodies target epitopes on the animal cells, causing rejection and failure of the transplanted organs, cells or tissue. Other roadblocks include delayed xenograft rejection, acute cellular rejection, chronic rejection, risks of cross-species transmission of disease or parasites.

One cause of hyperacute rejection results from the expression of alpha-1,3-galactosyltransferase ("alpha-1,3-GT") in porcine cells, which causes the synthesis of alpha-1,3-galactose epitopes. Except for humans, apes and Old World monkeys, most mammals carry glycoproteins on their cell surfaces that contain galactose alpha 1,3-galactose (see, e.g., Galili et al., "Man, apes, and old world monkeys differ from other mammals in the expression of α-galactosyl epitopes on nucleated cells," *J. Biol. Chem.* 263: 17755-17762 (1988). Humans, apes and Old World monkeys have a naturally occurring anti-alpha gal antibody that is produced and binds to glycoproteins and glycolipids having galactose alpha-1,3 galactose (see, e.g., Cooper et al., "Genetically engineered pigs," *Lancet* 342:682-683 (1993). Accordingly, when natural type swine products are utilized in xenotransplantation, human antibodies will be invoked to confront the foreign alpha-1,3-galactose epitopes, and hyperacute rejection normally follows.

A variety of methods have been attempted to modify swine to eliminate expression of alpha-1,3-galactosyltransferase, which has been shown to decrease hyperacute rejection as compared to wild-type swine. For example, "knockout" and "knock-in" swine are disclosed in U.S. Pat. No. 7,795,493 ("Phelps"), U.S. Pat. No. 7,547,816 ("Day"), and, 547,522 ("Hawley"). Each of those references is incorporated herein by reference in its entirety.

Other genetic modifications to swine besides eliminating expression of alpha-1,3-galactosytransferase can also serve to decrease immunological rejection of transplanted swine cells, tissues, and/or organs, by a human recipient. For example, eliminating expression of Neu5Gc is another approach to reduce immunological rejection. See, e.g., Scobie, L., "Long-Term IgG Response to Porcine Neu5Gc Antigens without Transmission of PERV in Burn Patients Treated with Porcine Skin Xenografts," The Journal of Immunology, 191: 2907-2915 (2013) ("Scobie"), the entire disclosure of which is incorporated herein by reference. All mammals express Neu5Ac, a sialic acid. All animals except humans convert Neu5Ac to Neu5Gc using Neu5Ac hydroxylase, which is encoded by the CMAH gene. Thus, similar to the alpha-1,3-galactosyltransferase epitope, Neu5Gc is expressed on swine cells, but is recognized as foreign by human recipients of xenotransplant products, leading to eventual rejection. Thus, eliminating CMAH, the enzyme responsible for the Neu5Ac to Neu5Gc conversion, could further engineer the cells of organs derived from swine for xenotransplantation and reduce risk of rejection in human recipients.

In addition to alpha-1,3-galactosytransferase and Neu5Gc, eliminating expression of β1,4-N-acetylgalactosaminyltransferase (B4GALNT2) is another approach to reduce immunological rejection. B4GALNT2 may contribute to the antibody response observed in swine to human transplants, and in the swine to baboon model indicate that it produces a glycan that elicits an immune response from the recipient. See, e.g., Byrne, G., "Cloning and expression of porcine β1,4-N-acetylgalactosaminyl transferase encoding q new xenoreactive antigen," Xenotransplantation, 21: 543-554 (2014) ("Byrne"), the entire disclosure of which is incorporated herein by reference. Disrupting the B4GALNT2 gene may reduce the immune response to swine cells, particularly when those cells have also had alpha-1,3-galactosytransferase and CMAH removed. See, e.g., Byrne. Aspects of the combined removal of alpha-1,3-galactosyltransferase, Neu5Gc, and β1,4-N-acetylgalactosaminyltransferase, also referred to as "triple knockout," are described in U.S. Patent Publication No. US2017/0311579, the entire disclosure of which is incorporated herein by reference. In many cases, the prior art methods involved attempts to address the resultant negative effects of the xenotransplantation, e.g., via administration of immunosuppressants. While the previously used methods require immunosuppressive drugs, use of immunosuppressants often lead to life-threatening malignancies and infections. In other cases, the prior art methods resolved to knockout animal genes and/or to insert human genes to create transgenic animals, but doing so resulted in animals that were unable to survive and thrive due to compromised immune systems and other phenotypic complications. In such cases, disruption of swine glycan and/or SLA genes made the cells vulnerable to lysis by natural killer cells. Natural killer cells are quick, versatile lymphocytes that function in innate immunity, adaptive immunity, and reproduction. Each human has a large diversity of natural killer cells. Prior xenotransplantation studies have reported problems including natural killer cell-mediated lysis after transplantation, as well as difficulties maintaining antiviral immunity, and autoimmune disorders in the donor animals.

Despite such publications, complex issues concerning xenotransplantation products in humans remain unsolved and guidance for providing viable xenotransplantation products remains vague, contradictory, and generic where specificity is required for safety and efficacy. There is no xenotransplantation product comprising live animal cells, tissues, or organs approved for marketing and very few clinical trials. The industry has faced safety concerns, e.g., potential transmission of pathogens, coupled with the lack of meaningful regulatory guidance on approved manufacturing procedures and product characteristics. While various publications have reported advances, e.g., in academic settings, none has resulted in an approved xenotransplantation product comprising live animal cells, tissues, or organs, and good manufacturing practice (GMP) regulations have not been promulgated for such products or manufacturing processes.

The present invention therefore addresses long-felt but unmet need for translating the science of xenotransplantation into a clinical reality.

SUMMARY OF THE INVENTION

In accordance with one aspect of the invention a method is provided for producing a biological product for xenotransplantation into a human recipient, said biological product comprising live cells and tissues that vascularize after xenotransplantation, the method including: producing a non-wild type, biologically engineered swine, wherein said swine has a biologically engineered genome such that it does not express one or more extracellular surface glycan epitopes; confirming that said swine is free of at least the following zoonotic pathogens:

(i) *Ascaris* species, *cryptosporidium* species, *Echinococcus*, *Strongyloids sterocolis*, and *Toxoplasma gondii* in fecal matter;

(ii) *Leptospira* species, *Mycoplasma hyopneumoniae*, porcine reproductive and respiratory syndrome virus (PRRSV), pseudorabies, transmissible gastroenteritis virus (TGE)/Procine Respiratory Coronavirus, *Toxoplasma Gondii* in antibody titers;

(iii) Porcine Influenza;

(iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), Microphyton and *Trichophyton* spp.;

(v) Porcine cytomegalovirus; and (vi) *Brucella suis*;

maintaining the swine according to a bioburden-reducing procedure, said procedure comprising maintaining the swine in an isolated closed herd, wherein all other animals in the isolated closed herd are confirmed to be free of said zoonotic pathogens, wherein the swine is isolated from contact with any non-human animals and animal housing facilities outside of the isolated closed herd; harvesting a biological product from said swine, wherein said harvesting comprises euthanizing the swine and aseptically removing the biological product from the swine; processing said biological product comprising sterilization after harvesting using a sterilization process that does not reduce cell viability to less than 50% cell viability in a 3-(4,5-dimethylthiazol-2-yl)-2,5-diphenyltetrazolium bromide (MTT)-reduction assay and does not reduce mitochondrial activity to less than 50% mitochondrial activity; and storing said biological product in a sterile container.

In accordance with one aspect of the invention, a method is provided for producing a biological product suitable for xenotransplantation into a human recipient, the method including: producing a non-wild type, biologically engineered swine, wherein said swine is produced through natural breeding and natural birthing, wherein said swine has a biologically engineered genome such that it does not express one or more extracellular surface glycan epitopes, and wherein said swine is free of at least the following pathogens: *Ascaris* species, *cryptosporidium* species, *Echnococcus*, *Strongyloids sterocolis*, *Toxoplasma gondii*, *Brucella suis*, *Leptospira* species, *mycoplasma hyopneumoniae*, pseudorabies, *Toxoplasma Gondii*, *staphylococcus* species, *Microphyton* species, and *Trichophyton* species, porcine influenza, cytomegalovirus, arterivirus, and coronavirus; rearing the swine and maintaining the swine according to a bioburden-reducing procedure, said procedure comprising maintaining the swine in a closed herd, wherein all other animals in the closed herd are confirmed to be free of at least the following pathogens: *Ascaris* species, *cryptosporidium* species, *Echnococcus, Strongyloids sterocolis, Toxoplasma gondii, Brucella suis, Leptospira* species, *mycoplasma hyopneumoniae*, pseudorabies, *Toxoplasma Gondii, staphylococcus* species, *Microphyton* species, and *Trichophyton* species, porcine influenza, cytomegalovirus, arterivirus, and coronavirus, wherein the swine is isolated from contact with any non-human animals and animal housing facilities outside of the closed herd; harvesting a biological product from said swine, wherein said harvesting comprises euthanizing the swine and aseptically removing the biological product from the swine; processing said biological product comprising sterilization within 15 hours of harvesting and storing said biological product in a sterile container, wherein said biological product does not contain one or more extracellular surface glycans, wherein said product is free of *Ascaris* species, *cryptosporidium* species, *Echnococcus, Strongyloids sterocolis, Toxoplasma gondii, Brucella suis, Leptospira* species, *mycoplasma hyopneumoniae*, pseudorabies, *Toxoplasma Gondii, staphylococcus* species, *Microphyton* species, and *Trichophyton* species, porcine influenza, cytomegalovirus, arterivirus, and coronavirus, and wherein said product is biologically active and comprises live cells and tissues capable of vascularizing after xenotransplantation, wherein cellular mitochondrial activity of said product is greater than 50% as measured by MTT assay; wherein said product is less immunogenic when transplanted into a human xenotransplant recipient as compared to a biological product obtained a xenotransplantation product made from conventional Gal-T knockout swine, from conventional triple knockout swine, from transgenic swine, from wild-type animals, and/or allograft, wherein said product is less antigenic when transplanted into a human xenotransplant recipient as compared to a biological product obtained from a xenotransplantation product made from conventional Gal-T knockout swine, from conventional triple knockout swine, from transgenic swine, from wild-type animals, and/or allograft, and
wherein said product is resistant to rejection by the human xenotransplant recipient in the absence of administration of immunosuppressant drugs or other immunosuppressant therapies to the human xenotransplant recipient.

In a further aspect of the invention, following the clinical xenotransplantation of the product into a human recipient, the product exhibits a clinical benefit that is on par or enhanced above an allograft product. In a further aspect of the invention, the product comprises an organ or tissue, for example, including a liver, a kidney, lung, skin or nerve. In a further aspect of the invention, the product is compatible with vascularization in the region of the transplant in the patient following the xenotransplantation. In a further aspect of the invention, with regard to skin, the product is compatible with the production of collagen in the region of the transplant in the patient following the xenotransplantation. In some aspects, clinical benefits may include decreased graft dislocation, increased graft adherence, granulation at level with surrounding tissue; less than 20%, 10%, 5% or 2% hyper-granulation, hematoma less than 20%, 10%, 5% or 2% of wound size; and fibrin deposition of less than 20%, 10%, 5% or 2% of wound size, reduced bacterial infection compared to allograft, e.g., colony counts of less than $10^5$ g/tissue, reduced cellulitis, reduced erythema, reduced edema, reduced hyperesthesia, reduced induration, reduced tenderness, reduced itching, reduced abscesses, reduced incidence of toxic shock syndrome, reduced colonization of toxin-1 producing *S. aureus*, reduced incidence of sepsis and septic shock, reduced colonization by *E. coli, P. aeruginosa, Klebsiella* spp., *Providencia* spp., enterobacteriaceae, and yeasts such as *C. albicans*. In a further aspect, the product may form an occlusive fibrin seal. In a further aspect, the product may incorporate into the transplantation site or healing site. In a further aspect, the product may reduce or prevent infection at the transplantation site or the healing site, increase or retain fluids at the transplantation site or the healing site, increase or retain electrolytes at the transplantation site or the healing site, increase or retain temperature homeostasis at the transplantation site or the healing site, reduce scarring at the transplantation site or the healing site, reduce or eliminate sepsis, reduce or eliminate protein losses, provide, improve or facilitate restoration of normal bodily functions, or a combination thereof. In a further aspect of the invention, the product is capable of being transplanted in the absence of immunosuppressant drugs or other immunosuppressant therapies. In some aspects, immunosuppressants are not used according to the present disclosure prior to, during, and/or after transplantation of the xenotransplantation product of the present disclosure. In some aspects, immunosuppressants may be used according to the present disclosure prior to, during, and/or after transplantation of the xenotransplantation product of the present disclosure. In some aspects, immunosuppressants are used according to the present disclosure after transplantation of the xenotransplantation product of the present disclosure to prolong the adherence of an already transplanted xenotransplantation product.

In accordance with another exemplary aspect of the invention, the present disclosure provides a method of preparing biological product for clinical xenotransplantation into a human comprising selecting a known human major histocompatibility complex gene sequence or sequencing a human recipient's major histocompatibility complex gene, genetically modifying cells of a swine to replace a portion of the swine's major histocompatibility complex gene sequence with a corresponding portion of the known human major histocompatibility complex gene sequence or a corresponding portion of the human recipient's major histocompatibility complex gene sequence such that the swine's cells express the corresponding portion of the known human major histocompatibility complex gene sequence or the corresponding portion of the human recipient's major histocompatibility complex gene sequence, isolating one or more cells, tissues, and/or organs from the swine that express the corresponding portion of the known human major histocompatibility complex gene sequence or the corresponding portion of the human recipient's major histocompatibility complex gene sequence, wherein the isolated cells, tissues, and/or organs are the biological product.

In accordance with another exemplary aspect of the invention, the present disclosure provides a method of preparing a genetically reprogrammed swine comprising a nuclear genome having disrupted alpha-1,3 galactosyltransferase gene, and genetically modified such that it expresses a major histocompatibility complex of a known human sequence or a human recipient of a cell, a tissue, and/or an organ isolated from said genetically reprogrammed swine, the method comprising selecting a known human major histocompatibility complex sequence or sequencing the human recipient's major histocompatibility complex gene, obtaining a swine comprising a nuclear genome having at least one disrupted swine surface glycan gene, genetically modifying cells of the swine to replace portions of the swine's major histocompatibility complex gene with corresponding portions of the known human major histocompatibility complex gene or corresponding portions of the human recipient's major histocompatibility complex gene such that the swine's cells express portions of the human recipient's major histocompatibility complex.

In accordance with another exemplary aspect of the invention, the present disclosure provides a method of delaying, reducing, or preventing rejection, separation, or adverse reactions to xenotransplanted tissues in a human recipient, comprising selecting a known human major histocompatibility complex gene sequence or sequencing the human recipient's major histocompatibility complex gene, obtaining a swine comprising a nuclear genome having disrupted alpha-1,3 galactosyltransferase gene, genetically modifying cells of the swine to replace a portion of the swine's major histocompatibility complex gene with a corresponding portion of the known human major histocompatibility complex gene sequence or the corresponding portion of the human recipient's major histocompatibility complex gene sequence such that the swine's cells express the corresponding portion of the known human major histocompatibility complex gene sequence or the corresponding portion of the human recipient's major histocompatibility complex gene sequence, isolating cells, tissue, and/or an organ from the genetically reprogrammed swine that express the corresponding portion of the known human major histocompatibility complex gene sequence or the corresponding portion of the human recipient's major histocompatibility complex gene sequence, and transplanting the isolated cells, tissue, and/or an organ from the genetically reprogrammed swine into the human recipient.

In accordance with another exemplary aspect of the invention, the present disclosure provides a biological product for clinical xenotransplantation derived from a non-wild type, biologically engineered, non-human organism, wherein said organism from which said biological product is derived is produced through natural breeding and/or assisted reproductive technologies, and wherein said organism has a biologically engineered genome such that it does not express one or more extracellular surface glycan epitopes, and wherein said organism is free of at least the following pathogens: *Ascaris* species, *cryptosporidium* species, *Echnococcus, Strongyloids sterocolis, Toxoplasma gondii, Brucella suis, Leptospira* species, *mycoplasma hyopneumoniae*, pseudorabies, *Toxoplasma Gondii, staphylococcus* species, *Microphyton* species, and *Trichophyton* species, porcine influenza, cytomegalovirus, arterivirus, and coronavirus, wherein said organism is not transgenic, wherein said product does not contain one or more extracellular surface glycans, wherein said product is free of: *Ascaris* species, *cryptosporidium* species, *Echnococcus, Strongyloids sterocolis, Toxoplasma gondii, Brucella suis, Leptospira* species, *mycoplasma hyopneumoniae*, pseudorabies, *Toxoplasma Gondii, staphylococcus* species, *Microphyton* species, and *Trichophyton* species, porcine influenza, cytomegalovirus, arterivirus, and coronavirus, wherein said product has not been terminally sterilized, wherein said product is less immunogenic compared to biological product obtained from a xenotransplantation product made from conventional Gal-T knockout swine, from conventional triple knockout swine, from transgenic swine, from wild-type animals, and/or allograft, wherein said product is less antigenic when transplanted into a human xenotransplant recipient as compared to a biological product obtained from a xenotransplantation product made from conventional Gal-T knockout swine, from conventional triple knockout swine, from transgenic swine, from wild-type animals, and/or allograft, and wherein said product is biologically active and comprises live cells and tissues capable of vascularizing after xenotransplantation.

In accordance with another exemplary aspect of the invention, the present disclosure provides a method for the production of a second-generation non-wild type, biologically engineered piglet, the method including: delivering a non-wild type, biologically engineered piglet from a pregnant sow through Cesarean section, wherein said sow was produced through natural breeding and/or assisted reproductive technologies, and holding said delivered piglet in an isolated closed herd wherein all other pigs in the isolated closed herd are confirmed to be free of at least the following pathogens: cytomegalovirus, arterivirus, and coronavirus, and wherein said piglet is free of at least the following pathogens: cytomegalovirus, arterivirus, and coronavirus; rearing said piglet in said isolated closed herd; mating said piglet, upon sexual maturity, with another pig that is also maintained in said isolated closed herd and free of said pathogens; and delivering a new piglet resulting from said mating, wherein said new piglet is the second-generation non-wild type, biologically engineered piglet that is also free of said pathogens.

In accordance with another exemplary aspect of the invention, the present disclosure provides a method of treating a human subject who has suffered an injury requiring an organ, nerve, cell, or tissue transplant, the method including transplanting an organ, nerve, cell, or tissue from a second-generation non-wild type, biologically engineered piglet to the subject, wherein the second-generation non-wild type, biologically engineered piglet is produced by the method of the present disclosure and wherein immunosuppressant drugs or other immunosuppressant therapies are not administered to the subject.

In accordance with another exemplary aspect of the invention, the present disclosure provides a method for the production of a piglet is provided, comprising: delivering a piglet from a pregnant sow through Cesarean section, wherein the sow was produced through natural breeding and/or assisted reproductive technologies, and holding the delivered piglet in an environment maintained to be designated pathogen free, wherein the piglet is free of at least the following pathogens: cytomegalovirus, arterivirus, and coronavirus; rearing the piglet in the environment; mating the piglet, upon sexual maturity, with another pig that is also maintained in the environment and free of the pathogens; and delivering a new piglet resulting from the mating, wherein the new piglet is also free of the pathogens. In a further aspect of the invention, a pig is produced by such a method. Further aspects of the method include harvesting a biological product from the new piglet, wherein the product comprises an organ or tissue, the organ comprises a liver, kidney, or skin, and/or the tissue comprises a nerve.

In accordance with another exemplary aspect of the invention, method for the xenotransplantation of a product into a human patient is provided, which comprises obtaining a product derived from a non-wild type, genetically engineered, non-human organism having a genome with a disrupted alpha-1,3 galactosyltransferase gene, wherein the organism is maintained in a designated pathogen free environment and is free of at least the following pathogens: cytomegalovirus, arterivirus, and coronavirus, and wherein the product is biologically active; and transplanting the product into a human recipient, wherein upon the transplantation, the product exhibits a clinical benefit. Further aspects of the method include the product comprising an organ or tissue, the organ comprising a liver, kidney or skin, the tissue comprising a nerve, the transplantation occurring in the absence of immunosuppressant drugs or other immunosuppressant therapies, the product being compatible with vascularization in the region of the transplant in the patient following the xenotransplantation, the product, e.g., skin being compatible with the production of collagen in the region of the transplant in the patient following the xenotransplantation, the clinical benefit being enhanced above an allograft product, the organism from which the biological product is derived being produced through natural breeding and/or assisted reproductive technologies. In some aspects, the method for the xenotransplantation of a product into a human patient may further include archiving human recipient samples, such as blood and tissue samples, to allow future monitoring for potential infections, following recipients for their lifetimes to detect any unusual symptoms, and/or archiving samples of the xenotransplantation product. Any non-human animal cells used for a co-culture process should also be archived.

Yet other genetic modifications to swine can also serve to decrease immunological rejection of transplanted swine cells, tissues, and/or organs, by a human recipient. For example, the major histocompatibility complex (MHC) (including subgroups Class I, Class II and Class III) comprises a set of cell surface proteins essential for the acquired immune system to recognize foreign molecules in vertebrates, and MHC molecules bind to antigens derived from pathogens and display them on the cell surface for recognition by the appropriate T-cells. See FIG. 25.

Major histocompatibility complex class I (MHCI) and class II (MHCII) molecules display peptides on antigen-presenting cell surfaces for subsequent T-cell recognition. See FIG. 22. Within the human population, allelic variation among the classical MHCI and II gene products is the basis for differential peptide binding, thymic repertoire bias and allograft rejection. MHC molecules are cell-surface glycoproteins that are central to the process of adaptive immunity, functioning to capture and display peptides on the surface of antigen-presenting cells (APCs). MHC class I (MHCI) molecules are expressed on most cells, bind endogenously derived peptides with sizes ranging from eight to ten amino acid residues and are recognized by CD8 cytotoxic T-lymphocytes (CTL). See FIG. 18 and FIG. 27. On the other hand, MHC class II (MHCII) are present only on specialized APCs, bind exogenously derived peptides with sizes varying from 9 to 22 residues, and are recognized by CD4 helper T-cells. See FIG. 28. These differences indicate that MHCI and MHCII molecules engage two distinct arms of the T-cell-mediated immune response, the former targeting invasive pathogens such as viruses for destruction by CD8 CTLs, and the latter inducing cytokine-based inflammatory mediators to stimulate CD4 helper T-cell activities including B-cell activation, maturation and antibody production. In some aspects, the biological product of the present disclosure is not recognized by CD8+ T cells, do not bind anti-HLA antibodies, and are resistant to NK-mediated lysis.

In the human, MHC molecules are referred to as HLA, an acronym for human leukocyte antigens, and are encoded by the chromosome 6p21.3-located HLA region.8,9 The HLA segment is divided into three regions (from centromere to telomere), class II, class III and class I. See FIG. 19. Classical class I and class II HLA genes are contained in the class I and class II regions, respectively, whereas the class III locus bears genes encoding proteins involved in the immune system but not structurally related to MHC molecules. The classical HLA class I molecules are of three types, HLA-A, HLA-B and HLA-C. Only the α chains of these mature HLA class I molecules are encoded within the class I HLA locus by the respective HLA-A, HLA-B and HLA-C genes. See FIG. 13. In contrast, the beta-2 microglobulin β2m chain encoded by the β2m gene is located on chromosome 15. The classical HLA class II molecules are also of three types (HLA-DP, HLA-DQ and HLA-DR), with both the α and β chains of each encoded by a pair of adjacent loci. In addition to these classical HLA class I and HLA class II genes, the human MHC locus includes a long array of HLA pseudogenes as well as genes encoding non-classical MHCI and MHCII molecules. HLA-pseudogenes are an indication that gene duplication is the main driving force for HLA evolution, whereas non-classical MHCI and MHCII molecules often serve a restricted function within the immune system quite distinct from that of antigen presentation to αβ TCRs.

In transplantation, MHC molecules act themselves as antigens, provoking an immune response from a recipient, leading to transplant rejection. Accordingly, eliminating the expression of specific MHC molecules from the donor animals will serve to reduce immunological rejection of transplanted swine cells, tissues, and/or organs, into a human recipient. Human MHC class I and II are also called human leukocyte antigen (HLA). The present inventors have found that in order for the donor animals to survive and thrive, it is necessary to retain certain MHC molecules (e.g., SLAs) that provide the donor animals with a minimally competent immune system. Prior art strategies that rely on deletion of the MHC gene pose significant risks to the donor animals, e.g., severe combined immune deficiency (SCID). Prior art strategies that do not reprogram the swine genome pose significant risks of rejection to the human recipient, or require significant and endless use of antisuppressants. The biological products of the present disclosure avoid many human immune pathways including antigen presentation and generation of adaptive immunity, natural killer cell-mediated lysis, T cell-mediated lysis, and/or macrophage phagocytosis. Accordingly, the biological product of the present disclosure provides long-term survival of xenotransplanted products in human recipients without the need for systemic immunosuppression.

The human leukocyte antigen (HLA) system or complex is a gene complex encoding the major histocompatibility complex (MHC) proteins in humans. These cell-surface proteins are responsible for the regulation of the immune system in humans. The HLA gene complex resides on a 3 Mbp stretch within chromosome 6p21. See FIG. 14. HLA genes are highly polymorphic, which means that they have many different alleles, allowing them to fine-tune the adaptive immune system. See FIG. 15. The proteins encoded by certain genes are also known as antigens, as a result of their historic discovery as factors in organ transplants. Different classes have different functions. See FIG. 16 and FIG. 17.

HLAs corresponding to MHC class I (A, B, and C) which all are the HLA Class1 group present peptides from inside the cell. For example, if the cell is infected by a virus, the HLA system brings fragments of the virus to the surface of the cell so that the cell can be destroyed by the immune system. These peptides are produced from digested proteins that are broken down in the proteasomes. In general, these particular peptides are small polymers, about 9 amino acids in length. Foreign antigens presented by MHC class I attract killer T-cells (also called CD8 positive- or cytotoxic T-cells) that destroy cells. MHC class I proteins associate with β2-microglobulin, which unlike the HLA proteins is encoded by a gene on chromosome 15.

HLAs corresponding to MHC class II (DP, DM, DO, DQ, and DR) present antigens from outside of the cell to T-lymphocytes. These particular antigens stimulate the multiplication of T-helper cells (also called CD4 positive T cells), which in turn stimulate antibody-producing B-cells to produce antibodies to that specific antigen. Self-antigens are suppressed by regulatory T cells. The affected genes are known to encode 4 distinct regulatory factors controlling transcription of MHC class II genes. These transacting factors are the class II transactivator and 3 subunits of regulatory factor X (RFX): RFX containing ankyrin repeats (RFXANK), the fifth member of the RFX family (RFX5), and RFX-associated protein (RFXAP). Mutations in one of each define 4 distinct complementation groups termed A, B, C, and D, respectively.

HLAs corresponding to MHC class III encode components of the complement system. HLAs have other roles. They are important in disease defense. They are the major cause of organ transplant rejections. They may protect against or fail to protect (if down-regulated by an infection) against cancers. Mutations in HLA may be linked to autoimmune disease (examples: type I diabetes, coeliac disease). HLA may also be related to people's perception of the odor of other people, and may be involved in mate selection, as at least one study found a lower-than-expected rate of HLA similarity between spouses in an isolated community.

Aside from the genes encoding the 6 major antigen-presenting proteins, there are a large number of other genes, many involved in immune function, located on the HLA complex. Diversity of HLAs in the human population is one aspect of disease defense, and, as a result, the chance of two unrelated individuals with identical HLA molecules on all loci is extremely low. HLA genes have historically been identified as a result of the ability to successfully transplant organs between HLA-similar individuals.

Each human cell expresses six MHC class I alleles (one HLA-A, -B, and -C allele from each parent) and six to eight MHC class II alleles (one HLA-DP and -DQ, and one or two HLA-DR from each parent, and combinations of these). The MHC variation in the human population is high, at least 350 alleles for HLA-A genes, 620 alleles for HLA-B, 400 alleles for DR, and 90 alleles for DQ. In humans, MHC class II molecules are encoded by three different loci, HLA-DR, -DQ, and -DP, which display ~70% similarity to each other. Polymorphism is a notable feature of MHC class II genes. The present disclosure includes identifying the nucleotide sequence to be reprogrammed into the donor animal, finding and selectively replacing corresponding sections of SLA with the nucleotide sequence to be reprogrammed, e.g., 50-80 nucleotides, 60-72 nucleotides, 62-68 nucleotides. In some aspects, MHC class II genes are reprogrammed. Maps of SLA genes are available. See FIGS. 25 and 26. Thus, the present disclosure includes reprogramming small sections of genetic code rather than making a transgenic animal having human genes inserted into the animal's genome. Advantages of the present disclosure over prior art MHC-silencing techniques include providing a biologically reprogrammed swine that has a well-functioning immune system, is substantially free of a specific group of pathogens that have been identified by the inventors to be critical to exclude in order to achieve the advantages of the disclosed invention, and provides xenotransplantation products that are "invisible" to the human recipient's immune system, i.e. significantly delay or avoid rejection by the human recipient's immune system.

Any two individuals who are not identical twins will express differing MHC molecules. While MHC-knockout cells have been made, such cells suffer from issues including compromise of activation of downstream adaptive immune responses due to the deletion of MHC alleles. By replacing MHC alleles of the swine, the present disclosure provides improved donor-recipient matching because full immunological functionality is maintained. Specifically, by modifying the swine donor cells, through gene editing techniques, to cause the donor cells to express the human recipient's MHC molecules will serve to reduce immunological rejection of transplanted swine cells, tissues, and/or organs, into a human recipient. This is desirable since MHC variation in the human population is very high and having a transplanted cell, tissue, or organ that expresses MHC molecules practically identical to the recipient will serve to decrease immunological rejection of such transplanted swine cells, tissues, and/or organs.

According to an aspect of the present disclosure, gene editing is performed to knock-in HLA-E and HLA-G constructs into the swine MHC region Class I region. According to an aspect of the present disclosure, gene editing is performed to knock-in HLA-C, HLA-E, and HLA-G constructs into the swine MHC region Class I region. CD94/NKG2 is a heterodimer expressed on natural killer (NK) and a small subset of T cells. This receptor varies in function as an inhibitor or activator depending on which isoform of NKG2 is expressed. The ligand for CD94/NKG2 is HLA-E in human, which binds leader peptides from other class I molecules. Similar to NK cells, most CD8 T cells that express high levels of CD94 co-express NKG2A, the inhibitory isoform. The engagement of this receptor can lead to a blocking of cytotoxicity. However, these receptors have also been implicated in the cell survival of both NK and CD8 T cells. The level of CD94 expression is inversely correlated with the level of apoptosis in culture. Thus, CD94/NKG2 receptors may regulate effector functions and cell survival of NK cells and CD8 T cells, thereby playing a crucial role in the innate and adaptive immune response to a pathogen. In certain aspects, the present disclosure includes testing donor animals and/or xenotransplantation product recipients for natural killer cell increase, e.g., by mass cytometry.

Other genetic modifications to swine can also decrease immunological rejection. For example, a number of transgenic modifications to swine have been implemented to reduce immunogenicity and immunological rejection (see, e.g., Denner J, "Xenotransplantation-Progress and Problems: A Review," *J Transplant Technol Res* 4(2):133 (2014) ("Denner")), the entire disclosure of which is incorporated herein by reference). These include, but are not limited to, hCD46 (hMCP, human membrane cofactor), hCD55, hCD59, hCD39, thrombomodulin, heme oxygenase 1, A20, HLA-E, and CD47, and combinations thereof for inhibition of human complement regulation, and other modifications as set forth in Denner and herein. Further modifications have been described in US2018/0184630, US2017/0216358, US2019/0004063, and U.S. Pat. No. 9,888,673, which are incorporated herein by reference in their entireties.

As will also be understood from the present invention, other characteristics of products derived from swine for xenotransplantation invoke an increased immune response from the human body. For example, swine may carry a multitude of pathogens, including, but not limited to, Porcine Cytomegalovirus ("pCMV"), *Leptospira* species, arterivirus, Porcine coronavirus, *Toxoplasma gondii* and other pathogens. The inventors have identified a specific group of pathogens that are critical to exclude in order to achieve the advantages of the disclosed invention. It is therefore an object of the present invention that products derived from swine for pig to human xenotransplantation procedures are free of the specific group of pathogens described herein.

The innate immune system, through human pattern recognition receptors (PRRs) and toll-like receptors (TLRs), detect structures located on cell surfaces or otherwise associated with such pathogens (e.g., pathogen-associated molecular patterns (PAMPs)), that are non-self, causing rejection of the subject xenotransplantation product. It is therefore an object of the present invention to remove, eliminate, kill, destroy, and/or otherwise neutralize, such structures from the subject products to minimize or even eliminate immunological reaction and/or rejection upon xenotransplantation of such products.

It is a further object of the present invention to produce such specific pathogen free swine products from swine having one or more unique characteristics (e.g., being non-wild-type genetically reprogrammed, engineered and/or modified), including, but not limited to, swine that lack expression of surface glycan epitopes, genetically modified swine, biologically reprogrammed, and other swine as described and disclosed herein.

It is a further object of the present invention that such products be minimally manipulated. Manipulation of xenotransplantation products beyond their natural state (e.g., fixing in aldehyde) contributes to making such products non-viable. Hence, it is an object of the present invention that the products disclosed and described herein be minimally manipulated, viable, live cell, and capable of making an organic union with the transplant recipient, including, but not limited to, inducing vascularization and/or collagen generation in the transplant recipient.

It is a further object of the present invention that such products in some instances are preserved, including, but not limited to, through cryopreservation, in a manner that maintains viability and live cell characteristics of such products. It will be understood that such products may also be stored as continually fresh, from harvesting to transplantation, and not cryopreserved. It is a further object of the present invention that such products have at least 50%, 55%, 60%, 65%, 70%, 75%, 80%, 85%, 90%, 95%, 98%, or 99% mitochondrial activity after a freeze-thaw cycle prior to transplantation. It is a further object of the present invention that such products have at least 80%, 85%, 90%, 95%, 98%, or 99% mitochondrial activity in fresh products for transplantation. It is a further object of the present invention that such products have at least 50%, 55%, 60%, 65%, 70%, 75%, 80%, or 85% cell viability in a 3-(4,5-dimethylthiazol-2-yl)-2,5-diphenyltetrazolium bromide (MTT)-reduction assay. The present invention is not limited to detection using the MTT-reduction assay and other detection assays may also be used. In such an exemplary assay, a level of 100% metabolic activity is defined, e.g., as the results of MTT-reduction assay from fresh (non-cryopreserved) tissue samples obtained from the single source animal donor, which constitutes the baseline, positive control for viability of the product lot. The absence of metabolic activity (0%) is defined as the results of MTT-reduction assay from heat-deactivated (boiling, or similar) tissue samples obtained from the single source animal donor, which constitutes the baseline, negative control for the viability of product lot. Product viability is a comparison of the metabolic activity in the test article, as compared to the 100% and 0% boundary conditions described above. Industry norms and published reference standards support that 50% biologic activity is acceptable to provide consistent, clinically useful materials.

It is a further object of the present invention that such products be for homologous use, i.e., the repair, reconstruction, replacement or supplementation of a recipient's organ, cell and/or tissue with a corresponding organ, cell and/or tissue that performs the same basic function or functions as the donor (e.g., swine skin is used as a transplant for human skin, swine kidney is used as a transplant for human kidney, swine liver is used as a transplant for human liver, swine nerve is used as a transplant for human nerve and so forth).

It is a further object of the present invention that the utilization of such products in xenotransplantation be performed with or without the need to use immunosuppressant drugs or therapies which inhibit or interfere with normal immune function. While it is known immunosuppressive drugs may be used to prevent rejection of xenotransplantation products, such drugs also inhibit immune responses against, for example, viral and bacterial infections, thereby placing the recipient at risk. Xenotransplantation has typically been followed by rejection of the transplanted tissue. The rejection may be a cellular rejection (lymphocyte mediated) or humoral (antibody mediated) rejection including but not limited to hyperacute rejection, an acute rejection, a chronic rejection, may involve survival limiting thrombocytopenia coagulopathy and an acute humoral xenograft reaction (AHXR). While not being limited by mechanism, both humoral and cellular rejection processes may target MHC molecules. The human hyperacute rejection response to swine glycans and proteins present on transplanted tissue is so strong that the transplant tissue is typically damaged by the human immune system within minutes or hours of transplant into the human.

Furthermore, different rejection mechanisms may predominate in an organ-preferred manner. An acute or rapid humoral rejection may begin within minutes of transplant; an acute or rapid cellular rejection may begin within days of the transplant. Both humoral and cellular rejections may also have a slower or chronic rejection phase; the chronic phases may occur for years. See Demetris et al. 1998 "Antibody-mediated Rejection of Human Orthotopic Liver Allografts. A study of liver transplantation across ABO blood group barriers", *Am J. Pathol* 132:489-502; Nakamura et al 1993 "Liver allograft rejection in sensitized recipients. Observations in a Clinically Relevant Small Animal Model" *Am J. Pathol.* 142:1383-91; Furuya et al 1992. "Preformed Lymphocytotoxic Antibodies: the Effects of Class, Titer and Specificity on Liver v Heart Allografts" *Hepatology* 16:1415-22; Tector et al 2001. "Rejection of Pig Liver Xenografts in Patients with Liver Failure: Implications for Xenotransplantation", *Liver Transpl* pp. 82-9; herein incorporated by reference in their entirety.

Pig cells express multiple proteins which are not found in human cells. These include, but are not limited to, $\alpha 1,3$-galactosyltransferase ($\alpha$Gal), cytidine monophosphate-N-acetylneuraminic acid hydroxylase (CMAH) and $\beta 1$-4 N-acetylgalactosaminyltransferase. Antibodies to the CMAH (and Neu5GC), $\alpha$-Gal, and Sda-like antigens are present in human blood prior to implantation of xeno-tissue, and are involved in the intense and immediate antibody-mediated rejection of implanted tissue. Additionally, pig cells express multiple swine leukocyte antigens (SLAs). Unlike humans, pigs constitutively express class I and class II SLAs on endothelial cells. SLAs and HLAs share considerable sequence homology (Varela et al 2003 *J. Am. Soc. Nephrol* 14:2677-2683). Anti-HLA antibodies present in human serum prior to implantation of porcine tissue cross-react with SLA antigens on porcine tissues. The SLA cross-reacting antibodies contribute to the intense and immediate rejection of the implanted porcine tissue. SLA antigens may also be involved with the recipient's T-cell mediated immune response. Porcine SLAs may include, but are not limited to, antigens encoded by the SLA-1, SLA-2, SLA-3, SLA-4, SLA-5, SLA-6, SLA-8, SLA-9, SLA-11 and SLA-12 loci. Porcine Class II SLAs include antigens encoded by the SLA-DQ and SLA-DR loci. See FIG. 26.

The present disclosure includes reprogramming donor animal cells so that full immune functionality in the donor animal is retained, but the cell surface-expressing proteins and glycans are reprogrammed such that they are not recognized as foreign by the human recipient's immune system. Accordingly, in contrast to prior art disclosures which called for knocking out MHCs and SLAs or inserting transgenes into the animal's genomes, the present disclosure relates to reprogramming the animal's genome by reprogramming only discrete and small portions so that the animal retains a functional immune system, but the animal's reprogrammed cells do not express cell surface-expressing proteins and glycans that elicit attack by the human recipient's immune system.

For immunogenic reprogramming using CRISPR, a guide RNA first binds to a complementary sequence of genomic DNA at the target site. Cas9 then makes a double-strand break (DSB) at the targeted site. However, the cleavage of the target is contingent upon the initial binding of the nuclease to a protospacer adjacent motif (PAM) 3-4 nucleotides downstream of the cut site. The PAM motif for SpCas9 is 5'-NGG-3' (with N signifying any nucleotide). Different types of CRISPR nucleases recognize different PAM sequences. Once a DSB is made, the cell will activate machinery to repair the cut site. It is during this repair when edits to the genome take place.

In some aspects, knockouts are achieved so as to make mutations that render a gene inoperative. In eukaryotic cells, DSBs are often repaired through non-homologous end joining (NHEJ), a quick-fix repair mechanism that involves ligating the ends of each DNA strand together. Prone to error, NHEJ often results in the insertion or deletion of nucleotides (called indels) at the break site. Indels in protein-coding regions that are not multiples of three induce frameshift mutations. Because the reading frame of the gene is altered, these mutations often lead to loss of gene function (i.e., knockout, no functional protein is made). This type of alteration can be used for a variety of loss-of-function applications.

In some aspects, knock-ins are achieved so as to insert a foreign genetic sequence.

Importantly, persons of ordinary skill are now fully enabled to genetically modify cells with commercially available CRISPR kits as well as via a multitude of commercial service organizations that provide design, consulting, and laboratory services with guaranteed results for any desired knock out or knock in experiments using CRISPR technology. Thus, persons skilled in the art can use the present disclosure to make and use the disclosed invention without undue experimentation.

In certain aspects, the present disclosure includes sequencing the recipient's HLA/MHC gene, preparing template HLA/MHC sequences, preparing CRISPR-Cas9 plasmids, e.g., using polymerase chain reaction, cloning template HLA/MHC sequences into the plasmids, determining CRISPR cleavage sites at the HLA/MHC locus in the swine cells, cloning gRNA sequences into one or more CRISPR-Cas9 plasmids, administering CRISPR-Cas9 plasmids into the swine cells, performing CRIPSR/Cas9 cleavage at the MHC locus of the swine cells, replacing the HLA/MHC locus in the swine cells with one or more template HLA/MHC sequences matching the recipient's sequenced HLA/MHC genes. In the Cas9 system, many Cas9-like nucleases were developed given the natural diversity of bacterial CRISPR systems. Cpf1, a putative Class 2 CRISPR effector, mediates target DNA editing with distinct features from Cas9. In contrast to Cas9 which generates blunt ends, Cpf1 generates a 5-nt staggered cut with a 5' overhang, which is particularly advantageous in facilitating a NHEJ-based gene insertion (knock-in) into a genome. A hybrid enzyme combining the Cas9-nickase and PmCDA1, an activation-induced cytidine deaminase could perform targeted nucleotide substitution (C-U) without the use of template DNA, providing a novel route for point mutation. A CRISPR system (Cas13a) that targets RNA has also been developed recently. A structure-guided endonuclease (SGN) consisting of flap endonuclease-1 that recognizes the 3' flap structure and the cleavage domain of Fok I, which cleaves DNA strands, may also be used. A guide DNA complementary to the target with an unpaired 3' end is needed to form a 3' flap structure. SGN recognizes and cleaves the target DNA on the basis of the 3' flap structure of a double-flap complex formed between the target and the guide DNA. The SGN offers a strategy for a structure-based recognition, capture, and editing of any desired target DNA, thereby expanding the toolkit for genetic modification. In certain aspects, the present disclosure further includes sequencing cells of the swine after performing the HLA/MHC replacement steps in order to determine if the HLA/MHC sequences in the swine cells have been successfully replaced. In certain aspects, the present disclosure further includes transplanting one or more cells, tissues, and/or organs from the HLA/MHC sequence-replaced swine into a human recipient. In certain aspects, the present disclosure further includes breeding HLA/MHC sequence-replaced swine for at least one generation, or at least two generations, before their use as a source for live tissues, organs and/or cells used in xenotransplantation.

In certain aspects, known human sequence information is available, e.g., in the IPD-IMGT/HLA database or library (available at ebi.ac.uk/ipd/imgt/hLa/) and the international ImMunoGeneTics information System® (available at imgt.org). Nomenclature for such genes is illustrated in FIG. 20. For example, HLA-A1, B8, DR17 is the most common HLA haplotype among Caucasians, with a frequency of 5%. Further, maps of human genomic information to animal genomic information are available. For example, as shown in FIG. 23 and FIG. 24, maps of the human and swine major histocompatibility complex class I and claim II regions are known and can be used to reprogram swine cells according to the present disclosure so as to retain the donor animal's immune function while reducing or eliminating reactivity of the human recipient's body to the xenotransplanted products from the donor animal. Thus, the disclosed method can be performed using the known MHC/HLA sequence information.

In certain aspects, the present disclosure includes a biological product for clinical xenotransplantation derived from a non-wild type, genetically engineered, swine, wherein said swine has a genome with a disrupted alpha-1,3 galactosyltransferase gene, and wherein a cell from the swine has been genetically modified such that it expresses a major histocompatibility complex of a recipient of said biological product.

The above and other various aspects and aspects are described below with reference to the accompanying drawings.

BRIEF DESCRIPTION OF THE DRAWINGS

The accompanying drawings, which are incorporated herein and form part of the disclosure, help illustrate various aspects of the present invention and, together with the description, further serve to describe the invention to enable a person skilled in the pertinent art to make and use the aspects disclosed herein. In the drawings, like reference numbers indicate identical or functionally similar elements.

FIG. 2 illustrates a method for preparing a skin product in accordance with the present invention.

FIG. 3 illustrates a combination skin product in accordance with the present invention.

FIG. 9A depicts POD-15. H&E, H&E, high power image depicts tissue viability with surface and follicular epithelial necrosis. FIG. 9B depicts POD-22 H&E, high power image demonstrating residual autograft (asterisks) with good overall viability. No surface epithelium and some surface necrosis noted, along with extensive fibrosis with infiltration into the autograft (arrows).

FIG. 15 is a table listing numbers of serological antigens, proteins, and alleles for human MHC Class I and Class II isotypes.

(FIG. 21A) AA contact energies were assigned respectively to these rungs (AA pairs) by the M-J matrix, and the binding energy between CDR3 and the presented peptide could be calculated by summing these values. (FIG. 21B) Actual 3-dimensional structure of a TCR-pMHC complex (PDBID: 1AO7) is shown. Both CDR3 loops comprise α and β chains running across rather than parallel to the presented peptide. CDR2 mainly interacts with helices, whereas CDR1 interacts with both MHC helix and presented peptide. The TCR-pMHC binding mode also varies widely.

FIG. 24 is a comparative genomic organization of the human and swine MHC Class II region.

FIG. 30 shows a cryovial used to store a xenotransplantation product.

FIG. 32 shows a Clinical Wound Assessment Scale in accordance with one aspect of the present invention.

DETAILED DESCRIPTION OF THE INVENTION

Figure 1:
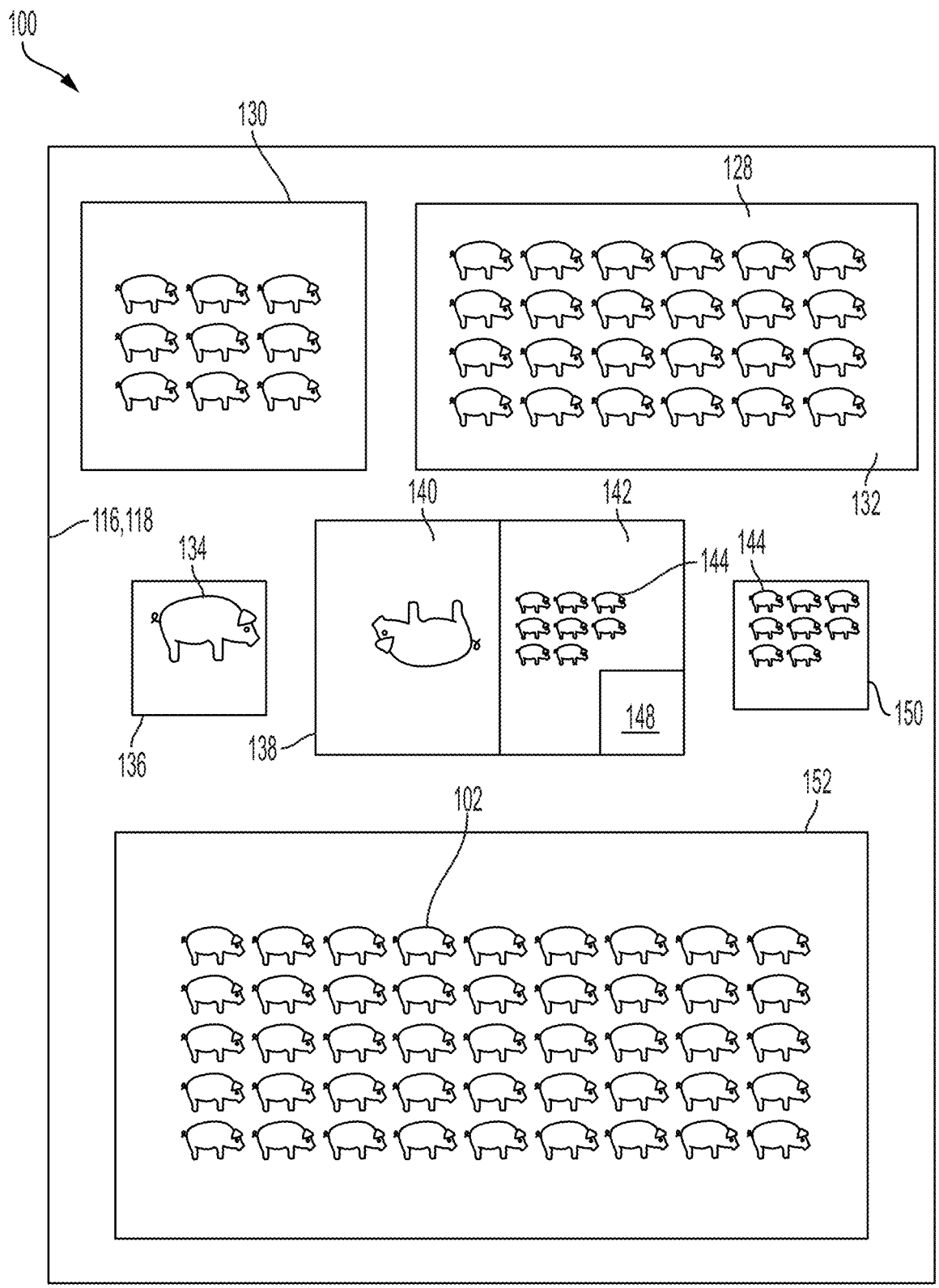
FIG. 1 illustrates a source animal facility and corresponding designated pathogen free facilities, animals, and herds in accordance with the present invention.

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or aspects so described.

The singular forms "a," "an," and "the" include plural referents unless the context clearly dictates otherwise.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

Generally, herein, the term "or" includes "and/or."

As used herein, a plurality of compounds or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The present disclosure provides a continuous manufacturing process for a xenotransplantation product that has reduced immunogenicity, reduced antigenicity, increased viability, increased mitochondrial activity, a specifically required pathogen profile, and unexpectedly long shelf-life in xenotransplantation tissues subject to cryopreservation. The continuous manufacturing process is surprisingly and unexpectedly effective in avoiding hyperacute rejection, delayed xenograft rejection, acute cellular rejection, chronic rejection, cross-species transmission of diseases, cross-species transmission of parasites, cross-species transmission of bacteria, cross-species transmission of fungi, cross-species transmission of viruses. The continuous manufacturing process is surprisingly and unexpectedly effective in creating a closed herd in which the donor animals survive normally without detectable pathological changes.

Source Animal Facility ("SAF")

Referring to FIG. 1, a barrier source animal location, including, but not limited to, a Source Animal Facility ("SAF") 100, that can be used for the housing, propagation, maintenance, care and utilization of a closed colony swine, including a closed colony that is designated pathogen free ("DPF") ("DPF Closed Colony") 102, is shown. As contained herein, the SAF has positive pressure, biocontainment characteristics is operated under specific isolation-barrier conditions.

As described herein, the DPF Closed Colony 102 is comprised of source animals maintained and propagated for harvesting various biological products for use in human xenotransplantation and other therapies, wherein such products have reduced bioburden and demonstrate reduced immunogenicity resulting from xenotransplantation and other therapeutic procedures. In some aspects, xenotransplantation products of the present disclosure are less immunogenic than a xenotransplantation product made from conventional Gal-T knockout swine, from conventional triple knockout swine, from transgenic swine, from wild-type animals, and/or allograft. For example, as shown in Examples 1 and 2, biological products made according to the present disclosure provided unexpectedly high clinical benefit when using a single knockout pig as the donor animal in that, despite the presence of Neu5Gc and porcine B4GALNT2, the biological product made according to the present disclosure had less immunogenicity than allograft, vascularized, and was resistant to rejection for the entire duration of the study period.

As further described herein, the SAF 100 and each of its accompanying areas (e.g., rooms, suites or other areas) can be utilized to house and maintain source animals from which biological products are harvested and/or processed. The SAF 100 and its areas are designed to minimize and eliminate the potential for contamination of the harvested and/or processed biological products and cross-contamination between such products.

Within the SAF 100, in some aspects, utilized animal areas are ventilated. For example, animal areas are ventilated with high efficiency particulate air (HEPA)-filtered fresh air from the roof of the building, for example, having at least 10-15 air changes per hour. Additionally, one or more laminar flow hoods (e.g., Class II Type A2 Laminar Airflow Biosafety Cabinets) are utilized in the SAF rooms, including in a xenotransplantation drug processing suite to providing additional ventilation to minimize or eliminate cross contamination.

In some aspects, utilized areas are also temperature controlled and monitored. For example, the areas are heated and cooled to maintain temperature within the range specified by, for example, the Guide for the Care and Use of Laboratory Animals. Utilized animal holding rooms are also alarmed and centrally monitored for high or low temperatures, and staff are notified immediately if temperatures are beyond required temperature.

In some aspects, the SAF 100 has multiple levels of containment for the source animals. For example, source animals are contained in a primary level of containment consisting of pens and cages which are secured by stainless steel latches. With respect to secondary level of containment, functionally designated areas (e.g., rooms, suites or other areas) can have latched inner doors, and an ante-room with card-controlled access to a hallway. A tertiary level of containment can include outside perimeter fencing.

The entire SAF is located within a single building. Primary entrance is through a single door via programmable identification (ID) card. All other external doors are alarmed, remain locked, and are for emergency use only.

Security is also a consideration to ensure security of the SAF 100 in general, and to control individuals entering the SAF 100 to minimize the risk of outside contaminants entering the SAF 100 and reaching the source animals. Therefore, in one aspect, the primary entrance to the SAF 100 is through a single door 116 via programmable identification (ID) card 118. All other external doors 120 are alarmed, remain locked, and are for emergency use only.

It will be understood that the SAF 100 and its features as disclosed herein are set out as examples, and it will be further understood that other facilities with various features can also be utilized to perform the methods and produce the products disclosed herein.

In some aspects, the SAF 100 animal program is licensed and/or accredited and overseen, evaluated and operated by a team of highly experienced, professional staff. For example, the program is registered and/or accredited with the USDA Animal and Plant Health Inspection Service (as a licensed animal research facility), National Institute of Health (NIH) Office of Laboratory Animal Welfare (OLAW) (confirming compliance with Public Health and Safety (PHS) regulations, Association for Assessment and Accreditation of Laboratory Animal Care (AAALAC) (with veterinary care of the source animals housed at the SAF under the direction of an attending veterinarian), and other federal, state and local regulatory authorities.

In some aspects, to ensure the welfare of the source animals, SAF personnel, and caretakers of source animals adhere to procedures for animal husbandry, tissue harvesting, and termination of animals that are approved by an appropriate Institutional Animal Care and Use Committee, in accordance with the Animal Welfare Act (7 U.S.C. 2131, et seq.), accredited by the AAALAC, and in compliance of the standards as set forth in the Guide for the Care and Use of Laboratory Animals.

In some aspects, caretakers have extensive training and experience in handling and caring for the source animals being managed in accordance with the present invention. For example, each caretaker undergoes a documented training program covering the standard operating procedures governing handling and care of these source animals, and be skilled in making daily health assessments and insuring prompt care is directed to any animal in need. In addition, the caretakers can be trained in scrubbing and gowning procedures prior to entry into the isolation areas (e.g., rooms, suites or other areas) as described herein, and under a medical surveillance program to ensure staff health and the health of the source animals.

To minimize and eliminate contamination risk to the SAF, any personnel or visitors entering the SAF wear personnel protective equipment or change into facility dedicated clothing and footwear before entry into any containment areas. Visitors who wish to enter animal areas must not have had any contact with live swine for at least 24 hours preceding the visit or must shower at the facility prior to entry.

It will be understood that the approaches and procedures set forth herein are examples as to how to ensure contamination does not reach the source animals within SAF 100. It will be further understood that a multitude of approaches can also be utilized to achieve a designated pathogen free environment for source animals.

Source Animals

In some aspects, as described herein, swine can be utilized as source animals. As used herein, unless otherwise specified, the terms "swine," "pig" and "porcine" are generic terms referring to the same type of animal without regard to gender, size, or breed. It will be understood that any number of source animals could be utilized in accordance with the present invention, including, but not limited to, pigs, non-human primates, monkeys, sheep, goats, mice, cattle, deer, horses, dogs, cats, rats, mules, and any other mammals. Source animals could also include any other animals including, but not limited to, birds, fish, reptiles, and amphibians. It will be understood that the term "disrupting" or "disrupt" or "disrupted" or like terms as used herein can include any and/or all modifications to a gene and related materials, including, but not limited to, removing, editing, silencing, modifying, reprogramming, immunogenomic reprogramming, altering, changing, engineering, knocking in, adding, knocking out, and/or any or all other such modifications.

Swine Lacking Expression of Extracellular Surface Glycan Epitopes

In some aspects, the swine source animals are genetically modified (i.e., non-wild-type). For example, in some aspects, the swine include "knockout" and/or "knock-in" swine having one or more characteristics of swine disclosed in U.S. Pat. No. 7,795,493 ("Phelps"), the entire disclosure of which is incorporated herein by reference. Such swine lack active (and/or have disrupted) $\alpha$-(1,3) galactosyl epitopes responsible for hyperacute rejection in humans upon transplantation. Multiple methods of production of knockout/knock-in swine are disclosed in Phelps including: the inactivation of one or both alleles of the alpha-1,3-GT gene by one or more point mutations (for example by a T-to-G point mutation at the second base of exon 9) and/or genetic targeting events as disclosed at col. 9, line 6 to col. 10, line 13; col. 21, line 53 to col. 28, line 47; and col. 31, line 48 to col. 38, line 22. The creation of such swine through the described methods, and/or the utilization of such swine and progeny following creation, can be employed in the practice of the present invention, including, but not limited to, utilizing organs, tissue and/or cells derived from such swine.

Similarly, in other aspects, the swine source animals include "knockout" and "knock-in" swine having one or more characteristics of swine disclosed in U.S. Pat. No. 7,547,816 ("Day"), the entire disclosure of which is incorporated herein by reference. Such swine also lack active (and/or have disrupted) $\alpha$-(1,3) galactosyl epitopes responsible for hyper-acute rejection in humans upon transplantation. Multiple methods of production of knockout/knock-in swine are disclosed in Day including: enucleating an oocyte, fusing the oocyte with a porcine cell having a non-functional alpha-1,3-GT gene, followed by implantation into a surrogate mother, as described more fully at col. 4, line 61 to col. 18, line 55. The creation of such swine through the described methods, and/or the utilization of such swine and progeny following creation, can be employed in the practice of the present invention, including, but not limited to, utilizing organs, tissue and/or cells derived from such swine.

Similarly, in other aspects, the swine source animals include GGTA Null ("knockouts" and "knock-ins") swine having one or more characteristics of swine disclosed in U.S. Pat. No. 7,547,522 ("Hawley"), the entire disclosure of which is incorporated herein by reference. Such swine also lack active (and/or have disrupted) $\alpha$-(1,3) galactosyl epitopes responsible for hyper-acute rejection in humans upon transplantation. As disclosed in Hawley, production of knockout/knock-in swine includes utilizing homologous recombination techniques, and enucleating oocytes followed by fusion with a cell having a non-functional alpha-1,3-GT gene and implantation into a surrogate mother (as disclosed more fully at col. 6, line 1 to col. 14, line 31). The creation of such swine through the described methods, and/or the utilization of such swine and progeny following creation, can be employed in the practice of the present invention, including, but not limited to, utilizing organs, tissue and/or cells derived from such swine.

In yet other aspects, the swine source animals include swine and swine that lack active (and/or have disrupted) $\alpha$-(1,3) galactosyl epitopes having one or more characteristics of swine as described in U.S. Pat. No. 9,883,939 ("Yamada"), the entire disclosure of which is incorporated by reference herein. In certain aspects, the swine source animals for use or modification in accordance with the present disclosure include the swine having one or more characteristics of swine described in U.S. 2018/0184630 (Tector, III), the disclosure of which is incorporated by reference herein in its entirety. The creation of such swine through the described methods, and/or the utilization of such swine and progeny following creation, can be employed in the practice of the present invention, including, but not limited to, utilizing organs, tissue and/or cells derived from such swine.

In yet other aspects, swine source animals include the swine having one or more characteristics of swine disclosed in U.S. Pat. No. 8,106,251 (Ayares), U.S. Pat. No. 6,469,229 (Sachs), U.S. Pat. No. 7,141,716 (Sachs), each of the disclosures of which are incorporated by reference herein. The creation of such swine through the described methods, and/or the utilization of such swine and progeny following creation, can be employed in the practice of the present invention, including, but not limited to, utilizing organs, tissue and/or cells derived from such swine.

In some aspects, the swine can originate from one or more highly inbred herds of pigs (whether genetically modified or not (i.e., wild-type)) with a co-efficient of inbreeding of 0.50 or greater. A higher coefficient of inbreeding indicates the products derived from the source animals may have more consistent biological properties for use in pig-to-human xenotransplantation (e.g., a coefficient of inbreeding of 0.80 or greater in one aspect). Coefficients of inbreeding for animals are disclosed in Mezrich et al., "Histocompatible Miniature Swine: An Inbred Large-Animal Model," *Transplantation,* 75(6):904-907 (2003). An example of a highly inbred herd of swine includes miniature swine descendant from the miniature swine disclosed in Sachs, et al., "Transplantation in Miniature Swine. I. Fixation of the Major Histocompatibility Complex," *Transplantation* 22:559 (1976), which is a highly inbred line possessing reasonable size matches particularly for organs eventually utilized for clinical transplantation. The creation of such swine through the described methods, and/or the utilization of such swine and progeny following creation, can be employed in the practice of the present invention, including, but not limited to, utilizing organs, tissue and/or cells derived from such swine.

Source animals can also include animals swine that lack active (and/or have disrupted) alpha-1,3-galactosyltransferase, Neu5Gc, and β1,4-N-acetylgalactosaminyltransferase as described in U.S. Patent Publication No. US2017/0311579 (Tector), the entire disclosure of which is incorporated herein by reference. The creation of such swine through the described methods, and/or the utilization of such swine and progeny following creation, can be employed in the practice of the present invention, including, but not limited to, utilizing organs, tissue and/or cells derived from such swine.

Immunogenomic Reprogrammed Swine Lacking Expression of Extracellular Surface Glycan Epitopes As used herein "immunogenomic reprogramming" includes replacing, silencing, altering or disrupting conserved genetic material of a donor animal's genome through, for example, the use of site-specific endonucleases for targeted manipulation of a donor swine's genome. The genetic modification can be made utilizing known genome editing techniques, such as zinc-finger nucleases (ZFNs), transcription activator-like effector nucleases (TALENs), adeno-associated virus (AAV)-mediated gene editing, and clustered regular interspaced palindromic repeat Cas9 (CRISPR-Cas9). These programmable nucleases enable the targeted generation of DNA double-stranded breaks (DSB), which promote the upregulation of cellular repair mechanisms, resulting in either the error-prone process of non-homologous end joining (NHEJ) or homology-directed repair (HDR), the latter of which can be used to integrate exogenous donor DNA templates. In one aspect, certain regions of the donor swine's genome are reprogrammed including, but not limited to, the MHC regions of the donor swine that are homologous/analogous/orthologous to the MHC regions of a human. For example, according to one non-limiting aspect, a pig's genome may be immunogenomically reprogrammed to express HLA-DQ ($\alpha\beta$) instead of SLA-DQ. Identification of corresponding regions between pigs and humans can be found in the literature including, for example, in Ando et al. Immunogenetics (2005) 57:864-873; Lunney, J., "Molecular genetics of the swine major histocompatibility complex, the SLA complex," Developmental and Comparative Immunology 33: 362-374 (2009); Shigenari et al., Immunogenetics (2004) 55:696-705; Gao et al., Developmental and Comparative Immunology, (2014) 45:87-96; Bentley et al., Tissue Antigens, (2009) 74, 393-403, each of which is incorporated herein by reference in its entirety for all purposes including, but not limited to, genetic information, sequences, and mapping.

Such "immunogenomic reprogramming," as described herein, does not create transgenic characteristics in the donor animal since the conserved region or regions of the donor animal genome that are reprogrammed are native and naturally occurring within the donor animal. This is contrasted with transgenic animals which have genomes that have been modified to introduce non-native genes from a different species of animal (for example, but not limited to, swine having or expressing hCD46-human membrane cofactor protein, MCP; hCD55-human decay-accelerating factor, DAF and other human genes set forth in Table 1 herein and otherwise known in the art).

In some aspects an immunogenomically reprogrammed swine lacking expression of extracellular surface glycan epitopes is provided. In some aspects, the source animals can include swine whose genomes, through genetic modification, include the removal of alpha-1,3-galactosyltransferase (single knockout) plus immunogenomic reprogramming to modify expression of MHC as described herein. In other aspects, the source animals can also include swine whose genomes, through genetic modification, include the removal of alpha-1,3-galactosyltransferase and Neu5Gc (double knockout), plus immunogenomic reprogramming to modify expression of MHC as described herein. In yet other aspects, the source animals can also include swine whose genomes, through genetic modification, include the removal of alpha-1,3-galactosyltransferase, Neu5Gc, and $\beta$1,4-N-acetylgalactosaminyltransferase (triple knockout), plus immunogenomic reprogramming to modify expression of MHC as described herein. In yet other aspects, source animals can also include animals whose genome expresses one or more specific MHC molecules of the human recipient or a known human sequence, as described herein.

In some aspects, the immunogenomic reprogramming results in MHC expression, non-expression, or modulated expression in the source animal as described herein. For these additional immunogenomic reprogrammed aspects, three general approaches can be employed to create hypo-immunogenic tolerant donor cells. These approaches are complementary and synergistic to achieving such a hypo-immunogenic tolerant donor cell for xenotransplantation which is distinct from "downstream" approach utilized by others in the xenotransplantation space as described herein.

In a first approach, the present invention utilizes immunogenomic reprogramming to reduce or eliminate MHC-I (Class A) components to avoid provocation of natural cellular mediated immune response by the recipient. In another aspect, exon regions in the donor animal (e.g., swine) genome corresponding to exon regions of HLA-A and HLA-B are silenced, wholly removed, or knocked-out of the genome of the donor animal. In another aspect, exon regions in the donor animal (e.g., swine) genome corresponding to exon regions of HLA-A and HLA-B are silenced, wholly removed, or knocked-out of the genome of the donor animal and exon regions in the donor animal (e.g., swine) genome corresponding to exon regions of HLA-C may be modulated, e.g., reduced. In one aspect, the present disclosure includes silencing, knocking out, or causing the minimal expression of source animal's homologous/analogous/orthologous HLA-C (as compared to how such would be expressed without such immunogenomic reprogramming). In another aspect, the immunogenomic reprogramming includes the swine donor cell to have modulatory expression of Class II Major Histocompatibility Complex Transactivator (CIITA) (to affect the alternate expression of HLA-C in the source animal while retaining immunological function of the source animal).

In an additional or alternative approach, the present disclosure includes reprogramming, or leveraging the inhibitory and co-stimulatory effects of the MHC-I (Class B) molecules. Specifically, the present disclosure includes a process that "finds and replaces" portions of the donor animal genome corresponding to portions of the HLA gene, e.g., to overexpress HLA-G where possible, retaining and overexpressing portions corresponding to HLA-E, and/or "finding and replacing" portions corresponding to HLA-F. As used herein, the term "find and replace" includes identification of the homologous/analogous/orthologous conserved genetic region and replacement of the section or sections with the corresponding human components through gene editing techniques. Another aspect includes finding and replacing the beta-2 microglobulin protein which is expressed in HLA-A, -B, -C, -E, -F, and -G. Homologous/analogous/orthologous conserved cytokine mediating complement inhibiting or otherwise immunomodulatory cell markers, or surface proteins, that would enhance the overall immune tolerance at donor-recipient cellular interface. In certain aspects, hCD55 may be knocked in combination with any of aspects disclosed herein. In certain aspects, hCD46 may be knocked in combination with any of aspects disclosed herein.

In a third approach, the present invention utilizes "find and replace" in order to express or overexpress specific ligands and other immunomodulatory molecules to create a localized environment of immune suppression in a region proximate to the donor-recipient cell interface in the manner exhibited by trophoblasts and placental cells in the region of the decidua. Whereby, donor cells would have the ability to induce apoptosis of T cells to include, but not be limited to, CD8+ T cells and NK cells and have a tolerogenic impact on TRegs and CD4+ T cells. These include, but are not limited to, Fas-L, TRAIL, PDL-1 (death ligand), and PDL-2.

In certain aspects, the present disclosure includes knocking-out: SLA-11; SLA-6,7,8; SLA-MIC2; and SLA-DQA; SLA-DQB1; SLA-DQB2, and knocking-in: HLA-C; HLA-E; HLA-G; and HLA-DQ. In certain aspects, the present disclosure includes knocking-in HLA-C, HLA-E, HLA-G. In certain aspects, the present disclosure includes knocking-out: swine genes corresponding to HLA-A, HLA-B, HLA-C, HLA-F, DQ, and DR, and knocking-in: HLA-C, HLA-E, and HLA-G. In certain aspects, the present disclosure includes knocking-out: swine genes corresponding to HLA-A, HLA-B, HLA-C, HLA-F, DQ, and DR, and knocking-in: HLA-C, HLA-E, HLA-G, HLA-F, and DQ. In certain aspects, expression of HLA-C may be modulated, e.g., reduced. In certain aspects, beta-2 microglobulin may be knocked in combination with any of aspects disclosed herein. In certain aspects, hCD55 may be knocked in in combination with any of aspects disclosed herein. In certain aspects, hCD46 may be knocked in combination with any of aspects disclosed herein. In certain aspects, the present disclosure includes overexpression of one or more apoptosis-inducing ligands (e.g., FasL, TRAIL, Programmed death-ligand 1 (PD-L1), Programmed death-ligand 2 (PD-L2)) to attenuate the T cell Response in combination with any of aspects disclosed herein. In certain aspects, the present disclosure includes any combination of the foregoing genetic modifications in combination with a single, double, or triple-knockout of swine surface glycan epitopes. In certain aspects, the present disclosure does not involve knocking-out genes coding for PERV-A, PERV-B, and/or PERV-C.

In certain aspects, expression of HLA-C may be modulated, e.g., reduced. In certain aspects, beta-2 microglobulin may be knocked in combination with any of aspects disclosed herein. In certain aspects, hCD55 may be knocked in combination with any of aspects disclosed herein. In certain aspects, hCD46 may be knocked in combination with any of aspects disclosed herein. In certain aspects, the present disclosure includes overexpression of one or more apoptosis-inducing ligands (e.g., FasL, TRAIL, Programmed death-ligand 1 (PD-L1), Programmed death-ligand 2 (PD-L2)) to attenuate the T cell Response in combination with any of aspects disclosed herein. In certain aspects, the present disclosure includes any combination of the foregoing genetic modifications in combination with a single, double, or triple-knockout of swine surface glycan epitopes.

In certain aspects, the present disclosure includes knocking-in HLA-C, HLA-E, HLA-G. In certain aspects, the present disclosure includes knocking-out: swine genes corresponding to HLA-A, HLA-B, HLA-C, HLA-F, DQ, and DR, and knocking-in: HLA-C, HLA-E, and HLA-G. In certain aspects, the present disclosure includes knocking-out: swine genes corresponding to HLA-A, HLA-B, HLA-C, HLA-F, DQ, and DR, and knocking-in: HLA-C, HLA-E, HLA-G, HLA-F, and DQ.

In some embodiments, such non-transgenic engineered swine have fewer than 10 genetic manipulations, such as no more than about 8, or no more than about 5 genetic manipulations. In some embodiments, the engineered swine include fewer than 20 such genetic manipulations, or in some embodiments, no more than about 15 or no more than about 10 genetic manipulations.

Considering xenotransplantation in a parallel lens with the interactions between maternal immune cells and fetal trophoblast cells of the placenta during pregnancy, the mechanisms that permit maternal-fetal tolerance are translated and modified by the present inventors to prepare the hypoimmunogenic xenotransplantation product of the present disclosure. By genetically reprogramming SLA genes as described herein, knocking out one or more surface glycans, and optionally introducing a limited subset of apoptosis-inducing proteins and complement regulatory proteins, the xenotransplantation product mimics the permit maternal-fetal tolerance dynamic of fetal trophoblast cells during pregnancy.

In certain aspects, the present disclosure centralizes (predicates) the creation of hypoimmunogenic and/or tolerogenic cells, tissues, and organs that does not necessitate the transplant recipients' prevalent and deleterious use of exogenous immunosuppressive drugs (or prolonged immunosuppressive regimens) following the transplant procedure to prolong the life-saving graft. Instead, the central theorem of this approach is countervailing to the existing and previous dogmatic approaches; instead, of accepting that innate and immovable disparity between donor and recipient, and thus focusing on interventions, gene alterations, and/or concomitant exogenous immunosuppressive medications used as a method of reducing/eliminating/negatively-altering the recipients' naturally resulting immunologic response, we intentionally choose to reverse the focus of the otherwise area of fundamental scientific dogma. Rather than accept the immunological incompatibilities between the donor and recipient, specifically (but not limited to) those mismatches of the Major Histocompatibility Complex(es), we intend to alter these catalytic antigens at the source, thereby eliminating all of the precipitating mechanisms that are the causative effectors of cell, tissue, and organ rejection between donor and recipient.

Thereby eliminating the rate-limiting step which requires burdensome levels of immunosuppressive drugs/regimens, we indirectly (but substantially) address one of the central hindrances of the entire field of xenotransplantation. Namely, since 1996 (Patience, et al, 1997) concern regarding the infectious capacity of an otherwise (innocuous) endogenous retrovirus (PERV), ubiquitously expressed in all porcine cells, significantly limited the advancement of the present field of science. Moreover, refractory compromise or intentional suppression of the natural immunological capacity of the recipient—primarily via requisite drugs to permit long-term organ/graft survival—further exacerbated concern regarding the potential clinical risk of xenotransplantation therapeutics. Since, in the prevailing two decades extensive research in has largely dispelled the concern regarding PERV; in tandem, efforts to eradicate all PERV(s) from the genome of potential swine source donors. Our approach, which eliminates by the mechanism of addressing (and significantly reduces) the underlying, fundamental cause of organ-rejection phenomena, the existence and/or presence of PERV RNA do not pose a credible risk to patients.

Restated, the former/previous approach to this unmet clinical need has precisely followed the classic medical dogma of "one-size fits all". Instead, we vigorously thwart this limited view and pragmatically demonstrate the ability to harness present technological advances and fundamental principles to achieve a "patient-specific" solution which dramatically improves clinical outcome measures. The former, we refer as the "downstream" approach—which must contend with addressing all of the natural immune processes in sequence. The latter, our approach, we optimistically term the "upstream" approach—one which represents the culmination of unfilled scientific effort into a coordinated translational effort.

Modification Techniques

It will be further understood that disruptions and modifications to the genomes of source animals provided herein can be performed by several methods including, but not limited to, through the use of clustered regularly interspaced short palindromic repeats ("CRISPR"), which can be utilized to create animals having specifically tailored genomes. See, e.g., Niu et al., "Inactivation of porcine endogenous retrovirus in pigs using CRISPR-Cas-9," Science 357:1303-1307 (22 Sep. 2017). Such genome modification can include, but not be limited to, disrupted or eliminated expression of α-(1,3) galactosyl epitopes, any of the genetic or transgenic modifications disclosed herein (e.g., as disclosed in Denner), and/or any other tailored genome modifications designed to reduce the bioburden and immunogenicity of products derived from such source animals to minimize immunological rejection.

Clustered regularly interspaced short palindromic repeats (CRISPR)/CRISPR-associated protein (Cas), originally known as a microbial adaptive immune system, has been adapted for mammalian gene editing recently. The CRISPR/Cas system is based on an adaptive immune mechanism in bacteria and archaea to defend the invasion of foreign genetic elements through DNA or RNA interference. Through mammalian codon optimization, CRISPR/Cas has been adapted for precise DNA/RNA targeting and is highly efficient in mammalian cells and embryos. The most commonly used and intensively characterized CRISPR/Cas system for genome editing is the type II CRISPR system from *Streptococcus pyogenes*; this system uses a combination of Cas9 nuclease and a short guide RNA (gRNA) to target specific DNA sequences for cleavage. A 20-nucleotide gRNA complementary to the target DNA that lies immediately 5' of a PAM sequence (e.g., NGG) directs Cas9 to the target DNA and mediates cleavage of double-stranded DNA to form a DSB. Thus, CRISPR/Cas9 can achieve gene targeting in any N20-NGG site.

In some aspects, genome modification protein can be selected from a RNA-guided clustered regularly interspersed short palindromic repeats (CRISPR)/CRISPR-associated (Cas) (CRISPR/Cas) nuclease system, a CRISPR/Cas dual nickase system, a zinc finger nuclease (ZFN), a transcription activator-like effector nuclease (TALEN), a meganuclease, a fusion protein comprising a programmable DNA binding domain linked to a nuclease domain (i.e., generates a double-stranded DNA break), and combinations thereof. With the use of such genome modification techniques, a high rate of double-stranded breaks (DSB) for a high rate of modification either in somatic cells or in embryos is obtained and a large number of genetically modified pigs are generated, e.g., through somatic cell nuclear transfer (SCNT) of modified somatic cells or direct microinjection of engineered nucleases into the embryos. Somatic cell nuclear transfer or cloning involves screening of somatic cells (typically fetal fibroblasts), which carry the intended genetic alterations, and the nuclear transfer of the modified cells in a cloning process. Engineered nuclease can be easily applied to create either NHEJ- or HDR-induced mutations within a donor cell in vitro through a pre-screening or selection strategy, which enables enrichment of cells carrying the desired mutation. An alternative to SCNT is the method involving direct gene editing in single-cell embryos. The mRNA of editors (for knockout) or together with donor DNA (for knock-in) can be microinjected into the cytoplasm or pronucleus of zygotes, which are then transferred into the synchronized surrogates to generate edited animals. This procedure is vastly simple compared with SCNT.

In other aspects, a fusion protein comprising a programmable DNA binding domain linked to a non-nuclease modification domain may be used for modifying genetic material. In certain aspects, the programmable DNA binding domain of the fusion protein can be catalytically inactive CRISPR/Cas system, a catalytically inactive meganuclease, a zinc finger protein, or a transcription activator-like effector, and the non-nuclease modification domain of the fusion protein can have acetyltransferase activity, deacetylase activity, methyltransferase activity, demethylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, citrullination activity, helicase activity, amination activity, deamination activity, alkylation activity, dealkylation activity, oxidation activity, transcriptional activation activity, or transcriptional repressor activity. In specific aspects, the non-nuclease modification domain of the fusion protein has cytosine deaminase activity, histone acetyltransferase activity, transcriptional activation activity, or transcriptional repressor activity.

The methods may involve introducing into a eukaryotic cell (a) a programmable DNA modification protein or nucleic acid encoding the programmable DNA modification protein and (b) at least one programmable DNA binding protein or nucleic acid encoding the at least one programmable DNA binding protein. The programmable DNA modification protein is targeted to a target chromosomal sequence and each of the at least one programmable DNA binding proteins is targeted to a site proximal to the target chromosomal sequence. Binding of the at least one programmable DNA binding protein to the site proximal to the target chromosomal sequence increases accessibility of the programmable DNA modification protein to the target chromosomal sequence, thereby increasing targeted genome modification efficiency and/or specificity.

Transgenic Approaches

In other aspects, swine source animals include transgenic animals modified to express human traits. Such additional modifications are disclosed in, for example, in Denner J, "Xenotransplantation-Progress and Problems: A Review," *J Transplant Technol Res* 4(2):133 (2014) ("Denner"), the entire disclosure of which is incorporated herein by reference. Such modifications may include, but are not limited to, hCD46-human membrane cofactor protein, MCP; hCD55-human decay-accelerating factor, DAF; hCD59-human protectin; H-transferase, competing for the substrates needed by the alpha-1,3-galactosyltransferase; hCTLA4-Ig-human cytotoxic T-murine lymphocyte antigen 4 fused with Ig heavy chains, as a surrogate ligand used to block CD28/CTLA4 T-cell costimulation; hTM-human thrombomodulin, anticoagulation, activates protein C; hA20-tumor necrosis factor-alpha-(TNF-alpha)-inducible gene, may control the AVR; HLA-E/beta-microglobulin-protection against human natural killer cell cytotoxicity; TRAIL-tumor necrosis factor related apoptosis inducing ligand, induces apoptosis; hHO-1, human heme oxygenase-1, anti-apoptotic, cell protective, Fas-L-Fas ligand, belongs to the tumor necrosis factor (TNF) family, its binding with its receptor induces apoptosis; GnT-III-β-1,4-N acetylglucosaminyltransferase III, catalyzes the formation of a bisecting GlcNAc structure in N-glycans; shRNA PERV-PERV-specific short hairpin RNA, inhibits PERV expression by RNA interference and other modifications. Such modifications may also include those set out in the following Table 1, reproduced from Denner as follows.

TABLE 1

| Gene | Effect |
|---|---|
| 1,3 Gal (alpha-1,3-galactosyltransferase) knock out (GalTKO) | Reduced Galalpha-1,3-Gal (Gal) expression, reduced hyperacute rejection |
| hCD46 (hMCP, human membrane cofactor) | Human complement regulation |
| hCD46 + GalTKO | Human complement regulation + Reduced Gal expression |
| hCD55 (hDAF, human decay accelerating factor) | Human complement regulation |
| hCD55 + endo-beta-galactosidase C | Human complement regulation + Reduced Gal expression |
| hCD59 | Human complement regulation |
| hCD55 + hCD59 | Human complement regulation |
| hCD46 + hCD55 + hCD59 | Human complement regulation |
| H-transferase (alpha-1,2-fucosyltransferase) | Reduced Gal expression |
| hCD59 + H-transferase (alpha-1,2-fucosyltransferase) | Human complement regulation + reduced Gal expression |
| hCTLA4-Ig (cytotoxic T lymphocyte-associated antigen) | Inhibits T-cell activity |
| hTM (human thrombomodulin) | Activate human anticoagulant protein C |
| hA20 (humanA20, tumor necrosis factor-alpha inducible gene) | Controls acute vascular rejection |
| HLA-E/(human leukocyte antigen-E) + human beta2 - macroglobulin | Protection from NK cell- mediated cytotoxicity |
| TRAIL (tumor necrosis factor-alpha-related apoptosis-inducing ligand) | Reduced posthyperacute cellular rejection |
| GnT-III (beta-d-mannoside beta-1,4-N-acetylglucosaminyltransferase III) | Reduced antigenicity to human natural antibodies |
| hHO-1 (human heme oxygenase-1) | Antiapoptosis |
| Fas ligand (Fas L) | Antiapoptosis |
| GalTKO + CD55 + CD59 | Control of instant blood- mediated inflammatory reaction (IBMIR) when transplanting neonatal isle T-cell clusters |
| GalTKO + CD55 + CD59 + H-Transferase | Reduced xenoantibody response to isle T-cells from transgenic animals |
| GalTKO + H-transferase | Reduced expression of alpha Gal antigen |
| Soluble TNFRI-Fc-hHO | Protection against oxidative and inflammatory injury |
| Optimized hTM | Overcome coagulation incompatibilities in pig-to-primate xenotransplantation. |
| GalTKO + CD46 | Suppress in vitro human anti-pig cellular responses |
| HLA-E | Suppression of inflammatory macrophage-mediated cytotoxicity and proinflammatory cytokine production |
| CD55, CD59 + H-transferase genes | Enhanced protective response to human serum-mediated cytolysis |

In some embodiments, such transgenic engineered swine have fewer than 10 genetic manipulations, such as no more than about 8, or no more than about 5 genetic manipulations. In some embodiments, the engineered swine include fewer than 20 such genetic manipulations, or in some embodiments, no more than about 15 or no more than about 10 genetic manipulations.

It is therefore understood that multiple source animals, with an array of biological properties including, but not limited to, genome modification and/or other genetically engineered properties, can be utilized to reduce immunogenicity and/or immunological rejection (e.g., acute, hyperacute, and chronic rejections) in humans resulting from xenotransplantation. In certain aspects, the present disclosure can be used to reduce or avoid thrombotic microangiopathy by transplanting the biological product of the present disclosure into a human patient. In certain aspects, the present disclosure can be used to reduce or avoid glomerulopathy by transplanting the biological product of the present disclosure into a human patient. It will be further understood that the listing of source animals set forth herein is not limiting, and the present invention encompasses any other type of source animal with one or more modifications (genetic or otherwise) that serve(s) to reduce immunogenicity and/or immunological rejection, singularly or in combination.

Single Knockout Swine that Includes PERV

It will be further understood that in some aspects, swine whose genomes lack or do not express active α-(1,3) galactosyl epitopes, whose genomes includes PERV A, B, and C, and are produced by the processes described herein, yield superior biological products derived from such source animals to reduce immunogenicity in humans following xenotransplantation enhancing increased transplant longevity. Such production aspects include, but are not limited to, the products being derived from designated pathogen free animals maintained and propagated in designated pathogen free facilities (including, but not limited to, facilities as described herein); the animals and resulting products being free of certain pathogens including, but not limited to, *ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*; the products being minimally manipulated from the time of harvest to xenotransplantation; the products being live cell (e.g., vital, biologically active); the products being able to induce vascularization in a subject following xenotransplantation; and/or the transplantation of the products not requiring concomitant immunosuppressant drugs and/or other immunosuppressant therapies.

Such reduced immunogenicity of the products described herein is supported by at least two studies (set forth in Example 1 herein) which show skin grafts derived from swine whose genome lacks one or more extracellular surface glycans including active α-(1,3) galactosyl epitopes that were produced and prepared in accordance with the present invention performed significantly better on monkeys than prior studies utilizing swine whose genome lacks active α-(1,3) galactosyl epitopes on monkeys not produced and/or prepared in accordance with the present invention. See, e.g., Albritton et al., *Lack of Cross-Sensitization Between alpha-1, 3-Galactosyltransferase Knockout Porcine and Allogeneic Skin Grafts Permits Serial Grafting*, Transplantation & Volume 97, Number 12, Jun. 27, 2014, (Gal-T-KO skin grafts on recipient baboons fully rejected by 12 or 13 days); Barone et al., *Genetically modified porcine split-thickness skin grafts as an alternative to allograft for provision of temporary wound coverage: preliminary characterization*, Burns 41 (2015) 565-574 (Gal-T-KO skin grafts on recipient baboons fully rejected by 11 days); and Weiner et al., *Prolonged survival of Gal-T-KO swine skin on baboons*, Xenotransplantation, 2010, 17(2): 147-152 (Gal-T-KO xenogeneic split-thickness skin grafts on baboons fully rejected by 11 days). Moreover, surprisingly, at least one study shows skin grafts derived from a DPF Closed Colony, α-1,3-galactosyltransferase [Gal-T] knockout pigs produced in accordance with the present invention performed better than allograft. See Example 1 herein. While the working examples herein demonstrate the advantageous results of the present disclosure using skin as a model organ, persons skilled in the art have recognized that the same factors that result in successful skin xenotransplantation product correlate to success with xenotransplantation of other organs. Accordingly, the ability to xenotransplant various types of cells, tissues, and different organs is recognized by persons of skill in the art where harvested xenotransplantation tissue is shown to be resistant to rejection by the recipient's body for some period of time. These factors include the product of the present invention being viable, biologically active, non-terminally sterilized, having low immunogenicity, having low bioburden, having low pathogenicity, inducing vascularization, collagen growth, and/or other interactions from the transplant recipient inducing organ or tissue adherence, organic union, or other temporary or permanent acceptance by the recipient. As used herein, the phrase "terminally sterilized" refers to a product that has been sterilized in its final container and the phrase "non-terminally sterilized" refers to a product that has not been sterilized in its final container. Terminal sterilization typically involves filling and sealing product containers under high-quality environmental conditions. Products are filled and sealed in this type of environment to minimize the microbial and particulate content of the in-process product and to help ensure that the subsequent sterilization process is successful. The product in its final container is then subjected to a sterilization process such as heat or irradiation. In contrast to a terminal sterilization process, in an aseptic process, the drug product, container, and closure are first subjected to sterilization methods separately, as appropriate, and then brought together. Due to their nature, certain products are aseptically processed at an earlier stage in the process, or in their entirety. Because there is no process to sterilize the product in its final container, it is containers are filled and sealed in a high sterility environment. Aseptic processing involves more variables than terminal sterilization. Before aseptic assembly into a final product, the individual parts of the final product are generally subjected to various sterilization processes. For example, glass containers may be subjected to dry heat; containers may be subjected to UV irradiation and/or anti-pathogen baths; rubber closures may be subjected to moist heat; and liquids may be subjected to filtration. Each of these manufacturing processes requires validation and control. Each process could introduce an error that ultimately could lead to the distribution of a contaminated product.

Closed Colonies

General Closed Colony

Referring now to FIG. 1, in one aspect, animals are secured from the outside to consider as candidates to add to the General Closed Colony 128 that is housed within the SAF 100 to help propagate the DPF Closed Colony 102 also housed within the SAF 100 in a separate isolation area 152. Transportation of the animals secured from the outside to the SAF is controlled to mitigate exposure to potential infectious agents. Such mitigation techniques include, but are not limited to, using a sterilized HEPA filtered cage during transport using a van cleaned with chlorhexidine and containing no other animals.

Candidate animals are initially quarantined to check health status and suitability for intake into the General Closed Colony 128. For example, in some aspects, animals coming from the outside are first housed in a quarantine intake area 130 within the SAF and accompanied by a complete health record (including, but not limited to, date of birth, vaccinations, infections, and antibiotic history), pedigree, and results of genetic tests. These animals reside in the quarantine intake area 130 for at least seven (7) days as the accompanying records are evaluated and other health screening measures are taken, including screening for some infectious agents.

In some aspects, animals with poor health, questionable medical status, or are not able to be treated for such medical issues, will not be accepted into the General Closed Colony 128 and/or will otherwise be culled from the quarantine area 130. Examples of acceptance criteria include, but are not limited to: (a) source animals are not born with any congenital defect that was unanticipated from the herd and that could have impacted the quality of health of the animal; (b) source animals have received all vaccinations according to age and the vaccinations were killed agents; (c) any infections that occurred in the source animal's lifetime have been reviewed as well as the clinical intervention, and it was determined that the infection and any treatment (if applicable) did not impact the quality of the health of the animal; (d) results of the surveillance testing has been reviewed and it has been verified that the source animal has been tested within the last 3 months (with all source animals tested at sacrifice and all tests must be negative); (e) if the animal was injured in any way which required medical attention, a review has been conducted and it has been confirmed that the impact of the injury and the medical intervention (if applicable) had no impact on the health of the animal; and/or (f) PERV tests have been performed and results recorded.

In some aspects, animals that pass this screening process and timetable are moved out of the quarantine intake area 130 and into a general holding area 132 within the SAF 100 to join or create an existing or newly formed General Closed Colony 128. It will be understood that the general holding area 132 is kept under closed colony conditions substantially similar to the conditions applied to the DPF Closed Colony 102 in the DPF Isolation Area 152.

It will be further understood that, excluding their offspring, candidate animals secured from the outside will never become members of the DPF Closed Colony. Piglets from the General Closed Colony 128 animals will be utilized to create and/or propagate the DPF Closed Colony as further described herein.

DPF Closed Colony

Pregnant Sows and DPF Piglets

In one aspect, pregnant sows 134 (or gilts) are obtained from the outside or from the General Closed Colony 128 to produce piglets to create and/or add to the DPF Closed Colony 102 herd. For example, in one aspect, sows 134 are placed in a sow quarantine area 136 within the SAF until the time to give birth, in this aspect via Cesarean section in order to avoid exposing the piglet to potential pathogens, including Porcine Cytomegalovirus (pCMV). Contraction of pCMV in piglets can occur when the piglets travel through the vagina of the sow during natural birth. The piglets, by virtue of their birthing through Cesarean section as described herein, prevents such contraction and the piglets produced through the methods described herein are pCMV-free.

Prior to the Cesarean section procedure, for example the morning of the procedure, an operating room 138 within the SAF 100 prepared according to standard operating room protocols in a sterile environment with 2 sides: Side A 140 for the Cesarean section of the sow, and Side B 142 to receive the piglets 144 that are candidates to either found or add to the DPF Closed Colony.

The sow 134 is brought into the operating room 138 for captive bolt euthanasia. Immediately following this, the sow 134 is placed in the left lateral decubitus position and the abdomen and torso are prepped widely with chlorhexidine and draped in a sterile fashion. A flank incision is expeditiously made and the abdominal muscles are split in order to gain access into the peritoneum. The uterus is exteriorized, incised and the piglets 144 are removed after doubly clamping and dividing the umbilical cord. Immediate execution of the surgical procedures following captive bolt euthanasia is critical to the survival of the piglets 144.

Infection controls for the piglets 144 are implemented at birth. The piglets 144 are placed in a warmed 1% chlorhexidine (or other sterilization agent, such as betadine) in sterile saline bath solution and then passed over to piglet handlers to a resuscitation area 148 for resuscitation, rewarming and gavage feeding of the first dose of colostrum. The sow's 134 carcass is closed by staff with suture and disposed of following appropriate procedures.

The piglets 144 are subsequently quarantined in a separate sterile piglet quarantine room 150 then transferred to a designated pathogen free isolation area ("DPF Isolation Area") 152 to either create or join the DPF Closed Colony 102. It will be understood that the DPF Isolation Area 152 can be of any size suitable to manage and maintain the DPF Closed Colony to the extent needed for breeding, rearing, birthing, harvesting, and overall management as described herein.

In one aspect, the DPF Isolation Area 152 that supports the DPF Closed Colony is a restricted access, positive-pressure barrier isolation suite, approximately 500 ft$^2$, with an animal husbandry capacity to support at least 9 animals (up to 20 kg each), inside the larger SAF 100. It will be understood that the DPF Isolation Area 152 can be significantly larger than this, and can include multiple areas (including, but not limited to, multiple rooms and suites), depending on the need of the number of source animals and demand for products, in accordance with the products and methods as described herein.

In some aspects, tracking of piglets is performed and piglets are handled under designated pathogen free conditions in the DPF Isolation Area 152. For example, handling of piglets is performed wearing personal protective equipment ("PPE") in the DPF Isolation Area 152, including face mask, gloves, shoe covers, and hair bonnet. The animals are handled by clean personnel, personnel who have not entered any animal room or facility where other swine are housed. For tracking, piglets are ear notched 3 days after birth and ear tagged with hand-labeled plastic ear tags at weaning (usually 3-5 weeks).

It will be understood that some piglets are raised in the DPF Closed Colony 102 in the DPF Isolation Area 152 as a source for xenotransplantation products, and some piglets in the DPF Closed Colony 102 are allowed to mature and be used to propagate the General Closed Colony 128. In the event of propagation of the General Closed Colony 128, the matured animal is removed from the DPF Isolation Area 152 and added to the General Closed Colony 128 for breeding. Since the DPF Isolation Area 152 is controlled to be DPF, once these or any other animals leave DPF Isolation Area 152, those animals never return to the DPF Isolation Area 152.

Precautions are taken to prevent the exposure of any animals within the DPF Closed Colony 102 to contamination (for example, blood, blood products or tissues obtained from animals outside the DPF Closed Colony 102). If any animals within the DPF Closed Colony 102 are inadvertently exposed to blood, blood products, or tissues obtained from animals outside the DPF Closed Colony 102, those animals are removed from the DPF Closed Colony 102 and will never return to the DPF Closed Colony 102. Aseptic techniques and sterile equipment for all parenteral interventions are used, and routine procedures such as vaccinations, treatment with drugs or biologics, phlebotomy, and biopsies are performed. The DPF Isolation Area 152 is restricted by card access only to specially authorized and trained staff.

In another aspect of the invention, in some aspects, newborn piglets are handled and hand-reared by trained and gowned staff in the DPF Isolation Area 152 to ensure their health and that they are maintained as designated pathogen free.

Propagation

The DPF Closed Colony 102 can be propagated in multiple ways. For example, as described herein, sows 134 may be taken from the outside or General Closed Colony 128, quarantined, and have their piglets 144 delivered via Cesarean section, with the piglets resuscitated, sterilized, quarantined, and placed into the DPF Isolation Area 152. Newborn piglets may be maintained at 26-30° C. or 80-85° F. In some aspects, heat lamps are used to keep animals warm. Newborn piglets are initially housed in sterilized medium crates in the SAF with sterile towels/drapes on the bottom.

The DPF Closed Colony 102 may also be propagated in other ways. For example, in one aspect, the DPF Closed Colony 102 is propagated through natural intercourse amongst the animals in the DPF Closed Colony 102 occurring entirely within the DPF Isolation Area 152. It will be understood that pregnancies may also occur in the DPF Closed Colony 102 within the DPF Isolation Area 152 as a result of artificial insemination or other breeding techniques that do not involve natural intercourse.

In such aspects, pregnant sows 154 (or gilts) in the DPF Closed Colony 102 within the DPF Isolation Area 152 carry the entire pregnancy and piglets are delivered through live vaginal birth and Caesarian section is not necessary. Importantly, the piglets resulting from natural intercourse and live vaginal birth within the DPF Isolation Area 152 are designated pathogen free, including no infection by pCMV.

Following the live vaginal birth, piglets are immediately taken away from the sows to prevent the sows from harming the piglets. The piglets are then hand-reared from birth by humans within the DPF Isolation Area 152 in the methods as described herein.

In the case of mating in the DPF Closed Colony 102 or General Closed Colony 128, the breeding of swine disclosed herein is typically homozygous to homozygous breeding. Females are given hormones two weeks before gestation then throughout pregnancy. Furthermore, as with the DPF Closed Colony 102, the General Closed Colony 128 may also be propagated through natural intercourse amongst the animals in the General Closed Colony 128, and may also occur as a result of artificial insemination or other assisted reproductive technologies (ARTs) that do not involve natural intercourse.

Various techniques have been developed and refined to obtain a large number of offspring from genetically superior animals or obtain offspring from infertile (or subfertile) animals. These techniques include: artificial insemination, cryopreservation (freezing) of gametes or embryos, induction of multiple ovulations, embryo transfer, in vitro fertilization, sex determination of sperm or embryos, nuclear transfer, cloning, etc.

Artificial insemination (AI) has been used to obtain offspring from genetically superior males for more than 200 years. Improvements in methods to cryopreserve (freeze) and store semen have made AI accessible to more livestock producers. In the same manner as cryopreservation of semen, embryo freezing allowed for the global commercialization of animals with high genetic qualities.

Multiple ovulation and embryo transfer: Development of embryo transfer technology allows producers to obtain multiple progeny from genetically superior females. Depending on the species, fertilized embryos can be recovered from females (also called embryo donors) of superior genetic merit by surgical or nonsurgical techniques. The genetically superior embryos are then transferred to females (also called embryo recipients) of lesser genetic merit. In cattle and horses, efficient techniques recover fertilized embryos without surgery, but only one or sometimes two embryos are produced during each normal reproductive cycle. In swine and sheep, embryos must be recovered by surgical techniques. To increase the number of embryos that can be recovered from genetically superior females, the embryo donor is treated with a hormone regimen to induce multiple ovulations, or superovulation.

In vitro Fertilization: As an alternative to collecting embryos from donor animals, methods have been developed recently to produce embryos in vitro (in the laboratory). The methods are also called in vitro embryo production. Immature oocytes (female eggs) can be obtained from ovaries of infertile or aged females, or from regular embryo donors (described above). Ovum (egg) pick up is a nonsurgical technique that uses ultrasound and a guided needle to aspirate immature oocytes from the ovaries. Once the immature oocytes have been removed from the ovary, they are matured, fertilized, and cultured in vitro for up to seven days until they develop to a stage that is suitable for transfer or freezing.

Since the mid 1980s, technology has been developed to transfer the nucleus from either a blastomere (cells from early, and presumably undifferentiated cleavage stage embryos) or a somatic cell (fibroblast, skin, heart, nerve, or other body cell) to an enucleated oocyte (unfertilized female egg cell with the nucleus removed). This "nuclear transfer" produces multiple copies of animals that are themselves nearly identical copies of other animals (transgenic animals, genetically superior animals, or animals that produce high quantities of milk or have some other desirable trait, etc.). This process is also referred to as cloning. To date, somatic cell nuclear transfer has been used to clone cattle, sheep, pigs, goats, horses, mules, cats, rabbits, rats, and mice.

The technique involves culturing somatic cells from an appropriate tissue (fibroblasts) from the animal to be cloned. Nuclei from the cultured somatic cells are then microinjected into an enucleated oocyte obtained from another individual of the same or a closely related species. Through a process that is not yet understood, the nucleus from the somatic cell is reprogrammed to a pattern of gene expression suitable for directing normal development of the embryo. After further culture and development in vitro, the embryos are transferred to a recipient female and ultimately result in the birth of live offspring. The success rate for propagating animals by nuclear transfer is often less than 10 percent and depends on many factors, including the species, source of the recipient ova, cell type of the donor nuclei, treatment of donor cells prior to nuclear transfer, the techniques used for nuclear transfer, etc.

Most commonly used ARTs rely on fertilization as a first step. This joining of egg and sperm is accompanied by the recombination of the genetic material from the sire and dam, and is often referred to as "shuffling the genetic deck." It will be understood that these breeding techniques can be used either within the DPF Closed Colony, as a breeding step within the DPF Isolation Area 152, or could be used as a breeding step for females in the General Closed Colony and/or from the outside.

In the case of utilization of ART to impregnate females in the General Closed Colony, and/or a female from the outside, the birthing of piglets from such females can be as described herein, i.e., sows 134 may be taken from the outside or General Closed Colony 128, quarantined, and have their piglets 144 delivered via Cesarean section, with the piglets resuscitated, sterilized, quarantined, and placed into the DPF Isolation Area 152.

Maintenance of Closed Colonies

It will be understood that the phrase "designated pathogen free," as used herein, can be used to describe animals, animal herds, animal products derived therefrom, and/or animal facilities that are free of one or more specified pathogens. Preferably, such "designated pathogen free" animals, animal herds, animal products derived therefrom, and/or animal facilities are maintained using well-defined routines of testing for such designated pathogens, utilizing proper standard operating procedures (SOPs) and practices of herd husbandry and veterinary care to assure the absence and/or destruction of such designated pathogens, including, but not limited to, routines, testing, procedures, husbandry, and veterinary care disclosed and described herein. It will be further understood that as used herein the terms "free," "substantially free" and like terms when used in connection with "pathogen free" are meant to indicate that the subject pathogens are not present, not alive, not active, or otherwise not detectable by standard or other testing methods for the subject pathogens.

Designated pathogens may include any number of pathogens, including, but not limited to, viruses, bacteria, fungi, protozoa, parasites, and/or prions (and/or other pathogens associated with transmissible spongiform encephalopathies (TSEs)). Designated pathogens could include, but not be limited to, any and all zoonotic viruses and viruses from the following families: adenoviridae, anelloviridae, astroviridae, caliciviridae, circoviridae, coronaviridae, parvoviridae, picornaviridae, and reoviridae.

Designated pathogens could also include, but not be limited to, adenovirus, arbovirus, arterivirus, bovine viral diarrhea virus, calicivirus, cardiovirus, circovirus 2, circovirus 1, coronavirus, encephalomyocarditis virus, eperytherozoon, *haemophilus* suis, herpes and herpes-related viruses, iridovirus, kobuvirus, leptospirillum, *listeria, mycobacterium* TB, *mycoplasma*, orthomyxovirus, papovirus, parainfluenza virus 3, paramyxovirus, parvovirus, pasavirus-1, pestivirus, picobirnavirus (PBV), picornavirus, porcine circovirus-like (po-circo-like) virus, porcine astrovirus, porcine bacovirus, porcine bocavirus-2, porcine bocavirus-4, porcine enterovirus-9, porcine epidemic diarrhea virus (PEDV), porcine polio virus, porcine lymphotropic herpes virus (PLHV), porcine stool associated circular virus (PoSCV), posavirus-1, pox virus, rabies-related viruses, reovirus, rhabdovirus, *rickettsia*, sapelovirus, sapovirus, *Staphylococcus hyicus, Staphylococcus intermedius, Staphylococcus epidermidis*, coagulase-negative staphylococci, suipoxvirus, swine influenza, teschen, torovirus, torque teno sus virus-2 (TTSuV-2), transmissible gastroenteritus virus, vesicular stomatitis virus, and/or any and/or all other viruses, bacteria, fungi, protozoa, parasites, and/or prions (and/or other pathogens associated with TSEs). In some aspects, particularly in swine herds, testing for TSEs is not performed because TSEs are not reported in natural conditions in swine. In other aspects, testing for TSEs is performed as part of the methods of the present disclosure.

There are huge numbers of pathogens that could possibly be tested for in animal herds, and there is no regulatory guidance or standard, or understanding in the field as to what specific group of pathogens should be tested for in donor animals, and which specific group of pathogens should be removed from donor animal populations in order to ensure safe and effective xenotransplantation. In other words, before the present disclosure, there was no finite number of identified, predictable pathogens to be tested for and excluded. The present disclosure provides a specific group of pathogens identified by the present inventors that are critical to exclude for safe and effective xenotransplantation, as set forth in the following Table 2.

TABLE 2

| Test | Pathogen |
|---|---|
| Parasite Fecal Float | Ascaris species |
| | Cryptosporidium species |
| | Echinococcus |
| | Strongyloids sterocolis |
| | Toxoplasma gondii |
| Brucella BAPA (buffered acidified plate agglutination test) | Brucella suis |
| Lepto6 Screen | Leptospira species |
| M Hyo | Mycoplasma Hyopneumoniae |
| PRRS x3 ELISA | Porcine Reproductive and Respiratory Syndrome Virus (PRRSV) |
| PRVgb Test | Pseudorabies |
| TGE/PRCV Test | Porcine Respiratory Coronavirus |
| Toxoplasmosis ELISA | Toxoplasma Gondii |
| Porcine Cytomegalovirus PCR | Porcine CMV |
| Porcine Influenza PCR | Porcine Influenza A |
| Nasal swab | *Bordetella bronchiseptica* |
| Skin culture | Coagulase-positive staphylococci |
| Skin culture | Coagulase-negative staphylococci |

TABLE 2-continued

| Test | Pathogen |
|---|---|
| Skin culture | Livestock-associated methicillin resistant *Staphylococcus aureus* (LA MRSA) |
| Skin culture | *Microphyton* and *Trichophyton spp.* |
| Porcine Endogenous Retrovirus RT-PCR Assay | Porcine Endogenous Retrovirus (PERV) C (PERV C) |

In certain aspects, a product of the present disclosure is sourced from animals having antibody titer levels below the level of detection for a plurality of or all of the pathogens discussed in the present disclosure. In certain aspects, subjects transplanted with a product of the present disclosure are tested and found to have antibody titer levels below the level of detection for a plurality of or all of the pathogens discussed in the present disclosure.

In some aspects, the present disclosure includes a method of testing for a specific group of pathogens consisting of no more than 18-35, e.g., 35, 34, 33, 32, 31, 30, 29, 28, 27, 26, 25, 24, 23, 22, 21, 20, 19, or 18 pathogens, the specific group of pathogens including each of the pathogens identified in Table 2. In some aspects, the present disclosure includes creating, maintaining and using donor animals that are free of the 18-35, e.g., 35, 34, 33, 32, 31, 30, 29, 28, 27, 26, 25, 24, 23, 22, 21, 20, 19, or 18 pathogens, the specific group of pathogens including each of the pathogens identified in Table 2.

As described herein, piglets born via live vaginal birth within the DPF Closed Colony 102 are not infected with pCMV, but are nonetheless tested for pCMV on a continuous basis. Testing for Porcine Cytomegalovirus (pCMV) and Porcine Endogenous Retrovirus (PERV), should be routine and continuous for screening and maintenance as described herein, and should occur routinely and continuously for the DPF Closed Colony. In some aspects of the present invention, the source animals described herein are positive for PERV A and B only, and some are positive for PERV A, B, and C. In other aspects, the source animals are free of PERV A, B and/or C (through utilization of CRISPR and other techniques).

With respect to PERV, it is understood that most, if not all, swine are known to be positive for PERV A and B. While PERV is recognized, the risk of transmission of PERV from treatment with swine derived tissue is expected to be rare. To date eight PERV mRNAs are expressed in all porcine tissues and in all breeds of swine and preclinical and clinical xenotransplantation studies of humans exposed to pig cells, tissues, and organs including pancreatic islets have failed to demonstrate transmission of PERV. See, e.g., Morozov V A, Wynyard S, Matsumoto S, Abalovich A, Denner J, Elliott R, "No PERV transmission during a clinical trial of pig islet cell transplantation," *Virus Res* 2017; 227:34-40. In the unlikely event that a human infection should occur, PERV is susceptible in vitro to nucleoside and non-nucleoside reverse transcriptase inhibitors in common clinical use. See, e.g., Wilhelm M, Fishman J A, Pontikis R, Aubertin A M, Wilhelm F X, "Susceptibility of recombinant porcine endogenous retrovirus reverse transcriptase to nucleoside and non-nucleoside inhibitors," *Cellular &Molecular Life Sciences* 2002; 59:2184-90; Schuurman, H., "Regulatory aspects of clinical xenotransplantation," Int. J. Surg., 23, (2015), pp. 312-321. Experimental data using the xenotransplantation product of the present disclosure indicated that PERV genetic material was not detected in the recipient's organs and that porcine DNA and cells did not migrate into the circulation of the recipient from the xenotransplanted organ.

The DPF Closed Colony 102 is maintained to ensure that the animals remain designated pathogen free and that appropriate standards of animal care and well-being are applied at all levels of the SAF 100 (i.e., breeding, maintenance, propagation). For example, continuous testing for pathogens and other biological markers occurs including the numerous pathogens identified herein (including, but not limited to, pCMV and other pathogens). Environmental and blood samples are collected as necessary for genotyping and testing for pathogens. Test result(s) obtained for pathogens or other health concerns are evaluated by the facility veterinarian who may recommend follow-up testing and observations, and quarantine of the facility or areas (e.g., rooms, suites or other areas) within a facility as needed. Careful documentation of any antimicrobial agents used during routine care of the source animals should be maintained, and exclusive use of killed vaccines used. Examples of antimicrobial agents include cefazolin, bacitracin, neomycin, and polymyxin.

In some aspects, routine health surveillance and screening for pathogens (e.g., adventitious agents) of source animals is performed every 3 months. Samples of serum, nasal swabs, and stool for each animal in the General and DPF Closed Colonies are obtained and provided for analytical tests for detection of such pathogens every 3 months. Source animal samples of serum, nasal swabs, and stool for testing are obtained immediately after euthanasia via captive bolt and evaluated as disclosed herein including one or more of: conducting a sterility assay and confirming that aerobic and anaerobic bacteria do not grow in the sterility assay; conducting a *mycoplasma* assay and confirming that *mycoplasma* colonies do not grow in the *mycoplasma* assay; conducting an endotoxin assay and confirming that the biological product is free of endotoxins in the endotoxin assay, conducting the MTT-reduction assay and confirming that the product has at least 50% cell viability in the MTT-reduction assay; conducting flow cytometry and confirming that the product does not have galactosyl-a-1,3-galactose epitopes as determined by the flow cytometry; conducting pathogen-detection assays specific for 18 to 35 pathogens and confirming that the product is free of *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

In some aspects, all swine undergo routine health monitoring, which includes documentation of all illnesses, medical care, procedures, drugs administered, vaccinations, physical examinations, any treatments received, and general health assessments and observations each day at time of feeding with a visual health inspection indicating the animal is able to stand, move freely and appears clinically normal, as well as observations relating to the animal's appearance, activity and appetite, recording on the Animal Husbandry Log any deficiencies. In some aspects, animals are vaccinated against *Mycoplasma hyopneumoniae, Hemophilus parasuis, Streptococcus suis, Pasteurella multocida, Bordatella bronchiseptica* and *Erysipelothrix rhusiopathiae*. All swine six months or older may be vaccinated against *Erysipelothrix rhusiopathiae, Leptospira (canicola-grippotyphosa-hardjo-icterohaemorrhagiae-pomona)*, Influenza and Parvovirus. Repeat vaccination may be performed, e.g., every six months.

In some aspects, health monitoring will normally be performed as part of daily husbandry procedures for cleaning and feeding to minimize entry into swine holding areas (e.g., rooms, suites or other areas). Prior to entering, personnel must wear personal protective equipment (PPE) and ensure that their footwear is free from gross contamination (e.g. visible dirt or mud). They will then don disposable shoe/boot covers prior to entry. Personnel in contact with any animals not housed in the designated pathogen free facility will change PPE if contaminated. All implements (shovel, other necessary tools) will undergo chlorhexidine immersion of no less than 2 minutes if exogenous to vivarium and judged necessary. Solid waste and soiled bedding is removed. Animal holding areas are sanitized with diluted Quat-PV or bleach a minimum of once every two weeks.

In some aspects, bedding is replaced daily using irradiated bedding wood shavings. The replacement amount is an approximate equal amount to that which was removed. All bedding is completely replaced on a weekly basis at a minimum. Daily activities including health status checks, cleaning and water levels are documented in the Animal Husbandry log. Appropriately labeled trash and biological waste is picked up by staff daily and incinerated.

With regard to piglet, newborns are handled and cared for by trained and gowned staff in an isolation suite. All supplies, room and crates are sanitized prior to housing of the piglets. Sterile drapes and towels are used to line the bottom of the crates. Room temperature is controlled to 80-85° F. Animals crates are maintained at 85-95° F. through the use of heat lamps. Piglets are maintained in the crates through the first 2 weeks after which time piglets are housed on the floor with irradiated wood shavings. Crates are cleaned daily and shavings are removed and replenished daily. Piglets are initially fed fresh-made, sterile colostrum (Bovine Colostrum IgG formulated for swine, Sterling Nursemate ASAP or equivalent) using a feeding tube every 1 to 2 hours until piglet is self-feeding from feeder. During the early days, the piglet is weighed twice a day and well-being is checked and recorded twice a day. Starting at day 14, piglets are fed 3 times per day with a Milk Replacer (Ralco Birthright or equivalent) that is further supplemented with irradiated piglet grain (antibiotic free creep feed, Blue Seal 813 or equivalent). The amount each piglet eats at each feeding is recorded. Vaccinations, genotyping, ear notching, and needle teeth trimming are performed within the first 7 days after birth of the piglet. In some aspects, vaccines use killed agents. Piglets are vaccinated against *Mycoplasma hyopneumoniae, Hemophilus parasuis, Streptococcus suis, Pasteurella multocida, Bordatella bronchiseptica* and *Erysipelothrix rhusiopathiae* at day 7 after birth, with a booster vaccination at 28 days of age. In one aspect, vaccines are killed agents. All swine six months or older are vaccinated against *Erysipelothrix Rhusiopathiae, Leptospira (canicola-grippotyphosa-hardjo-icterohaemorrhagiae-pomona)*, Influenza and Parvovirus. Repeat vaccination is performed every six months.

The source animals for the xenotransplantation product are maintained in a positive pressure, biocontainment establishment, under specific isolation-barrier conditions governed by standard operation procedures adopted by the managers of the given program, and receive specialized care, under controlled conditions in order to mitigate adventitious agents. To ensure the welfare of the closed colony of source animals intended for xenotransplantation use, the SAF, personnel, and the caretakers of source animals adhere to procedures for animal husbandry, tissue harvesting, and sacrifice of animals. The source animals are housed in a positive pressure, biocontainment establishment, under specific isolation-barrier conditions.

In some aspects, food and bedding are delivered to a loading dock, transported, and stored in a specific feed room off of the clean cage wash area accessible only to staff in the inner hallway. All bedding and feed are sterilized by irradiation and double bagged to insure sterility. Feed used for the piglets and more mature animals is defined grain feed by a specific manufacturer. It does not contain any cattle protein. Water supply is provided either by use of the facility sterile water system or purchased sterile water which is dispensed into sterile pans. Records for storage and delivery of feed, water, and other consumables are maintained, and include manufacturer, batch numbers, and other pertinent information, per protocol.

In some aspects, animal records are maintained to describe the feed provided to source animals for at least two generations before their use as a source for live tissues, organs and/or cells used in xenotransplantation. This includes source, vendor, and the type of feed used (including its contents). Use of feed that has been derived from animals is prohibited. Source animals are not provided feeds containing animal proteins or other cattle materials that are prohibited by the FDA feed ban as expanded in 2008 as source animals (21 CFR 589.2000) or feeds containing significant drug contamination or pesticide or herbicide residues for source animals (21 CFR 589.2001).

In some aspect, purified water is provided in sufficient quality to prevent unnecessary exposure of animals to infectious pathogens, drugs, pesticides, herbicides, and fertilizers. Newborn animals are provided colostrum specifically qualified for herd qualification. In some aspects, Bovine Colostrum IgG formulated for swine, Sterling Nursemate ASAP or equivalent is used to feed newborn animals.

Biological Products Derived from DPF Closed Colony

Biological Products

As described herein, biological products for xenotransplantation are derived from source animals produced and maintained in accordance with the present invention, including from the DPF Closed Colony 102 as described herein. Such biological products include, but are not limited to, liver, kidney, skin, lung, heart, pancreas, intestine, nerve and other organs, cells and/or tissues.

Harvesting of such biological products occurs in a single, continuous, and self-contained, segregated manufacturing event that begins with the sacrifice of the source animal through completion of the production of the final product. The animal is euthanized via captive bolt euthanasia, may be moved, if necessary, in a sterile, non-porous bag, to an operating room where the procedure to harvest biological product from the source animal will occur. All members of the operating team should be in full sterile surgical gear, e.g., dressed in sterile dress to maintain designated pathogen free conditions prior to receiving the source animal and in some instanced be double-gloved to minimize contamination, and surgical areas and tools are sterilized. The source animal is removed from the bag and container in an aseptic fashion. The source animal is scrubbed by operating staff, e.g., for at least 1-10 minutes with antiseptic, e.g., Chlorhexidine, brushes over the entire area of the animal where the operation will occur, periodically pouring Chlorhexidine over the area to ensure coverage. Surgical area(s) of the animal are scrubbed with opened Betadine brushes and sterile water rinse over the entire area of the animal where the operation will occur for, e.g., 1-10 minutes. For surgery, operators will be dressed in sterile dress in accordance with program and other standards to maintain designated pathogen free conditions. All organs, cells or tissue from the source animal that will be used for xenotransplantation is harvested within 15 hours of the animal being sacrificed.

Biological products can also include, but are not limited to, those disclosed herein (e.g., in the specific examples), as well as any and all other tissues, organs, and/or purified or substantially pure cells and cell lines harvested from the source animals. In some aspects, tissues that are utilized for xenotransplantation as described herein include, but are not limited to, areolar, blood, adenoid, bone, brown adipose, cancellous, cartaginous, cartilage, cavernous, chondroid, chromaffin, connective tissue, dartoic, elastic, epithelial, Epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue. In some aspects, organs that are utilized for xenotransplantation as described herein include, but are not limited to, skin, kidneys, liver, brain, adrenal glands, anus, bladder, blood, blood vessels, bones, cartilage, cornea, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, and vagina.

In some aspects, purified or substantially pure cells and cell lines that are utilized for xenotransplantation as describe herein include, but are not limited to, blood cells, blood precursor cells, cardiac muscle cells, chondrocytes, cumulus cells, endothelial cells, epidermal cells, epithelial cells, fibroblast cells, granulosa cells, hematopoietic cells, Islets of Langerhans cells, keratinocytes, lymphocytes (B and T), macrophages, melanocytes, monocytes, mononuclear cells, neural cells, other muscle cells, pancreatic alpha-1 cells, pancreatic alpha-2 cells, pancreatic beta cells, pancreatic insulin secreting cells, adipocytes, epithelial cells, aortic endothelial cells, aortic smooth muscle cells, astrocytes, basophils, bone cells, bone precursor cells, cardiac myocytes, chondrocytes, eosinophils, erythrocytes, fibroblasts, glial cells, hepatocytes, keratinocytes, Kupffer cells, liver stellate cells, lymphocytes, microvascular endothelial cells, monocytes, neuronal stem cells, neurons, neutrophils, pancreatic islet cells, parathyroid cells, parotid cells, platelets, primordial stem cells., Schwann cells, smooth muscle cells, thyroid cells, tumor cells, umbilical vein endothelial cells, adrenal cells, antigen presenting cells, B cells, bladder cells, cervical cells, cone cells, egg cells, epithelial cells, germ cells, hair cells, heart cells, kidney cells, leydig cells, lutein cells, macrophages, memory cells, muscle cells, ovarian cells, pacemaker cells, peritubular cells, pituitary cells, plasma cells, prostate cells, red blood cells, retinal cells, rod cells, Sertoli cells, somatic cells, sperm cells, spleen cells, T cells, testicular cells, uterine cells, vaginal epithelial cells, white blood cells, ciliated cells, columnar epithelial cells, dopaminergic cells, dopaminergic cells, embryonic stem cells, endometrial cells, fibroblasts fetal fibroblasts., follicle cells, goblet cells, keratinized epithelial cells, lung cells, mammary cells, mucous cells, non-keratinized epithelial cells, osteoblasts, osteoclasts, osteocytes, and squamous epithelial cells.

An organ is a group of related cells that combine together to perform one or more specific functions within the body. Biologically, skin is the body's largest and fastest-growing organ, and is classified as the primary component of the integumentary system, one of the ten macro-organ systems found in "advanced" animals. Skin fulfills several critical roles including regulating temperature, providing a dynamic barrier to the external world, and serving as a conduit to support an immense network of sensory receptors. The skin performs several functions that are vital to the survival and health of the body. The skin heals to prevent the loss of blood after wounds, regulates body temperature by dissipating heat and as a layer against cold, absorption, secretion, thermal-regulation, sensory detection and orientation, and barrier protection. In fact, not only has success in transplantation of skin been recognized to correlate to transplantation of other organs, but skin transplants appear to be more sensitive to rejection than other organs, e.g., immune privileged organs such as liver, and skin transplants have even been suggested for use as "sentinel transplants," i.e., use of skin grafts in a human recipient as early predictors of rejection of transplanted solid organs in the same recipient. For example, as reported in Ali et al. *Transplant Proc.* 2016 October; 48(8): 2565-2570, evidence provided by experience with abdominal wall transplantation in some intestinal and multivisceral transplant recipients suggest that rejection may manifest in the skin component before emergence in the intestinal allograft, providing a "lead time" during which treatment of rejection of the abdominal wall could prevent the emergence of intestinal rejection.

Further, United States Code Title 42, Section 274 and Section 301, explicitly list skin its formal definition of human organs, i.e., "'Human organ,' as covered by section 301 of the National Organ Transplant Act, as amended, means the human (including fetal) kidney, liver, heart, lung, pancreas, bone marrow and other hematopoietic stem/progenitor cells without regard to the method of their collection, cornea, eye, bone skin, and intestine, including the esophagus, stomach, small and/or large intestine, or any portion of the gastrointestinal tract." Similarly, the Human Organ Transplant Ordinance (HOTO), an internationally ratified ordinance to prevent organ trading and protect donor and recipient rights to self-determination. This global legislation lists skin—and whole segments of the integumentary system—formally as an organ, and more broadly defines an organ as "any part of the human body consisting of a structured arrangement of tissues which, if wholly removed, cannot be regenerated by the body . . . ." Following, the formal medical definition of a transplant is: "the removal of tissue from one part of the body or from one individual and its implantation or insertion in another especially by surgery." The HOTO defines a transplant as "the transfer of an organ from one person to another during a transplant operation, regardless of permanence."

With regard to skin, grafts typically consist of decellularized and/or reconstituted sheets of homogenized dermis that are used to achieve temporary, superficial wound coverage. Such grafts do not retain the original tissue structure nor the metabolically active, otherwise naturally present cells, and thus do not become vascularized; no capillary ingrowth or vessel-to-vessel connections are made. Consequently, immune rejection is not a concern—the skin graft becomes "ejected" rather than rejected by the growth of a complete host epithelium underneath the graft. Thus, while the term graft can be correctly applied to such solutions, the primary qualities that differentiate a transplant from a graft are that of heightened complexity, organization, and inclusion of one or more types of tissue. In the present case, a skin transplant is fundamentally differentiated from grafts known in the prior art. For example, a skin xenotransplant is comprised of live cells that perform the same function as the patient's original skin before eventually experiencing immune-mediated rejected. Thus, in this context, a skin xenotransplant according to the present disclosure is an organ transplant rather than a graft.

Product Characteristics and Therapeutic Uses

In some aspects, the xenotransplantation products described and disclosed herein are temporary, i.e., their use in patients for xenotransplantation is non-permanent, utilized primarily for the treatment of acute ailments and injuries, able to be utilized for longer periods of time as compared to products that are not produced in accordance with the present invention. It will be understood that some of the aspects of the products described and disclosed herein may also be permanent or more permanent, with transplanted organs, tissues and/or cells being accepted by human recipients over much longer periods of time without adverse rejection.

In other aspects, the xenotransplantation products described and disclosed herein are viable, live cell (e.g., vital, biologically active) products; distinct from synthetic or other tissue-based products comprised of terminally sterilized, non-viable cells which are incapable of completing the vascularization process. Further, in some aspects, the product of the present disclosure is not devitalized, or "fixed" with glutaraldehydes or radiation treatment.

In yet other aspects, the xenotransplantation products described and disclosed herein are minimally manipulated (e.g., without physical alteration of the related cells, organs or tissues) such that such products are substantially in their natural state.

In yet other aspects, the xenotransplantation products described and disclosed herein are capable of making an organic union with the human recipient, including, but not limited to, being compatible with vascularization, collagen growth (e.g., in regard to skin), and/or other interactions from the transplant recipient inducing graft adherence, organic union, or other temporary or permanent acceptance by the recipient.

In yet other aspects, the xenotransplantation products described and disclosed herein are utilized in xenotransplantation without the need to use immunosuppressant drugs or other immunosuppressant therapies to achieve desired therapeutic results.

In other aspects, some of the xenotransplantation products described and disclosed herein (e.g., skin) are stored by cryopreservation, stored fresh (without freezing), or stored via other methods to preserve such products consistent with this invention. Storage involves using conditions and processes that preserve cell and tissue viability.

In some aspects, storage may involve storing organs, tissues, or cells, in any combination of a sterile isotonic solution (e.g., sterile saline with or without antibiotics), on ice, in a cryopreservation fluid, cryopreserved at a temperature of around $-40°$ C. or around $-80°$ C., and other methods known in the field. Such storage can occur in a primary containment system and secondary containment system.

In yet other aspects, the xenotransplantation products described and disclosed herein are for homologous use, i.e., the repair, reconstruction, replacement or supplementation of a recipient's organ, cell and/or tissue with a corresponding organ, cell and/or tissue that performs the same basic function or functions as the donor (e.g., swine kidney is used as a transplant for human kidney, swine liver is used as a transplant for human liver, swine skin is used as a transplant for human skin, swine nerve is used as a transplant for human nerve and so forth).

In yet other aspects, the xenotransplantation products described and disclosed herein have a low bioburden, minimizing pathogens, antibodies, genetic markers, and other characteristics that may serve to increase the product's bioburden and the human body's immunological rejection of the product upon xenotransplantation. This may include the innate immune system, through PRRs TLRs, detecting PAMPs and rejecting the subject xenotransplantation product.

It will be understood that the aspects disclosed and described herein can be applied in any number of combinations to create an array or different aspects comprising one or more of the features and/or aspects of the aspects encompassed by the present invention.

It will be understood that there are numerous therapeutic applications for products derived from DPF Closed Colony in accordance with the present invention. For example, such products may be utilized to treat acute and/or chronic disease, disorders, or injuries to organ, cells or tissue, and any and all other ailments that can utilize the products disclosed herein. Such treatments and/or therapies can include utilizing such products to repair, reconstruct, replace or supplement (in some aspects on a temporary basis and in other aspects a permanent basis), a human recipient's corresponding organ, cell and/or tissue that performs the same basic function or functions as the donor.

Specific treatment applications include, but are not limited to, lung transplants, liver transplants, kidney transplants, pancreas transplants, heart transplants, nerve transplants and other full or partial transplants. With regard to skin, treatment applications also include, but are not limited to, treatment of burn wounds, diabetic ulcerations, venous ulcerations, chronic skin conditions, and other skin ailments, injuries and/or conditions (including, but not limited to, severe and extensive, deep partial and full thickness injuries, ailments and/or conditions) (see, e.g., Example 2 herein); use in adult and pediatric patients who have deep dermal or full thickness burns comprising a total body surface area greater than or equal to 30%, optionally in conjunction with split-thickness autografts, or alone in patients for whom split-thickness autografts may not be an option due to the severity and extent of their wounds/burns; treatment of liver failure, wounds, ailments, injuries and/or conditions with liver products derived in accordance with the present invention; treatment of peripheral nerve damage, and other nerve ailments, injuries and/or conditions; and cell and other therapies utilizing materials harvested from the DPF Closed Colony, including the therapeutic uses disclosed in U.S. Pat. No. 7,795,493 ("Phelps"), including cell therapies and/or infusion for certain disorders (as disclosed in col. 30, line 1 to col. 31, line 9) and treatment or certain disorders or pathologies (as disclosed in col. 31, lines 10 to 42), the disclosure of which is incorporated by reference herein.

It will be understood that the specific recitation of therapies herein in no way limits the types of therapeutic applications for the products disclosed and described herein, which encompass acute and/or chronic disease, disorders, injuries to the following organs, tissues and/or cells: skin, kidneys, liver, brain, adrenal glands, anus, bladder, blood, blood vessels, bones, brain, brain, cartilage, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, uterus, vagina, areolar, blood, adenoid, bone, brown adipose, cancellous, cartaginous, cartilage, cavernous, chondroid, chromaffin, connective tissue, dartoic, elastic, epithelial, Epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue; blood cells, blood precursor cells, cardiac muscle cells, chondrocytes, cumulus cells, endothelial cells, epidermal cells, epithelial cells, fibroblast cells, granulosa cells, hematopoietic cells, Islets of Langerhans cells, keratinocytes, lymphocytes (B and T), macrophages, melanocytes, monocytes, mononuclear cells, neural cells, other muscle cells, pancreatic alpha-1 cells, pancreatic alpha-2 cells, pancreatic beta cells, pancreatic insulin secreting cells, adipocytes, epithelial cells, aortic endothelial cells, aortic smooth muscle cells, astrocytes, basophils, bone cells, bone precursor cells, cardiac myocytes, chondrocytes, eosinophils, erythrocytes, fibroblasts, glial cells, hepatocytes, keratinocytes, Kupffer cells, liver stellate cells, lymphocytes, microvascular endothelial cells, monocytes, neuronal stem cells, neurons, neutrophils, pancreatic islet cells, parathyroid cells, parotid cells, platelets, primordial stem cells, Schwann cells, smooth muscle cells, thyroid cells, tumor cells, umbilical vein endothelial cells, adrenal cells, antigen presenting cells, B cells, bladder cells, cervical cells, cone cells, egg cells, epithelial cells, germ cells, hair cells, heart cells, kidney cells, leydig cells, lutein cells, macrophages, memory cells, muscle cells, ovarian cells, pacemaker cells, peritubular cells, pituitary cells, plasma cells, prostate cells, red blood cells, retinal cells, rod cells, Sertoli cells, somatic cells, sperm cells, spleen cells, T cells, testicular cells, uterine cells, vaginal epithelial cells, white blood cells, ciliated cells, columnar epithelial cells, dopaminergic cells, dopaminergic cells, embryonic stem cells, endometrial cells, fibroblasts fetal fibroblasts., follicle cells, goblet cells, keratinized epithelial cells, lung cells, mammary cells, mucous cells, non-keratinized epithelial cells, osteoblasts, osteoclasts, osteocytes, and squamous epithelial cells. This listing is in no way meant to limit the array of therapeutic uses to treat acute and/or chronic disease, disorders, injuries, organ or tissue failures, and any and all other ailments that can utilize the products disclosed herein.

With respect to the treatment of burns, including but not limited to e.g., second- and third-degree burns, in some aspects, skin products derived in accordance with the present invention are used to treat human patients with severe and extensive deep partial and/or full thickness burn wounds. Such products contain terminally-differentiated cell types that are not expanded ex vivo prior to use and do not migrate from the site of application during intended duration of treatment. Therefore, potential for tumorigenicity is negligible.

Such products adhere to the wound bed and provides a barrier function in the immediate post-burn period. Such products have non-terminally sterilized, viable cells, allowing for vascularization of the graft tissue with the recipient. In some aspects, the epidermis remains fully intact, and dermal components are maintained without change to structural morphology or organization of the various cells and tissues. This physiologic mechanism supports the prolonged survival of the graft material, and provides at least a temporary barrier function with significant clinical impact on par with, or better than, allograft. In some aspects, if clinical signs of infection, e.g., pain, edema, erythema, warmth, drainage, odor or unexplained fever, are present or developing, the product of the present disclosure is not applied until the clinical signs of the infection are reduced or eliminated for a predetermined period of time, e.g., 1, 2, 3, 4, 5, 6, or 7 days, 1, 2, 3, or 4 weeks, or if the subject has tested negative for the infection. In some aspects, the wound is cleaned, confirmed to be well-vascularized and nonexuding. If a dermal substitute such as cadaver allograft is also being used, the epidermal layer is removed from engrafted allograft prior to the application of the product without removing the engrafted dermis. The epidermal layer may be removed with a dermatome or other instrument according to standard operating procedures of the facility.

Grafts conventionally used in clinical practice consist of decellularized and/or reconstituted sheets of homogenized dermis that are used to achieve temporary, superficial wound coverage. Such conventional grafts do not retain the original tissue structure nor the metabolically active, otherwise naturally present cells, and thus do not become vascularized; no capillary ingrowth or vessel-to-vessel connections are made. In contrast, skin products described herein are fundamentally differentiated from such grafts because the product of the present disclosure includes live cells that perform the same function as the patient's original skin, i.e., the product acts as an organ transplant. Skin performs additional, critical roles related to homeostasis, temperature regulation, fluid exchange, and infection prevention. The absence of a sufficient amount of skin can compromise the ability to perform these functions leading to high incidences of mortality and morbidity from infections and fluid loss. Skin transplants have been reliably used with notable clinical benefit to prevent these outcomes in patients with significant wounds; regardless of whether the graft is temporary or permanent. Thus, unlike other proposed transplants, use of immunosuppressive drugs would not be necessary. In fact, such regimens would be contraindicated in burn patients whose injuries already exhibit some level of comprised immune function. Thus, the xenotransplantation product of the present disclosure should not be confused with traditional "xenograft" products consisting of econstituted, homogenized wild-type porcine dermis fashioned into sheets or meshed, such as EZ-Derm™ or Medi-Skin™. Such porcine xenografts do not vascularize and are primarily only useful for temporary coverage of superficial burns. In stark contrast, the xenotransplantation product of the present disclosure contains metabolically active, minimally manipulated cells in identical conformations and unchanged morphologies as the source tissue.

In some aspects, the present disclosure includes using xenotransplanted donor skin as a test for prediction of rejection of other organs from the same animal donor. Techniques for performing such predictive tests using human donor skin have previously been described, e.g., in Moraes et al., Transplantation. 1989; 48(6):951-2; Starzl, et al., Clinical and Developmental Immunology, vol. 2013, Article ID 402980, 1-9; Roberto et al., Shackman et al., Lancet. 1975; 2(7934):521-4, the disclosures of which are incorporated herein by reference in their entireties for all purposes. Moraes reported that the crossmatch procedure was highly accurate in predicting early kidney transplant rejection. Shackman reported that the fate of skin grafts taken from live human prospective kidney donors correlates well with the outcome of kidney transplantation from the same donors. According to the present disclosure, in one aspect, the present disclosure includes a method of using a xenotransplanted skin sample in a human patient in order to determine whether there is a risk of rejection of other organs xenotransplanted from the same animal donor in the human patient.

In some aspects, the xenotransplantation product of the present disclosure has pharmacokinetic and pharmacodynamics properties that meet regulatory requirements. Characterization of such properties requires a unique approach with respect to classical meanings of drug absorption, distribution, metabolism, and excretion. "Absorption" of the xenotransplantation product for the purposes of consideration of pharmacokinetics, may be described by the vascularization process the xenotransplantation product experiences. For example, shortly after surgery, skin xenotransplantation products may present as warm, soft, and pink, whereas wild-type or traditional xenografts appear as non-vascularized "white grafts." In some aspects, the distribution of the transplant is limited to the site of transplant as confirmed by DNA PCR testing to demonstrate the presence or absence of pig cells in peripheral blood beyond the transplantation site.

In other aspects, the cells of the biological products produced in accordance with the present invention do not migrate following xenotransplantation into the recipient, including into the circulation of the recipient. This includes that PERV or PERV-infected porcine cells do not migrate into the recipient. Confirmation that such cells do not migrate into the recipient can be performed in a number of ways, including via DNA-PCR analysis of peripheral blood mononuclear cells (PBMCs) and samples from the transplantation site and of highly perfused organs (e.g., liver, lung, kidney and spleen) to determine and otherwise demonstrate that migrations of porcine cells (DNA) or porcine retroviral (RNA) components in the peripheral blood did not occur in the recipient.

Moreover, bioavailability and mechanism of action of the xenotransplantation product is not affected by size. The distribution of the xenotransplantation product is limited to the site of the administration. For example, in the case of a skin transplant, the debrided wound bed initially created by the trauma or burn injury is the site of administration. The present disclosure includes testing to detect distribution of cells from the xenotransplantation product in the peripheral blood, wound beds, spleen and/or kidney beyond the site of administration. In certain aspects, such testing will demonstrate an absence of cells from the xenotransplantation product in the peripheral blood, wound beds, spleen and/or kidney beyond the site of administration. Such testing may include DNA PCR testing for various cellular markers present in the type of animal from which the product is obtained, e.g., PERV, swine MHC, and other swine DNA sequences. In certain aspects, cells and nucleic acids from the xenotransplantation product remain limited to the site of administration.

The metabolism of the xenotransplantation product, traditionally defined as the metabolic breakdown of the drug by living organisms, typically via specialized enzymes or enzymatic systems, may be congruent with the aforementioned natural host rejection phenomenon, which occurs in the absence of exogenous immunosuppressive drugs. Via the same formulation and identical route of administration as intended for future human use, such xenotransplantation products undergo a delayed, immune rejection course similar to allograft comparators for clinically useful durations.

In similar fashion, excretion of the xenotransplantation product could be modeled and experientially monitored by the clinical "sloughing" phenomenon as a result of necrotic ischemia of the transplant, due to antibody-mediated vascular injury, ultimately leading to the death of the tissue.

The demonstrated efficacy of the xenotransplantation product of the present disclosure, along with safety, availability, storage, shelf-life, and distribution, provide significant advantages over current standards of care.

In some aspects, the "dosage" of the xenotransplantation product of the present disclosure is expressed as percentage of viable cells in the product per unit area of transplantation. As such, in some aspects, the xenotransplantation product of the present disclosure can be considered as analogous to the active pharmaceutical ingredient in a pharmaceutical drug product.

Survival of the xenogeneic cells, tissues, or organs of the present disclosure is increased by avoiding: (a) infiltration of immune or inflammatory cells into the xenotransplantation product or alteration of such cells in other relevant compartments, such as the blood and cerebrospinal fluid; (b) fibrotic encapsulation of the xenotransplantation product, e.g., resulting in impaired function or xenotransplantation product loss; (c) xenotransplantation product necrosis; (d) graft versus host disease (GVHD); and (e) in vivo function and durability of encapsulation or barriers intended to diminish rejection or inflammatory responses.

Blood samples from piglets are obtained and tested for phenotype, lack of expression of alpha galactose on the cell surface of blood cells using FITC-IB4 labeling and flow cytometry. At this stage of development, all progeny will be genotyped at birth. A PCR assay has been established to determine if a pig has a wild type galactose-α1,3galactose transferase gene (Gal-T) or if it is heterozygous or homozygous for the Gal-T knockout (Gal-T-KO) using DNA isolated from ear notches or PBMC. Genomic DNA is isolated from PBMC (or skin tissues) using DNeasy Kit following the Qiagen DNeasy kit directions. PCR is performed on genomic DNA and control template DNA, Wild type Gal-T (+/+) Heterozygote Gal-T-KO (+/−) and Homozygous Gal-T-KO (−/−).

Punch biopsies of skin grafts are co-cultured with subconfluent target cells, human 293 (kidney epithelium) and porcine ST-IOWA cell lines maintained in culture medium (Dulbecco's modified Eagle's medium supplemented with 10% fetal bovine serum and glutamine, penicillin, and streptomycin) in a 75-cm2 flask. The biopsies are kept in contact with the target cells for 5 days, after which the culture medium and remaining tissue are removed and the target cell co-cultures are maintained by subculturing as necessary. PERV infection of target cells is determined by the presence of reverse transcriptase (RT) activity in the culture supernatants. Transmission assays are maintained for a minimum of 60 days before being considered negative.

Product characterization to measure safety, identity, purity and potency is performed. Safety tests include bacterial and fungal sterility, *mycoplasma*, and viral agents. The present disclosure includes cryopreserving and archiving for further testing, as needed, samples of all final xenotransplantation products (i.e., cells or tissues or biopsies of organs), whether fresh or from culture ex vivo. In some cases, for example if the xenotransplantation product is a whole intact organ, a relevant surrogate sample (e.g., adjacent tissues or contra-lateral organ) is archived.

With regard to skin, storage and cryopreservation of porcine skin has not been fully characterized, especially with regards to viability, as most porcine xenografts are intentionally devitalized, or "fixed" with glutaraldehydes or radiation treatment. Such information is necessary to support the use of vital porcine skin grafts—or porcine skin transplants—as a temporary and clinically advantageous option.

In procedures in which the xenotransplantation product is transplanted immediately after removal from the source animal, such as xenotransplantation of whole organs, results of testing of the xenotransplantation product may not be available before its clinical use. In such cases, testing of the source animal, itself, may be all the testing that is possible before the procedure. Testing of samples taken from such xenotransplantation products or appropriate relevant biological surrogates, e.g., adjacent tissues or contra-lateral organs, may be performed according to the present disclosure. Microbiological examination methods may include aspects set forth in the following Table 3:

TABLE 3

| TEST DETAILS | | GROWTH PROMOTION | | SUITABILITY OF COUNTING METHOD IN THE PRESENCE OF PRODUCT | |
| --- | --- | --- | --- | --- | --- |
| Microorganism | Preparation of Test Strain | Total Aerobic Microbial Count | Total Yeasts and Molds Count | Total Aerobic Microbial Count | Total Yeasts and Molds Count |
| *Staphylococcus aureus* such as ATCC 6538, NCIMB 9518, CIP 4.83, or NBRC 13276 | Soybean-Casein Digest Agar or Soybean-Casein Digest Broth 30°-35° 18-24 hours | Soybean-Casein Digest Agar and Soybean-Casein Digest Broth ≤100 cfu 30°-35° ≤3 days | | Soybean-Casein Digest Agar/MPN Soybean-Casein Digest Broth ≤100 cfu 30°-35° ≤3 days | |
| *Pseudomonas aeruginosa* such as ATCC 9027, NCIMB 8626, CIP 82.118, or NBRC 13275 | Soybean-Casein Digest Agar or Soybean-Casein Digest Broth 30°-35° 18-24 hours | Soybean-Casein Digest Agar and Soybean-Casein Digest Broth ≤100 cfu 30°-35° ≤3 days | | Soybean-Casein Digest Agar/MPN Soybean-Casein Digest Broth ≤100 cfu 30°-35° ≤3 days | |
| *Bacillus subtilis* such as ATCC 6633, NCIMB 8054, OP 52.62, or NBRC 3134 | Soybean-Casein Digest Agar or Soybean-Casein Digest Broth 30°-35° 18-24 hours | Soybean-Casein Digest Agar and Soybean-Casein Digest Broth ≤100 cfu 30°-35° ≤3 days | | Soybean-Casein Digest Agar/MPN Soybean-Casein Digest Broth ≤100 cfu 30°-35° ≤3 days | |
| *Candida albicans* such as ATCC 10231, NCPF 3179, IP 48.72, or NBRC 1594 | Sabouraud Dextrose Agar or Sabouraud Dextrose Broth 20°-25° 2-3 days | Soybean-Casein Digest Agar ≤100 cfu 30°-35° ≤5 days | Sabouraud Dextrose ≤100 cfu 30°-35° ≤5 days | Soybean-Casein Digest Agar ≤100 cfu 30°-35° ≤5 days MPN: not applicable | Sabouraud Dextrose Agar ≤100 cfu 20°-25° ≤5 days |
| *Aspergillus brasiliensis* such as ATCC16404, IMI 149007, IP 1431.83, NBRC 9455 | Sabouraud Dextrose Agaror Potato-Dextrose or Agar 20°-25° 5-7 days, or until good sporulation is achieved | Soybean-Casein Digest Agar ≤100 cfu 30°-35° ≤5 days | Sabouraud Dextrose ≤100 cfu 30°-35° ≤5 days | Soybean-Casein Digest Agar ≤100 cfu 30°-35° ≤5 days MPN: not applicable | Sabouraud Dextrose Agar ≤100 cfu 20°-25° ≤5 days |

The present disclosure includes using Buffered Sodium Chloride-Peptone Solution pH 7.0 or Phosphate Buffer Solution pH 7.2 to make test suspensions; to suspend *A. brasiliensis* spores, 0.05% of polysorbate 80 may be added to the buffer. The present disclosure includes using the suspensions within 2 hours, or within 24 hours if stored between 2° C. and 8° C. As an alternative to preparing and then diluting a fresh suspension of vegetative cells of *A. brasiliensis* or *B. subtilis*, a stable spore suspension is prepared and then an appropriate volume of the spore suspension is used for test inoculation. The stable spore suspension may be maintained at 2° to 8° for a validated period of time. To verify testing conditions, a negative control is performed using the chosen diluent in place of the test preparation. There must be no growth of microorganisms. A negative control is also performed when testing the products as described under Testing of Products. A failed negative control requires an investigation. Microbiological Examination may be performed according to USP 61, USP 63, USP 71, USP 85 EP section 2.6.13 Microbial Examination of Non-sterile Products (Test for Specified Microorganisms), each of which is incorporated herein by reference in its entirety.

With regard to testing for porcine cytomegalovirus (PCMV), source animals are screened for PCMV on a quarterly basis. However, caesarian derived piglets, which are then consistently raised in the closed colony are not infected with PCMV. Analysis for PCMV was conducted during the studies in Example 1 herein and no PCMV was detected in the punch biopsies using the following PCR method. These results were consistent to the PCR results from nasal swabs. Quantitative Real-Time PCR is utilized for PCMV testing. Target DNA sequences were quantified by real-time PCR using a Stratagene Mx3005P. Sequence-specific primers and TaqMan probe were generated for each gene target. Each 25 uL PCR reaction included target DNA, 800 nM primers 200 nMTaqMan probe, 20 nM Rox reference and 1× Brilliant III Ultra Fast Master Mix. The PCR cycling conditions were as follows: 1 cycle at 95° C. for 5 min followed by 50 cycles of denaturation at 95° C. for 10 seconds, and annealing-extension at 60° C. for 30 seconds with data collection following each extension. Serial dilutions of gel-extracted amplicon cloned into Invitrogen TOPO plasmid served as quantifying standards. Target DNA is detected with a linear dynamic range of 10 to 106 copies. For quantification of PCMV DNA, 300 ng of xenograft pig kidney DNA was run in a TaqMan PCR in triplicate. Primers and probes specific for PCMV DNA polymerase gene have been shown to have no cross-reactivity with PLHV-1. Utilization of cesarean-derived swine as source animals, combined with animal husbandry of the resulting closed colony and maintenance of the barrier-isolation conditions is attributed the animals being PCMV free. With regard to skin, the inventors noted that the safety and efficacy results achieved in Example 1 using single knockout swine (as opposed to triple knockout or even further genetically modified swine) were quite surprising given the comparable performance to allograft.

In some aspects, the analytical procedures used to test the xenotransplantation product can also include:

a. USP<71> Sterility. Samples are transferred to Tryptic Soy Broth (TSB) or Fluid Thioglycollate Medium (FTM) as appropriate. For Bacteriostasis and fungistasis, TSB samples are spiked with an inoculum of <100 Colony Forming Units (CFUs) of 24-hour cultures of *Bactillus subtilis, Candida albicans*, and with <100 spores of *Aspergilius braseiliensis*. The FTM samples will be spiked with an inoculum of <100 CFU's of 24-hour cultures of *Staphyloccocus aureus, Pseudomonas aeruginosa*, and *Clostridium sporogenes*. If growth is not observed, the product is found to be bacteriostatic or fungistatic and fails the USP <71> Sterility Test.

b. Aerobic and Anaerobic Bacteriological Cultures. Samples are transferred to Tryptic Soy Broth (TSB) or Fluid Thioglycollate Medium (FTM) as appropriate. Vessels will be incubated to allow for potential growth. If no evidence of microbial growth is found, the product will be judged to comply with the test for sterility as described by USP<71>.

c. *Mycoplasma* Assay USP <63>. Fresh samples will be added to 100 mL of *Mycoplasma hayflick* broth and incubated at 37° C. for up to 21 days. The sample is subcultured after 2-4 days, 7-10 days, 14 days, and 21 days. The plates are then incubated at 37° C. for up to 14 days and checked for the presence of *Mycoplasma* colonies. If none are detected, the product is found to be in compliance with USP<63> and is *mycoplasma* free.

d. Endotoxin USP<85>. Three samples from the same lot will be tested for the Inhibition/Enhancement of the Limulus amoebocyte lysate (LAL) test. Samples will be extracted with 40 mL of WFI per sample at 37° C. for 1 hour. Samples will then be tested in the LAL Kinetic Chromogenic Test with a standard curve ranging from 5-50 EU/mL at a validated dilution. Assays will be performed in compliance with USP<85>.

e. MTT Assay for Cell Viability. The metabolic activity of the drug product is tested relative to control tissue samples using a biochemical assay for [3-4,5 dimethylthiazol-2-yl]-2,5 diphenyltetrazolium bromide (MTT) metabolism. Positive and negative control samples of fresh xenotransplantation product tissue (positive control) or heat inactivated discs of xenotransplantation product tissue (negative control) or the test article of Xenotransplantation product are placed in amber microcentrifuge tubes containing MTT solution (0.3 m g/mL in DMEM, 0.5 mL). The discs are treated with MTT formazan and incubated for 180±15 minutes at 37° C. and an atmosphere of 5% CO 2 in air. The reaction is terminated by removal of the discs and the formazan is extracted by incubation at either ambient temperature for ≤24 hours or refrigerated at 4° C. for ≤72 hours. Samples are protected from light during this time. Aliquots are taken after the extraction is complete and the absorbance at 550 nm (with a reference wavelength of 630 nm) is measured and compared to a standard curve.

f. IB4 Assay for Extracellular Glycan Epitope. The absence of the galactosyl-α-1,3-galactose (Alpha-Gal) epitope on cells will be determined using fluorescence activated flow cytometry. White blood cells in whole blood are stained with a fluorochrome labeled isolectin-B4 (FITC-I-B4) and comparisons are made against blood obtained from wild type positive controls and the Gal-T-KO source animal twice. First, all source animals are tested at birth. Second, the same test will be performed from whole blood collected at sacrifice of the source animal and tested for stability of the gene knockout, and the negative phenotype for Alpha-Gal. The isolectin binds to the epitope on cells from the wild type pig but no binding occurs on the cells from the Gal-T-KO pigs. The assay serves to confirm alpha-gal epitope is not present in the genetically engineered source animal. Spontaneous re-activation of the gene, and re-expression of the Alpha-Gal moiety post sacrifice is highly improbable and unreasonable to expect; its inclusion would only deteriorate the efficacy of the xenotransplantation product causing it to resemble wild-type porcine tissue and hyperacutely reject as previously demonstrated.

g. PERV Viral Assay. PERV pol quantitation 10 uL of a 1:625 dilution of the RT reaction was amplified in a 50 cycle PERV polymerase quantitative TaqMan PCR in triplicate using a Stratagene MX300P real-time thermocycler (Agilent Technologies). 10 uL of a 1:25 dilution of the "No RT enzyme" control RT reaction was similarly treated. PCR conditions included PERV pol forward and reverse primers at 800 nM final concentration and PERV pol probe at 200 nM final concentration. Brilliant III Ultra Fast master mix (600880 Agilent Technologies) was used supplemented to 20 nM with ROX reporter dye (600880 Agilent Technologies) and 0.04 U nits/µL UNG nuclease (N8080096, Life Technologies). Cycling conditions included 1 cycle of 10 minutes at 50° C. followed by one cycle of 10 minutes at 95° C. and 50 cycles of 10 seconds at 95° C. followed by 30 seconds at 60° C. with data collected at the end of each cycle. Absolute copies of PERV pol, and of porcine MHC-I and porcine GAPDH nucleic acids were measured per nanogram of input cDNA. Punch biopsies of thawed as described herein and washed xenotransplantation product are tested for the presence of PERV DNA and RNA.

h. Histology and Morphology. Samples of the xenotransplantation product, following the described manufacturing process, are sampled for examination for cell morphology and organization. Verification under microscope via visible examination to ensure correct cell morphology and organization of xenotransplantation product tissues and absent for abnormal cell infiltrate populations.

i. Release Assay Sampling Methodology. Once all units of the final xenotransplantation product lot have been created, units are independently, randomly selected for use in manufacturing release assays for the required acceptance criteria. These units will be marked for lot release to the various laboratory contractors, and the various analytical tests will be performed per the required cGMP conditions.

Similarly, prior to validation for human clinical use, all final xenotransplantation product must meet acceptance criteria for selecting a donor pig for material including (i) reviewing the medical record for a defined pedigree, (ii) reviewing the medical record for the test results for alpha-1,3-galactose by Flowmetrics, (iii) reviewing the medical record for a history of full vaccinations; (iv) reviewing the medical record for the surveillance tests performed over the lifetime of the pig; (v) adventitious agent screening of source animal; (vi) reviewing the medical record for infections over the lifetime of the pig; and (vi) reviewing the medical record for any skin abnormalities noted in the animal's history.

The final xenotransplantation product control strategy and analytical testing is conducted at the conclusion of the manufacturing process prior to release for clinical use. Results of the required analytical tests will be documented via a xenotransplantation product drug product Certificate of Analysis (COA) that is maintained with a master batch record pertaining to each lot of xenotransplantation product drug product.

The following Table 4 is a list of the assays and results of the battery of tests performed on the xenotransplantation product materials.

TABLE 4

| Test | Test Method | Sample Material Tested | Result |
|---|---|---|---|
| Sterility Testing Aerobic Bacteria Anaerobic Bacteria Fungi Acid fast cultures Specific bacterial screen | Tissue Culture | 3 mm Punch Biopsy of Xenotransplantation product (Post Thaw) | No growth detected |
| Mycological Screen | Mycoplasma Assay | 3 mm Punch Biopsy of Xenotransplantation product (Post Thaw) | No growth detected after 28 days |
| Bacteriostasis & Fungistasis | USP<71> Gibraltar Laboratory | Xenotransplantation product (Post Thaw) | Bacteriostatic, no growth of specific indicator organism |
| Endotoxin Test | USP<85>LAL, Kinetic Chromogenic Test | Xenotransplantation product (Post Thaw) | <0.2 EU/unit |
| Endogenous Viral Testing (PERV) | RT-qPCR Co-culture Assay MGH - Infectious Disease - Fishman Laboratory | 3 mm Punch Biopsy of Xenotransplantation product (Post Thaw) | Presence of PERV A, B, C confirmed |
| Viability Testing | MTT and Phenyl Acetate Assays | 3 mm Punch Biopsy of Xenotransplantation product (Post Thaw) | Greater than 70% Mitochondrial Activity remaining following freeze - thaw cycle, confirmed by both assays |
| Identity Cell Morphology | Histology, Hematoxylin and Eosin Staining | 3 mm Punch Biopsy of Xenotransplantation product (Post Thaw) | No abnormalities noted. Cell morphology and organization consistent with skin graft No presence of Alpha - GAL detected |

TABLE 4-continued

| Test | Test Method | Sample Material Tested | Result |
|---|---|---|---|
| Confirmation of absence of Alpha-GAL (Gal-T-Knockout confirmation) | Flow Cytometry, isolectin-B4 (FITC-I-B4) | Whole Blood, 2 ml, obtained from source animal, at sacrifice. | |

In another aspect it will be understood that there includes an adventitious agent control strategy developed based on the source animal, including the species, strain, geographic origin, type of tissue, and proposed indication. Analytical Tests are conducted for adventitious agents, to include bacteria, fungi, *mycoplasma*, and viral microorganisms, including as follows:

a. Bacteriological Free Status—The bacteriological screen is conducted to confirm the drug product is free of potential biological agents of concern Humans. Both Aerobic and Anaerobic screens are conducted to ensure sterility. Samples are thawed as described herein and transferred to Tryptic Soy Broth (TSB) or Fluid Thioglycollate Medium (FTM) as appropriate. Vessels will be incubated to allow for potential growth. If no evidence of microbial growth is found, the product will be judged to comply with the test for sterility.

b. Mycological (Fungal) Free Status—The mycological screen is conducted to confirm the Drug Product is free of potential fungal agents of concern. Samples are thawed as described herein. After thawing, samples are transferred to a soybean-casein digest agar. Vessels will be incubated to allow for potential growth. If no evidence of fungal growth is found, the product will be judged to comply with the test for sterility per USP<71>.

c. *Mycoplasma* Free Status—The *mycoplasma* screen is conducted to confirm the drug product is free of *mycoplasma*. Samples are thawed as described herein and added to 100 mL of *Mycoplasma* broth and incubated at 37° C. for up to 21 days. The sample is subcultured after 2-4 days, 7-10 days, 14 days, and 21 days. The plates are then incubated at 37° C. for up to 14 days and checked for the presence of *Mycoplasma* colonies. If none are detected, the product is found to be in compliance with USP<63> and is *mycoplasma* free.

d. Endotoxin Free Status—The endotoxin free status is conducted to confirm the drug product is free of endotoxins and related agents of concern. Three samples from the same lot will be tested for the Inhibition/Enhancement of the Limulus amoebocyte lysate (LAL) test. Samples will be thawed as described herein and extracted with 40 mL of WFI per sample at 37° C. for 1 hour. Samples will then be tested in the LAL Kinetic Chromogenic Test with a standard curve ranging from 5-50 EU/mL at a validated dilution. Assays will be performed in compliance with USP<85>.

e. Viral Assays Conducted—The viral assays are conducted to confirm the source animal is free of potential viral agents of concern, confirmation of endogenous viruses (see below). This includes co-culturing and RT-PCR testing for specific latent endogenous viruses including PERV. In vivo assays are also conducted on the animal source to monitor animal health and freedom from viral infection as key aspects of the lot release criteria. Due to the endemic nature of PERV in porcine tissue, this qualifies as a positive result that does not preclude the use of such tissue. However, the virus is identified and characterized in lot release to provide information for monitoring the recipient of the xenotransplantation product.

f. Cell Viability Assay—The MTT assay is conducted to confirm the biologically active status of cells in the xenotransplantation product. Evidence of viability is provided through surrogate markers of mitochondrial activity as compared to positive (fresh, not cryopreserved) and negative (heat-denatured) controls. The activity of the cells is required for the xenotransplantation product to afford the intended clinical function. This is required as a lot release criteria, and is currently established that tissue viability should not be less than 50% of the metabolic activity demonstrated by the fresh tissue control comparator.

g. Histology and Morphology—Verification under microscope via visible examination of Hematoxylin and Eosin (H&E) section staining of the epidermal and dermal layers, to ensure correct cell morphology and organization of the xenotransplantation product tissues and cell infiltrate populations. This is conducted to confirm the appropriate physiologic appearance and identity of cells present in the xenotransplantation product. The xenotransplantation product is composed of minimally manipulated porcine dermal and epidermal tissue layers. This is required as a lot release criteria. Evidence of the following cell layers (from most superficial to deepest), in the epidermal layer are verified:
  i. Stratum Corneum
  ii. Stratum Granulosum
  iii. Stratum Spinosum
  iv. Stratum Basale Evidence of the following cellular structures in the dermal layer are verified:
  v. Blood vessels, evidence of vasculature
  vi. Nerves
  vii. Various glands
  viii. Hair follicles
  ix. Collagen The genetically engineered source animals do not contain any foreign, introduced DNA into the genome; the gene modification employed is exclusively a knock-out of a single gene that was responsible for encoding for an enzyme that causes ubiquitous expression of a cell-surface antigen. It will be understood that the xenotransplantation product in one or more aspects do not incorporate transgene technologies, such as CD-46 or CD-55 transgenic constructs.

An endotoxin free status is conducted to confirm the drug product is free of endotoxins and related agents of concern. Protocols for the assurance of Endotoxin free status are as follows: Three samples from the same lot are tested for Inhibition/Enhancement of the Limulus amoebocyte lysate (LAL) test. Samples are thawed, extracted, and tested in the LAL Kinetic Chromogenic Test with a standard curve ranging from 5-50 EU/mL at a validated dilution in compliance with USP<85>.

The MTT assay is conducted to confirm the biologically active status of cells in the product. Evidence of viability is provided through surrogate markers of mitochondrial activity as compared to positive (fresh, not cryopreserved) and negative (heat-denatured) controls. The activity of the cells is required for the product to afford the intended clinical function and the viability parameters for one aspect ranging from 50% to 100% mitochondrial activity.

Verification under microscope via visible examination of Hematoxylin and Eosin (H&E) section staining of the epidermal and dermal layers, to ensure correct cell morphology and organization of the xenotransplantation product tissues and cell infiltrate populations. This is conducted to confirm the appropriate physiologic appearance and identity of cells present in the product.

For skin xenotransplantation products, evidence of the following cell layers (from most superficial to deepest), in the epidermal layer are verified: Stratum Corneum; Stratum Granulosum; Stratum Spinosum; Stratum Basale. Evidence of the following cellular structures in the dermal layer are verified: Blood vessels, evidence of vasculature; Nerves; Various glands; Hair follicles; Collagen.

The xenotransplantation product may be further processed to ensure that it remains free of aerobic and anaerobic bacteria, fungi, viruses, and *mycoplasma*. Under sterile conditions in a laminar flow hood in a drug product processing suite using applicable aseptic techniques, immediately after, within 1, 2, 3, 4, 5, 6, 7, 8, 9, 10 seconds, within 10 seconds to 1 minute, within 1 minute to 1 hour, within 1 hour to 15 hours, or within 15 hours to 24 hours following harvest, the xenotransplantation product is sterilized, e.g., using one or more of UV irradiation or an anti-microbial/anti-fungal. In one aspect, the product may be placed into an anti-microbial/anti-fungal bath ("antipathogen bath"). The antipathogen bath may include: one or more anti-bacterial agents, e.g., ampicillin, ceftazidime, neomycin, streptomycin, chloramphenicol, cephalosporin, penicillin, tetracycline, vancomyocin, and the like; one or more anti-fungal agents, e.g., amphotericin-B, azoles, imidazoles, triazoles, thiazoles, candicidin, hamycin, natamycin, nystatin, rimocidin, allylamines, echinocandins, and the like; and/or one or more anti-viral agents. The anti-pathogen bath may include a carrier or medium as a diluent, e.g., RPMI-1640 medium. In some aspects, the anti-pathogen bath may include at least 2 anti-bacterial agents. In some aspects, the anti-pathogen bath may include at least 2 anti-bacterial agents and at least one anti-fungal agent. In some aspects, the anti-pathogen bath may include at least four agents. In some aspects, the anti-pathogen bath may include no more than 4, 5, 6, 7, 8, 9, or 10 agents. In some aspects, the anti-pathogen bath may include any combination of the foregoing.

The product may be sterilized using UV light sterilization. For example, the product is placed under the UV lamp for a desired period of time, e.g., 0.5, 1, 1.5, 2, 3, 4, 5, 6, minutes or more, then turned over to the other side, and put under the UV lamp for the same or a different period of time on opposite side. The time period for exposing a given sample to the UV may be varied based on the specific biological agents or the types of biological agents to be sterilized, e.g., as shown in the following Table 8 below. For example, the product may be sterilized using a UV lamp having a UV-C intensity of at least 100 uW/cm$^2$ for at least 2 minutes and up to 15, 12, 10, 8, 6, 5, 4, 3, or 2.5 minutes, and turned over such that its opposite surface is exposed to the UV lamp for at least 2 minutes and up to 15, 12, 10, 8, 6, 5, 4, 3, or 2.5 minutes to obtain a UV-treated product; a UV-C dosage of at least 100,000 uW sec/cm$^2$ and up to 800,000, 700,000, 600,000, 500,000, 400,000, 300,000 or 200,000 uW sec/cm$^2$; a UV-C dosage of at least 200,000 uW sec/cm$^2$ and up to 800,000, 700,000, 600,000, 500,000, 400,000, or 300,000 uW sec/cm$^2$; a UV lamp having a UV-C intensity of at least 100 uW/cm$^2$ for at least 2 minutes and up to 15, 12, 10, 8, 6, 5, 4, 3, or 2.5 minutes.

Product processing occurs in a single, continuous, and self-contained, segregated manufacturing event that begins with the sacrifice of the source animal through completion of the production of the final product. The animal is euthanized via captive bolt euthanasia, may be moved, if necessary, in a sterile, non-porous bag, to an operating room where the procedure to harvest biological product from the source animal will occur. All members of the operating team should be in full sterile surgical gear, e.g., dressed in sterile dress to maintain designated pathogen free conditions prior to receiving the source animal and in some instanced be double-gloved to minimize contamination, and surgical areas and tools are sterilized. The source animal is removed from the bag and container in an aseptic fashion. The source animal is scrubbed by operating staff, e.g., for at least 1-10 minutes with antiseptic, e.g., Chlorhexidine, brushes over the entire area of the animal where the operation will occur, periodically pouring Chlorhexidine over the area to ensure coverage. Surgical area(s) of the animal are scrubbed with opened Betadine brushes and sterile water rinse over the entire area of the animal where the operation will occur for, e.g., 1-10 minutes.

In one aspect, with regard to skin, a full thickness skin graft wound dressing consisting of dermal tissue derived from a swine in accordance with the present invention is used in conjunction or combination with cultured epidermal autografts to produce a product according to the present disclosure and that can be used in methods of the present disclosure. Prior to application of the epidermal autografts, significant debridement of wound bed is required to ensure an adequate substrate. To confirm a wound bed is ready for an epidermal autograft, apply the skin products described herein, e.g., biological skin products derived from animals of the present disclosure to confirm adherence. Once adherence is confirmed, the temporary wound coverage product is removed, and in some aspects, the wound bed is covered with a meshed autograft, and one or more cultured epidermal autograft products are placed on top to close the gaps in the autograft mesh.

The debridement may include mechanical debridement, chemical debridement, enzymatic debridement, or a combination thereof. Mechanical debridement may include surgical excision, e.g., tangential excision to remove thin layers of dermis until healthy tissue is visualized, or fascial excision to remove the full thickness of dermis down to the underlying fascia. Tangential excision allows less viable tissue to be removed with the necrotic tissue, but typically results in higher blood loss, is a larger physiologic stressor than fascial excision, and is more likely to result in "incomplete" debridement, with some devitalized tissue remaining in place. In fascial excision, blood loss and operative time are minimized, but often a large amount of healthy tissue is removed with the burned tissue. Debriding agents may include agents capable of cleaning a burn wound by removing foreign material and dead tissue. Many such agents are known. In enzymatic debridement, collagenases or other proteolytic enzymes are employed that break down proteins of the extracellular matrix, allowing devitalized tissue to be wiped away without the need for surgery while preferably leaving healthy tissue substantially intact. Enzymatic debridement involves the application of proteolytic and optionally other exogenous enzymes to a wound surface to break down necrotic tissue. Enzymatic debridement may be a relatively slow process, carried out over a period of a number of weeks in combination with other topical preparations, soakings and repeated dressings. Alternately, rapid enzymatic debridement can be accomplished using multi-enzyme products, for example, those extracted from the stem of the pineapple plant, as disclosed for example in WO 98/053850 and WO 2006/0006167, and as provided in the product marketed under the trade name Debrase®. A procedure for enzymatic debridement generally utilizes an enzyme such as bromelain derivatives, debridase, collagenase, papain derivatives, streptokinase, sutilains, fibrinolysin, deoxyribonuclease, hill derivatives, trypsin or combinations thereof. Autolytic debridement relies on enhancing the natural process of selective liquefaction, separation and digestion of necrotic tissue and eschar from healthy tissue that occurs in wounds due to macrophage and endogenous proteolytic activity. This is achieved by the use of occlusive, semi-occlusive or moist interactive dressings. Enzymatic debridement agents include a bromelain enriched enzyme product, other collagenases, or other enzyme products capable of clearing devitalized tissue or wound debris. NexoBrid™ (MediWound Ltd.) is one such bromelain enriched product that specifically targets heat-denatured collagen for degradation, resulting in partial-thickness and full-thickness wounds requiring a wound coverage or dressing product. Such products and methods are described in U.S. Pat. Nos. 8,540,983; 8,119,124; 7,128,719; 7,794,709; 8,624,077; and US2009/0010910A1, each of which is incorporated by reference herein.

In some aspects, the wound bed may include or be a chronic wound or an acute wound. Chronic wounds include but are not limited to venous leg ulcers, pressure ulcers, and diabetic foot ulcers. Acute wounds include but are not limited to burns, traumatic injuries, amputation wounds, skin graft donor sites, bite wounds, frostbite wounds, dermabrasions, and surgical wounds.

In the cases where there is no dermis, biological products produced in accordance with the present invention are utilized. The epidermis is removed from such products (e.g., before dermis harvesting on the pig with a VERSAJET™ Hydrosurgery system), so that just the dermis remains. Then, the subject biological product is placed on the patient's subcutaneous tissue, serving as a substrate for the cultured epidermal autograft process described herein.

In one aspect, a liver derived in accordance with the present disclosure is utilized for extracorporeal perfusion as a temporary filter for a human patient until a patient receives a human transplant. In an operating area within the DPF Isolation Area, a source animal is placed under a general anesthetic (ketamine, xylazine, enflurane) or euthanized by captive bolt. A hepatectomy is then performed on the source animal in designated pathogen free conditions. The liver product derived from the source animal can be packaged and transported to the location of the procedure in accordance with current practice with human donor livers. The procedure to utilize the liver filtration product can be performed, for example, by percutaneously cannulating a human patient's internal jugular vein for venous return with an arterial cannula and percutaneously cannulating a patient's femoral vein for venous outflow with an artery cannula. These cannulas are connected to a bypass circuit, having a centrifugal pump, a heat exchanger, an oxygenator, and a roller pump incorporated therein. This circuit is primed with crystalloids and run for a period of time (e.g., 10-30 minutes) before the liver from an animal according to the present disclosure is incorporated at a stabilized flow rate, e.g., 600-1000 ml/min, maintained in a crystalloid bath occasionally supplemented with warm solution, e.g., 30-40° C.

It will be understood that, in the context of swine-to-human xenotransplantation, each human recipient will have a major histocompatibility complex (MHC) (Class I, Class II and/or Class III) that is unique to that individual and will not match the MHC of the donor swine. Accordingly, it will be understood that when a donor swine graft is introduced to the recipient, the swine MHC molecules themselves act as antigens, provoking an immune response from the recipient, leading to transplant rejection.

Human leukocyte antigen (HLA) genes show incredible sequence diversity in the human population. For example, there are >4,000 known alleles for the HLA-B gene alone. The genetic diversity in HLA genes in which different alleles have different efficiencies for presenting different antigens is believed to be a result of evolution conferring better population-level resistance against the wide range of different pathogens to which humans are exposed. This genetic diversity also presents problems during xenotransplantation where the recipient's immune response is the most important factor dictating the outcome of engraftment and survival after transplantation.

In accordance with one aspect the present invention, a donor swine is provided with a genome that is biologically engineered to express a specific set of known human HLA molecules. Such HLA sequences are available, e.g., in the IPD-IMGT/HLA database (available at ebi.ac.uk/ipd/imgt/hla/) and the international ImMunoGeneTics information System® (available at imgt.org). For example, HLA-A1, B8, DR17 is the most common HLA haplotype among Caucasians, with a frequency of 5%. Thus, the disclosed method can be performed using the known MHC/HLA sequence information in combination with the disclosures provided herein.

In some aspects, the recipient's human leukocyte antigen (HLA) genes and MHC (Class I, II and/or III), are identified and mapped. It will be understood that ascertaining the human recipient's HLA/MHC sequence can be done in any number of ways known in the art. For example, HLA/MHC genes are usually typed with targeted sequencing methods: either long-read sequencing or long-insert short-read sequencing. Conventionally, HLA types have been determined at 2-digit resolution (e.g., A*01), which approximates the serological antigen groupings. More recently, sequence specific oligonucleotide probes (SSOP) method has been used for HLA typing at 4-digit resolution (e.g., A*01:01), which can distinguish amino acid differences. Currently, targeted DNA sequencing for HLA typing is the most popular approach for HLA typing over other conventional methods. Since the sequence-based approach directly determines both coding and non-coding regions, it can achieve HLA typing at 6-digit (e.g., A*01:01:01) and 8-digit (e.g., A*01:01:01:01) resolution, respectively. HLA typing at the highest resolution is desirable to distinguish existing HLA alleles from new alleles or null alleles from clinical perspective. Such sequencing techniques are described in, for example, Elsner H A, Blasczyk R: (2004) Immunogenetics of HLA null alleles: implications for blood stem cell transplantation. Tissue antigens. 64 (6): 687-695; Erlich R L, et al (2011) Next-generation sequencing for HLA typing of class I loci. BMC genomics. 12: 42-10.1186/1471-2164-12-42; Szolek A, et al. (2014) OptiType: Precision HLA typing from next-generation sequencing data. Bioinformatics 30:3310-3316; Nariai N, et al. (2015) HLA-VBSeq: Accurate HLA typing at full resolution from whole-genome sequencing data. BMC Genomics 16:S7; Dilthey A T, et al. (2016) High-accuracy HLA type inference from whole-genome sequencing data using population reference graphs. PLoS Comput Biol 12:e1005151; Xie C., et al. (2017) Fast and accurate HLA typing from short-read next-generation sequence data with xHLA 114 (30) 8059-8064, each of which is incorporated herein in its entirety by reference.

The known human HLA/MHC or an individual recipient's sequenced HLA/MHC sequence(s) may be utilized as a template to modify the swine leukocyte antigen (SLA)/MHC sequence to match, e.g., to have 90%, 95%, 98%, 99%, or 100% sequence homology to a known human HLA/MHC sequence or the human recipient's HLA/MHC sequence. Upon identifying a known human recipient HLA/MHC sequence to be used or performing genetic sequencing of a human recipient to obtain HLA/MHC sequences, biological reprogramming may be performed to SLA/MHC sequences in cells of the swine based on desired HLA/MHC sequences. For example, several targeting guide RNA (gRNA) sequences are administered to the swine of the present disclosure to reprogram SLA/MHC sequences in cells of the swine with the template HLA/MHC sequences of the human recipient.

CRISPR-Cas9 is used to mediate rapid and scarless exchange of entire MHC alleles at specific native locus in swine cells. Multiplex targeting of Cas9 with two gRNAs is used to introduce single or double-stranded breaks flanking the MHC allele, enabling replacement with the template HLA/MHC sequence (provided as a single or double-stranded DNA template). In certain aspects, the CRISPR/Cas9 components are injected into swine oocytes, ova, zygotes, or blastocytes prior to transfer into foster mothers.

In certain aspects, the present disclosure includes embryogenesis and live birth of SLA-free and HLA-expressing biologically reprogrammed swine. In certain aspects, the present disclosure includes breeding SLA-free and HLA-expressing biologically reprogrammed swine to create SLA-free and HLA-expressing progeny. In certain aspects, the CRISPR/Cas9 components are injected into swine zygotes by intracytoplasmic microinjection of porcine zygotes. In certain aspects, the CRISPR/Cas9 components are injected into swine prior to selective breeding of the CRISPR/Cas9 genetically modified swine. In certain aspects, the CRISPR/Cas9 components are injected into donor swine prior to harvesting cells, tissues, zygotes, and/or organs from the swine. In certain aspects, the CRISPR/Cas9 components include all necessary components for controlled gene editing including self-inactivation utilizing governing gRNA molecules as described in U.S. Pat. No. 9,834,791 (Zhang), which is incorporated herein by reference in its entirety.

The genetic modification can be made utilizing known genome editing techniques, such as zinc-finger nucleases (ZFNs), transcription activator-like effector nucleases (TAL-ENs), adeno-associated virus (AAV)-mediated gene editing, and clustered regular interspaced palindromic repeat Cas9 (CRISPR-Cas9). These programmable nucleases enable the targeted generation of DNA double-stranded breaks (DSB), which promote the upregulation of cellular repair mechanisms, resulting in either the error-prone process of non-homologous end joining (NHEJ) or homology-directed repair (HDR), the latter of which can be used to integrate exogenous donor DNA templates. CRISPR-Cas9 may also be used to remove viral infections in cells. For example, the genetic modification via CRISPR-Cas9 can be performed in a manner described in Kelton, W. et. al., "Reprogramming MHC specificity by CRISPR-Cas9-assisted cassette exchange," Nature, Scientific Reports, 7:45775 (2017) ("Kelton"), the entire disclosure of which is incorporated herein by reference. Accordingly, the present disclosure includes reprogramming using CRISPR-Cas9 to mediate rapid and scarless exchange of entire alleles, e.g., MHC, HLA, SLA, etc.

In one aspect, the recipient's HLA/MHC gene is sequenced and template HLA/MHC sequences are prepared based on the recipient's HLA/MHC genes. In another aspect, a known human HLA/MHC genotype from a WHO database may be used for genetic reprogramming of swine of the present disclosure. CRISPR-Cas9 plasmids are prepared, e.g., using polymerase chain reaction and the recipient's HLA/MHC sequences are cloned into the plasmids as templates. CRISPR cleavage sites at the SLA/MHC locus in the swine cells are identified and gRNA sequences targeting the cleavage sites and are cloned into one or more CRISPR-Cas9 plasmids. CRISPR-Cas9 plasmids are then administered into the swine cells and CRIPSR/Cas9 cleavage is performed at the MHC locus of the swine cells.

The SLA/MHC locus in the swine cells are replaced with one or more template HLA/MHC sequences matching the known human HLA/MHC sequences or the recipient's sequenced HLA/MHC genes. Cells of the swine are sequenced after performing the SLA/MHC reprogramming steps in order to determine if the HLA/MHC sequences in the swine cells have been successfully reprogrammed. One or more cells, tissues, and/or organs from the HLA/MHC sequence-reprogrammed swine are transplanted into a human recipient.

In certain aspects, HLA/MHC sequence-reprogrammed swine are bred for at least one generation, or at least two generations, before their use as a source for live tissues, organs and/or cells used in xenotransplantation. In certain aspects, the CRISPR/Cas9 components can also be utilized to inactivate genes responsible for PERV activity, e.g., the pol gene, thereby simultaneously completely eliminating PERV from the swine donors.

For purposes of modifying donor SLA/MHC to match recipient HLA/MHC, comparative genomic organization of the human and swine histocompatibility complex has been mapped. For example, such SLA to HLA mapping can be found in: Lunney, J., "Molecular genetics of the swine major histocompatibility complex, the SLA complex," Developmental and Comparative Immunology 33: 362-374 (2009) ("Lunney"), the entire disclosure of which is incorporated herein by reference. Accordingly, a person of ordinary skill in the art effectively and efficiently genetically reprogram swine cells in view of the present disclosure and using the mapping of Lunney et al. as a reference tool.

The modification to the donor SLA/MHC to match recipient HLA/MHC causes expression of specific MHC molecules from the swine cells that are identical, or virtually identical, to the MHC molecules of a known human genotype or the specific human recipient. In one aspect, the present disclosure involves making modifications limited to only specific portions of specific SLA regions of the swine's genome to retain an effective immune profile in the swine while biological products are hypoimmunogenic when transplanted into human recipients such that use of immunosuppressants can be reduced or avoided. In contrast to aspects of the present disclosure, xenotransplantation studies of the prior art required immunosuppressant use to resist rejection. In one aspect, the swine genome is reprogrammed to knock-out swine genes corresponding to HLA-A, HLA-B, HLA-C, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G, HLA-F, and DQ. In one aspect, the swine genome is reprogrammed to knock-out SLA-11; SLA-6,7,8; SLA-MIC2; and SLA-DQA; SLA-DQB1; SLA-DQB2, and to knock-in HLA-C; HLA-E; HLA-G; and HLA-DQ. In certain aspects, HLA-C expression is reduced in the reprogrammed swine genome. By reprogramming the swine cells to be invisible to a human's immune system, this reprogramming thereby minimizes or even eliminates an immune response that would have otherwise occurred based on swine MHC molecules otherwise expressed from the donor swine cells.

It will therefore be understood that this aspect (i.e., reprogramming the SLA/MHC to express specifically selected human MHC alleles), when applied to swine cells, tissues, and organs for purposes of xenotransplantation will decrease rejection as compared to cells, tissues, and organs derived from a wild-type swine or otherwise genetically modified swine that lacks this reprogramming, e.g., transgenic swine or swine with non-specific or different genetic modifications.

It will be further understood that causing the donor swine cells, tissues, and organs to express a known human MHC genotype or the recipient's MHC specifically as described herein, combined with the elimination in the donor swine cells of alpha-1,3-galactosytransferase, Neu5Gc, and β1,4-N-acetylgalactosaminyltransferase (B4GALNT2) (e.g., "single knockout," "double knockout," or "triple knockout"), presents a swine whose cells will have a decreased immunological rejection as compared to a triple knockout swine that lacks the specific SLA/MHC reprogramming of the present disclosure.

Cryopreservation and storage according to the present disclosure includes preparing biological product according to the present disclosures, placing in a container, adding freeze media to the container and sealing. For example. 15% dimethyl sulfoxide (DMSO) cryoprotective media is combined with fetal porcine serum (FPS) or donor serum (if FPS is unavailable) in a 1:1 ratio, filtered (0.45 micron), and chilled to 4° C. prior to use. The containers are subsequently frozen in a controlled rate, phase freezer at a rate of 1° C. per minute to −40° C., then rapidly cooled to a temperature −80° C. DMSO displaces intracellular fluid during the freezing process. Cryoprotective media, e.g., CryoStor is used in an amount of about 40-80%, or 50-70% based on maximum internal volume of the cryovial (10 ml) less the volume of the xenotransplantation product. In order to thaw the cryopreserved biological product for surgical use, sealed vials were placed in ~37° C. water baths for approximately 0.5 to 2 minutes, at which point the container is opened and the product was removed using sterile technique. Subsequently, products undergo three, 1-minute serial washes, e.g., in saline with gentle agitation, in order to dilute and systematically remove ambient, residual DMSO and prevent loss of cell viability. The product may then be used surgically.

It will be understood that the xenotransplantation product may be processed, stored, transported, and/or otherwise handled using materials, containers and processes to ensure preserved sterility and prevent damage thereto. In some aspects, a sterile non-adhesive material may be used to protect the xenotransplantation product, e.g., to support the xenotransplantation product and prevent adhesive of the product to surfaces and/or to prevent self-adhesion of the xenotransplantation product during manipulation, storage, or transport. Unintentional adhesion of the xenotransplantation product may disrupt the integrity of the xenotransplantation product and potentially reduce its therapeutic viability. Inclusion of the sterile non-adhesive material provides protection and/or physical support and prevents adhesion. In some aspects, the sterile non-adhesive material is not biologically or chemically active and does not directly impact the metabolic activity or efficacy of the xenotransplantation product itself.

Aspects of the present disclosure are further described by the following non-limiting list of items:

1. A method of producing a biological product suitable for xenotransplantation into a human recipient comprising:

producing a non-wild type, biologically engineered swine, wherein said swine is produced through natural breeding and natural birthing, wherein said swine has a biologically engineered genome such that it does not express one or more extracellular surface glycan epitopes, and wherein said swine is free of at least the following pathogens: *Ascaris* species, *cryptosporidium* species, *Echnococcus*, *Strongyloids sterocolis*, *Toxoplasma gondii*, *Brucella suis*, *Leptospira* species, *mycoplasma hyopneumoniae*, pseudorabies, *Toxoplasma Gondii*, *staphylococcus* species, *Microphyton* species, and *Trichophyton* species, porcine influenza, cytomegalovirus, arterivirus, and coronavirus, rearing the swine and maintaining the swine according to a bioburden-reducing procedure, said procedure comprising maintaining the swine in a closed herd, wherein all other animals in the closed herd are confirmed to be free of at least the following pathogens: *Ascaris* species, *cryptosporidium* species, *Echnococcus*, *Strongyloids sterocolis*, *Toxoplasma gondii*, *Brucella suis*, *Leptospira* species, *mycoplasma hyopneumoniae*, pseudorabies, *Toxoplasma Gondii*, *staphylococcus* species, *Microphyton* species, and *Trichophyton* species, porcine influenza, cytomegalovirus, arterivirus, and coronavirus, wherein the swine is isolated from contact with any non-human animals and animal housing facilities outside of the closed herd, harvesting a biological product from said swine, wherein said harvesting comprises euthanizing the swine and aseptically removing the biological product from the swine, processing said biological product comprising sterilization within 15 hours of harvesting and storing said biological product in a sterile container, wherein said biological product does not contain one or more extracellular surface glycans, wherein said product is free of *Ascaris* species, *cryptosporidium* species, *Echnococcus*, *Strongyloids sterocolis*, *Toxoplasma gondii*, *Brucella suis*, *Leptospira* species, *mycoplasma hyopneumoniae*, pseudorabies, *Toxoplasma Gondii*, *staphylococcus* species, *Microphyton* species, and *Trichophyton* species, porcine influenza, cytomegalovirus, arterivirus, and coronavirus, and wherein said product is biologically active and comprises live cells and tissues capable of vascularizing after xenotransplantation, wherein cellular mitochondrial activity of said product is greater than 50% as measured by MTT assay;

wherein said product is less immunogenic when transplanted into a human xenotransplant recipient as compared to a biological product obtained a xenotransplantation product made from conventional Gal-T knockout swine, from conventional triple knockout swine, from transgenic swine, from wild-type animals, and/or allograft, wherein said product is less antigenic when transplanted into a human xenotransplant recipient as compared to a biological product obtained from a xenotransplantation product made from conventional Gal-T knockout swine, from conventional triple knockout swine, from transgenic swine, from wild-type animals, and/or allograft, and wherein said product is resistant to rejection by the human xenotransplant recipient in the absence of administration of immunosuppressant drugs or other immunosuppressant therapies to the human xenotransplant recipient.

2. The method of any item or combination of items disclosed herein, wherein the processing comprises ultraviolet (UV) sterilization within 15 hours of harvesting.

3. The method of any item or combination of items disclosed herein, wherein the product is laid flat on a sterile surface and exposed to a UV lamp having a UV-C intensity of at least 100 uW/cm$^2$ for at least 2 minutes and up to 15, 12, 10, 8, 6, 5, 4, 3, or 2.5 minutes, and turned over such that its opposite surface is exposed to the UV lamp for at least 2 minutes and up to 15, 12, 10, 8, 6, 5, 4, 3, or 2.5 minutes to obtain a UV-treated product.

4. The method of any item or combination of items disclosed herein, wherein the product is laid flat on a sterile surface and exposed to a UV-C dosage of at least 100,000 uW sec/cm$^2$ and up to 800,000, 700,000, 600,000, 500,000, 400,000, 300,000 or 200,000 uW sec/cm$^2$.

5. The method of any item or combination of items disclosed herein, wherein the product is laid flat on a sterile surface and exposed to a UV-C dosage of at least 200,000 uW sec/cm$^2$ and up to 800,000, 700,000, 600,000, 500,000, 400,000, or 300,000 uW sec/cm$^2$.

6. The method of any item or combination of items disclosed herein, further comprising placing the UV-treated product in a previously-sterilized container and subsequently exposing all surfaces of the container to a UV lamp having a UV-C intensity of at least 100 uW/cm$^2$ for at least 2 minutes and up to 15, 12, 10, 8, 6, 5, 4, 3, or 2.5 minutes, exposing all surfaces of a previously-sterilized cap of the sterile container to the UV-lamp for at least two minutes, and subsequently securing the cap onto the sterile container.

7. The method of any item or combination of items disclosed herein, wherein said processing step further comprises at least one of placing the biological product into an antimicrobial solution containing one or more of antibiotics such as placing the biological product into an antimicrobial solution containing one or more of antibiotics such as Ampicillin/Ceftazidime/Vancomycin/Amphotericin-B, flow cytometry to determine extracellular surface glycan epitope elimination, cryopreservation using cryoprotective-media packaging.

8. The method of any item or combination of items disclosed herein, wherein said storing step further comprises cryopreserving the product, wherein the cryopreserving step comprises a controlled-rate freezing technique beginning at about 4° C. and lowering by about 1° C. per minute until −40° C. followed by temperature reduction to about −80° C. within 5 minutes.

9. The method of any item or combination of items disclosed herein, wherein the xenotransplantation product is confirmed to be free of one or more extracellular surface glycan epitopes.

10. The method of any item or combination of items disclosed herein, wherein the organism is delivered by C-section.

11. The method of any item or combination of items disclosed herein, further comprising administering one or more anti-microbial agents and one or more vaccines to the organism.

12. The method of any item or combination of items disclosed herein, wherein the one or more vaccines are killed vaccines.

13. The method of any item or combination of items disclosed herein, further comprising feeding the organism sterile or purified water and a grain-based feed that does not contain animal proteins or cattle-based material.

14. The method of any item or combination of items disclosed herein, further comprising irradiation sterilizing bedding, cages, and feed for the organism.

15. The method of any item or combination of items disclosed herein, wherein the bioburden-reducing procedure further comprises air filtration of the closed herd, chemically sterilizing cages and vehicles used to house or transport the organism, bathing the organism in chlorhexidine, bathing the organism in sterile saline, bathing the organism in an anti-fungal solution, or a combination the method of any one of items 1-15, further comprising screening said organism for detectable levels of *rickettsia, mycoplasma*, transmissible spongiform encephalopathies (TSEs), and parasites before said rearing step.

16. The method of any item or combination of items disclosed herein, further comprising rearing a plurality of additional organisms in the same manner as the organism and performing periodic necropsy, histology, and pathology on the additional organisms to confirm that the closed herd remains free of pathogens and parasites.

17. The method of any item or combination of items disclosed herein, further comprising quarantining said organism for at least two weeks before the harvesting step and screening the organism for detectable levels of pathogens.

18. The method of any item or combination of items disclosed herein, where the quarantining step further comprises physical examination of the organism and one or more tests selected from complete blood count, peripheral blood smear, and fecal exam for parasites.

19. The method of any item or combination of items disclosed herein, wherein the organism is euthanized during the harvesting step and further comprising conducting a necropsy including gross, histopathological, and microbiological evaluation.

20. The method of any item or combination of items disclosed herein, further comprising collecting and cryopreserving tissue samples from at least one of spleen, liver, bone marrow, central nervous system, and lung from the organism at necropsy.

21. The method of any item or combination of items disclosed herein, further comprising collecting plasma and/or cerebrospinal fluid from the organism during the harvesting step.

22. The method of any item or combination of items disclosed herein, further comprising measuring at least one of cell viability in the biological product and biologically active molecules selected from cytokines, hormones, and neurotransmitters secreted or produced by the biological product.

23. The method of any item or combination of items disclosed herein, further comprising cutting said product to a desired size; bathing said cut product in an anti-pathogen bath; and storing said cut and bathed product at a temperature that will preserve said cut and bathed product.

24. The method of any item or combination of items disclosed herein, further comprising applying said product onto a scaffold or at least the same size as the product, rolling said product and said scaffold, placing said rolled product and scaffold into a sterile container, and storing the container at a temperature between about 10° C. to about −80° C.

25. A biological product for clinical xenotransplantation derived from a non-wild type, biologically engineered, swine produced according to the method of any item or combination of items disclosed herein, wherein a cell from the swine has been genetically modified such that it expresses a major histocompatibility complex of a known human sequence or a human recipient of said biological product.

26. The biological product of any item or combination of items disclosed herein, wherein said genome further comprises a disrupted cytidine monophosphate-N-acetylneuraminic acid hydroxylase (CMAH) gene.

27. The biological product of any item or combination of items disclosed herein, wherein said genome further comprises a disrupted β1,4-N-acetylgalactosaminyltransferase gene.

28. The biological product of any item or combination of items disclosed herein-28, wherein said genome further comprises a disrupted cytidine monophosphate-N-acetylneuraminic acid hydroxylase (CMAH) gene.

29. The biological product of any item or combination of items disclosed herein, wherein the cell from the swine has a genome including a scarless exchange of one or more endogenous swine leukocyte antigen alleles with one or more human leukocyte antigen alleles.

30. The biological product of any item or combination of items disclosed herein, wherein the cell from the swine has a genome including replacement of 60-70 nucleotides in length in one or more endogenous swine leukocyte antigens with a corresponding human leukocyte antigen nucleotide region from a known human sequence.

31. The biological product of any item or combination of items disclosed herein, wherein the one or more isotypes are DQ and DR.

32. The biological product of any item or combination of items disclosed herein, wherein the cell from the swine has been genetically reprogrammed at one or more of a Class I HLA, a MHCII, a B cell Fc receptor, glycoprotein galactosyltransferase 1,3 (GGTA1), NOD-like receptor family CARD domain containing 5 (NLRC5) and an immunoglobulin G (IgG).

33. The biological product of any item or combination of items disclosed herein, wherein cells from said genetically modified swine when co-cultured with human peripheral blood mononuclear cells (PBMCs) induce a lower production of cytokine Interleukin 6 (IL-6) and a lower CD8+ T cell immune response as compared to cells from said non-genetically modified counterpart swine, as measured by an in vitro mixed lymphocyte reaction assay.

34. The biological product of any item or combination of items disclosed herein, wherein said genetically modified swine further comprises reduced protein expression of an endogenous gene not expressed in a human and increased protein expression of a gene expressed in a human.

35. A combination product comprising an epidermal autograft product from a human subject and the product of any item or combination of items disclosed herein.

36. A method of preparing biological product for clinical xenotransplantation into a human comprising selecting a known human major histocompatibility complex gene sequence or sequencing a human recipient's major histocompatibility complex gene, genetically modifying cells of a swine to replace a portion of the swine's major histocompatibility complex gene sequence with a corresponding portion of the known human major histocompatibility complex gene sequence or a corresponding portion of the human recipient's major histocompatibility complex gene sequence such that the swine's cells express the corresponding portion of the known human major histocompatibility complex gene sequence or the corresponding portion of the human recipient's major histocompatibility complex gene sequence, isolating one or more cells, tissues, and/or organs from the swine that express the corresponding portion of the known human major histocompatibility complex gene sequence or the corresponding portion of the human recipient's major histocompatibility complex gene sequence, wherein the isolated cells, tissues, and/or organs are the biological product.

37. The method of any item or combination of items disclosed herein wherein the genetically modifying step comprises preparing template major histocompatibility complex sequences, preparing CRISPR-Cas9 plasmids, cloning template major histocompatibility complex sequences into the plasmids, determining CRISPR cleavage sites at the major histocompatibility complex locus in the swine cells, cloning gRNA sequences into one or more CRISPR-Cas9 plasmids, administering CRISPR-Cas9 plasmids into cells of a swine, performing CRIPSR/Cas9 cleavage at the major histocompatibility complex locus of the swine cells, replacing the major histocompatibility complex locus in the swine cells with one or more template major histocompatibility complex sequences matching the corresponding portion of the known human major histocompatibility complex gene sequence or the corresponding portion of the human recipient's major histocompatibility complex gene sequence.

38. The method of any item or combination of items disclosed herein, further comprising sequencing cells of the swine after performing the major histocompatibility complex replacement steps and comparing the sequence of the swine's major histocompatibility complex genes with the known human sequence or the human recipient's major histocompatibility complex genes, and if the major histocompatibility complex sequences in the swine cells have been successfully replaced, isolating one or more cells, tissues, and/or organs from the swine that express the known human sequence or the human recipient's major histocompatibility complex to prepare the biological product.

39. The method of any item or combination of items disclosed herein, further comprising transplanting the biological product from the major histocompatibility complex sequence-replaced swine into the human recipient.

40. The method of any item or combination of items disclosed herein, further comprising breeding major histocompatibility complex sequence-replaced swine for at least one generation to obtain progeny swine, and then isolating one or more cells, tissues, and/or organs from the progeny swine that express the known human sequence or the human recipient's major histocompatibility complex, wherein the isolated cells, tissues, and/or organs are the biological product.

41. The method of any item or combination of items disclosed herein, wherein the genome of said swine comprises a disrupted cytidine monophosphate-N-acetylneuraminic acid hydroxylase (CMAH) gene.

42. The method of any item or combination of items disclosed herein, wherein the genome of said swine comprises a disrupted β1,4-N-acetylgalactosaminyltransferase gene.

43. The method of any item or combination of items disclosed herein, wherein said genome further comprises a disrupted cytidine monophosphate-N-acetylneuraminic acid hydroxylase (CMAH) gene.

44. The method of any item or combination of items disclosed herein, wherein the cell from the swine has a genome including a scarless exchange of one or more endogenous swine leukocyte antigen alleles with one or more human leukocyte antigen alleles.

45. The method of any item or combination of items disclosed herein, wherein the cell from the swine has a genome including replacement of 60-70 nucleotides in length in one or more endogenous swine leukocyte antigens with a corresponding human leukocyte antigen nucleotide region from a known human sequence.

46. The method of any item or combination of items disclosed herein, wherein the human leukocyte antigen nucleotide region from the known human sequence is one or more of DQ and DR, preferably one or more of $DQ_\beta$ and $DR_\beta$.

47. The method of any item or combination of items disclosed herein, wherein the cell from the swine has been genetically reprogrammed at one or more of a Class I HLA, a MHCII, a B cell Fc receptor, glycoprotein galactosyltransferase 1,3 (GGTA1), NOD-like receptor family CARD domain containing 5 (NLRC5) and an immunoglobulin G (IgG).

48. The method of any item or combination of items disclosed herein, wherein cells from said genetically modified swine when co-cultured with human peripheral blood mononuclear cells (PBMCs) induce a lower production of cytokine Interleukin 6 (IL-6) and a lower CD8+ T cell immune response as compared to cells from said non-genetically modified counterpart swine, as measured by an in vitro mixed lymphocyte reaction assay.

49. The method of any item or combination of items disclosed herein, wherein said genetically modified swine further comprises reduced protein expression of an endogenous gene not expressed in a human and increased protein expression of a gene expressed in a human.

50. A genetically reprogrammed swine comprising a nuclear genome having disrupted surface glycan(s), e.g., alpha-1,3 galactosyltransferase gene, and genetically modified such that it expresses a portion of a major histocompatibility complex of a known human sequence or a human recipient of cells, tissue, and/or an organ isolated from the genetically reprogrammed swine and optionally further modified according to any item or combination of items disclosed herein.

51. The genetically reprogrammed swine of any item or combination of items disclosed herein, wherein said genetically reprogrammed swine's genome further comprises a disrupted cytidine monophosphate-N-acetylneuraminic acid hydroxylase (CMAH) gene.

52. The genetically reprogrammed swine of any item or combination of items disclosed herein, wherein said genetically reprogrammed swine's genome further comprises a disrupted β1,4-N-acetylgalactosaminyltransferase gene.

53. The genetically reprogrammed swine of any item or combination of items disclosed herein, comprising a nuclear genome with at least two SLA gene deletions and at least two HLA gene insertions from corresponding portions of HLA genes, wherein the HLA genes are from the known human sequence or the human recipient, from a consensus sequence for a given population group, or from a library sequence.

54. The genetically reprogrammed swine of any item or combination of items disclosed herein, wherein said genome further comprises a disrupted cytidine monophosphate-N-acetylneuraminic acid hydroxylase (CMAH) gene.

55. The genetically reprogrammed swine of any item or combination of items disclosed herein, wherein the cell from the swine has a genome including a scarless exchange of one or more endogenous swine leukocyte antigen alleles with one or more human leukocyte antigen alleles.

56. The genetically reprogrammed swine of any item or combination of items disclosed herein, wherein the cell from the swine has a genome including replacement of 60-70 nucleotides in length in one or more endogenous swine leukocyte antigens with a corresponding human leukocyte antigen nucleotide region from a known human sequence.

57. The genetically reprogrammed swine of any item or combination of items disclosed herein, wherein the human leukocyte antigen nucleotide region from the known human sequence is one or more of DQ and DR, preferably one or more of $DQ_\beta$ and $DR_\beta$.

58. The genetically reprogrammed swine of any item or combination of items disclosed herein, wherein the cell from the swine has been genetically reprogrammed at one or more of a Class I HLA, a MHCII, a B cell Fc receptor, glycoprotein galactosyltransferase 1,3 (GGTA1), NOD-like receptor family CARD domain containing 5 (NLRC5) and an immunoglobulin G (IgG).

59. The genetically reprogrammed swine of any item or combination of items disclosed herein, wherein cells from said genetically modified swine when co-cultured with human peripheral blood mononuclear cells (PBMCs) induce a lower production of cytokine Interleukin 6 (IL-6) and a lower CD8+ T cell immune response as compared to cells from said non-genetically modified counterpart swine, as measured by an in vitro mixed lymphocyte reaction assay.

60. The genetically reprogrammed swine of any item or combination of items disclosed herein, wherein said genetically modified swine further comprises reduced protein expression of an endogenous gene not expressed in a human and increased protein expression of a gene expressed in a human.

61. A method of preparing a genetically reprogrammed swine comprising a nuclear genome having disrupted surface glycan(s), e.g., alpha-1,3 galactosyltransferase gene, and genetically modified such that it expresses a major histocompatibility complex of a known human sequence or a human recipient of a cell, a tissue, and/or an organ isolated from said genetically reprogrammed swine, the method comprising selecting a known human major histocompatibility complex sequence or sequencing the human recipient's major histocompatibility complex gene, obtaining a swine comprising a nuclear genome having at least one disrupted swine surface glycan gene, genetically modifying cells of the swine to replace portions of the swine's major histocompatibility complex gene with corresponding portions of the known human major histocompatibility complex gene or corresponding portions of the human recipient's major histocompatibility complex gene such that the swine's cells express portions of the human recipient's major histocompatibility complex.

62. The method of any item or combination of items disclosed herein, wherein said genetically reprogrammed swine's genome further comprises a disrupted gene encoding β1,4-N-acetylgalactosaminyltransferase.

63. The method of any item or combination of items disclosed herein, wherein said genetically reprogrammed swine comprises a nuclear genome with at least two SLA gene deletions and at least two HLA gene insertions, wherein the HLA genes are from the human recipient, from a consensus sequence for a given population group, or from a library sequence.

64. The method of any item or combination of items disclosed herein, wherein said genome further comprises a disrupted cytidine monophosphate-N-acetylneuraminic acid hydroxylase (CMAH) gene.

65. The method of any item or combination of items disclosed herein, wherein the cell from the genetically reprogrammed swine has a genome including a scarless exchange of one or more endogenous swine leukocyte antigen alleles with one or more human leukocyte antigen alleles.

66. The method of any item or combination of items disclosed herein, wherein the cell from the genetically reprogrammed swine has a genome including replacement of 60-70 nucleotides in length in one or more endogenous swine leukocyte antigen nucleotide regions with a corresponding human leukocyte antigen nucleotide region from a known human sequence.

67. The method of any item or combination of items disclosed herein, wherein the human leukocyte antigen nucleotide region from the known human sequence is one or more of DQ and DR, preferably one or more of $DQ_\beta$ and $DR_\beta$.

68. The method of any item or combination of items disclosed herein, wherein the cell from the swine has been genetically reprogrammed at one or more of a Class I HLA, a MHCII, a B cell Fc receptor, glycoprotein galactosyltransferase 1,3 (GGTA1), NOD-like receptor family CARD domain containing 5 (NLRC5) and an immunoglobulin G (IgG).

69. The method of any item or combination of items disclosed herein, wherein cells from said genetically modified swine when co-cultured with human peripheral blood mononuclear cells (PBMCs) induce a lower production of cytokine Interleukin 6 (IL-6) and a lower CD8+ T cell immune response as compared to cells from said non-genetically modified counterpart swine, as measured by an in vitro mixed lymphocyte reaction assay.

70. The method of any item or combination of items disclosed herein, wherein said genetically modified swine further comprises reduced protein expression of an endogenous gene not expressed in a human and increased protein expression of a gene expressed in a human.

71. A method of delaying, reducing, or preventing rejection, separation, or adverse reactions to xenotransplanted tissues in a human recipient, comprising selecting a known human major histocompatibility complex gene sequence or sequencing the human recipient's major histocompatibility complex gene, obtaining a swine comprising a nuclear genome having disrupted alpha-1,3 galactosyltransferase gene, genetically modifying cells of the swine to replace a portion of the swine's major histocompatibility complex gene with a corresponding portion of the known human major histocompatibility complex gene sequence or the corresponding portion of the human recipient's major histocompatibility complex gene sequence such that the swine's cells express the corresponding portion of the known human major histocompatibility complex gene sequence or the corresponding portion of the human recipient's major histocompatibility complex gene sequence, isolating cells, tissue, and/or an organ from the genetically reprogrammed swine that express the corresponding portion of the known human major histocompatibility complex gene sequence or the corresponding portion of the human recipient's major histocompatibility complex gene sequence, and transplanting the isolated cells, tissue, and/or an organ from the genetically reprogrammed swine into the human recipient.

72. The method of any item or combination of items disclosed herein, wherein said genetically reprogrammed swine's genome further comprises a disrupted β1,4-N-acetylgalactosaminyltransferase gene.

73. The method of any item or combination of items disclosed herein, wherein said genome further comprises a disrupted cytidine monophosphate-N-acetylneuraminic acid hydroxylase (CMAH) gene.

74. The method of any item or combination of items disclosed herein, wherein the cell from the swine has a genome including a scarless exchange of one or more endogenous swine leukocyte antigen alleles with one or more human leukocyte antigen alleles.

75. The method of any item or combination of items disclosed herein, wherein the cell from the swine has a genome including replacement of 60-70 nucleotides in length in one or more endogenous swine leukocyte antigens with a corresponding human leukocyte antigen nucleotide region from a known human sequence.

76. The method of any item or combination of items disclosed herein, wherein the human leukocyte antigen nucleotide region from the known human sequence is one or more of DQ and DR, preferably one or more of $DQ_\beta$ and $DR_\beta$.

77. The method of any item or combination of items disclosed herein, wherein the cell from the swine has been genetically reprogrammed at one or more of a Class I HLA, a MHCII, a B cell Fc receptor, glycoprotein galactosyltransferase 1,3 (GGTA1), NOD-like receptor family CARD domain containing 5 (NLRC5) and an immunoglobulin G (IgG).

78. The method of any item or combination of items disclosed herein, wherein cells from said genetically modified swine when co-cultured with human peripheral blood mononuclear cells (PBMCs) induce a lower production of cytokine Interleukin 6 (IL-6) and a lower CD8+ T cell immune response as compared to cells from said non-genetically modified counterpart swine, as measured by an in vitro mixed lymphocyte reaction assay.

79. The method of any item or combination of items disclosed herein, wherein said genetically modified swine further comprises reduced protein expression of an endogenous gene not expressed in a human and increased protein expression of a gene expressed in a human.

80. A biological product for clinical xenotransplantation derived from a non-wild type, biologically engineered, non-human organism,
wherein said organism from which said biological product is derived is produced through natural breeding and/or assisted reproductive technologies, and
wherein said organism has a biologically engineered genome such that it does not express one or more extracellular surface glycan epitopes, and
wherein said organism is free of at least the following pathogens: *Ascaris* species, *cryptosporidium* species, *Echnococcus*, *Strongyloids sterocolis*, *Toxoplasma gondii*, *Brucella suis*, *Leptospira* species, *mycoplasma hyopneumoniae*, pseudorabies, *Toxoplasma Gondii*, *staphylococcus* species, *Microphyton* species, and *Trichophyton* species, porcine influenza, cytomegalovirus, arterivirus, and coronavirus,
wherein said organism is not transgenic,
wherein said product does not contain one or more extracellular surface glycans,
wherein said product is free of: *Ascaris* species, *cryptosporidium* species, *Echnococcus*, *Strongyloids sterocolis*, *Toxoplasma gondii*, *Brucella suis*, *Leptospira* species, *mycoplasma hyopneumoniae*, pseudorabies, *Toxoplasma Gondii*, staphylococcus species, *Microphyton* species, and *Trichophyton* species, porcine influenza, cytomegalovirus, arterivirus, and coronavirus, wherein said product has not been terminally sterilized, wherein said product is less immunogenic compared to biological product obtained from a xenotransplantation product made from conventional Gal-T knockout swine, from conventional triple knockout swine, from transgenic swine, from wild-type animals, and/or allograft, wherein said product is less antigenic when transplanted into a human xenotransplant recipient as compared to a biological product obtained from a xenotransplantation product made from conventional Gal-T knockout swine, from conventional triple knockout swine, from transgenic swine, from wild-type animals, and/or allograft, and wherein said product is biologically active and comprises live cells and tissues capable of vascularizing after xenotransplantation.

81. The product of any item or combination of items disclosed herein, wherein said product is resistant to rejection by a human xenotransplant recipient in the absence of administration of immunosuppressant drugs or other immunosuppressant therapies to the transplant recipient.

82. The product of any item or combination of items disclosed herein, wherein said product comprises an organ or tissue.

83. The product of any item or combination of items disclosed herein, wherein said organ comprises a liver, a lung, a kidney, or skin.

84. The product of any item or combination of items disclosed herein, wherein said tissue comprises a nerve.

85. The product of any item or combination of items disclosed herein, wherein said organ is capable of vascularizing in the region of the transplant in said patient following said xenotransplantation.

86. The product of any item or combination of items disclosed herein, wherein said skin is capable of promoting collagen production in the region of the transplant in said patient following said xenotransplantation.

87. The product of any item or combination of items disclosed herein, wherein said organism has a genome with at least one further disrupted gene selected from the group consisting of genes encoding: cytidine monophosphate-N-acetylneuraminic acid hydroxylase (CMAH), β1-4 N-acetylgalactosaminyltransferase, swine leukocyte antigens, alpha-1,2-fucosyltransferase, cytotoxic T lymphocyte-associated antigen, tumor necrosis factor-alpha-related apoptosis-inducing ligand (TRAIL), Fas ligand (Fas L), CD55, CD59, and CD46.

88. The product of any item or combination of items disclosed herein, wherein said organism has a genome with at least one further modification to express at least one protein selected from the group consisting of: human leukocyte antigens, MHC type I; MHC type II; hCD46-human membrane cofactor protein (MCP); hCTLA4-Ig-human cytotoxic T-murine lymphocyte antigen 4 fused with Ig heavy chains; hCD55-human decay-accelerating factor (DAF); hCD59-human protectin; H-transferase; hTM-human thrombomodulin; hA20-tumor necrosis factor-alpha-(TNF-alpha)-inducible gene; HLA-E/beta-microglobulin; human heme oxygenase-1 (hHO-1).

89. The product of any item or combination of items disclosed herein, wherein the product is biologically active and comprises live cells and tissues capable of vascularizing after cryopreservation at a temperature at or below −40° C. for at least one year.

90. The product of any item or combination of items disclosed herein, wherein said product is free of at least two of *Ascaris* species, *Cryptosporidium*, *Echinococcus*, *Strongyloids sterocolis*, *Toxoplasma gondii*, *Brucella suis*, *Leptospira* species, *Mycoplasma hyopneumoniae*, Porcine Reproductive and Respiratory Syndrome Virus (PRRSV), Pseudorabies, *Toxoplasma Gondii*, Porcine Influenza A virus, *Bordetella bronchiseptica*, staphylococci, *Microphyton* species, *Trichophyton* species, adenovirus, arbovirus, bovine viral diarrhea virus, calicivirus, cardiovirus, circovirus 2, circovirus 1, encephalomyocarditis virus, eperythero-zoon, *haemophilus* suis, herpes and herpes-related viruses, iridovirus, kobuvirus, leptospirillum, *listeria*, *mycobacterium* TB, *mycoplasma*, orthomyxovirus, papovirus, parainfluenza virus 3, paramyxovirus, parvovirus, pasavirus-1, pestivirus, picobirnavirus (PBV), picornavirus, porcine circovirus-like virus, porcine astrovirus, porcine bacovirus, porcine bocavirus-2, porcine bocavirus-4, porcine enterovirus-9, porcine epidemic diarrhea virus (PEDV), porcine polio virus, porcine lymphotropic herpes virus (PLHV), porcine stool associated circular virus (PoSCV), posavirus-1, pox virus, rabies-related viruses, reovirus, rhabdovirus, *rickettsia*, sapelovirus, sapovirus, *staphylococcus hyicus*, suipoxvirus, teschen, torovirus, torque teno sus virus-2 (TTSuV-2), transmissible gastroenteritus virus, vesicular stomatitis virus, and prions.

91. A method for the production of a second-generation non-wild type, biologically engineered piglet, comprising:
  delivering a non-wild type, biologically engineered piglet from a pregnant sow through Cesarean section, wherein said sow was produced through natural breeding and/or assisted reproductive technologies, and
  holding said delivered piglet in an isolated closed herd wherein all other pigs in the isolated closed herd are confirmed to be free of at least the following pathogens: cytomegalovirus, arterivirus, and coronavirus, and wherein said piglet is free of at least the following pathogens: cytomegalovirus, arterivirus, and coronavirus;
  rearing said piglet in said isolated closed herd;
  mating said piglet, upon sexual maturity, with another pig that is also maintained in said isolated closed herd and free of said pathogens; and
  delivering a new piglet resulting from said mating, wherein said new piglet is the second-generation non-wild type, biologically engineered piglet that is also free of said pathogens.

92. A pig produced by the method of item 91 or any item or combination of items disclosed herein.

93. The method of item 92 or any item or combination of items disclosed herein, which further comprises harvesting a biological product from said new piglet.

94. The method of item 93 or any item or combination of items disclosed herein, wherein said product comprises an organ or tissue.

95. The method of item 94 or any item or combination of items disclosed herein, wherein said organ comprises a liver, lung, kidney, or skin.

96. The method of item 95 or any item or combination of items disclosed herein, wherein said tissue comprises a nerve.

97. The method of item 92 or any item or combination of items disclosed herein, wherein said non-wild type, biologically engineered piglet has a genome with a disrupted alpha-1,3 galactosyltransferase gene.

98. The method of any one of items 92 and 94-98 or any item or combination of items disclosed herein, wherein said second-generation non-wild type, biologically engineered piglet has a genome with at least one further disrupted gene selected from the group consisting of genes encoding: cytidine monophosphate-N-acetylneuraminic acid hydroxylase (CMAH), β1-4 N-acetylgalactosaminyltransferase, swine leukocyte antigens, alpha-1,2-fucosyltransferase, cytotoxic T lymphocyte-associated antigen, tumor necrosis factor-alpha-related apoptosis-inducing ligand (TRAIL), Fas ligand (Fas L), CD55, CD59, and CD46.

99. The method of any one of items 92 and 94-99 or any item or combination of items disclosed herein, wherein said second-generation non-wild type, biologically engineered piglet has a genome with at least one further modification to express at least one protein selected from the group consisting of: human leukocyte antigens, MHC type I; MHC type II; hCD46-human membrane cofactor protein (MCP); hCTLA4-Ig-human cytotoxic T-murine lymphocyte antigen 4 fused with Ig heavy chains; hCD55-human decay-accelerating factor (DAF); hCD59-human protectin; H-transferase; hTM-human thrombomodulin; hA20-human tumor necrosis factor-alpha-(TNF-alpha)-inducible gene; HLA-E/beta-microglobulin; human heme oxygenase-1 (hHO-1).

100. The method of any one of items 92 and 94-100 or any item or combination of items disclosed herein, further comprising after each of said delivering steps, placing each of the non-wild type, biologically engineered piglet and the second-generation non-wild type, biologically engineered piglet in a warmed sterilization agent solution bath.

101. The method of any one of items 92 and 94-101 or any item or combination of items disclosed herein, wherein the non-wild type, biologically engineered piglet and the second-generation non-wild type, biologically engineered piglet are maintained in a closed herd such that the non-wild type, biologically engineered piglet, the second-generation non-wild type, biologically engineered piglet, and human care personnel are quarantined from contact with any pigs and pig housing facilities outside of the closed herd.

102. The method of any one of items 92 and 94-102 or any item or combination of items disclosed herein, further comprising administering one or more anti-microbial agents and one or more vaccines to the non-wild type, biologically engineered piglet and the second-generation non-wild type, biologically engineered piglet.

103. The method of any one of items 92 and 94-103 or any item or combination of items disclosed herein, further comprising irradiation sterilizing bedding and feed for the non-wild type, biologically engineered piglet and the second-generation non-wild type, biologically engineered piglet.

104. The method of any one of items 92 and 94-104 or any item or combination of items disclosed herein, further comprising the non-wild type, biologically engineered piglet and the second-generation non-wild type, biologically engineered piglet with sterile or purified water and a grain-based feed that does not contain animal proteins or cattle-based material.

105. A method of treating a human subject who has suffered an injury requiring a skin graft, the method comprising transplanting a skin graft from a second-generation non-wild type, biologically engineered piglet to the subject, wherein the second-generation non-wild type, biologically engineered piglet is produced by the method of item 92 or any item or combination of items disclosed herein, wherein the skin graft is free of at least the following pathogens: cytomegalovirus, arterivirus, and coronavirus, wherein immunosuppressant drugs or other immunosuppressant therapies are not administered to the subject.

106. The method of item 106 or any item or combination of items disclosed herein, further comprising monitoring the skin graft for clinical signs of rejection, after detection of one or more clinical signs of rejection of the skin graft, removing the skin graft and replacing it with an allogeneic skin graft or an autologous skin graft.

107. The method of item 107 or any item or combination of items disclosed herein, wherein the one or more clinical signs of rejection are selected from the group consisting of lack or loss a vascularization; sloughing; white color; darker or pale color compared to normal skin; cooler temperature as compared to normal skin; granulation; crust or scab formation; discharge; and loss or lessening of pliability.

108. The method of any one of items 106-108 or any item or combination of items disclosed herein, wherein the injury is a partial thickness wound or a full thickness wound.

109. The method of any one of items 106-108 or any item or combination of items disclosed herein, wherein the injury comprises burns; avulsed skin; diabetic wounds; and/or venous stasis ulcers.

110. A method of treating a subject in need of a functioning liver comprising: obtaining a liver derived from a piglet made according to any one of items 92 and 94-105 or a swine made according to of any one of items 37-50 or any item or combination of items disclosed herein, creating an extracorporeal circuit between said subject and said liver, such that blood from said subject is capable of flowing through said liver and back to said subject; and permitting blood to flow from said subject through said extracorporeal circuit through said liver and back to said subject.

111. An undifferentiated cell for clinical xenotransplantation derived from a piglet made according to of any one of items 92 and 94-105 or a swine made according to of any one of items 37-50 or any item or combination of items disclosed herein, wherein said cell is capable of being utilized in a regenerative therapy to generate an organ or biological tissue.

112. A method for the xenotransplantation of a product into a human patient comprising:
obtaining the biological product of item 1; and
transplanting said product into a human recipient, wherein upon said transplantation, said product exhibits a clinical benefit.

113. The method of item 113 or any item or combination of items disclosed herein, wherein said product comprises an organ or tissue.

114. The method of item 114 or any item or combination of items disclosed herein, wherein said organ comprises a liver, lung, kidney or skin.

115. The method of item 115 or any item or combination of items disclosed herein, wherein said tissue comprises a nerve.

116. The method of any one of items 113-116 or any item or combination of items disclosed herein, wherein said transplanting step is performed in the absence of immunosuppressant drugs or other immunosuppressant therapies.

117. The method of item 115 or any item or combination of items disclosed herein, wherein the organ is skin and further comprising debriding the transplantation site before the transplanting step.

118. The method of item 115 or item 118 or any item or combination of items disclosed herein, wherein said skin vascularizes in the region of the transplant in said patient following said xenotransplantation.

119. The method of any one of items 115, and 118-119 or any item or combination of items disclosed herein, wherein said skin produces collagen in the region of the transplant in said patient following said xenotransplantation.

120. The method of any one of items 113-120 or any item or combination of items disclosed herein, wherein said clinical benefit is enhanced above an allograft product, wherein the clinical benefit compared to the allograft product is one or more of: decreased graft dislocation; increased graft adherence; granulation at level with surrounding tissue; less than 20% hyper-granulation; hematoma less than 20% of wound size; fibrin deposition of less than 20% of wound size; reduced bacterial infection compared to allograft; increased hemostasis; induced expression of at least one of transforming growth factors (TGFs), fibroblast growth factors (FGFs), epidermal growth factor (EGF), Insulin-like Growth Factor (IGF-1), Platelet-derived Growth Factors (PDGFs), and vascular endothelial growth factors (VEGFs); increased attraction and/or proliferation of at least one of human fibroblasts, human epidermal keratinocytes, human endothelial cells, and human pluripotent stem cells; inhibiting at least one of MMP-1, MMP-2, MMP-3, MMP-8, and MMP-9; treating, reducing or inhibiting at least one of hyperglycemia, neuropathy, vasculopathy, infection, fibrin cuff, and/or venous hypertension; reduced cellulitis; reduced erythema; reduced edema; reduced hyperesthesia; reduced induration; reduced tenderness; reduced itching; reduced abscesses; reduced incidence of toxic shock syndrome; reduced colonization of toxin-1 producing *S. aureus*; reduced incidence of sepsis; and reduced colonization by at least one of *E. coli, P. aeruginosa, Klebsiella* spp., *Providencia* spp., enterobacteriaceae, and *C. albicans*.

121. The method of any one of items 113-121 or any item or combination of items disclosed herein, wherein said organism from which said biological product is derived is produced through natural breeding and/or assisted reproductive technologies.

122. The method of any one of items 113-122 or any item or combination of items disclosed herein, wherein the non-human organism is genetically modified to disrupt at least one further disrupted gene selected from the group consisting of genes encoding: cytidine monophosphate-N-acetyl-neuraminic acid hydroxylase (CMAH), β1-4 N-acetylgalactosaminyltransferase, swine leukocyte antigens, alpha-1,2-fucosyltransferase, cytotoxic T lymphocyte-associated antigen, tumor necrosis factor-alpha-related apoptosis-inducing ligand (TRAIL), Fas ligand (Fas L), CD55, CD59, and CD46.

123. The method of any one of items 113-123 or any item or combination of items disclosed herein, wherein the non-human organism has a genome with at least one further modification to express at least one protein selected from the group consisting of: human leukocyte antigens, MHC type I; MHC type II; hCD46-human membrane cofactor protein (MCP); hCTLA4-Ig-human cytotoxic T-murine lymphocyte antigen 4 fused with Ig heavy chains; hCD55-human decay-accelerating factor (DAF); hCD59-human protectin; H-transferase; hTM-human thrombomodulin; hA20-tumor necrosis factor-alpha-(TNF-alpha)-inducible gene; HLA-E/beta-microglobulin; human heme oxygenase-1 (hHO-1).

124. The method of any one of items 113-124 or any item or combination of items disclosed herein, wherein the clinical benefit comprises forming an occlusive fibrin seal, reducing or preventing infection at the transplantation site or the healing site, increasing or retaining fluids at the transplantation site or the healing site, increasing or retaining electrolytes at the transplantation site or the healing site, increasing or retaining temperature homeostasis at the transplantation site or the healing site, reducing scarring at the transplantation site or the healing site, reducing or eliminating sepsis, reduce or eliminate protein losses, restoring bodily functions, or a combination thereof.

125. The method of any one of items 113-125 or any item or combination of items disclosed herein, wherein the transplanted product is resistant to rejection by the human recipient in the absence of administration of immunosuppressant drugs or other immunosuppressant therapies to the human recipient.

126. The method of any one of items 113-126 or any item or combination of items disclosed herein, further comprising performing one or more of toe-blood pressure readings, pulse volume recordings, transcutaneous oxygen measurements, and skin perfusion pressure measurements, or further comprising treating the human recipient after said transplanting step
with compression therapy, vacuum assisted closure (VAC), offloading, negative pressure, hyperbaric oxygen therapy, or a combination thereof.

127. A method of producing a biological product for xenotransplantation into a human recipient, said biological product comprising live cells and tissues that vascularize after xenotransplantation,
the method comprising:
A) producing a non-wild type, biologically engineered swine, wherein said swine has a biologically engineered genome such that it does not express one or more extracellular surface glycan epitopes,
B) confirming that said swine is free of at least the following zoonotic pathogens:
(i) *Ascaris* species, *cryptosporidium* species, *Echinococcus, Strongyloids sterocolis*, and *Toxoplasma gondii* in fecal matter;
(ii) *Leptospira* species, *Mycoplasma hyopneumoniae*, porcine reproductive and respiratory syndrome virus (PRRSV), pseudorabies, transmissible gastroenteritis virus (TGE)/Procine Respiratory Coronavirus, and *Toxoplasma Gondii* by determining antibody titers;
(iii) Porcine Influenza;
(iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), *Microphyton* and *Trichophyton* spp.;
(v) Porcine cytomegalovirus; and
(vi) *Brucella suis;*
C) maintaining the swine according to a bioburden-reducing procedure, said procedure comprising maintaining the swine in an isolated closed herd, wherein all other animals in the isolated closed herd are confirmed to be free of said zoonotic pathogens, wherein the swine is isolated from contact with any non-human animals and animal housing facilities outside of the isolated closed herd;
D) harvesting a biological product from said swine, wherein said harvesting comprises euthanizing the swine and aseptically removing the biological product from the swine;
E) processing said biological product comprising sterilization after harvesting using a sterilization process that does not reduce cell viability to less than 50% cell viability as determined by a 3-(4,5-dimethylthiazol-2-yl)-2,5-diphenyltetrazolium bromide (MTT)-reduction assay; and F) storing said biological product in a sterile container under storage conditions that preserve cell viability.

128. The method of item 127 or any item or combination of items disclosed herein, which does not include terminally sterilizing the biological product, wherein said biological product is free of *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

129. The method of item 127 or item 128 or any item or combination of items disclosed herein, wherein before step F), the method further comprises testing said processed biological product via:
   a. conducting a sterility assay and confirming that aerobic and anaerobic bacteria do not grow in the sterility assay
   b. conducting a *mycoplasma* assay and confirming that *mycoplasma* colonies do not grow in the *mycoplasma* assay,
   c. conducting an endotoxin assay and confirming that the biological product is free of endotoxins in the endotoxin assay,
   d. conducting the MTT-reduction assay and confirming that the product has at least 50% cell viability in the MTT-reduction assay,
   e. conducting flow cytometry and confirming that the product does not have galactosyl-a-1,3-galactose epitopes as determined by the flow cytometry,
   f. conducting pathogen-detection assays specific for 18 to 35 pathogens and confirming that the product is free of *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

130. The method of any one or combination of items 127-129 or any item or combination of items disclosed herein, wherein the biological product is free of two or more types of extracellular surface glycan epitopes as confirmed by flow cytometry.

131. The method of any one or combination of items 127-130 or any item or combination of items disclosed herein, wherein the biological product is free of alpha-1,3-galactosyltransferase epitopes and N-glycolylneuraminic acid epitopes as confirmed by flow cytometry.

132. The method of any one or combination of items 127-131 or any item or combination of items disclosed herein, wherein the biological product is free of alpha-1,3-galactosyltransferase epitopes, N-glycolylneuraminic acid epitopes, and β1,4-N-acetylgalactosaminyltransferase epitopes as confirmed by flow cytometry.

133. The method of any one or combination of items 127-132 or any item or combination of items disclosed herein, wherein said swine is produced through natural intercourse by parent swine also maintained in the isolated closed herd and also free of the following pathogens: *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*, and wherein said swine is birthed through live vaginal birth.

134. The method of any one or combination of items 127-133 or any item or combination of items disclosed herein, wherein following said live vaginal birth said swine is hand reared by one or more humans.

135. The method of any one or combination of items 127-134 or any item or combination of items disclosed herein, further comprising rearing a plurality of additional swine in the same manner as the swine and performing periodic necropsy, histology, and pathology on the additional swine to confirm that the closed herd remains free of *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

136. The method of any one or combination of items 127-135 or any item or combination of items disclosed herein, further comprising feeding the swine sterile or purified water and a grain-based feed that does not contain animal proteins or cattle-based material and irradiation sterilizing bedding, cages, and feed for the swine.

137. The method of any one or combination of items 127-136 or any item or combination of items disclosed herein, further comprising conducting a necropsy including gross, histopathological, and microbiological evaluation after the harvesting step and collecting and cryopreserving tissue samples from at least one of spleen, liver, bone marrow, central nervous system, and lung from the swine at necropsy.

138. The method of any one or combination of items 127-137 or any item or combination of items disclosed herein, wherein said biologically engineered genome further comprises a disrupted cytidine monophosphate-N-acetylneuraminic acid hydroxylase (CMAH) gene.

139. The method of any one or combination of items 127-138 or any item or combination of items disclosed herein, wherein said biologically engineered genome further comprises a disrupted β1,4-N-acetylgalactosaminyltransferase gene.

140. The method of any one or combination of items 127-139 or any item or combination of items disclosed herein, wherein said biologically engineered genome further comprises scarless exchange of one or more endogenous swine leukocyte antigen alleles with one or more human leukocyte antigen alleles.

141. The method of any one or combination of items 127-140 or any item or combination of items disclosed herein, wherein said biologically engineered genome further comprises replacement of 50-70 nucleotides in length in one or more endogenous swine leukocyte antigens with a corresponding human leukocyte antigen nucleotide region.

142. The method of any one or combination of items 127-141 or any item or combination of items disclosed herein, wherein the corresponding human leukocyte antigen nucleotide region is $DQ_\beta$, in combination with HLA-E, HLA-G, or both HLA-E and HLA-G.

143. The method of any one or combination of items 127-142 or any item or combination of items disclosed herein, wherein the biologically engineered genome has been genetically reprogrammed at one or more of a Class I human leukocyte antigen (HLA), a major histocompatibility complex (MHC) II, a B cell Fc receptor, glycoprotein galactosyltransferase 1,3 (GGTA1), NOD-like receptor family CARD domain containing 5 (NLRC5) and an immunoglobulin G (IgG).

144. The method of any one or combination of items 127-143 or any item or combination of items disclosed herein, wherein the biological product when co-cultured with human peripheral blood mononuclear cells (PBMCs) induces a lower production of cytokine Interleukin 6 (IL-6) and a lower CD8+ T cell immune response as compared to cells from said non-genetically modified counterpart swine, as measured by an in vitro mixed lymphocyte reaction assay.

145. The method of any one or combination of items 127-144 or any item or combination of items disclosed herein, wherein the biologically engineered genome comprises a nuclear genome with swine leukocyte antigen (SLA) deletions and HLA insertions, wherein the HLA genes are from the human recipient, from a consensus sequence for a given population group, or from a library sequence.

146. The method of any one or combination of items 127-145 or any item or combination of items disclosed herein, further comprising biologically reprogramming the swine's genome by preparing template major histocompatibility complex sequences, preparing CRISPR-Cas9 plasmids, cloning template major histocompatibility complex sequences into the plasmids, determining CRISPR cleavage sites at the major histocompatibility complex locus in the swine cells, cloning gRNA sequences into one or more CRISPR-Cas9 plasmids, administering CRISPR-Cas9 plasmids into cells of the swine, performing CRIPSR/Cas9 cleavage at the major histocompatibility complex locus of the swine cells, replacing the major histocompatibility complex locus in the swine cells with one or more template major histocompatibility complex sequences from a human template major histocompatibility complex sequence.

147. The method of any one or combination of items 127-146 or any item or combination of items disclosed herein, further comprising, prior to step A),
a. obtaining a candidate swine group from more than one swine from outside of the closed herd accompanied with a health record, pedigree, and genetic test results, and housing the more than one swine from outside of the closed herd in a quarantine intake area for at least 7 days, and wherein swine in the candidate swine group are non-wild type, biologically engineered swine having biologically engineered genomes such that they do not express one or more extracellular surface glycan epitopes,
b. screening the more than one swine from outside of the closed herd for infections to identify any swine that should be removed from the candidate swine group,
c. removing any identified swine from the candidate swine group to form a screened candidate swine group,
d. moving the screened candidate swine group to a holding area held wherein the swine is isolated from contact with any non-human animals and animal housing facilities outside of the holding area,
e. mating the screened candidate swine in the holding area,
f. delivering a non-wild type, biologically engineered piglet from a pregnant sow through Cesarean section, wherein said sow was produced through natural breeding and/or assisted reproductive technologies, and
g. holding said delivered piglet in an isolated closed herd wherein all other pigs in the isolated closed herd are confirmed to be free of at least the following pathogens: cytomegalovirus, arterivirus, and coronavirus, and wherein said piglet is free of at least the following pathogens: *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*, and then performing step A) of item 127.

148. The method of any one or combination of items 127-147 or any item or combination of items disclosed herein, wherein said piglet has a genome comprising a disrupted: (i) alpha-1,3 galactosyltransferase gene; (ii) cytidine monophosphate-N-acetylneuraminic acid hydroxylase (CMAH) gene; (iii) β1,4-N-acetylgalactosaminyltransferase gene; (i) and (ii); (i) and (iii); or (i), (ii), and (iii).

149. The method of any one or combination of items 127-148 or any item or combination of items disclosed herein, wherein said sterilization process does not include terminally sterilizing the biological product, and wherein said sterilization process comprises at least one of exposing the harvested biological product to UV-C radiation and bathing the harvested biological product in an anti-pathogen bath.

150. A method for the xenotransplantation of a product into a xenotransplant recipient comprising:
obtaining the biological product produced by the method of any preceding item;
transplanting said biological product into a xenotransplant recipient;
monitoring said recipient for at least one of:
  a. vascularization of the biological product;
  b. rejection of the biological product;
  c. increase in an immunogenic biomarker; and
  wherein upon said transplantation, said biological product exhibits a clinical benefit in the xenotransplant recipient.

151. The method of item 150 or any item or combination of items disclosed herein, wherein said transplanting step is performed in the absence of immunosuppressants.

152. The method of item 150 or item 151 or any item or combination of items disclosed herein, wherein said clinical benefit is enhanced above an allograft product, wherein the clinical benefit compared to the allograft product is one or more of: decreased graft dislocation; increased graft adherence; granulation at level with surrounding tissue; less than 20% hyper-granulation; hematoma less than 20% of wound size; fibrin deposition of less than 20% of wound size; reduced bacterial infection compared to allograft; increased hemostasis; induced expression of at least one of transforming growth factors (TGFs), fibroblast growth factors (FGFs), epidermal growth factor (EGF), Insulin-like Growth Factor (IGF-1), Platelet-derived Growth Factors (PDGFs), and vascular endothelial growth factors (VEGFs); increased attraction and/or proliferation of at least one of human fibroblasts, human epidermal keratinocytes, human endothelial cells, and human pluripotent stem cells; inhibiting at least one of MMP-1, MMP-2, MMP-3, MMP-8, and MMP-9; treating, reducing or inhibiting at least one of hyperglycemia, neuropathy, vasculopathy, infection, fibrin cuff, and/or venous hypertension; reduced cellulitis; reduced erythema; reduced edema; reduced hyperesthesia; reduced induration; reduced tenderness; reduced itching; reduced abscesses; reduced incidence of toxic shock syndrome; reduced colonization of toxin-1 producing *S. aureus*; reduced incidence of sepsis; and reduced colonization by at least one of *E. coli, P. aeruginosa, Klebsiella* spp., *Providencia* spp., enterobacteriaceae, and *C. albicans*.

153. The method of any one or combination of items 150-152 or any item or combination of items disclosed herein, wherein, after the transplanting step, the xenotransplant recipient has serum IgM and IgG levels of 1,000 to 20,000 µg/ml.

154. The method of any one or combination of items 150-153 or any item or combination of items disclosed herein, wherein, after the transplanting step, the xenotransplant recipient has a serum IgM level of 1,000 to 5,000 µg/ml.

155. The method of any one or combination of items 150-154 or any item or combination of items disclosed herein, wherein, after the transplanting step, the xenotransplant recipient has a serum IgG level of 8,000 to 15,000 µg/ml.

156. The method of any one or combination of items 150-155 or any item or combination of items disclosed herein, wherein, after the transplanting step, the xenotransplant recipient has serum IgM and IgG levels below serum IgM and IgG levels measured prior to transplantation or less than 10% higher than serum IgM and IgG levels measured prior to transplantation.

157. The method of any one or combination of items 150-156 or any item or combination of items disclosed herein, wherein, after the transplanting step, the xenotransplant recipient has a serum IgM level 20% to 50% lower than the xenotransplant recipient's serum IgM level measured prior to transplantation.

158. The method or product of any preceding item, wherein said product has at least 50%, 55%, 60%, 65%, 70%, 75%, 80%, 85%, 90%, 95%, 98%, or 99% mitochondrial activity.

159. The method or product of any preceding item, wherein said product has at least 50%, 55%, 60%, 65%, 70%, 75%, 80%, or 85% cell viability in a 3-(4,5-dimethylthiazol-2-yl)-2,5-diphenyltetrazolium bromide (MTT)-reduction assay.

160. The method, product, or swine of any preceding item, wherein the donor animal, e.g., swine, has a modified genome such that genes encoding sugar surface glycans and MHC I are knocked out.

161. The method, product, or swine of any preceding item, wherein the donor animal, e.g., swine, has a modified genome such that genes encoding MHC Class II DP, DQ, and $DR_\alpha$ are knocked out.

162. The method, product, or swine of any preceding item, wherein the donor animal, e.g., swine, has a modified genome such that genes encoding MHC Class II DP, DQ, and $DR_\alpha$ are knocked out and $DR_\beta$ is replaced with a human $DR_\beta$ gene sequence.

163. The method, product, or swine of any preceding item, wherein the donor animal, e.g., swine, has a modified genome such that genes encoding MHC Class II DQ, DR, and $DP_\alpha$ are knocked out.

164. The method, product, or swine of any preceding item, wherein the donor animal, e.g., swine, has a modified genome such that genes encoding MHC Class II DQ, DR, and $DP_\alpha$ are knocked out and $DP_\beta$ is replaced with a human $DP_\beta$ gene sequence.

165. The method, product, or swine of any preceding item, wherein the donor animal, e.g., swine, has a modified genome such that genes encoding MHC Class II DR, DP, and $DQ_\alpha$ are knocked out.

166. The method, product, or swine of any preceding item, wherein the donor animal, e.g., swine, has a modified genome such that genes encoding MHC Class II DR, DP, and $DQ_\alpha$ are knocked out and $DQ_\beta$ is replaced with a human $DQ_\beta$ gene sequence.

167. The method, product, or swine of any preceding item, wherein the donor animal, e.g., swine, has a modified genome such that genes encoding MHC Class I are knocked out and genes encoding MHC Class II $DQ_\alpha$ and $DQ_\beta$ are knocked out and $DR_\alpha$ and $DR_\beta$ are replaced with human $DR_\alpha$ and $DR_\beta$ gene sequences.

168. The method, product, or swine of any preceding item, wherein the donor animal, e.g., swine, has a modified genome such that genes encoding MHC Class I are knocked out and genes encoding MHC Class II $DR_\alpha$ and $DR_\beta$ are knocked out and $DQ_\alpha$ and $DQ_\beta$ are replaced with human $DQ_\alpha$ and $DQ_\beta$ gene sequences.

169. The method, product, or swine of any preceding item, wherein the donor animal, e.g., swine, has a modified genome such that genes encoding MHC Class I are knocked out, a gene encoding HLA-A is knocked-in, and genes encoding MHC Class II $DQ_\alpha$ and $DQ_\beta$ are knocked out and $DR_\alpha$ and $DR_\beta$ are replaced with human $DR_\alpha$ and $DR_\beta$ gene sequences.

170. The method, product, or swine of any preceding item, wherein the donor animal, e.g., swine, has a modified genome such that genes encoding MHC Class I are knocked out, a gene encoding HLA-A is knocked-in, and genes encoding MHC Class II $DR_\alpha$ and $DR_\beta$ are knocked out and $DQ_\alpha$ and $DQ_\beta$ are replaced with human $DQ_\alpha$ and $DQ_\beta$ gene sequences.

171. The method, product, or swine of any preceding item, wherein the donor animal, e.g., swine, has a modified genome such that genes encoding MHC Class I are knocked out, a gene encoding HLA-B is knocked-in, and genes encoding MHC Class II $DQ_\alpha$ and $DQ_\beta$ are knocked out and $DR_\alpha$ and $DR_\beta$ are replaced with human $DR_\alpha$ and $DR_\beta$ gene sequences.

172. The method, product, or swine of any preceding item, wherein the donor animal, e.g., swine, has a modified genome such that genes encoding MHC Class I are knocked out, a gene encoding HLA-B is knocked-in, and genes encoding MHC Class II $DR_\alpha$ and $DR_\beta$ are knocked out and $DQ_\alpha$ and $DQ_\beta$ are replaced with human $DQ_\alpha$ and $DQ_\beta$ gene sequences.

173. The method, product, or swine of any preceding item, wherein the donor animal, e.g., swine, has a modified genome such that genes encoding MHC Class I are knocked out, genes encoding HLA-A and HLA-B are knocked-in, and genes encoding MHC Class II $DQ_\alpha$ and $DQ_\beta$ are knocked out and $DR_\alpha$ and $DR_\beta$ are replaced with human $DR_\alpha$ and $DR_\beta$ gene sequences.

174. The method, product, or swine of any preceding item, wherein the donor animal, e.g., swine, has a modified genome such that genes encoding MHC Class I are knocked out, genes encoding HLA-A and HLA-B are knocked-in, and genes encoding MHC Class II $DR_\alpha$ and $DR_\beta$ are knocked out and $DQ_\alpha$ and $DQ_\beta$ are replaced with human $DQ_\alpha$ and $DQ_\beta$ gene sequences.

175. The method, product, or swine of any preceding item, wherein the donor animal, e.g., swine, has a modified genome such that genes encoding MHC Class I are knocked out and a gene encoding HLA-A is knocked-in.

176. The method, product, or swine of any preceding item, wherein the donor animal, e.g., swine, has a modified genome such that genes encoding MHC Class I are knocked out and a gene encoding HLA-B is knocked-in.

177. The method, product, or swine of any preceding item, wherein the donor animal, e.g., swine, has a modified genome such that genes encoding MHC Class I are knocked out and a gene encoding HLA-C is knocked-in.

178. The method, product, or swine of any preceding item, wherein the donor animal, e.g., swine, has a modified genome such that genes encoding MHC Class I are knocked out, genes encoding HLA-A, HLA-B and HLA-C are knocked-in, and genes encoding MHC Class II $DR_\alpha$ and $DR_\beta$ are replaced with human $DR_\alpha$ and $DR_\beta$ gene sequences and MHC Class II $DQ_\alpha$ and $DQ_\beta$ are replaced with human $DQ_\alpha$ and $DQ_\beta$ gene sequences.

179. The method, product, or swine of any preceding item, wherein the donor swine has a modified genome to knock-out: swine genes corresponding to HLA-A, HLA-B, HLA-C, and DR, and to knock-in: HLA-C; HLA-E; and HLA-G.

180. The method, product, or swine of any preceding item, wherein the donor swine has a modified genome to knock-out: swine genes corresponding to HLA-A, HLA-B, HLA-C, HLA-F, DQ, and DR, and to knock-in: HLA-C, HLA-E, HLA-G.

181. The method, product, or swine of any preceding item, wherein the donor swine has a modified genome to knock-out: swine genes corresponding to HLA-A, HLA-B, HLA-C, HLA-F, DQ, and DR, and to knock-in: HLA-C, HLA-E, HLA-G, HLA-F, and DQ.

182. The method, product, or swine of any preceding item, wherein the donor swine has a modified genome to knock-out: SLA-11; SLA-6,7,8; SLA-MIC2; and SLA-DQA; SLA-DQB1; SLA-DQB2, and to knock-in: HLA-C; HLA-E; HLA-G; and HLA-DQ.

183. The method, product, or swine of any preceding item, wherein the reprogramming is performed using a RNA-guided clustered regularly interspersed short palindromic repeats (CRISPR)/CRISPR-associated (Cas) (CRISPR/Cas) nuclease system, a CRISPR/Cas dual nickase system, a zinc finger nuclease (ZFN), a transcription activator-like effector nuclease (TALEN), a meganuclease, a fusion protein comprising a programmable DNA binding domain linked to a nuclease domain (i.e., generates a double-stranded DNA break), and combinations thereof.

184. The method or product of any preceding item, wherein the biological product has an antigenic profile and an immunogenic profile such that it is resistant to rejection by the human recipient's immune system in the absence of administration of immunosuppressant drugs to the human recipient.

The present invention is described in further detail in the following examples which are provided to be illustrative only, and are not intended to limit the scope of the invention.

Example 1

DPF Closed Colony Skin Graft (Monkey Studies)

It has been discovered that skin grafts derived from a DPF Closed Colony, α-1,3-galactosyltransferase [Gal-T] knock-out pigs produced in accordance with the present invention exhibit significantly longer rejection times than skin grafts derived from α-1,3-galactosyltransferase [Gal-T] knockout pigs but that were not derived from DPF Closed Colony pigs.

Numerous prior studies evaluating rejection time of α-1,3-galactosyltransferase [Gal-T] knockout pigs (not derived from a DPF Closed Colony) on monkeys show rejection times in the range of 11-13 days. See, e.g., Albritton et al., *Lack of Cross-Sensitization Between alpha-1, 3-Galactosyltransferase Knockout Porcine and Allogeneic Skin Grafts Permits Serial Grafting*, Transplantation & Volume 97, Number 12, Jun. 27, 2014, (Gal-T-KO skin grafts on recipient baboons fully rejected by 12 or 13 days); Barone et al., "*Genetically modified porcine split-thickness skin grafts as an alternative to allograft for provision of temporary wound coverage: preliminary characterization*," Burns 41 (2015) 565-574 (Gal-T-KO skin grafts on recipient baboons fully rejected by 11 days); and Weiner et al., *Prolonged survival of Gal-T-KO swine skin on baboons*, Xenotransplantation, 2010, 17(2): 147-152 (Gal-T-KO xenogeneic split-thickness skin grafts on baboons fully rejected by 11 days).

The subject invention has been shown in nonclinical studies to perform on par and surprisingly better than its allograft comparators, without the inherent disadvantage of inconsistent quality and unreliable and limited availability. That is, surprisingly, at least Study No. 1 shows skin grafts derived from a DPF Closed Colony, α-1,3-galactosyltransferase [Gal-T] knockout pigs produced in accordance with the present invention performed better than allograft.

Two recent studies (Study No. 1 and Study No. 2 set out below) by applicant demonstrate that skin grafts derived from DPF Closed Colony, α-1,3-galactosyltransferase [Gal-T] knockout pigs produced in accordance with the present invention on monkeys show significantly higher rejection times, in Study 2 longer than 30 days. The genetically engineered source animals in this example did not contain any foreign, introduced DNA into the genome; the gene modification employed was exclusively a knock-out of a single gene that was responsible for encoding for an enzyme that causes ubiquitous expression of a cell-surface antigen. The xenotransplantation product in this example does not incorporate transgene technologies, such as CD-46 or CD-55 transgenic constructs.

Study No. 1

This study evaluated DPF Closed Colony, α-1,3-galactosyltransferase [Gal-T] knockout porcine xenotransplantation product material compared to allografts as temporary wound grafts prior to autograft placement in cynomolgus monkeys (*Macaca fascicularis*) in an experimental model of full thickness skin lesions.

Primary end points included screening for porcine endogenous retrovirus (PERV) in the grafts and the recipient as well as evaluation of the xenotransplantation product and allograft rejection and their potential effects on ultimate autograft take. Secondary end points included microbiologic and histopathologic analysis of kidney, spleen, liver, lung, grafts, and wound bed tissues collected at necropsy.

Four (4) cynomolgus monkeys were enrolled in this study. Four (4), full thickness wound beds measuring approximately 2-3 cm×2-3 cm were created on the dorsal region of each animal on Day 0.

Initially, wounds were treated with either Xenogeneic skin (xenotransplantation product), a split-thickness Gal-T-transgenic porcine xenotransplantation product material, or Allogenic skin (allograft), a split-thickness allograft material, on Day 0.

On Day 15 of the study, the xenotransplantation product and allografts were removed and replaced with split-thickness autologous skin grafts (autografts), after which the animals were survived to Day 22 of study (with the exception of moribund sacrifice Animals 1001 and 1004).

Microscopic evaluation of full thickness wound beds in a cynomolgus monkey model treated with xenotransplantation product or allograft and removed on Day 12 or 15 (FIG. 9A) and survived up to Day 22 (FIG. 9B) demonstrated no evidence of acute tissue rejection with either the xenotransplantation product or allograft comparable to slightly better performance overall with the xenotransplantation product test article when compared to the allograft test article, and average to good autograft performance following pretreatment with either xenotransplantation product or allograft test articles. The significant survival times of the xenotransplantation product prompted a follow-on study (Study No. 2).

Study No. 2

The objective of this study was to evaluate the safety and immunogenicity of DPF Closed Colony, α-1,3-galactosyltransferase [Gal-T] knockout porcine xenotransplantation product material in cynomolgus monkeys (*Macaca fascicularis*).

Primary end points included screening for porcine endogenous retrovirus (PERV) pre- and post-graft placement and evaluation of the xenotransplantation product rejection.

Four (4) cynomolgus monkeys were enrolled in this study. Two (2) 9 cm$^2$ full thickness wound beds were created on the dorsal region of each animal created on Day 0.

Wounds were treated with split-thickness Gal-T-knockout porcine xenograft material consisting of dermal and epidermal tissue layers.

Figure 8:
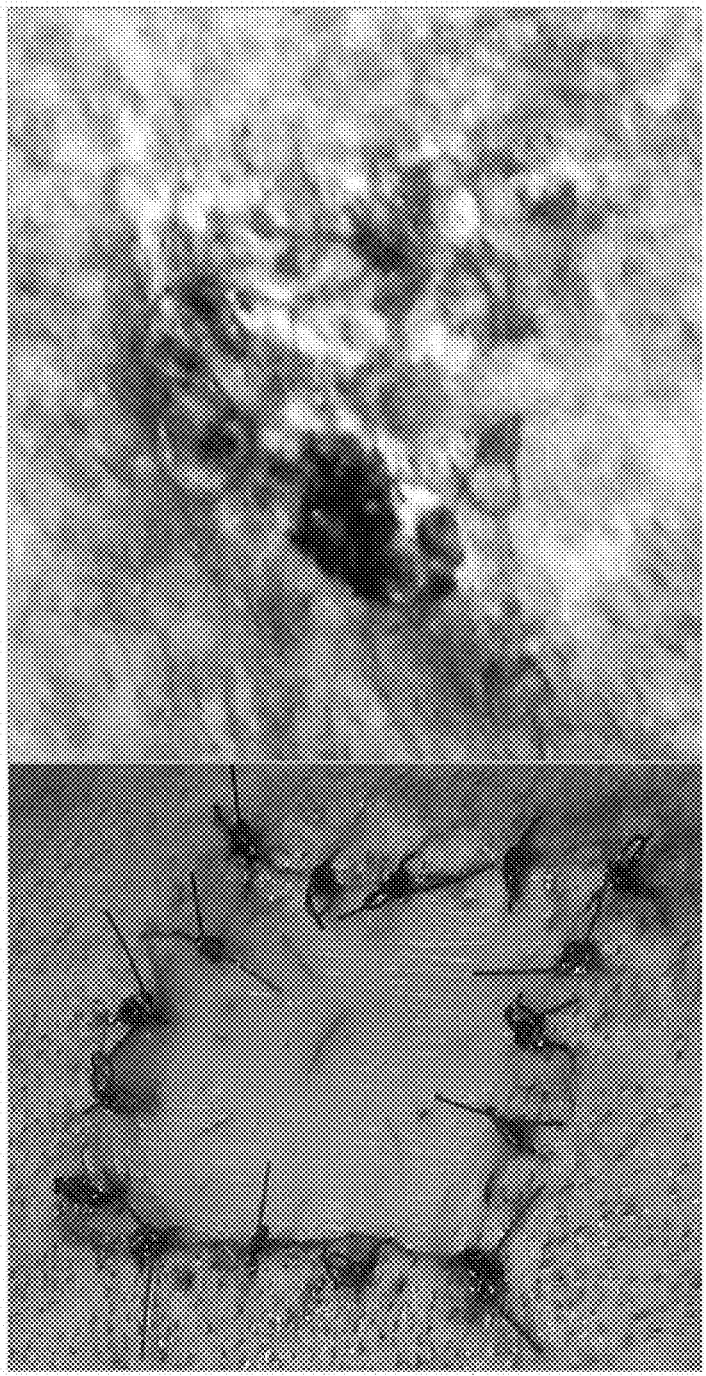
FIG. 8 depicts longitudinal progression of porcine split-thickness skin graft used as a temporary wound closure in treatment of full-thickness wound defects in a non-human primate recipient. Left: POD-0, xenotransplantation product at Wound Site 2. Right: POD-30, same xenotransplantation product at Wound Site 2.
Figure 10:
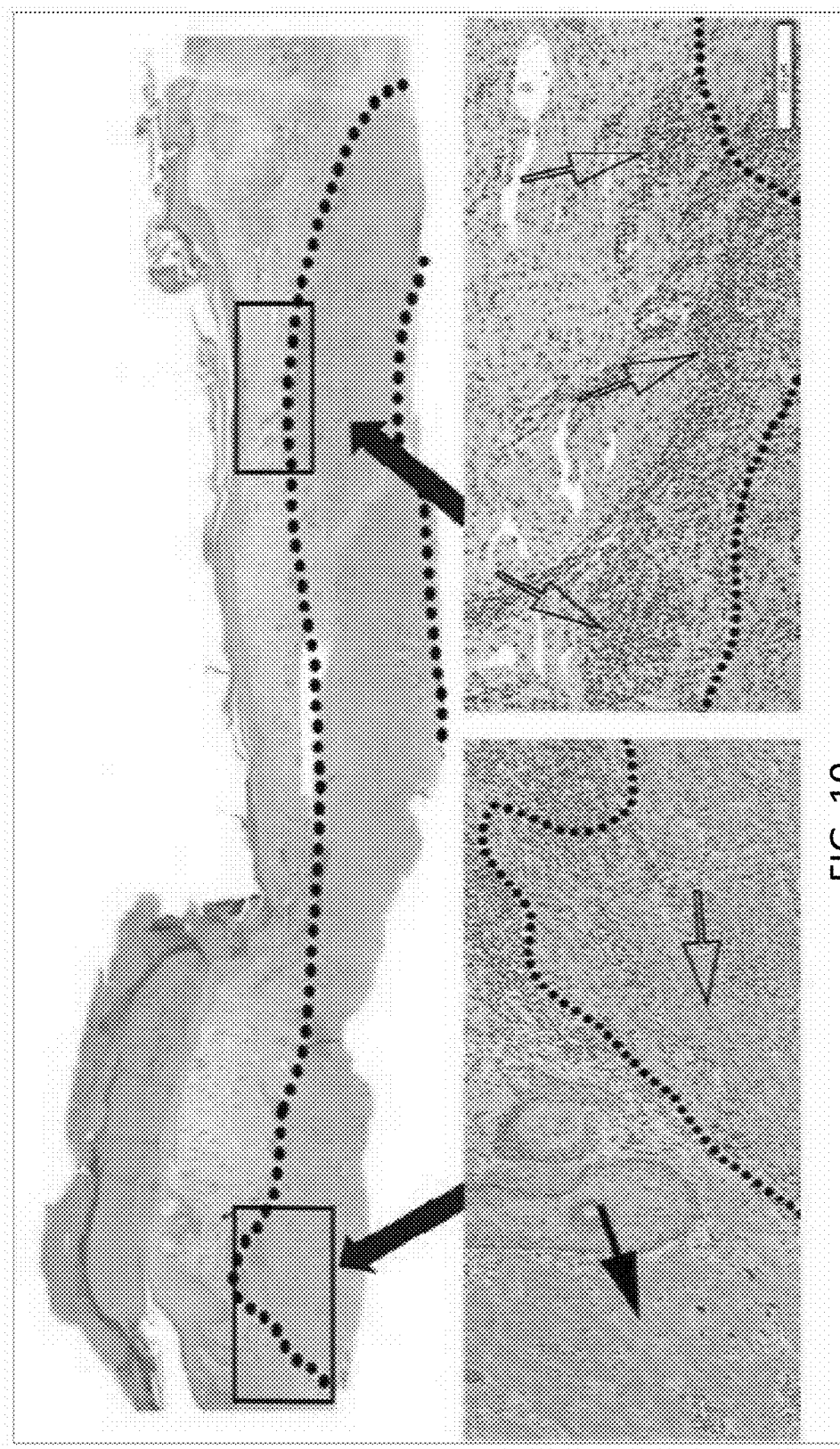
FIG. 10 shows POD-30 histological images for: Top, Center: H&E, Low power image of wound site depicts complete epithelial coverage. Dotted line surrounds the residual xenotransplantation product.

In some aspects, transgenic animals may be used in accordance with the present disclosure. FIG. 8 shows the longitudinal progression of porcine split-thickness skin graft used as a temporary wound closure in treatment of full-thickness wound defects in a non-human primate recipient. Left: POD-0, xenograft at Wound Site 2. Right: POD-30, same xenograft at Wound Site 2. FIG. 10 shows POD-30 histological images for: Top, Center: H&E, Low power image of wound site depicts complete epithelial coverage. Dotted line surrounds the residual xenograft tissue. Bottom, Left: H&E, Higher power image of the large inset box. To the right and below the dotted line is the dermal component of the xenograft, with the xenograft dermal matrix indicated by an open arrow. To the left of the dotted line is the host dermis (black arrow) and the host dermal matrix. Mild inflammation is present and interpreted to be in response to the xenograft test article. Bottom, Right: H&E, higher power image of the small inset box. The dotted line roughly demonstrates the junction between the xenograft test article (below dotted line) and new collagen tissue (above dotted line), with intact epithelium at the top of the image. Mild inflammation in response to the xenograft (open arrows) is observed.

Figure 11A:
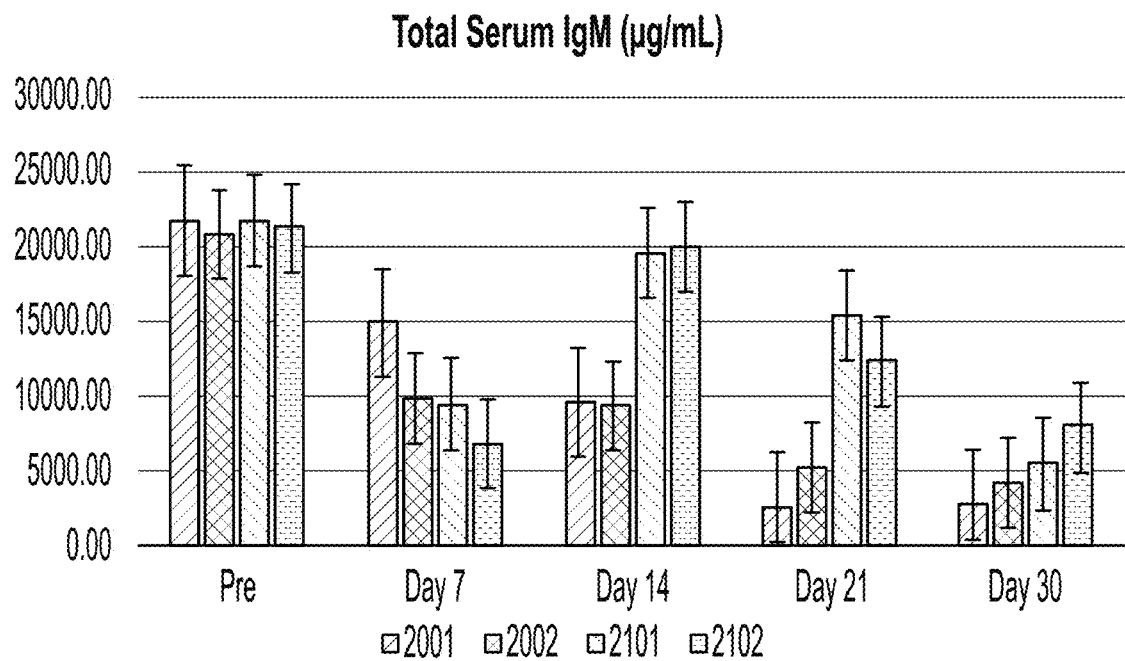
FIG. 11A graphs the total serum IgM ELISA (µg/mL) for all four subjects (2001, 2002, 2101, 2102) during the course of the study.
Figure 11B:
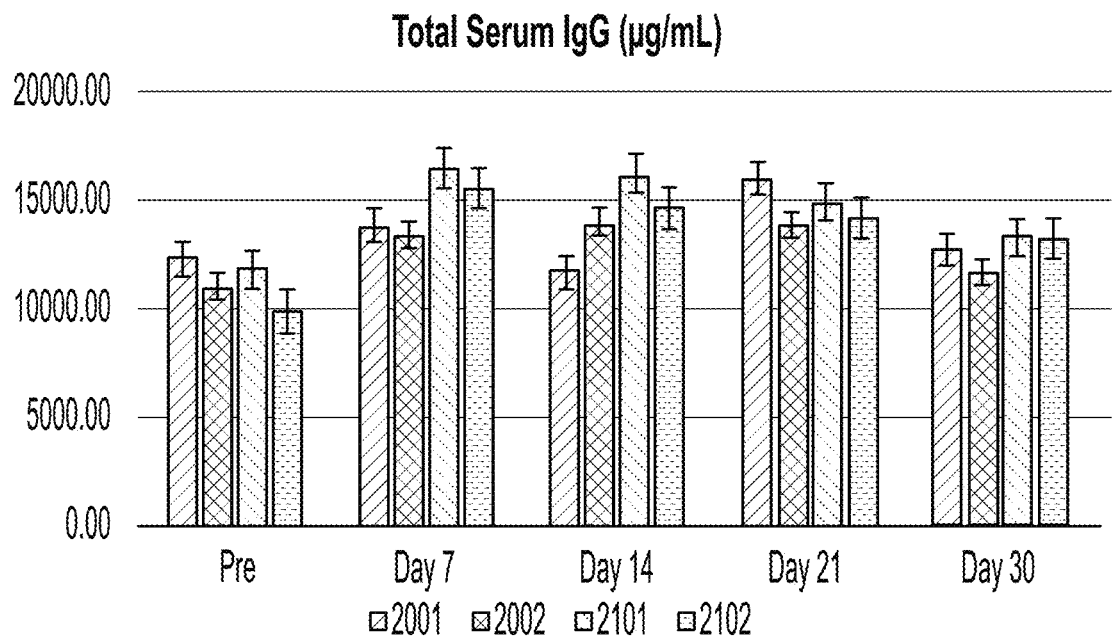
FIG. 11B graphs the total serum IgG ELISA (µg/mL) for all four subjects (2001, 2002, 2101, 2102) during the course of the study.

FIG. 11A graphs the total serum IgM ELISA (μg/mL) for all four subjects (2001, 2002, 2101, 2102) during the course of the study. FIG. 11B graphs the total serum IgG ELISA (μg/mL) for all four subjects (2001, 2002, 2101, 2102) during the course of the study. In some aspects, subjects transplanted with the product of the present disclosure will have serum IgM and IgG levels of less than 20,000 μg/ml each. In some aspects, subjects transplanted with the product of the present disclosure will have serum IgM and/or IgG levels below or less than 10%, 5%, 3%, or 1% higher than serum IgM and IgG levels measured prior to transplantation. In some aspects, the claimed method may demonstrate an immunoreactivity incidence rate of less than 5%, 3%, or 1% of subjects transplanted with the product of the present disclosure.

Figure 12A:
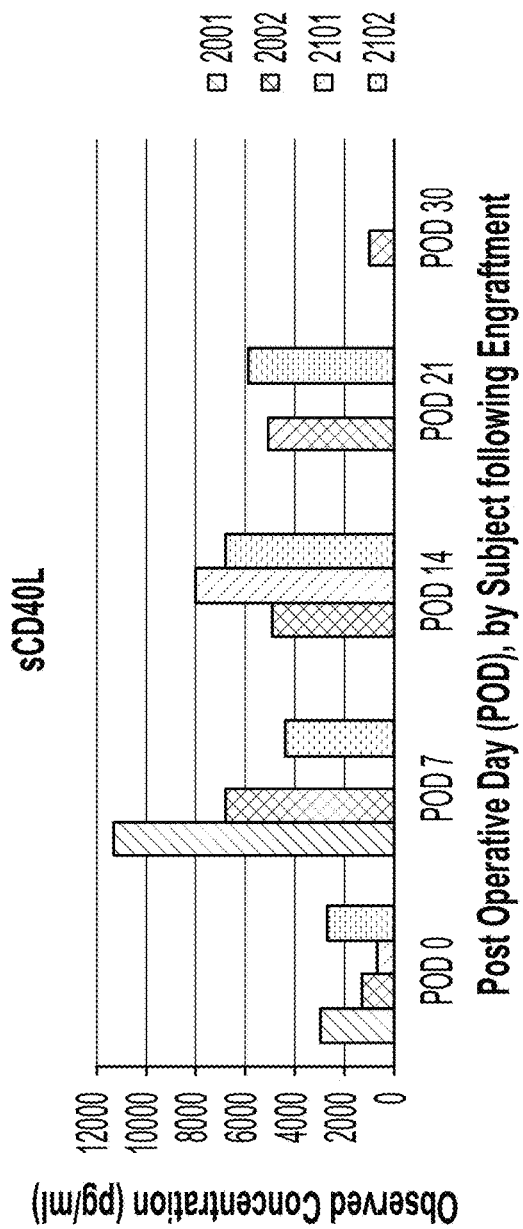
FIG. 12A graphs systemic concentrations of soluble CD40L as measured by Luminex 23-plex at POD-0, POD-7, POD-14, POD-21, and POD-30.
Figure 12B:
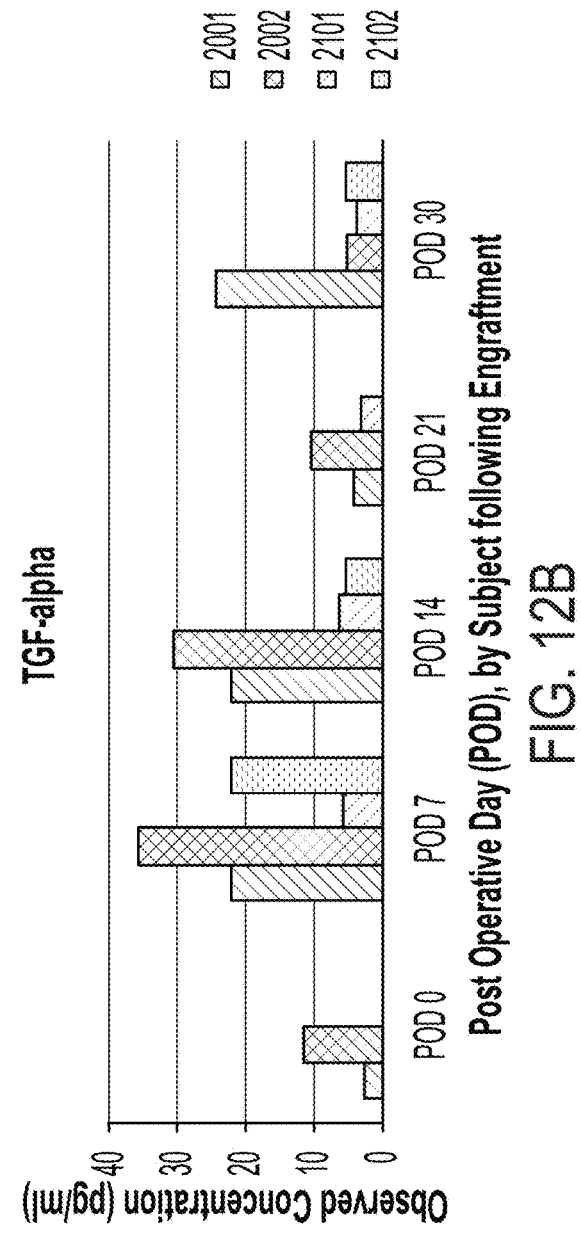
FIG. 12B graphs systemic concentrations of TGF-alpha as measured by Luminex 23-plex at POD-0, POD-7, POD-14, POD-21, and POD-30.
Figure 12C:
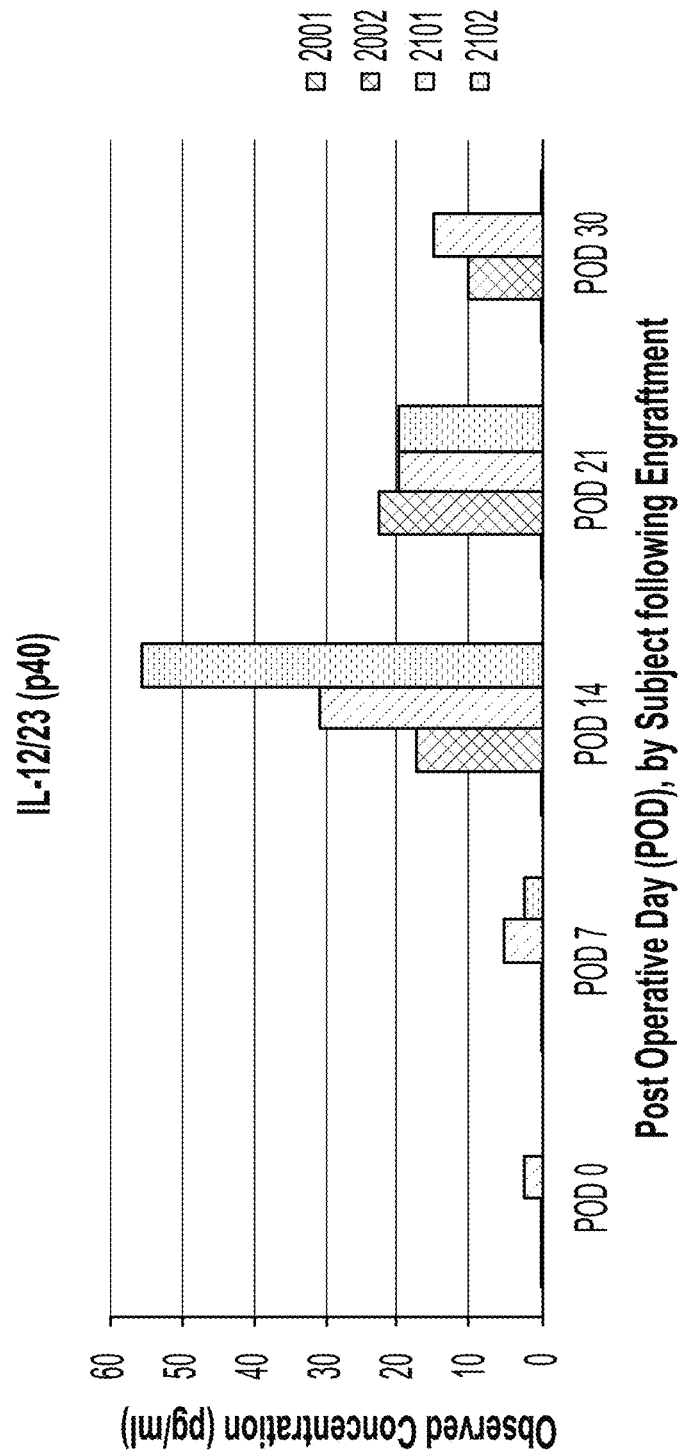
FIG. 12C graphs systemic concentrations of IL-12/23 (p40) as measured by Luminex 23-plex at POD-0, POD-7, POD-14, POD-21, and POD-30.
Figure 13:
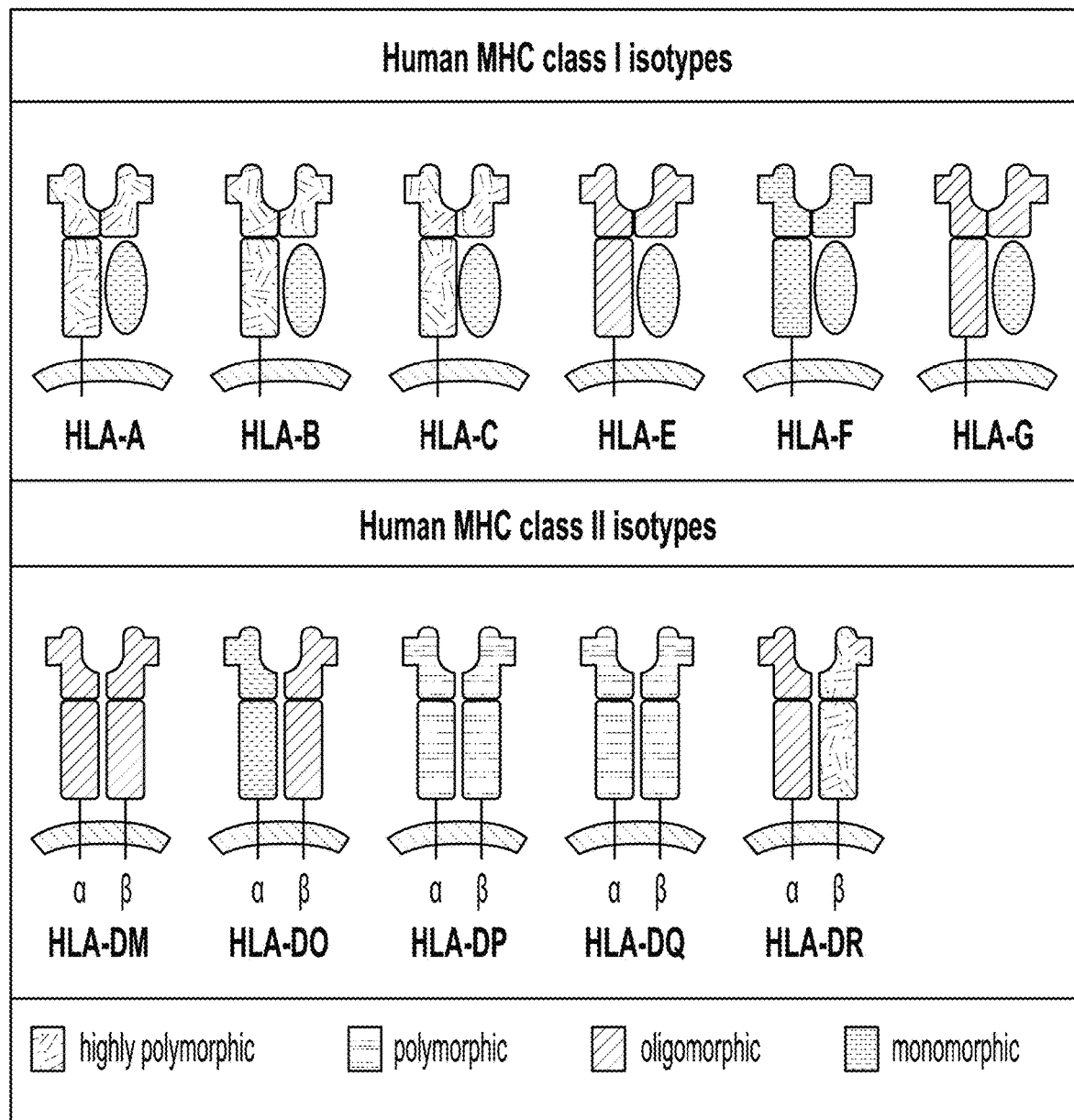
FIG. 13 schematically illustrates Human MHC Class I and Class II isotypes.
Figure 14:
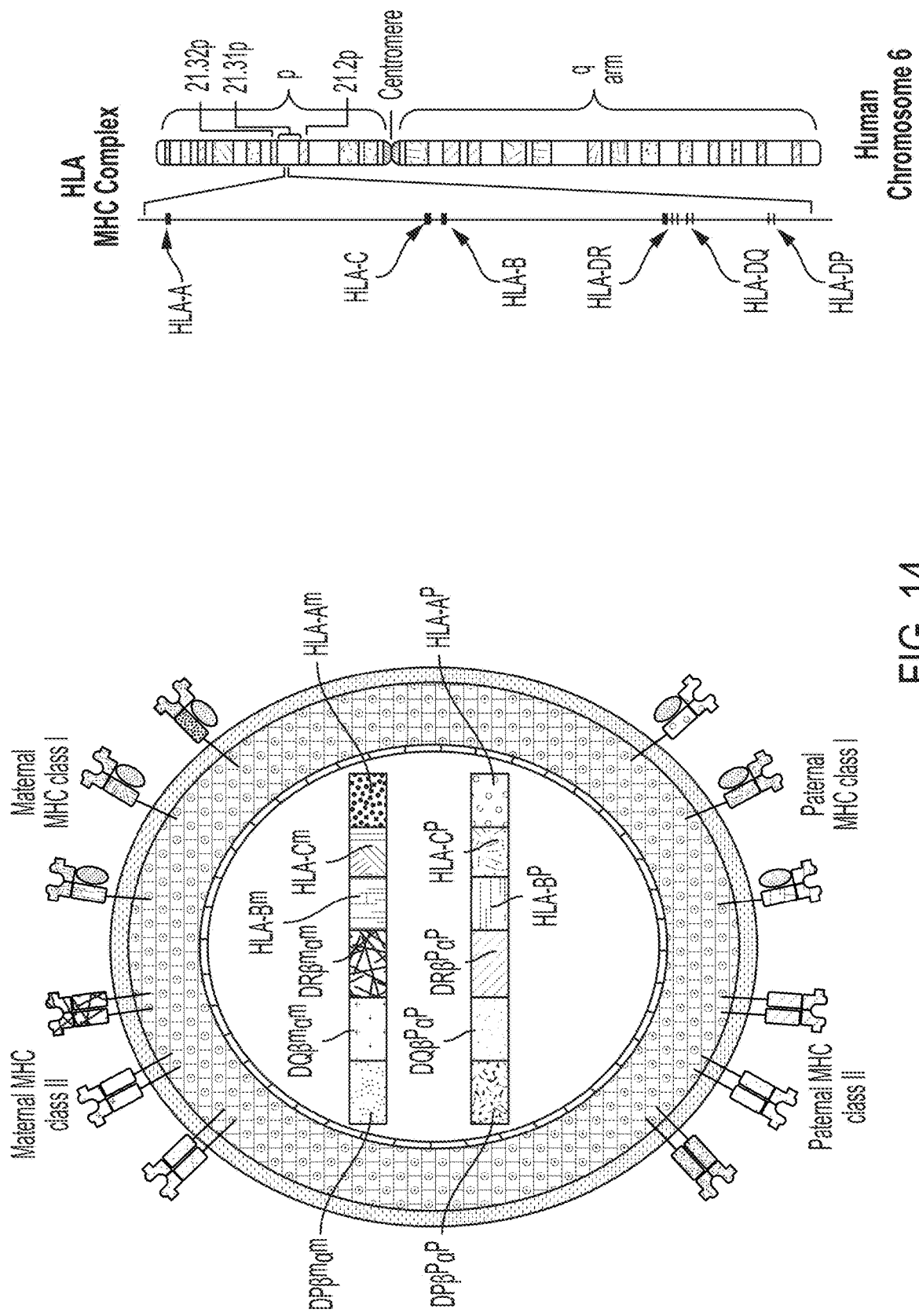
FIG. 14 schematically illustrates codominant expression of HLA genes and the position of HLA genes on human chromosome 6.
Figure 16:
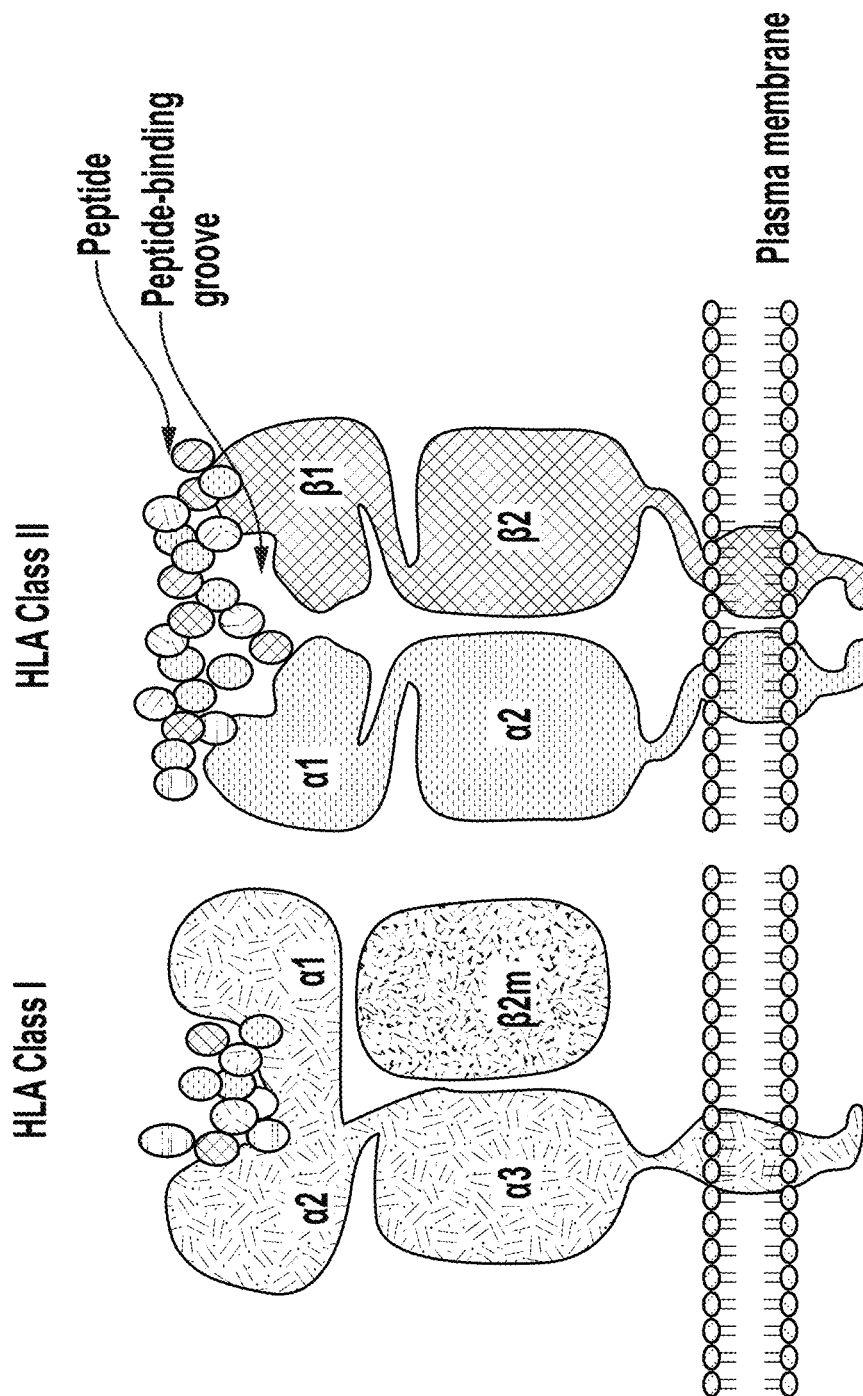
FIG. 16 schematically illustrates HLA Class I and Class II on the surface of a cell.
Figure 17:
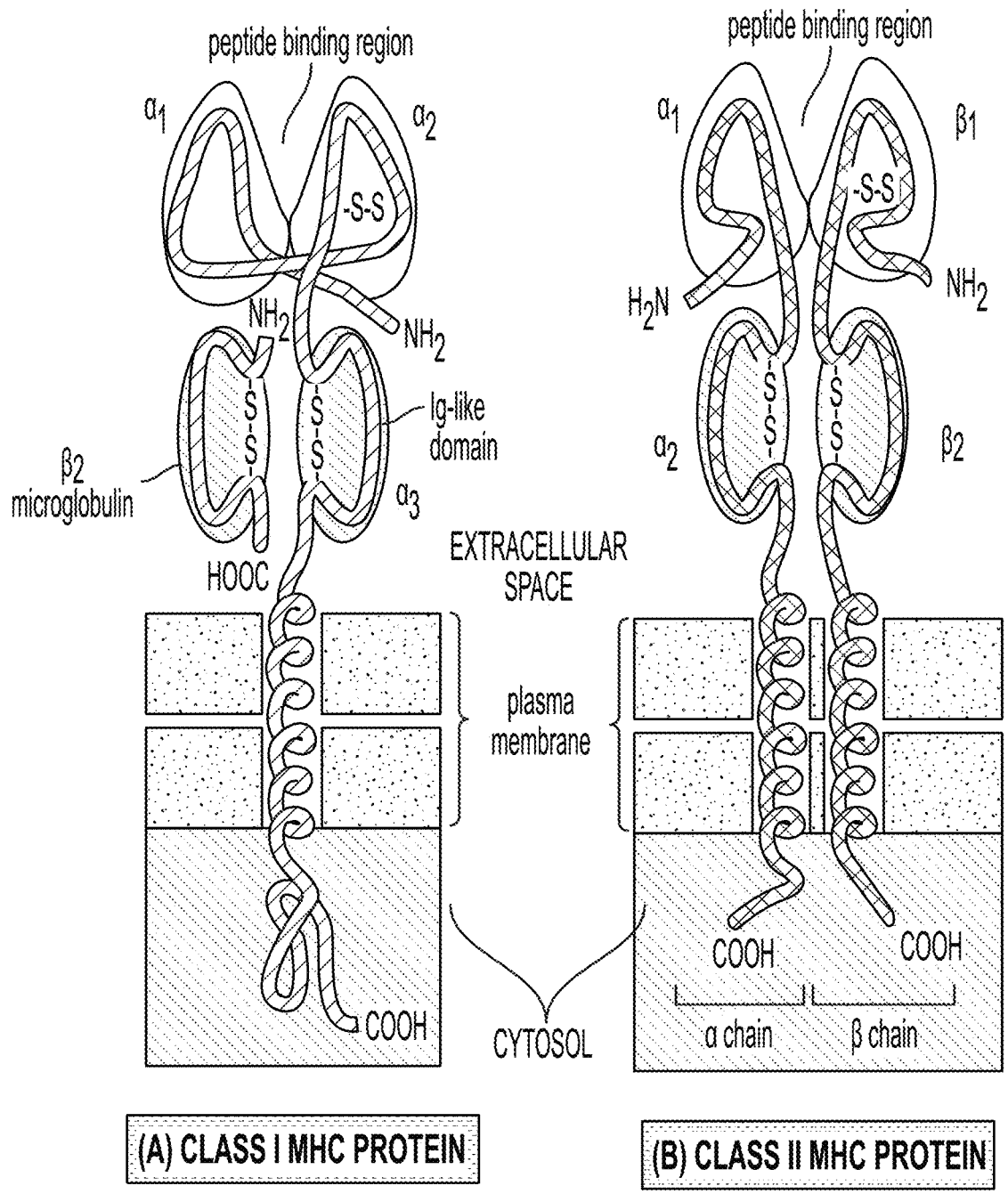
FIG. 17 shows the structure of MHC Class I (A) and class II proteins (B). The two globular domains furthest from the plasma membrane that form the peptide binding region (PBR) are shaded in blue. The two Ig-like domains, including the β2-microglobulin, are shaded in grey.
Figure 18:
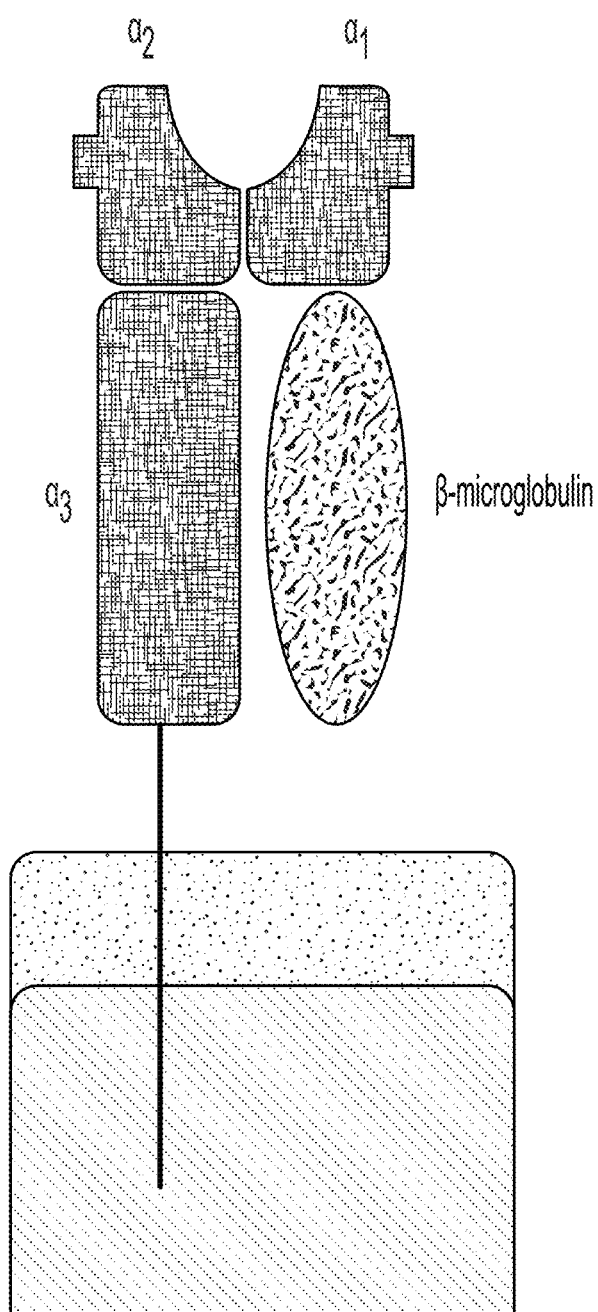
FIG. 18 schematically illustrates HLA Class I on the surface of a cell.
Figure 19:
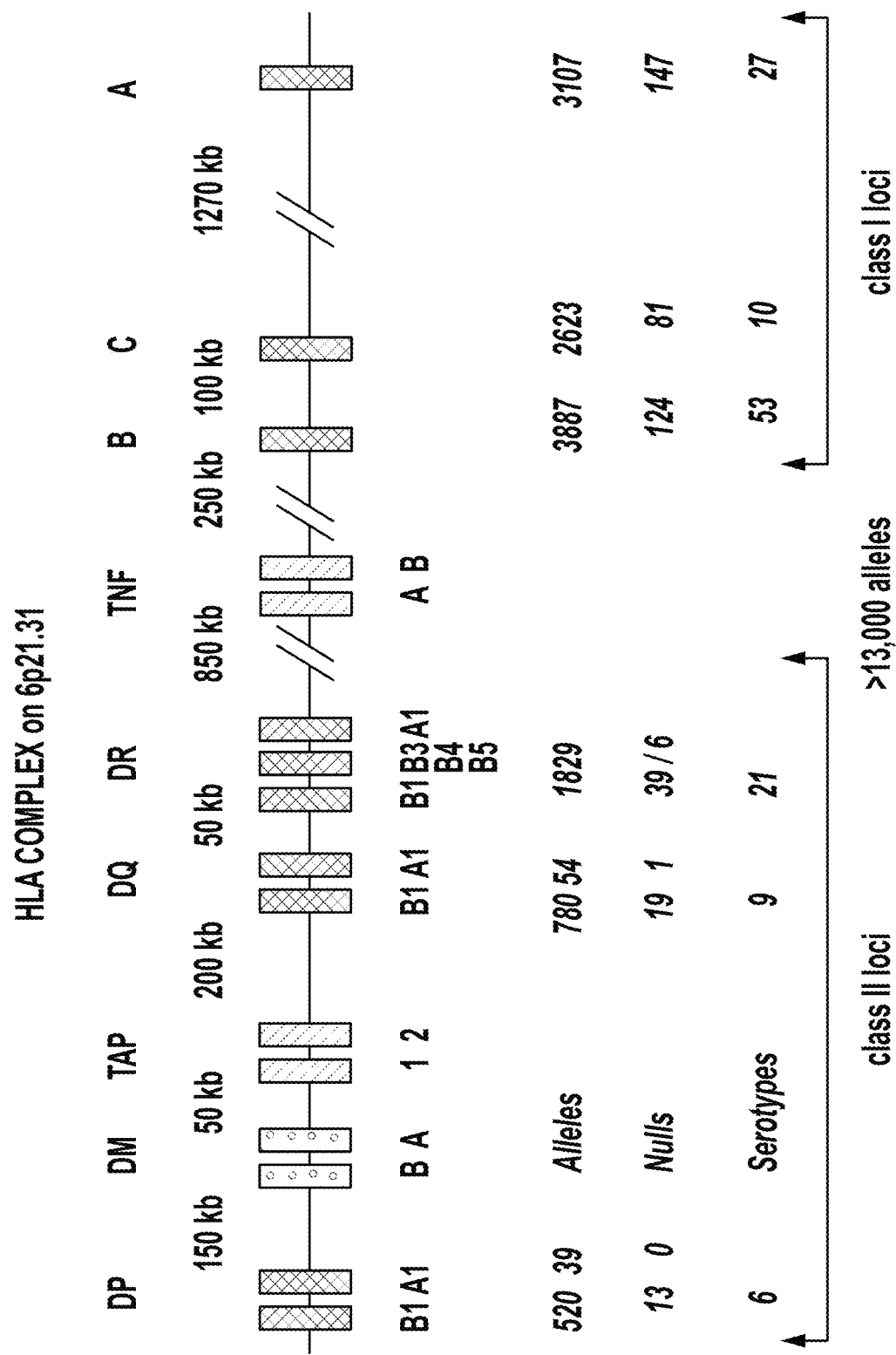
FIG. 19 shows the Human Leukocyte Antigen Complex (HLA). The HLA genes are the most polymorphic in the genome. The allelic diversity of the HLA class I and class II loci is extensive, with >13,000 alleles described.
Figure 20:
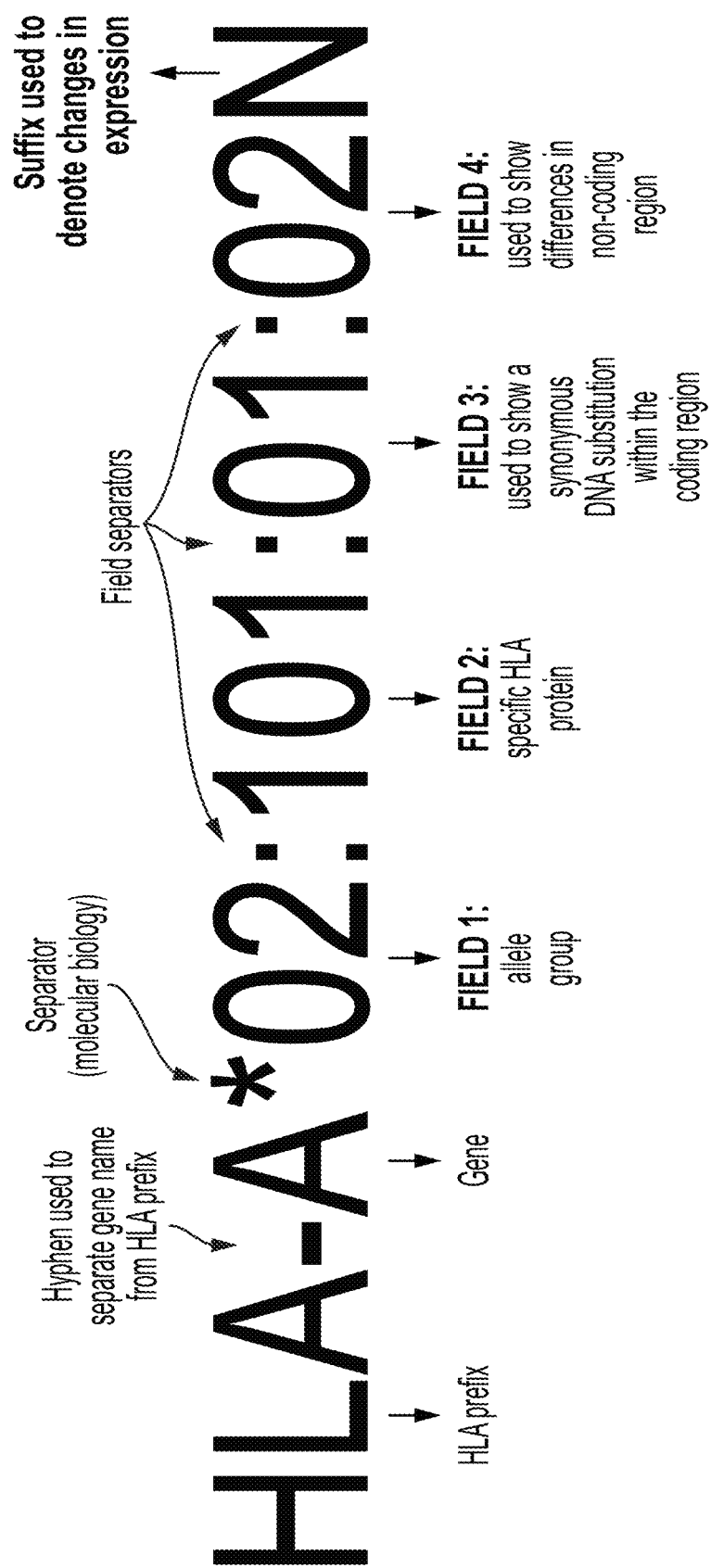
FIG. 20 illustrates nomenclature of HLA alleles. Each HLA allele name has a unique number corresponding to up to four sets of digits separated by colons. The length of the allele designation is dependent on the sequence of the allele and that of its nearest relative. All alleles receive at least a four digit name, which corresponds to the first two sets of digits, longer names are only assigned when necessary. The digits before the first colon describe the type, which often corresponds to the serological antigen carried by an allotype. The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns, or in the 5' or 3' untranslated regions that flank the exons and introns, are distinguished by the use of the fourth set of digits.
Figure 21B:
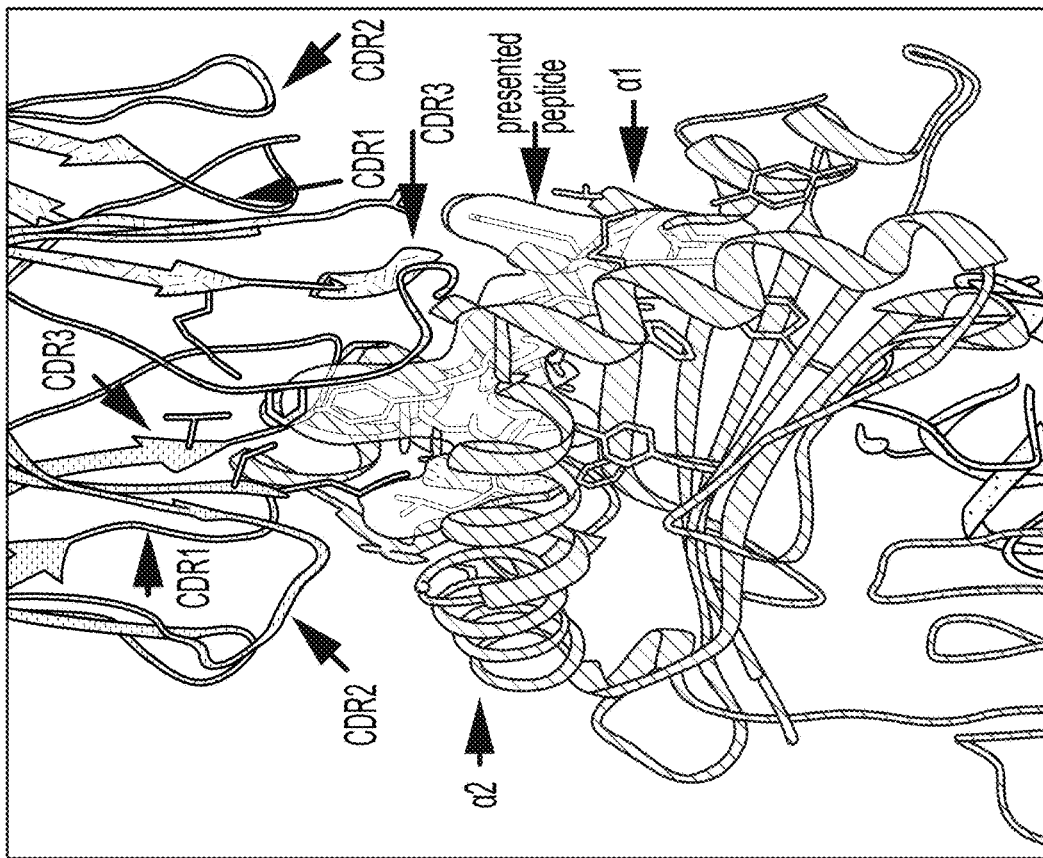
FIGS. 21A-21B show a string model for TCR-pMHC complex from Tsurui et al., General Med 2013, 2:1. In this simplified model, CDR1 and CDR2 of TCRs mainly interact with helices running along both sides of MHC molecules, between which the presented peptide is located. In this case, CDR3 (LKVEGTRVY) interacts with a presented peptide (LDIRASELT) so as to form a ladder with 9 rungs (L-L, K-D, V-I, E-R, G-A, T-S, R-E, V-L, Y-T). For simplicity, only the interaction between CDR3 and the presented peptide is considered (SI 1).
Figure 21A:
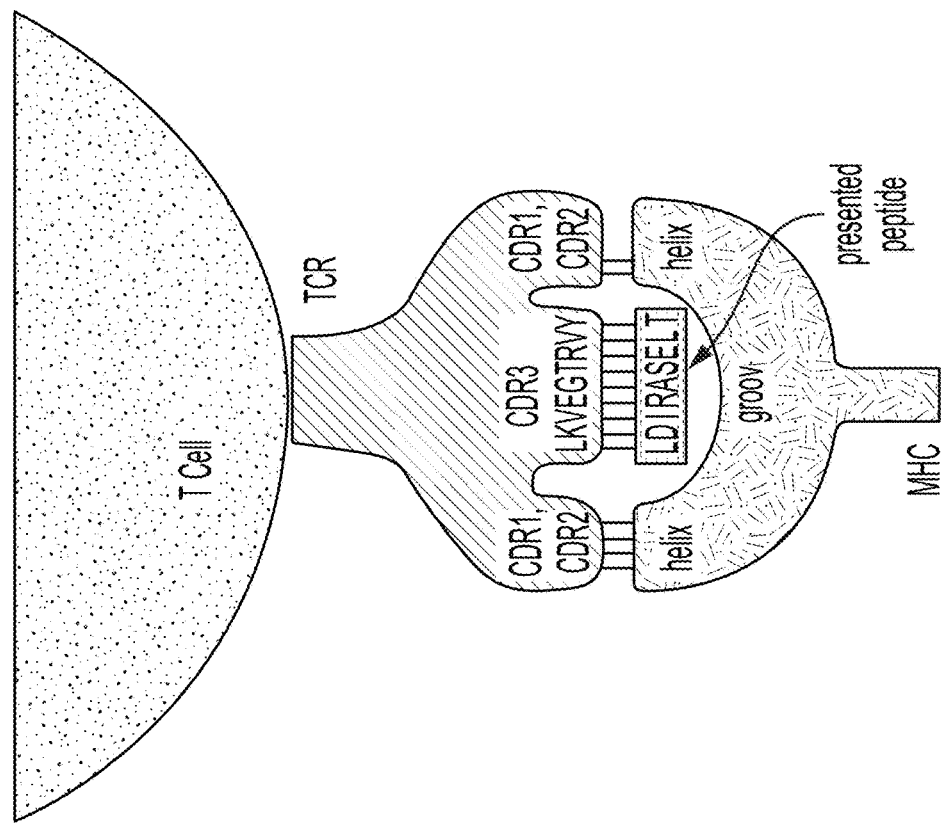
Figure 22:
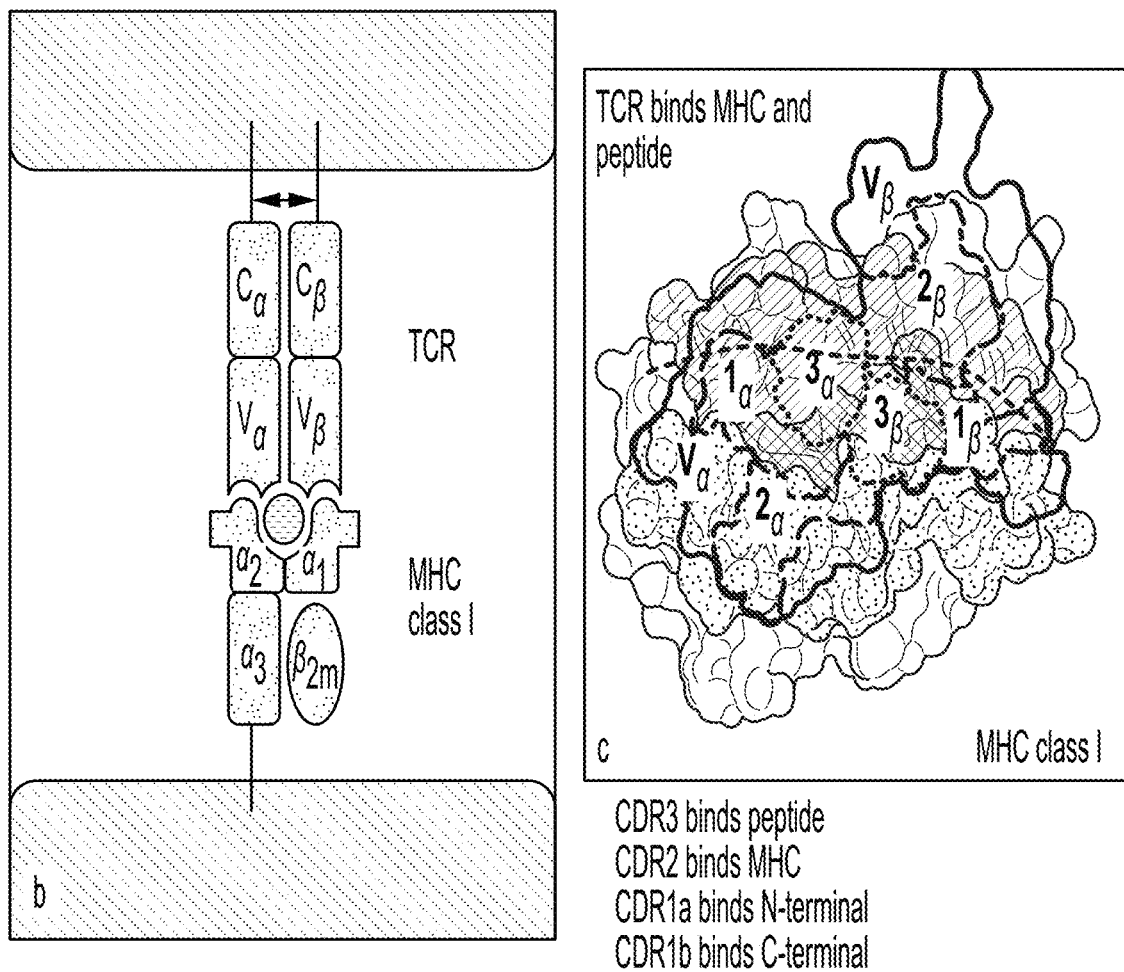
FIG. 22 schematically illustrates a T Cell Receptor (TCR) binding MHC class I and a peptide.
Figure 23:
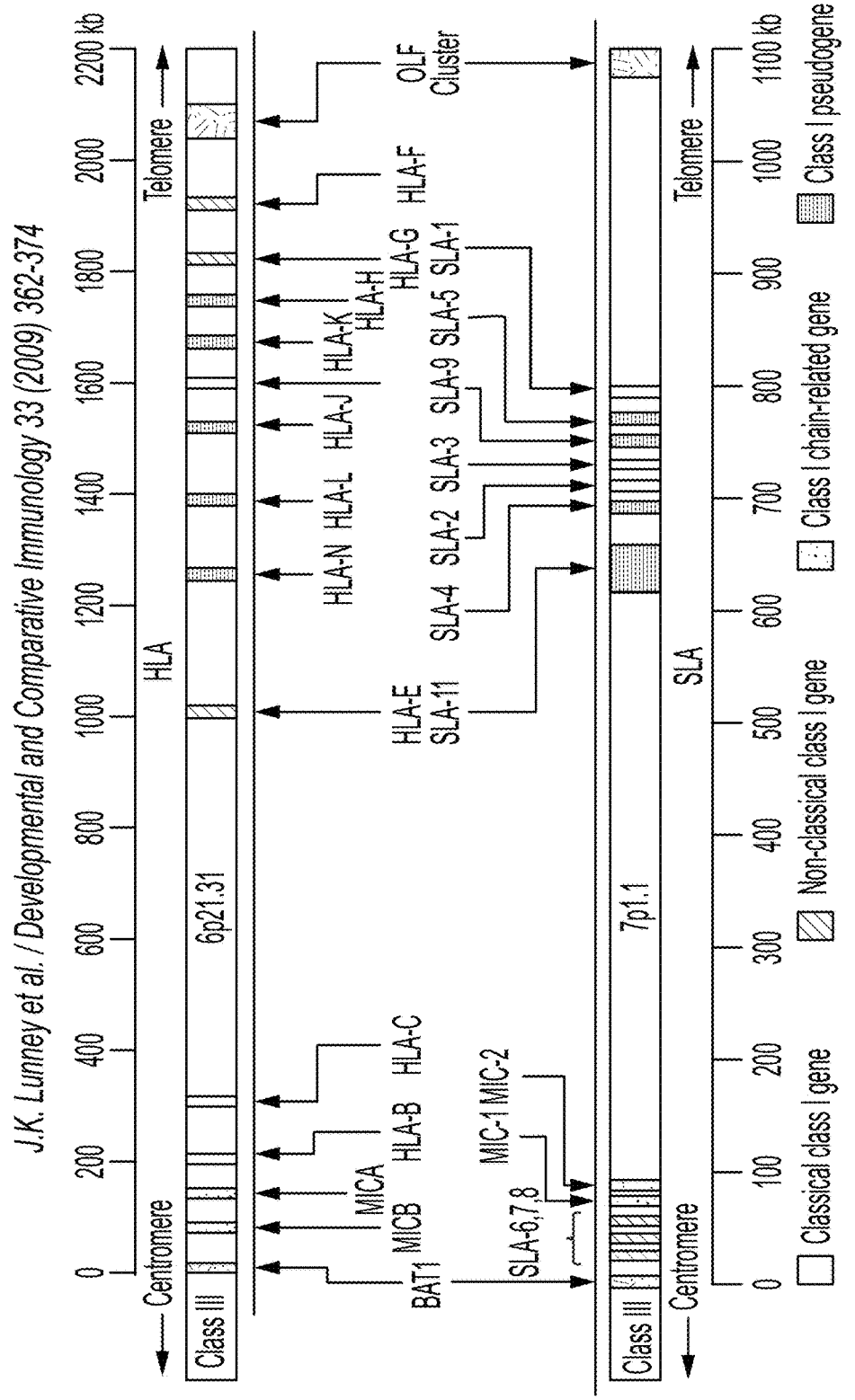
FIG. 23 is a comparative genomic organization of the human and swine MHC Class I region.
Figure 25:
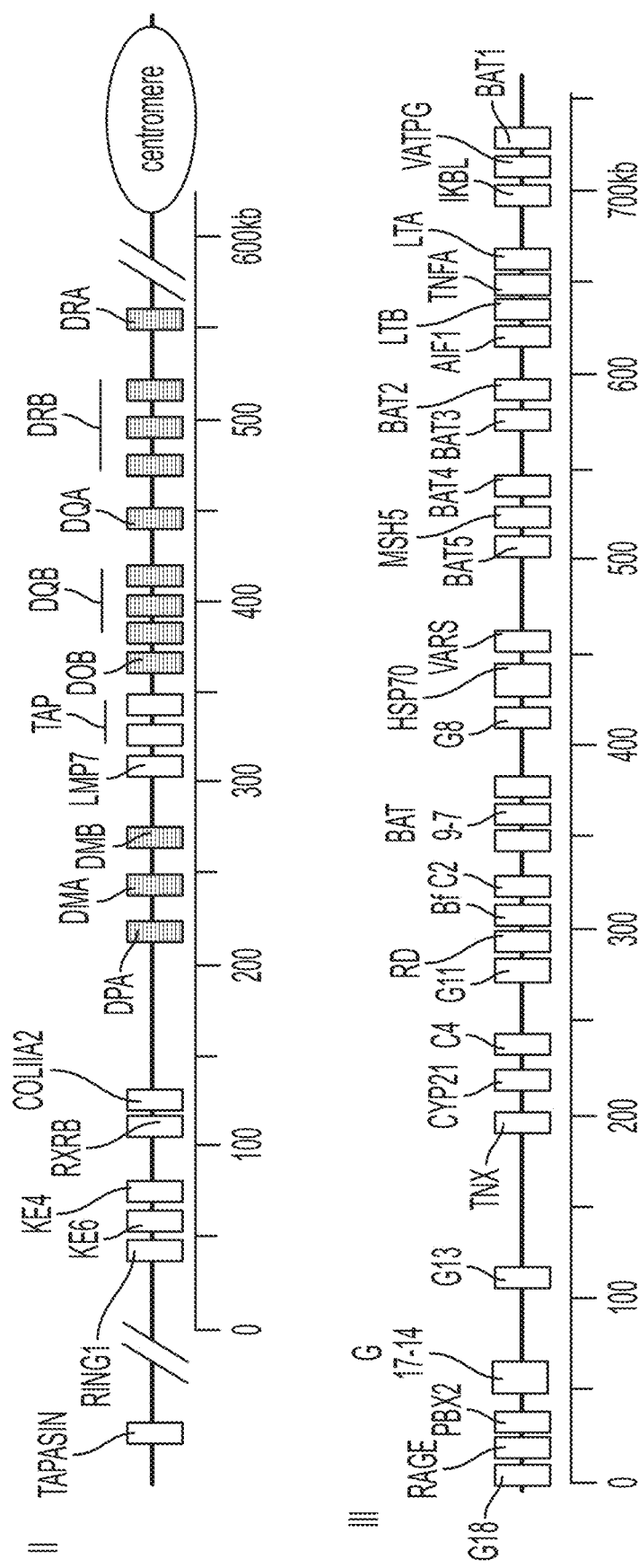
FIG. 25 shows a physical map of the SLA complex. Black boxes: loci containing MHC-related sequences. White boxes: loci without MHC-related sequences. From the long arm to the short arm of the chromosome, the order of the regions is class II (II), class III (III) and class I (I).
Figure 25:
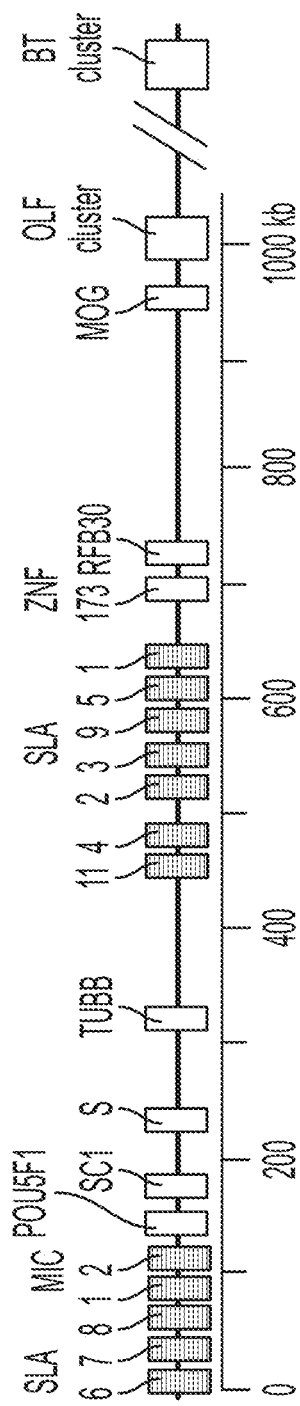
Figure 26:
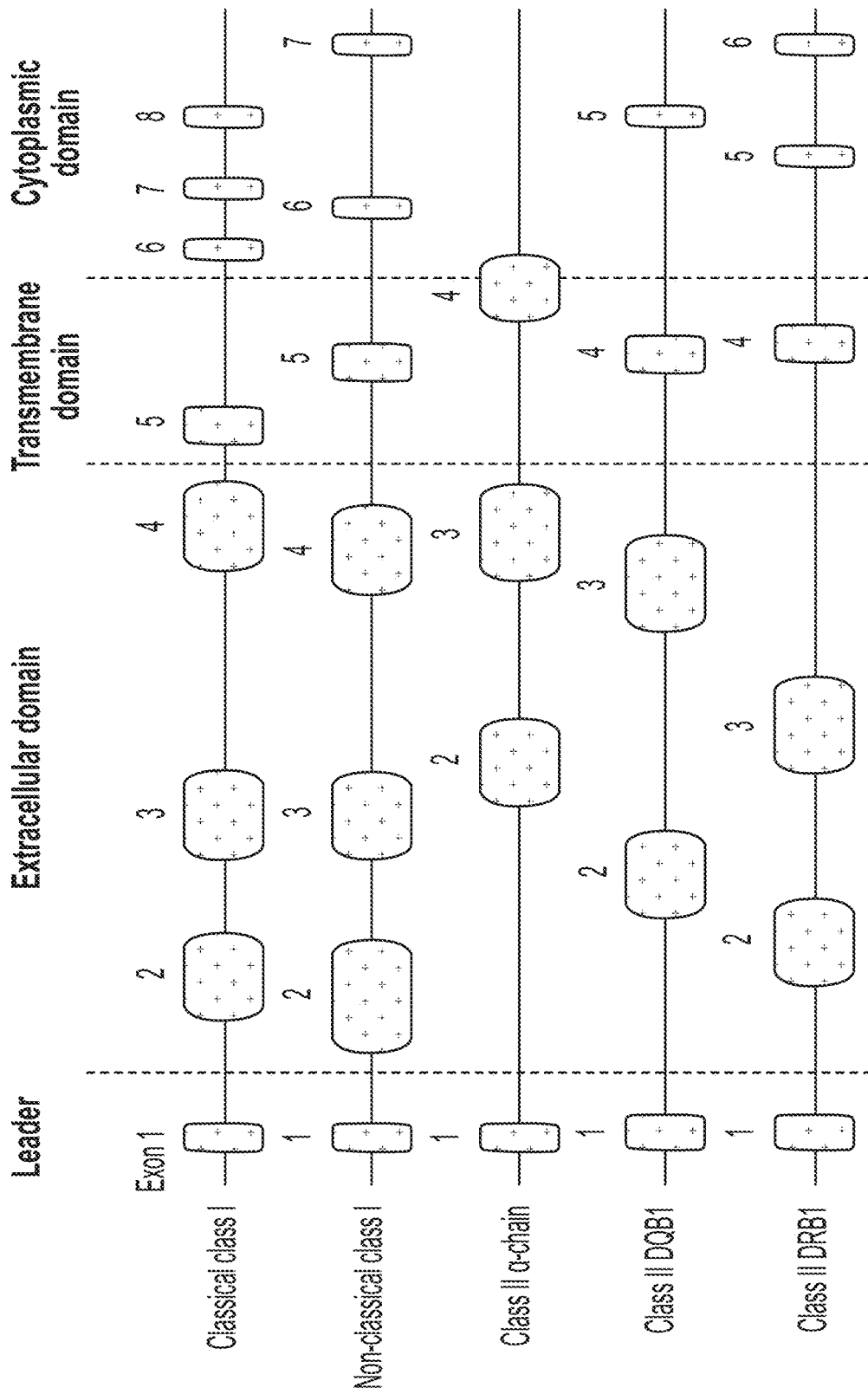
FIG. 26 shows the schematic molecular organization of the SLA genes. Exons are represented by the gray ovals and introns by lines. Gene length is approximate to that found for the Hp-1.1 genome sequence.
Figure 27:
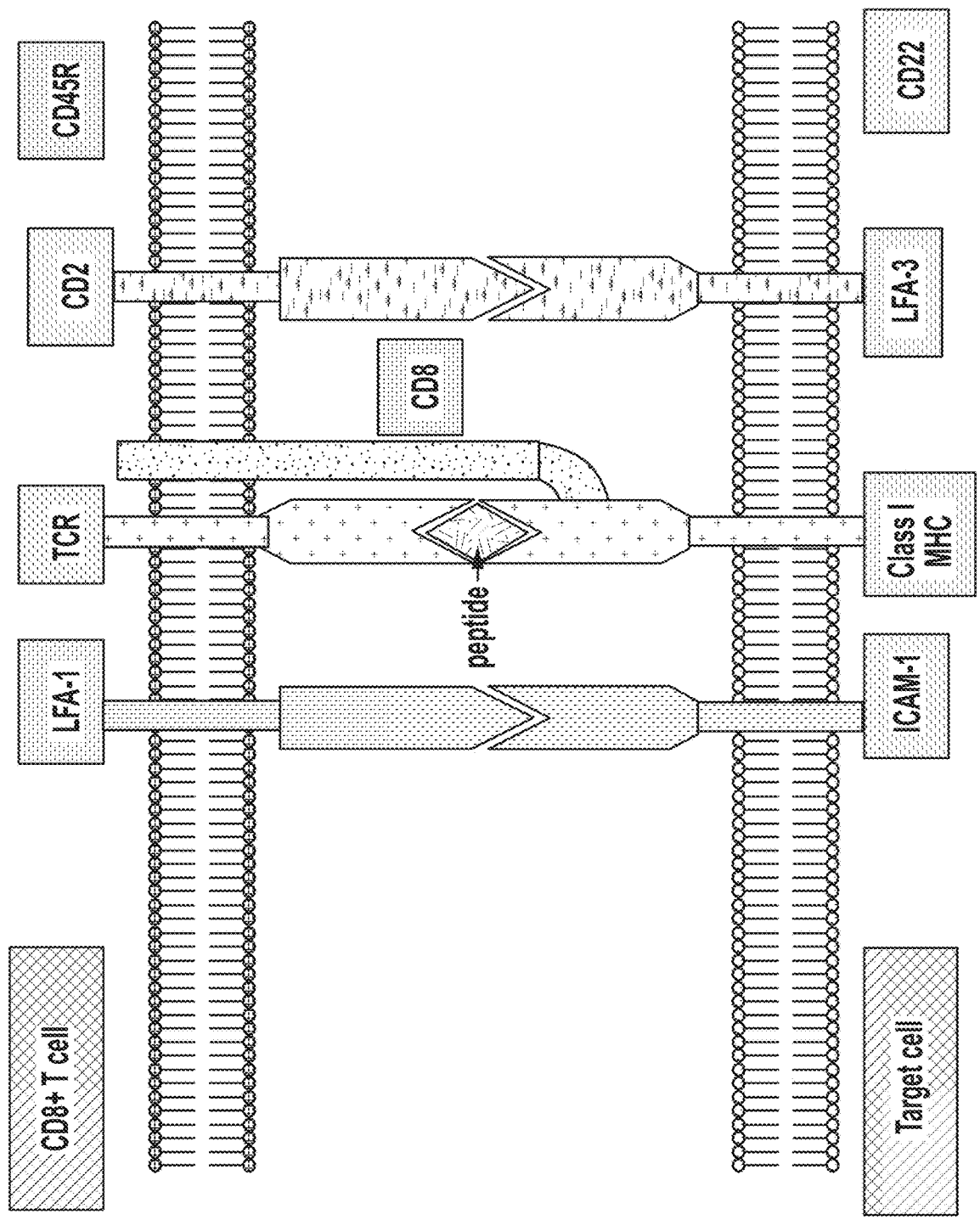
FIG. 27 schematically illustrates a Cytotoxic T Cell (CD8+)—Target Cell Interaction.
Figure 28:
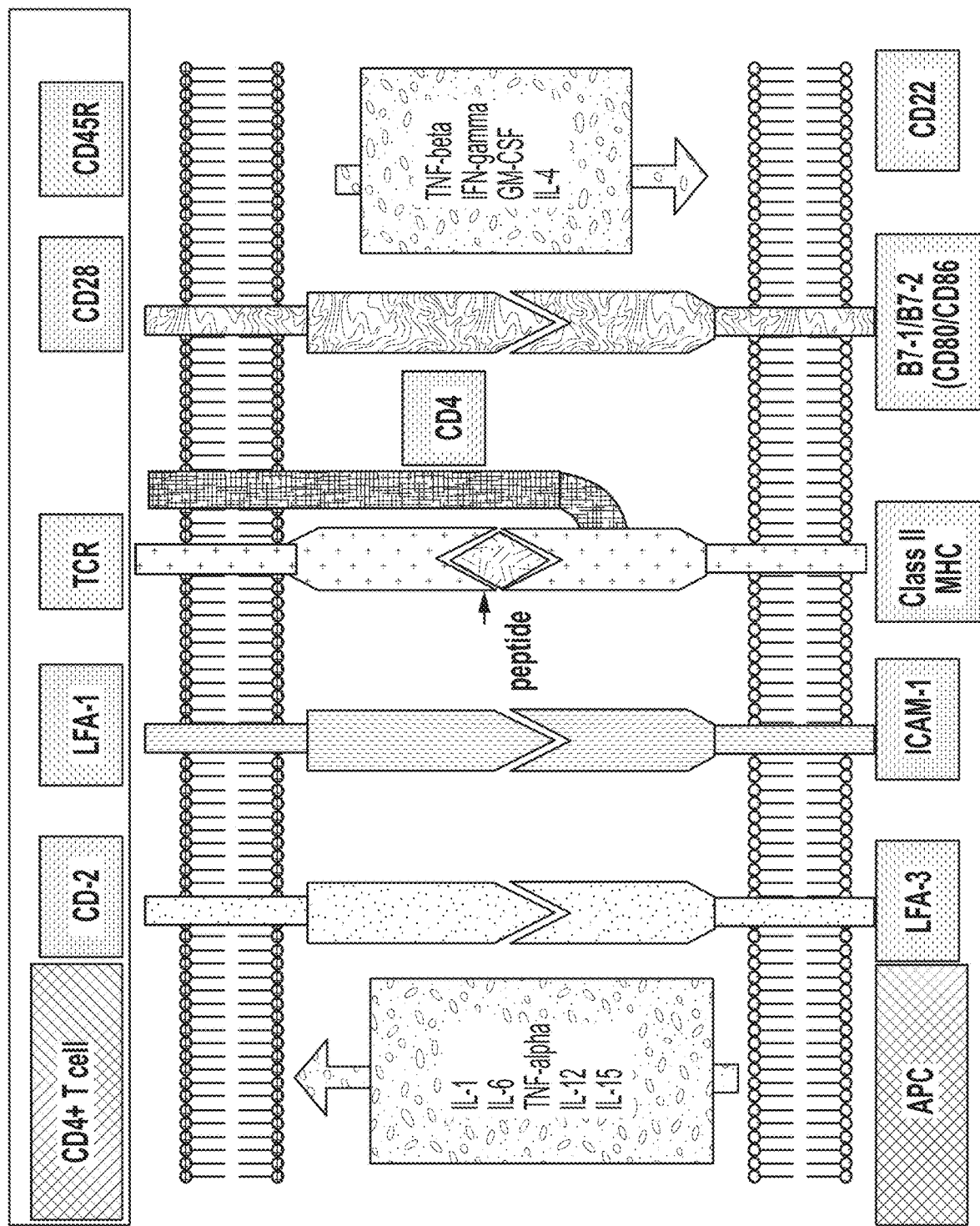
FIG. 28 schematically illustrates a Cytotoxic T Cell (CD4+)—Target Cell Interaction.

FIG. 12A graphs systemic concentrations of soluble CD40L as measured by Luminex 23-plex at POD-0, POD-7, POD-14, POD-21, and POD-30. FIG. 12B graphs systemic concentrations of TGF-alpha as measured by Luminex 23-plex at POD-0, POD-7, POD-14, POD-21, and POD-30. FIG. 12C graphs systemic concentrations of IL-12/23 (p40) as measured by Luminex 23-plex at POD-0, POD-7, POD-14, POD-21, and POD-30.

Animals were terminated at 30 or 31 Days, wound sites were collected and fixed in 10% neutral buffered formalin (NBF) or Modified Davidson's Solution for the testis and epididymis. It should be noted that while the animals were terminated at 30 or 31 days due to the study design and for comparison purposes, the xenotransplantation product of the present disclosure is capable of resisting rejection for longer than the study period used in this example.

Microscopic evaluation of full thickness wound beds in a cynomolgus monkey model treated with xenograft and terminated on Day 30 or 31 demonstrated good filling of the wound defect with host and xenograft tissue.

Screening for porcine endogenous retroviruses (PERV) and porcine cytomegalovirus (PCMV) was performed separately at specified post-operative intervals via specialized (porcine specific) polymerase chain reaction (PCR) and reverse transcriptase PCR (RT-PCR) testing of samples. The porcine xenografts, lysed PBMCS of the recipient, recipient wound bed, and highly perfused organs from the recipients at necropsy were evaluated for presence of porcine cell migration. All tests were performed in triplicate with internal controls for DNA and RNA, as well as assay performance. Microbiologic (bacterial, fungal, viral) assays and histopathologic analysis of kidney, spleen, liver, lung, xenografts, allografts, wound bed tissues collected at necropsy, and analysis of peripheral blood were performed to test for xenograft-related immunogenic biomarkers. DNA PCR was performed to test for porcine cell migration in PBMCs from the cynomolgus monkey model treated with the product of the present disclosure for the following samples: (A.) (3) full-thickness (xenograft) wound beds, (B) (3) full-thickness (allograft) wound beds; (C) (2) spleen samples; and (D)(2) kidney samples. There was no evidence of cell migration or zoonotic transmission systemically to the host. The presence of PERV is attributed to the residual pig cells in the wound bed, as verified with porcine MHC controls. Our results suggest that porcine DNA and cells did not migrate into the circulation of the graft recipients from the grafts, and likewise PERV or PERV-infected porcine cells did not migrate past the wound bed.

The following Table 5 shows the analysis for porcine cell migration and transmission:

TABLE 5

| Item No. | PSK17-01 Sample Analysis | PCMV | PERV | MHC (swine) | CCR5 (Control) |
|---|---|---|---|---|---|
| | PBMC @ End-of-Study Subject # (EoS Date) | | | | |
| 1 | NHP-1001 (POD-IS) | * | * | * | * |
| 2 | NHP-1002 (POD-22) | Neg (−) | Neg (−) | Neg (−) | Pos (+) |

TABLE 5-continued

| Item No. | PSK17-01 Sample Analysis | PCMV | PERV | MHC (swine) | CCR5 (Control) |
|---|---|---|---|---|---|
| 3 | NHP-1003 (POD-22) | Neg (−) | Neg (−) | Neg (−) | Pos (+) |
| 4 | NHP-1004 (POD-12) | Neg (−) | Neg (−) | Neg (−) | Pos (+) |
| | Wound Bed @ End-of-Study Subject # (Test Article) (EoS Date) | | | | |
| 5 | NHP-1001 (Xenograft) (POD-IS) | * | * | * | * |
| 6 | NHP-1001 (Allograft) (POD-IS) | * | * | * | * |
| 7 | NHP-1002 (Xenograft) (POD-22) | Neg (−) | Neg (−) | Neg (−) | Pos (+) |
| 8 | NHP-1002 (Allograft) (POD-22) | Neg (−) | Neg (−) | Neg (−) | Pos (+) |
| 9 | NHP-1003 (Xenograft) (POD-22) | Neg (−) | Neg (−) | Neg (−) | Pos (+) |
| 10 | NHP-1003 (Allograft) (POD-22) | Neg (−) | Neg (−) | Neg (−) | Pos (+) |
| 11 | NHP-1004 (Xenograft) (POD-12) | Neg (−) | Pos (+)[4] | Neg (−) | Pos (+) |
| 12 | NHP-1004 (Allograft) (POD-12) | Neg (−) | Neg (−) | Neg (−) | Pos (+) |
| | Spleen @ End-of-Study | | | | |
| 13 | NHP-1001 | Neg (−) | Neg (−) | Neg (−) | Pos (+) |
| 14 | NHP-1004 | Neg (−) | Neg (−) | Neg (−) | Pos (+) |
| | Kidney @ End-of-Study | | | | |
| 15 | NHP-1001 | Neg (−) | Neg (−) | Neg (−) | Pos (+) |
| 16 | NHP-1004 | Neg (−) | Neg (−) | Neg (−) | Pos (+) |

Key for Table 5:
Neg(−) = Negative
Pos(+) = Positive
* = Test Not Performed or Sample Not Acceptable, due to unrelated, study design-related logistical or preservation issue
Pos (+)[4] The wound bed for NHP 1004 (PERV positive) underwent co-culture studies to ascertain whether the detected virus present at the interface between graft and recipient (host) could infect permissive human cells.
Co-culture of the xenograft and recipient wound bed cells with permissive human cells for PERV infection and replication did not demonstrate productive infection in the target cells (HEK293), after a 23-day culture.

Example 2

The following example provides a description of a process of harvesting and processing skin from a designated pathogen free α-1,3-galactosyltransferase [Gal-T] knockout swine produced in accordance with the present invention, with the skin to be used as a xenogeneic skin product for human transplantation. In some of these aspects, the xenotransplantation product consists of split thickness grafts consisting of dermal and epidermal tissue layers containing vital, non-terminally sterilized porcine cells derived from specialized, genetically engineered, Designated Pathogen Free (DPF), source animals (alpha 1,3 galactosyltransferase knockout [Gal-T-KO] miniature swine).

The genetically engineered source animals in this example do not contain any foreign, introduced DNA into the genome; the gene modification employed is exclusively a knock-out of a single gene that was responsible for encoding for an enzyme that causes ubiquitous expression of a cell-surface antigen. The xenotransplantation product in this example does not incorporate transgene technologies, such as CD-46 or CD-55 transgenic constructs.

The process and techniques disclosed herein are but examples, and do not limit the scope of the invention. It will be fully understood that while this example is directed to xenotransplantation skin products, several of the steps in the following process and aspects of the overall approach can be applied to other organs or tissues, including, but not limited to, kidney, lung, liver, pancreas, nerve, heart, intestine, and other organs or tissue. It will be further understood that modifications to the processes and methods disclosed in this example (including additions or omissions of one or more process or method steps) can be made in relation to the harvesting and processing of other organs or tissue besides skin. This understanding is based in part on the fact that other organs and tissue will have different physical characteristics and so harvesting and processing steps for such other organs or tissue will be different from this example in certain practical ways (e.g., a kidney, heart, liver, lung, or other whole organ will not be cut to size and packaged in a cryovial supported by nylon mesh). Nonetheless, it will be further understood that additions or omissions of one or more process or method steps as applied to each such organ or tissue may be made to this example utilizing approaches known in the art (e.g., a harvested kidney, heart, liver, lung, or other whole organ will, in some aspects, be placed in an antipathogen bath or exposed to UV light as described herein for the removal of pathogens following harvest, and placed in one or more closure systems. For example, such one or more closure systems could include, but not be limited to, a first closure system (e.g., utilizing an inert material for initial closure to surround the organ to prevent the organ from coming into contact with or adhering to other materials proximate to the organ) and/or a second closure system (e.g., a sterile and secure outer container that contains the organ and first closure system (if a first closure system is utilized)). Such organs within such closure system(s) are configured to be transported to a clinical site as whole organs, stored, protected and transported in temperatures, sterility, and other conditions to maintain sterility and cell viability for transplantation as described herein at the clinical site.

Animal Preparation

Skin product processing occurs in a single, continuous, and self-contained, segregated manufacturing event that begins with the sacrifice of the source animal through completion of the production of the final product.

Xenogeneic skin grafts derived from the DPF Closed Colony is received, with the swine being recently euthanized via captive bolt euthanasia in another section of the DPF Isolation Area. The source animal is contained in a sterile, non-porous bag that is contained within a plastic container which is delivered into the DPF Isolation Area and placed in an operating room where the procedure to harvest skin from the source animal will occur. All members of the operating team should be in full sterile surgical gear dressed in sterile dress to maintain designated pathogen free conditions prior to receiving the source animal and in some instanced be double-gloved to minimize contamination.

The operating area is prepared with materials required for harvesting skin from the source animal prior to decontamination (e.g., 24 hours prior with chlorine dioxide gas treatment) and prior to the procedure. Dermatome (electronic skin harvesting device, e.g., Amalgatome by Exsurco) power supply, and extension cord are sterilized and placed in the operating area prior to the operation. Any materials not in the room during the chlorine dioxide gas treatment (and therefore non-sterile) will be sprayed with 70% ethanol or isopropanol prior to entering the room.

The source animal is removed from the bag and container in an aseptic fashion, for example, a human lifting the source animal from the bag and container using sterilized gloves and/or sterilized device to aid lifting and minimize contamination. The source animal is scrubbed by operating staff for at least 2 minutes with Chlorhexidine brushes over the entire area of the animal where the operation will occur, periodically pouring Chlorhexidine over the area to ensure coverage.

The source animal is placed on its right lateral flank and dorsum towards the operating table leaving the left lateral flank and dorsum exposed. The exposed surface is scrubbed to the extreme visible surgical borders, and constrained by sterile drapes secured with towel clamps. The source animal is then scrubbed with opened Betadine brushes and sterile water rinse over the entire area of the animal where the operation will occur for approximately 2 minutes.

This Chlorhexidine and Betadine mixture will sit on the source animal for approximately 2 minutes, and staff (dressed in sterile dress to maintain designated pathogen free conditions) will then rinse and dry the source animal with sterile water and sterile gauze. The source animal's hair is removed so as to not impact the membrane or introduce another element that would degrade the cells. Hair removal is done using sterilized clippers and/or straight razor in the designated pathogen free environment immediately post-mortem with a clean blade utilizing a chlorhexidine lather. Staff will use the clippers and/or straight razor (lubricated in a sterile bath) to remove any remaining hair on the operating site, taking care to not puncture the skin. This procedure will be repeated (scrubbing to shaving) by turning the source animal onto the left lateral flank so as to expose the right side. The source animal will be rinsed with sterile water and dried with sterile towels and sprayed with 70% ethanol. The source animal will be inspected visually by the surgeon to ensure proper coverage of scrubbing. After the sterile scrub and final shaving, the source animal is ready for skin harvest.

Skin Harvesting

Operators will be dressed in sterile dress in accordance with program and other standards to maintain designated pathogen free conditions. All tissue from the source animal that will be used for xenotransplantation is harvested within 15 hours of the animal being sacrificed.

In one aspect, the source animal is laid on its side on an operating table. In this aspect, harvesting is done utilizing a dermatome circular blade, (for example and Amalgatome® SD). As the staff secures the animal in place, the surgeon determines the most appropriate width (e.g., 1, 2, 3, or 4 inches) and uses the circular dermatome to remove strips of split thickness skin grafts at a chosen thickness (e.g., 0.50 mm, 0.55 mm, 0.62 mm).

By way of further example, the thickness of the skin grafts could range from 0.01 mm to 4 mm, depending on the therapeutic needs at issue. It will also be understood that in some aspects a full thickness graft may also be utilized harvested with alternative harvesting and grafting procedures known in the art. Graft sizes can range from 1 $cm^2$ to 1000 $cm^2$ (or approximately 1 $ft^2$). It will be understood that larger graft sizes are also possible depending on the application and harvesting technique utilized and size of the source animal. It will be understood that for all aspects, other depths could be utilized as well, depending on the application and needs of the task at hand for therapeutic and/or other purposes.

In another aspect, skin harvesting involves surgically removing a skin flap from the animal first, then the skin flap is placed dermis-side down onto a harvest board (e.g., a solid board made of metal, plastic or other appropriate material) set upon on the operating table. In this aspect, sterile padding material is added beneath the skin flap and on top of the harvest board, to allow appropriate give for proper dermatome device function. The skin flap is then affixed to the harvest board firmly with steel clamps. Curved towel clamps are utilized on the side of the skin flap opposite the clamps until the skin is firm and taut. The surgeon will choose the most appropriate thickness on the dermatome and adjust per harvest conditions. The surgeon will use the dermatome on the secured skin flap, with an assistant maintaining tension along the dermatome progress. A second assistant may also provide assistance with skin flap tension, and may use rat tooth forceps to pull the graft product emerging from the dermatome.

Grafts are trimmed to desired sizes. By way of example, sizes can be: 5 cm×5 cm, with a total surface area of 25 $cm^2$ and uniform thickness of approximately 0.55 mm; 5 cm×15 cm, with a total surface area of 75 $cm^2$ and uniform thickness of approximately 0.55 mm; 8 cm×7.5 cm, with a total surface area of 60 $cm^2$ and uniform thickness of approximately 0.55 mm; 8 cm×15 cm with a total surface area of 120 $cm^2$ and uniform thickness of approximately 0.55 mm. It will be further understood that customizable sizes (i.e., width, thickness and length) can be created depending on patient needs, including larger sheets of skin can be harvested for use in xenotransplantation procedures.

The xenotransplantation product is further processed to be free of aerobic and anaerobic bacteria, fungus, and mycoplasma. Under sterile conditions in a laminar flow hood in a drug product processing suite using applicable aseptic techniques, immediately after, within 1, 2, 3, 4, 5, 6, 7, 8, 9, 10 seconds, within 10 seconds to 1 minute, within 1 minute to 1 hour, within 1 hour to 15 hours, or within 15 hours to 24 hours following harvest, the xenotransplantation product is placed into an anti-microbial/anti-fungal bath ("antipathogen bath"). With regard to a skin product, this can occur after the skin product is trimmed to the proper dose size and shape (e.g., trimmed to squares, rectangles, or others shapes of desired size(s))

The antipathogen bath includes ampicillin, ceftazidime, vancomyocin, amphotericin-B placed in a sterile container and the xenotransplantation products are diluted as outlined in the following Table 6 and added to RPMI-1640 medium as outlined in the following Table 7. In one aspect, about 10 mL of medium is removed from the bottle before adding the above items.

TABLE 6

| Drug | Vial Mg | Diluent Vol | Diluent | Approx. Vol available | Approx. concentration |
|---|---|---|---|---|---|
| Ceftazidime | 1000 | 10.0 mL | Sterile water | 10.8 mL | 100 mg/mL |
| Ampicillin | 2000 | 10.0 mL | Sterile water | 11 mL | 180 mg/mL |
| Vancomycin | 500 | 10.0 mL | Sterile water |  | 50 ug/mL |
| Amphotericin B | 50 | 5.0 mL | Sterile water |  | 10 mg/mL |

TABLE 7

| Drug | Final Concentrations | mg/500 mL Media | Volume (mL) added to 500 mL RPMI 1640 |
|---|---|---|---|
| Ceftazidime | 500-2500 mg/L | 250-1250 mg | 2.5-10 |
| Ampicillin | 500-2500 mg/L | 250-1250 mg | 1-6 |
| Vancomycin | 25-125 mg/L | 10-75 mg | 0.25-2 |
| Amphotericin B | 40-200 mg/L | 20-100 mg | 2-10 |
|  |  | Total volume added | 5.75-28 |

It will be understood that while this example is directed to xenotransplantation skin products, other organs, including, but not limited to, kidney, lung, heart, liver, pancreas, and other organs can be bathed in the antipathogen bath in accordance with the present invention. The amounts of combination of drugs and other chemicals, and duration of exposure to such antipathogen bath, are performed to minimize the affect such exposure has on cell viability and mitochondrial activity to achieve both the desired antipathogen result and minimal manipulation of the xenotransplantation products in accordance with the present invention.

As an alternative, or in addition to, removing pathogens via the antipathogen bath, the products are made designated pathogen free by a process and system utilizing ultraviolet light. In this aspect, the operator is dressed in sterile dress in accordance with institutional standards to maintain designated pathogen free conditions. The operator wears eye protection safety glasses for ultraviolet light and lasers.

An ultraviolet laser lamp is set up in a laminar flow hood. Each of the four corners of the lamp is placed on two container lids that are stacked on top of each other, i.e., four pairs of lids are used to support the lamp, or other supporting items, able to position the lamp in a temporary or fixed position above the working surface of the hood. The distance from the lamp bulbs (2 bulb tubes total) to the floor of the hood is approximately 1.5 inches. The entire interior of the hood is sprayed with alcohol, e.g., ethanol or isopropanol. The lamp is turned on and the operator performs a calculation of time for desired exposure based on lamp specifications, number of bulbs, and distance between the bulbs and the xenotransplantation product.

The operator pours two baths (one chlorhexidine and one alcohol) into two separate bowls and places the two bowls under the hood.

A package of new sterilized cryovials is placed under the hood. Cryovial caps are unscrewed and placed into the chlorhexidine bath. Each cryovial (without cap) is then turned upside down and plunged open ended into the chlorhexidine bath, for one minute each and then set upright to air dry. Thereafter, the exterior of each cryovial is wiped with chlorhexidine and alcohol utilizing sterile gauze. The cryovial caps are removed from the chlorhexidine bath and placed on sterile gauze. The open ends of each vial were plunged into alcohol bath for 1 minute each and then set aside to air dry.

Xenotransplantation products recently obtained from the harvest/procurement phase in the surgical room are transferred into the product processing room, via a one-way entrance into the laminar flow hood. Anything entering the sterile field is wiped down with 70% ethanol prior to transfer to the operator. The operator will have access to all required materials in the laminar flow hood: xenotransplantation product (in sterile container), cryovials, 10 mL syringes and needles, phase freezer holding rack, and pre-cut nylon mesh. Only one size of the products is processed at a time to ensure proper control to final vials. The operator is seated at the laminar flow hood in compliance with sterile, aseptic techniques.

When using UV light sterilization, the product is placed under the UV lamp for a desired period of time, e.g., 2 minutes or more, then turned over to the other side, and put under the UV lamp for the same period of time, e.g., 2 minutes or more on opposite side. The time period for exposing a given sample to the UV is varied based on the specific biological agents or the types of biological agents to be sterilized, e.g., as shown in the following Table 8:

TABLE 8

| Biological Agent | Type of Biological Agent | UV-C Dosage (uW sec/cm$^2$) for 90% sterilization | Sterilization time (sec)* |
|---|---|---|---|
| Penicillium spp. | Fungus | 224,000 | 1800 |
| Aspergillus flavus | Fungus | 34,900 | 300 |
| Aspergillus niger | Fungus | 31,500 | 250 |
| Yeast | Fungus | 4000 | 30 |
| Influenza A | Virus | 1900 | 15 |
| HIV-1 | Virus | 28,000 | 220 |
| Vaccinia | Virus | 1500 | 10 |

TABLE 8-continued

| Biological Agent | Type of Biological Agent | UV-C Dosage (uW sec/cm$^2$) for 90% sterilization | Sterilization time (sec)* |
|---|---|---|---|
| *Escherichia coli* | Bacteria | 2000 | 20 |
| *Staphylococcus aureus* | Bacteria | 6600 | 50 |
| *Bacillus subtilis* | Bacteria | 6800 | 50 |
| *Mycoplasma spp.* | Bacteria | 8400 | 70 |
| *Pseudomonas aeruginosa* | Bacteria | 2200 | 20 |

*Using a UV-C intensity of 125 uW/cm$^2$

With regard to other whole organs, product yield will typically depend on how many of each such whole organ a given source animal may have (e.g., one liver, two lungs, two kidneys, one heart, one pancreas and so forth).

It will also be understood that while this example is directed to xenotransplantation skin products, other organs, including, but not limited to, kidney, heart, lung, liver, pancreas, and other organs can be exposed to ultraviolet light and made designated pathogen free in accordance with the present invention. The UV exposure dosages, intensity, and duration of exposure to such ultraviolet light, are performed to minimize the affect such exposure has on cell viability and mitochondrial activity to achieve both the desired antipathogen result and minimal manipulation of the xenotransplantation products in accordance with the present invention.

Manufacturing Process

Generally

Through the continuous manufacturing event, source animals are processed into aseptic xenotransplantation products. Several items are involved in the manufacture of the product relating to the source animals, including, but not limited to:

a. care and husbandry of the source animals (including, as described herein, providing certain vaccinations, carefully maintaining and analyzing pedigree records, performing proper animal husbandry, and maintaining the animals in isolation barrier conditions);

b. product manufacturing (including, as described herein, processing the source animals into the subject product from euthanizing to harvest);

c. analytical testing of the source animals (including, as described herein, screening for adventitious agents including parasitology, bacteriology, and virology assays);

d. analytical testing of the source animals (including, as described herein, confirming the source animal is an alpha-1,3-galactotransferase knockout or has other characteristics that are desired for a given application); and e. analytical testing of the source animals (including, as described herein, viral assay for Endogenous Viruses (PERV)).

Several items are also involved in the manufacture and release testing of the resulting products, including, but not limited to:

a. product manufacturing (including, as described herein, processing the drug product, storing the drug product, and releasing the drug product);

b. analytical testing of the drug product (including, as described herein, viability testing (via, e.g., MTT assay)), c. sterility testing (including, as described herein, aerobic bacteria culture, anaerobic bacteria culture, fungal culture, *mycoplasma* assay, endotoxin test, USP <71>)), d. adventitious agent testing (including, as described herein, PCR Assay for e.g., Endogenous Viruses (PERV)); and e. analytical testing of the drug product (including, as described herein, histology).

For skin, the quantity of product yield from each animal can vary depending on the size of each animal. By way of example, some animals could yield between 3,000 and 6,000 cm$^2$ in product. In one aspect, a single batch of skin product is harvested from a single source animal in a continuous process. A batch description of the xenotransplantation product is provided in Table 9 and batch formula for the xenotransplantation product is provided in Table 10.

TABLE 9

Batch Size

| Product (strength) | Lot Size |
|---|---|
| Xenotransplantation product Drug Product, Dosage Strength 1 (7.5 grams, 25 cm$^2$) | 200 Units (180-220) (1.5 kgs per lot) (1.35 kg to 1.65kg) |
| Xenotransplantation product Drug Product, Dosage Strength 2 (22.5 grams, 75 cm$^2$) | 67 units (60-75) (1.5 kgs per lot) (1.35 kg to 1.65kg) |

TABLE 10

Batch Formula

| Component | Nominal Amount per Vial | Nominal Amount per Lot |
|---|---|---|
| Xenotransplantation product Drug Substance Dosage Strength 1 | 25 cm$^2$ | 200 Units |
| CryoStor | 7 ml | 1.4 L |
| Nylon Mesh | 60 cm$^2$ | 1200 cm$^2$ |
| Total Batch Size | 7.5 grams | 1.5 kgs |
| Xenotransplantation product Drug Substance Dosage Strength 1 | 75 cm$^2$ | 67 Units |
| CryoS tor | 5 ml | 350 ml |
| Nylon Mesh | 180 cm$^2$ | 3600 cm$^2$ |
| Total Batch Size | 22.5 grams | 1.5 kgs |

Prior lot testing is performed under good laboratory practice ("GLP") conditions to ensure process sterility is maintained consistently. Assurance of sterility of the final product is determined prior to material release and clinical use. Prior to validation for human clinical use, all xenotransplantation products will meet certain acceptance criteria, including as described herein. The final drug product control strategy and analytical testing is conducted at the conclusion of the manufacturing process prior to release for clinical use. Results of the required analytical tests will be documented via a drug product certificate of analysis (COA) that is maintained with a master batch record pertaining to each lot of xenotransplantation products.

Source animal sample archives are generated and maintained through procurement of tissue samples of lung, liver, spleen, spinal cord, brain, kidney, and skin. These tissues are collected for source animal tissues for testing, archive, and stored for potential future testing. Archived samples of source animal tissue and bodily fluids should be stored at minus (−) 70 degrees Celsius or lower, as appropriate for preserving the sample. In other aspects, fixed samples can be maintained at room temperature. Appropriate tissue samples should be collected for formalin fixation and paraffin-embedding and for cryopreservation from source animals at the time the live cells, tissues, or organs are procured. Cryopreservation should be at least ten 0.5 cc aliquots of citrated- or EDTA-anticoagulated plasma; five aliquots of viable leukocytes (1×107/aliquot, for subsequent isolation of nucleic acids and proteins or for use as a source of viable cells for co-culture or other tissue culture assays.

Product Processing Following Harvesting

The previously harvested and minimally manipulated xenotransplantation skin product (here the skin integrity being minimally manipulated dermal and epidermal tissue layers with standard cellular morphology and organization) enters the separate, adjacent room with positive pressure above that of the surgical suite, designated as the Class 10,000 (ISO-7) product processing room.

The operating room will be setup per operating preparation procedures and the operating personnel will be dressed in Tyvex suits for fume hood work. If requested, an assistant will also be dressed in a Tyvex suit. Gowning and Dressing is done with aseptic techniques. Gloves and sleeves will be sprayed with alcohol if needed. The ABSL-2 laminar flow hood, having been prior sterilized via gaseous chlorine dioxide sterilization process, will be sprayed with alcohol, e.g, 70% ethanol, and the laminar flow exhaust will be initiated. Utilizing aseptic techniques, previously sterilized via autoclave, surgical instrument, cryovials, cryotray, flasks, syringes, needles, additional containers, and all processing equipment will be placed within the laminar flow hood. Exterior packaging is sprayed with alcohol prior to being transferred to the operator.

As described herein, prior to operation, nylon mesh graft backing should be cut into squares of appropriate size for the dosage levels, sealed in an autoclavable pouch, and sterilized via steam. Exterior of pouch will then be sterilized with 70% ethanol and placed in the fume hood. Exterior package of 10 mL Cryovials will be decontaminated with 70% ethanol and placed into the fume hood. Sterile, autoclaved surgical instrument package should be sprayed with 70% ethanol and transferred to the operator.

Sterile syringes and needles should be sprayed with 70% ethanol and transferred to the operator. Graft tissue recently harvest form the porcine donor will be transferred to the hood. Anything entering the sterile field is wiped down with 70% ethanol prior to transfer to the operator. Operator will have access to all required materials in the fume hood: Grafts (in sterile container), Cryovials, 10 mL syringes and needles, Phase Freezer holding rack, and cut Nylon mesh. Operator should be seated at the fume hood with in compliance with sterile, aseptic technique.

Referring to FIG. 2, each cryovial will be sterilized and labeled in advance to reduce processing time and unnecessary material exposure to DMSO prior to cryopreservation. Pans containing each xenotransplantation product and the RPMI 1640 Tissue Culture Media at room temperature with antibiotics (e.g., antipathogen bath) is placed under the laminar flow hood. The products had been bathing in the anti-pathogen bath for not less than 30 minutes to sterilize the xenotransplantation product.

In one aspect, when using UV light sterilization, the cryovials are sterilized using the UV lamp as described above. After the product is inserted into each vial, each new cap is placed on each new vial and screwed on securely. Each vial is placed under the lamp and periodically rolled for desired even exposure to light on the exterior of the vial. The vials are placed inside a glass jar that has an interior that has been previously sterilized and the exterior is sterilized by the operator with alcohol and chlorhexidine, including threads and caps. Vials are wiped down with alcohol and are placed into glass jars. The exteriors of the glass jars are drenched with alcohol outside of the hood. Under the hood, the operator bathes the glass jar lids and plunges the open ends of the jars into alcohol and wipes the exterior of the jars with alcohol (and optionally chlorhexidine) including threads of the jar. The vials are wiped with alcohol utilizing gauze and placed inside each glass jar with an instrument. The lids of the glass jars are then secured and the jars are handed to the assistant. Frequently and on a periodic basis throughout these processes, the assistant sprays the operator's gloves and arms with alcohol.

In this example, the xenotransplantation skin product, which was cut to form in the surgical suite with sterile scissors and was trimmed with 10-blade scalpel, will be re-measured with a sterile, stainless steel ruler to verify technical specifications and dimensions have been met. The xenotransplantation skin product is visually inspected to ensure no rips, tears, observable defects, or excessive or insufficient thickness are present.

Under the laminar flow hood the operator will use forceps to take a single xenotransplantation skin product from the antipathogen bath and place it upon a piece of nylon mesh that has been previously cut to fit the cryovial, centered on the nylon mesh, with the dermis side in contact with the mesh (e.g., dermis side down), taking 1 minute for each product (understanding the time could be less or more, and up to 5 minutes for each product). It will be understood that the sterile nylon mesh packaging component is utilized, among other things, to support the xenotransplantation product and prevent self-adhesion of the xenotransplantation product when rolled.

It will be further understood that the sterile nylon mesh packaging component can be of any dimension that would allow the xenotransplantation product to be placed onto the sterile nylon mesh packaging component and fit within the two dimensional surface area (i.e., the length and width not including the thickness) of the sterile nylon mesh packaging component (e.g., the two dimensional area dimension of the xenotransplantation product would be less than the two dimensional area dimension of the sterile nylon mesh packaging component).

It will be further understood that the dimensions of the sterile nylon mesh packaging component would be sized in accordance with the xenotransplantation product size and dosage. For example, the sterile nylon mesh packaging component is 8 cm×7.5 cm (60 cm$^2$) to fit a 5 cm×5 cm xenotransplantation skin product (25 cm$^2$) (7.5 grams) utilizing 7 ml of cryoprotective media when placed in the cryovial. It will be even further understood that the dimensions of the sterile nylon mesh packaging component is 8 cm×22.5 cm (180 cm$^2$) to fit a 5 cm×15 cm xenotransplantation skin product (75 cm$^2$) (22.5 grams) utilizing 5 ml of cryoprotective media when placed in the cryovial.

Unintentional adhesion of epidermal or dermal regions of the xenotransplantation skin product during packaging may disrupt the integrity of the xenotransplantation skin product and potentially reduce its therapeutic viability. Inclusion of the sterile nylon-mesh packaging component is intended to provide internal physical support to and prevent self-adhesion. The sterile nylon-mesh packaging component is not biologically or chemically active and does not directly impact the metabolic activity or efficacy of the xenotransplantation skin product itself.

During the course of numerous experiments, including the monkey studies described in Example 1 herein, use of this sterile nylon-mesh packaging component has never been observed to cause an adverse, undesired reaction with the xenotransplantation product, or degrade and contaminate the final xenotransplantation product causing adverse reactions or outcomes to the recipient. The sterile, nylon-mesh packaging component is not used in the grafting procedure. Following cryopreservation and thawing, and prior to use of the xenotransplantation product, it is discarded. Thus, selection of the specific material and associated specifications were carefully chosen for the given application. Medifab 100-Micron Nylon Mesh (Part #03-100/32-Medifab) is manufactured per cGMP standards, and was selected because of its physical characteristics and certified acceptability for human, clinical use.

Under the laminar flow hood, the operator will then tightly roll this combination of xenotransplantation product and nylon mesh packaging component and place the combination within a cryovial (e.g., 10 ml vial) taking 1 minute for each product (understanding the time could be less or more, and up to 5 minutes for each product). In this aspect, the mesh material is rolled to ensure that the vertical height of the cylinder is 8 cm and uniformly fits within the 10 ml cryovial (e.g., 10 cm length and 17 mm diameter) and once completed, can be secured with a threaded seal cap. The mesh material is oriented such that the protective mesh material is on the exterior of the xenotransplantation product, and that once the rolled is complete there is no exposed or visible xenotransplantation material and it is fully encased in the protective insert. The intrinsic tensile and material properties of the sterile nylon-mesh packaging component are homogenous, and the inelasticity or stiffness of the material causes it to expand to fill the volume of the cryovial. Thus, regardless of the initial "roll-density", the material will uniformly loosen and is therefore standardized.

Under the laminar flow hood the operator will then use a sterile syringe to draw up enough sterile cryoprotective media (e.g., 5-7 ml of the media with 5% dimethyl sulfoxide (DMSO) (Cryostor CS5, BioLife Solutions)) to fill the cryovial until the skin product roll is fully immersed, ensuring that the combination of xenotransplantation skin material, mesh backing, and cryoprotectant media is flush with the 10 ml fill line, taking 1 minute for each product (understanding the time could be less or more, and up to 5 minutes for each product).

Under the laminar flow hood, the operator will seal the cryovial with the threaded cap. The identity of the contents and label information are confirmed by the operator. Labels are prepopulated and applied to the exterior of the cryovials containing the product in advance of the product processing.

It will be understood that the preparation of the xenotransplantation products and packaging components described herein could be in the form of therapeutic dosages. For example, the xenotransplantation drug product consists of:
  a. Xenotransplantation split-thickness skin Drug Substance
  b. Primary Container Closure System which includes
    i. Primary Packaging Component: a sterile, clear, polypropylene 10 ml cryovial with threaded seal-cap
    ii. Sterile nylon-mesh packaging component
    iii. Cryoprotective media packaging component The indicated dosage of Xenotransplantation product is 300 mg of vital, metabolically active, porcine xenotransplantation drug substance per cm$^2$, with a constant thickness of 0.55 mm. Example formulations include:
  c. Dosage Strength 1: a 25 cm$^2$ split thickness skin graft, with uniform thickness of 0.55 mm, which weighs approximately 7.5 grams.
  d. Dosage Strength 2: a 75 cm$^2$ split thickness skin graft, with uniform thickness of 0.55 mm, which weights approximately 22.5 grams.

An example xenotransplantation drug product primary packaging component is a sterile, clear, polypropylene 10 ml cryovial with threaded seal-cap. For example, the Simport Cryovial, T310 (10-ml) is manufactured by Simport Scientific. This product is composed of medical grade resin that is BPA free, Heavy Metal Free, and LATEX Free and meets USP Class VI limits.

A nylon-mesh packaging component is utilized during the xenotransplantation drug product manufacturing process. The prepared xenotransplantation drug product is placed on sterile nylon-mesh packaging component (e.g., Medifab 100-Micron Nylon Mesh) that has been previously trimmed to the following dimensions:
  a. Dosage Strength 1: 7.5 cm in width by 8 cm in height; total area of 60 cm$^2$
  b. Dosage Strength 2: 22.5 cm in width by 8 cm in height; total area of 180 cm$^2$ A cryoprotective media packaging component is also utilized during the drug manufacturing process. The xenotransplantation drug product is immersed in the following volumes of cryoprotective media packaging component prior to cryopreservation:
  a. Dosage Strength 1: 7 ml of Cryostor CS5 (containing 5% DMSO).
  b. Dosage Strength 2: 5 ml of Cryostor CS5 (containing 5% DMSO).

With regard to the assurance of saturation of cryoprotective media, the indicated amount of CryoStor CS5 media (per Dosage Strength) is applied via 10 ml syringe with the cryovial (such as a type of cryovial shown in FIG. 30) in the vertical position, under a laminar flow hood (ISO-5, FED STD 209E Class 100 conditions) Cryomedia fills the voided space(s), and gravity ensures that the fill-process begins from the base of the vertically oriented cryovial towards the fill line at the apex. Volume is added until it reaches the manufacturers demarcated 10 ml fill line. Filling the vial in this manner also facilitates the removal of air bubbles. Once complete, the threaded cap is sealed. Visual and physical verification of saturation and fill is accomplished, ensuring that contents the xenotransplantation product are unable to shift internally.

Cryopreservation

Product materials will be placed in the appropriate freezer rack containing cryovials with product as described above, and placed in a certified, Q-A control rate-phase freezer. Using a certified, Q-A control rate-phase freezer, the entire product is cryopreserved via one standardized control-rate freezing process:
  a. Starting at 4° C., internal chamber and sample temperature probe will lower at a rate of 1° Celsius per minute until a temperature of −40° C. is achieved.
  b. Once temperature of −40° C. has been reached in a controlled rate, control-rate freezer sample temperature probe should lower rapidly from −40° C. to −80° C. c. Material is then transferred to a GLP certified, −80° C. freezer until use.

Taking 40 minutes per batch time from room temperature to −80° C. (understanding the time could be less or more, and up to 2 hours). In some aspects, penetrative cryoprotectants such as DMSO, may be used to protect morphology and tissue structure, and retain metabolic activity levels comparable to that of fresh skin. In some aspects, cryopreservation may alternatively or additionally include one or more of glycerol, gentamicin, Nystatin, L-glutamine, and other processing solutions. In some aspects, β-lactam antibiotics are not used.

Inclusion of the cryoprotective-media packaging component is intended to support cell survival during the freeze-thaw cycle required for the xenotransplantation product. Failure to include the cryoprotective media packaging component of xenotransplantation product during packaging may disrupt the integrity of the xenotransplantation product or impede the cryopreservation process, and may potentially reduce the xenotransplantation product viability below acceptance criteria. Cryopreservation of the xenotransplantation product without inclusion a cryoprotective media results in destruction of biologically active cells contained in the xenotransplantation product. Rapid formation of ice crystals and disruption of cellular membranes and mitochondrial organelle barriers occurs during the freezing process, and the dimethyl-sulfoxide ingredient acts to displace intracellular fluid. Thus, the cryoprotective media reduces the formation of such ice crystals and rapid, disruptive increase in total cellular volume that would negatively impact the cellular viability and, thus, the efficacy of the Drug Product.

During the course of a number of experiments, including the monkey studies in Example 1 herein, use of this cryoprotective-media packaging component has never been observed to cause an adverse, undesired reaction with the xenotransplantation product, or degrade and contaminate the final xenotransplantation product causing adverse reactions or outcomes to the recipient. Thus, selection of the specific material and associated specifications were chosen to meet appropriate standards necessary of a xenotransplantation product intended for human, clinical use. This including identifying a cryoprotective media with minimal, subclinical levels of DMSO, one that would satisfactorily perform without the need for inclusion of an additional xenotransplantation material (porcine serum) in the formulation. The cryoprotective media-packaging component is not used in the grafting procedure. Upon thawing, and prior to use of the xenotransplantation for therapeutic uses including as a drug product, it is discarded. CryoStor CS5 is manufactured per cGMP standards and was selected because of its certified acceptability for human, clinical use.

Shipping to Clinical Site

Shipping the product to the clinical site should be done to maintain the xenotransplantation skin product material at −80° C. storage condition. One example shipping container is the EXP-6 Standard Dry Vapor Shipper having an extensive, having the following specifications:
  Dynamic Holding Time 10 Days
  Holding Temperature −150° C. or Colder
  Core Technology Dry Vapor Liquid Nitrogen
  Specimen Chamber 2.8" (71 mm) Diameter
  11.5" (292 mm) Depth
  Weight Dry 9.7 lbs/4.4 kg
  Charged 18.3 lbs/8.3 kg
  Domestic Dimensional 21.07 lbs/9.56 kg
  International Dimensional 24.87 lbs/11.28 kg
  Outer Box 12"×12"×22"
  (305×305×559 mm)

Figure 29:
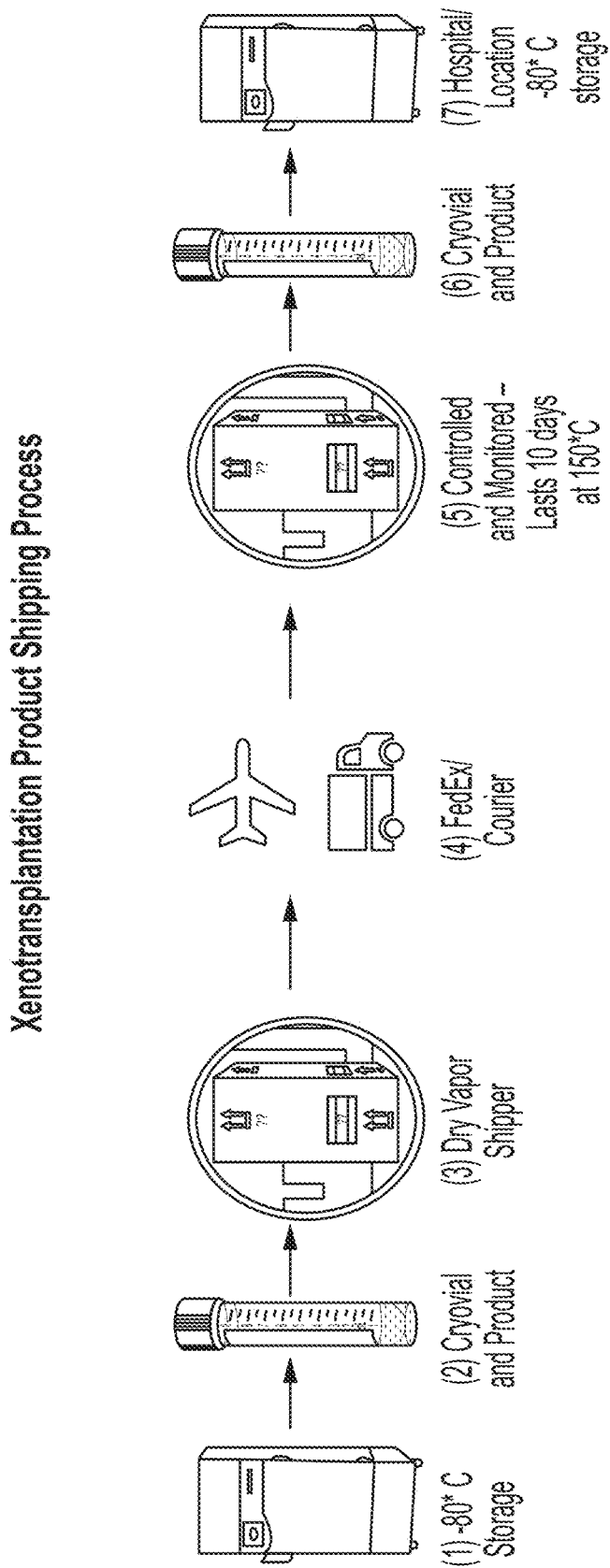
FIG. 29 shows a shipping process of a xenotransplantation product.

Aspects of the shipping process are also shown in FIG. 29 including, but not limited to, (1) cryopreservation storage; (2) xenotransplantation product in cryovial and media as described herein while in cryopreservation storage; (3) cryovial placed in dry vapor shipping container (or secondary closure system); (4) container and vial shipped via courier; (5) xenotransplantation product controlled and monitored at delivery location (can last at least 10 days at minus (−) 150 degrees Celsius or colder); (6) xenotransplantation product in cryovial and media as described herein removed from container/secondary closure system; (7) xenotransplantation product in cryovial and media as described herein placed in freezer at location being stored at −80° C.

Clinical Site Preparation

In one aspect, the drug product arrives at the clinical site as a cryopreserved xenotransplantation product. Prior to use, the xenotransplantation product must be thawed in a 37° C. water bath, removed from the vial and washed in a series of 3 sterile 0.9% saline baths at room temperature.

For the thawing process, sterile equipment and aseptic techniques are used:
  a. Prepare 200 mL of normal saline into each of three 500 mL sterile, surgical bowls.
  b. Place the unopened cryovial with the skin product in water bath having a temperature of about 25° C. In some embodiments, the temperature is about 37° C.
  c. In the bath, swirl gently for approximately 5 minutes or until tissue is mobile within the cryovial, taking care to minimize unnecessary exposure time the xenotransplantation skin product tissue is suspended in the thawed DMSO as much as possible.
  d. Open the cryovial and use sterile forceps to quickly remove tissue and mesh to transfer into a bowl of normal saline.
  e. Using sterile forceps, ensure tissue is fully submerged in saline for 15 seconds, agitating by swirling gently to maximize coverage. The underlying, supportive mesh material should be separated from the skin xenotransplantation skin product material. Use a second pair of sterile forceps to separate if necessary. Mesh can be left in the bowl, or discarded.
  f. Using sterile forceps, transfer the skin into a second bowl wash. Submerge fully and gently swirl for 15 seconds; this is a serial dilution or "rinse".
  g. Repeat the previous step, using sterile forceps to transfer the skin into a third wash of normal saline. Submerge fully and gently swirl for about 15 seconds.
  h. The entire duration of the rinse process should be completed within 60 seconds to minimize unnecessary exposure time the product is suspended in thawed DMSO in order to maximize product efficacy.

i. Tissue is now thawed, rinsed, and ready for application. Leave in normal saline until use, not to exceed 2 hours at about 25° C.

After the complete, thaw and rinse process is complete, the xenotransplantation product is ready for placement on the wound site. Serial washes in saline, once thawed provide ample dilutive solvent to remove the residual cryoprotectant (5% DMSO solution, CryoStor CS5) and replace the intracellular fluid levels to normal homeostatic conditions. Such dilution and use of a cryoprotective media containing a sub-clinical level of DMSO ensures that any minimal, residual DMSO remaining on the xenotransplantation skin product material post-thaw would be non-appreciable and would be highly unlikely to be clinically significant. This process also ensures retention of the maximum amount of metabolically active cells, and thereby maximizing the efficacy of the xenotransplantation product.

Example of Thawing. Following is one example of a thawing procedure for a xenotransplantation product. Thawing can occur in a BioSafety Cabinet with operator in sterile gloves as follows: (i) prepare 200 mL of Normal saline into each of three 500 mL surgical bowls; (ii) prepare the water bath by wiping it clean with chlorhexidine then spraying it down with 70% ethanol; (iii) after the ethanol has dried add sterile water solution into the water bath and heat to 37° C.+/−2° C.; (iv) the xenotransplantation drug product is in a double bag, leave it unopened and place it into the 37° C. water bath; (v) swirl gently for approximately 5 minutes or until the tissue is mobile within the cryovial; (vi) minimize the time the tissue spends in thawed DMSO as much as possible; (vii) spray the outside bags with ethanol and remove the vial from the outer bags and spray the xenotransplantation drug product cryovials with 70% ethanol before placing into Biosafety Cabinet; (viii) unscrew the cryovial and use forceps to quickly remove tissue and mesh to transfer into a bowl of normal saline; (ix) use forceps to ensure tissue is fully submerged in saline for 60 seconds, agitating by swirling gently to maximize coverage; (x) the mesh should be separated from the skin, using a second pair of forceps to separate if necessary; (xi) the mesh can be left in the bowl, or discarded; (xii) using forceps transfer the skin into the second bowl wash; (xiii) submerge fully and gently swirl for 60 seconds; (xiv) using forceps transfer the skin into the third bowl wash and submerge fully and gently swirl for 60 seconds. Tissue is now thawed and ready for application. Keep it moist with sterile saline in a sterile pan.

The process of rolling the inert, nylon mesh backing and the xenotransplantation skin product results in uniform "roll-density" of the xenotransplantation product. All mesh materials are cut to uniform dimensions, according to the prescribed dimensions for the given application, and are obtained from the same material lot, thus affording uniform material properties for all units of the skin product manufactured within a specific lot.

The intrinsic tensile and material properties of the nylon mesh insert are homogenous, and the inelasticity or stiffness of the material causes it to expand to fill the volume of the primary container closure system (cryovial). Thus, regardless of the initial "roll-density", the material will uniformly loosen and is therefore standardized.

The indicated amount of CryoStor CS5 media (per Dosage Strength) is applied via 10 ml-syringe with the cryovial in the vertical position, under Class 100, ISO5 conditions within an ABSL-2 laminar flow hood.

Cryomedia fills the voided space(s), and gravity ensures that the fill-process begins from the base of the vertically oriented cryovial towards the fill line at the apex. Volume is added until it reaches the manufacturers demarcated 10 ml fill line. Filling the vial in this manner also facilitates the removal of air bubbles.

Once complete, the threaded cap is sealed. Visual and physical assurance of saturation and fill is accomplished by the shaking the skin product ensuring that contents are unable to shift internally. Aspects of the cryovial are also shown in FIG. 30, with aspects that can include, among other things, 10 ml volume, size of 17 mm×84 mm, vertical ribs facilitating cap removal, silicone washer, cap and tube made of the same polypropylene material with the same coefficient of expansion ensuring seal at all temperatures, 1 and ¼ turn thread design, thick wall, large white marking area, and round bottom allowing for ease of emptying contents.

Figure 31:
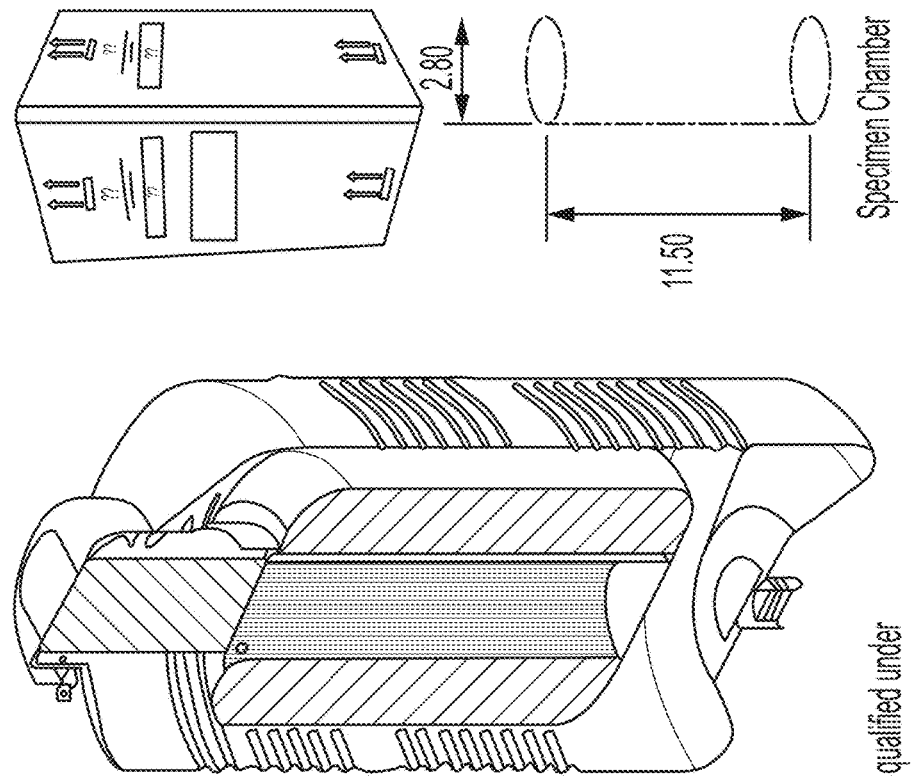
FIG. 31 shows a secondary closure or container system for storing a xenotransplantation product at temperatures below ambient temperature, including, but not limited to, −150 degrees Celsius and other temperatures.

Aspects of the secondary closure system is shown in FIG. 31, with aspects that can include, among other things, Tyvek—1073B medical grade construction, 5 inches wide× 12" high, storage ability of 15 canes or 2 cryovial boxes, holding temperature of −150 degrees Celsius or colder, utilization of dry vapor liquid nitrogen, IATA rated 10 days of dynamic holding time under normal shipping conditions, specimen chamber diameter of 2.8 inches (71 mm), specimen chamber depth of 11.5 inches (292 mm), dry weight of 9.7 lbs./4.4 kg, charged weight of 18.3 lbs./8.3 kg, domestic dimensional weight of 21.07 lbs./9.56 kg, international dimensional weight of 24.87 lbs./11.28 kg, outer box dimensions of 12"×12"×22."

No additional or external impurities in the product are anticipated to be present since processing involves only the minimal mechanical manipulation of the product, and no other chemical or biological agents are introduced during this closed process. Acceptance criteria testing required for use of the source animals for the product manufacturing process is conducted as described herein and documented via the Drug Product COA. The final product is evaluated for viral adventitious agents as described herein.

In terms of shelf life, continuous storage of the xenotransplantation product as described support a shelf life long-term stability (cell-viability) of up to at least 7 years (in one embodiment is a shelf life of 6 months) when stored continuously at −80° C. The shelf-life duration of continued cryopreservation of the xenotransplantation product with of at least 7 years. Table 11 shows stability time points that the xenotransplantation product will be tested.

TABLE 11

Stability Study Time Points

| | Time points (Months) | | | | |
|---|---|---|---|---|---|
| Assay | 0 | 12 | 24 | 36 | 60 |
| Histology | A | B | B | B | B |
| Sterility | A | B | B | B | B |
| Endotoxin | A | B | B | B | B |
| Viability | A | B | B | B | B |

A = initial product release testing
B = stability testing for Xenotransplantation product In accordance with one aspect, following in Table 12 are items that can be utilized in a certificate of analysis and release.

TABLE 12

Test Results

| Test | Method | Acceptance Criteria | Results |
|---|---|---|---|
| Appearance | Visual Inspection | Clear, colorless to slightly yellow liquid with no visible particulates | Conforms |
| pH | TM5110 USP <791> | 7.5 to 7.7 | 7.6 |
| Metabolic Activity Assay | TMS100 | Cell viability is 75% to 200% of cells preserved in the internal standard at Day 1 recovery following preservation. | 87 |
| Endotoxin | Kinetic Chromogenic USP <85> | ≤ 0.5 EU/ml | Conforms |
| Sterility | Membrane Filtration USP <71> | Sterile | Conforms |
| Identification | TMS111 FT-IR | Conforms to CryoStor CSS Reference Standard | Conforms |
| Osmolality | TM 5112 USP <785> | 1360-1390 mOsm/kgH2O | 1388 |
| Specific Gravity | TM5114 | 1.055-1.063 | 1.059 |
| DMSO Content | Gas Chromatography (FID) | 4.0%-7.0% | 5.0 |

Example 3

Dermis Epidermus Combo Product

The following example provides a description of a skin product derived from a designated pathogen free α-1,3-galactosyltransferase [Gal-T] knockout swine for use in human transplantation produced in accordance with the present invention. The product, process and techniques disclosed herein are but examples, and do not limit the scope of the invention.

Some skin transplantation products for the treatment of burns and other ailments utilize cultured epidermal autografts (see, e.g., products produced by Vericel Corporation under the Epicel® brand name). Such epidermal autografts can be utilized for patients with burns (including severe burns) and result in reduced or no rejection in the transplanted epidermal material since the material is derived from the patient's own skin.

However, such products are limited to the epidermis only, and do not include the dermis portion of the skin. Referring to FIG. 3, it will be understood that the dermis (which typically accounts for 95% of the thickness of the skin) performs significantly different functions than the epidermis (which is the outer portion of the skin that typically accounts for 5% of the thickness of the skin).

Since epidermal autografts alone lack the ability to perform the critical functions of the dermis, such products are used in combination with a viable dermis. In some injuries, the wound bed includes remaining portions of the patient's own dermis, which is the ideal dermis to utilize in a procedure grafting cultured epidermal autografts onto a patient. However, in some cases the burn is more severe, and the patient's own dermis no longer exists or is no longer viable. In those instances, a different dermis is required since an epidermal autograft alone will not suffice.

In one aspect, a full thickness skin graft wound dressing consisting of dermal tissue derived from designated pathogen free α-1,3-galactosyltransferase [Gal-T] knockout swine in accordance with the present invention is used in conjunction or combination with cultured epidermal autografts. One treatment process utilizing this combination is as follows.

A patient with severe burn wounds is taken to an operating room within 48-72 hours of injury. A biopsy is taken as soon as possible after the patient undergoes care, and the epidermis skin cells are isolated and grown separately according to the known procedures for creating cultured epidermal autografts (see, e.g., products produced by Vericel Corporation under the Epicel® brand name).

Depending on how much of the patient's body is damaged, epidermal autografts are taken from healthy areas to treat burned areas and/or to later create an epidermal autograft mesh used in the grafting process.

Areas of severe burns are treated with the skin products described herein, e.g., skin products derived from a designated pathogen free α-1,3-galactosyltransferase [Gal-T] knockout swine produced in accordance with the present invention. Such treatments comprise temporary wound coverage until sufficient autografts are utilized to treat the patient long-term.

Prior to application of the epidermal autografts, significant debridement of wound bed is required to ensure an adequate substrate. To confirm a wound bed is ready for an epidermal autograft, apply the skin products described herein, e.g., skin products derived from a designated pathogen free α-1,3-galactosyltransferase [Gal-T] knockout swine produced in accordance with the present invention to confirm adherence. Once adherence is confirmed, the temporary wound coverage product is removed, and in some aspects, the wound bed is covered with a meshed autograft, and one or more cultured epidermal autograft products are placed on top to close the gaps in the autograft mesh.

The debridement may include mechanical debridement, chemical debridement, enzymatic debridement, or a combination thereof. Mechanical debridement may include surgical excision, e.g., tangential excision to remove thin layers of dermis until healthy tissue is visualized, or fascial excision to remove the full thickness of dermis down to the underlying fascia. Tangential excision allows less viable tissue to be removed with the necrotic tissue, but typically results in higher blood loss, is a larger physiologic stressor than fascial excision, and is more likely to result in "incomplete" debridement, with some devitalized tissue remaining in place. In fascial excision, blood loss and operative time are minimized, but often a large amount of healthy tissue is removed with the burned tissue. Debriding agents may include agents capable of cleaning a burn wound by removing foreign material and dead tissue. Many such agents are known. In enzymatic debridement, collagenases or other proteolytic enzymes are employed that break down proteins of the extracellular matrix, allowing devitalized tissue to be wiped away without the need for surgery while preferably leaving healthy tissue substantially intact. Enzymatic debridement involves the application of proteolytic and optionally other exogenous enzymes to a wound surface to break down necrotic tissue. Enzymatic debridement may be a relatively slow process, carried out over a period of a number of weeks in combination with other topical preparations, soakings and repeated dressings. Alternately, rapid enzymatic debridement can be accomplished using multi-enzyme products, for example, those extracted from the stem of the pineapple plant, as disclosed for example in WO 98/053850 and WO 2006/0006167, and as provided in the product marketed under the trade name Debrase®. A procedure for enzymatic debridement generally utilizes an enzyme such as bromelain derivatives, debridase, collagenase, papain derivatives, streptokinase, sutilains, fibrinolysin, deoxyribonuclease, hill derivatives, trypsin or combinations thereof. Autolytic debridement relies on enhancing the natural process of selective liquefaction, separation and digestion of necrotic tissue and eschar from healthy tissue that occurs in wounds due to macrophage and endogenous proteolytic activity. This is achieved by the use of occlusive, semi-occlusive or moist interactive dressings. Enzymatic debridement agents include a bromelain enriched enzyme product, other collagenases, or other enzyme products capable of clearing devitalized tissue or wound debris. NexoBrid™ (MediWound Ltd.) is one such bromelain enriched product that specifically targets heat-denatured collagen for degradation, resulting in partial-thickness and full-thickness wounds requiring a wound coverage or dressing product. Such products and methods are described in U.S. Pat. Nos. 8,540,983; 8,119,124; 7,128,719; 7,794,709; 8,624,077; and US2009/0010910A1, each of which is incorporated by reference herein.

In some aspects, the wound bed may include or be a chronic wound or an acute wound. Chronic wounds include but are not limited to venous leg ulcers, pressure ulcers, and diabetic foot ulcers. Acute wounds include but are not limited to burns, traumatic injuries, amputation wounds, skin graft donor sites, bite wounds, frostbite wounds, dermabrasions, and surgical wounds.

In the cases where there is no dermis, skin products derived from a designated pathogen free α-1,3-galactosyltransferase [Gal-T] knockout swine produced in accordance with the present invention are utilized. The epidermis is removed from such products (e.g., before dermis harvesting on the pig with a VERSAJET™ Hydrosurgery system), so that just the dermis remains. Then, the subject swine dermis is placed on the patient's subcutaneous tissue, serving as a substrate for the cultured epidermal autograft process described above.

Example 4

DPF Xenogeneic Liver Filter

Use of transgenic pig livers to serve as extracorporeal filters in humans is disclosed in Levy, et al., "Liver allotransplantation after extracorporeal hepatic support with transgenic (hCD55/hCD59) porcine livers: Clinical results and lack of pig-to-human transmission of the porcine endogenous retrovirus," Transplantation, 69(2):272-280 (2000) ("Levy"), the entire contents of which are incorporated herein by reference.

In that study, whole organ extracorporeal perfusion of a genetically modified transgenic porcine liver was proposed to sustain patients awaiting human liver transplantation for fulminant hepatic failure. The pig livers used were reported to be transgenic for human CD55 (decay-accelerating factor) and human CD59, however, the livers failed to suppress marked increase of [alpha]-gal antibodies.

In accordance with the present invention, in one aspect, a liver derived from a DPF Closed Colony, α-1,3-galactosyltransferase [Gal-T] knockout pig in accordance with the present invention is utilized for extracorporeal perfusion as a temporary filter for a human patient until a patient receives a human transplant. It will be understood that pigs with additional genetic modifications may also be utilized, including pigs genetically reprogrammed for any number of traits listed in Table 1 and elsewhere herein.

Figure 4:
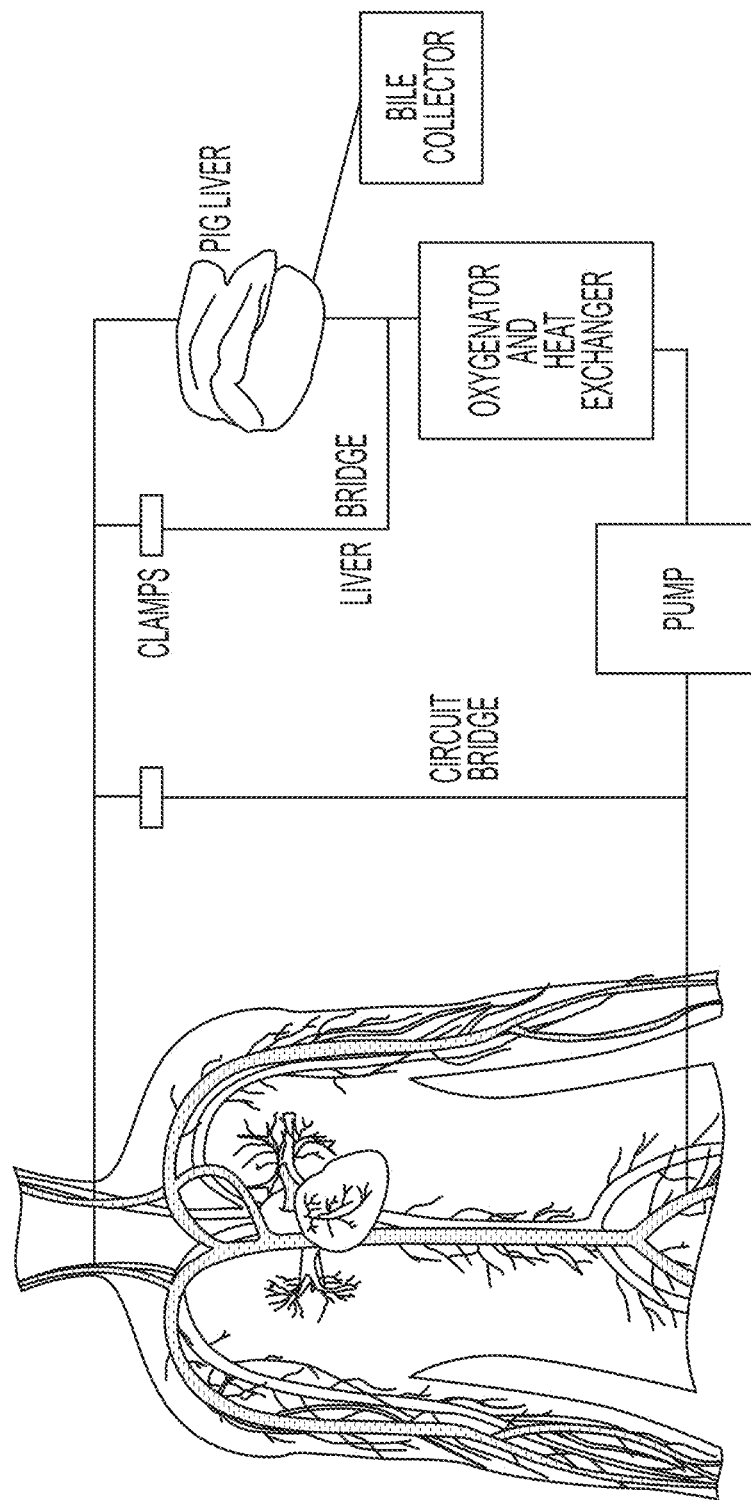
FIG. 4 illustrates an extracorporeal liver filter and circuit in accordance with the present invention.

In one aspect, as shown in FIG. 4, an extracorporeal circuit utilizes an oxygenator (e.g., Minimax Plus® hollow fiber oxygenator), a pump (e.g., Bio-Medicus model 540 Bio-Console® with a BP50 Pediatric Bio Pump® centrifugal pump), and a warmer (Bio-Medicus model 370 BioCal™ Temperature Controller). The circuit also utilizes a roller pump (e.g., Sarns model 7000; Sarns, Ann Arbor, Mich.) to supplement for lack of gravity return to the patient. Bridges and clamps are utilized to isolate both the perfused liver and the patient.

In an operating area within the DPF Isolation Area, a source animal is placed under a general anesthetic (ketamine, xylazine, enflurane) or euthanized by captive bolt. A hepatectomy is then performed on the source animal in designated pathogen free conditions.

The livers can be preserved in any number of ways known in the art prior to use as an extracorporeal filter, including, but not limited to, as disclosed in Levy (e.g., "a 4° C. lactated Ringer's/albumin solution and cannulated in the portal vein (28F Research Medical, model SPC-641-28) and the inferior vena cava (36F Research Medical, model SPC-641-36)").

The common bile duct can be intubated in any number of ways, including, but not limited to, as set forth in Levy (e.g., "with an intravenous extension tube (Extension Set 30, Abbott Hospitals, Inc., Chicago, Ill.) to allow subsequent quantification of bile production.")

The liver product derived from the source animal can be packaged and transported to the location of the procedure in accordance with current practice with human donor livers.

The procedure to utilize the liver filtration product can be performed, for example, by percutaneously cannulating a patient's internal jugular vein for venous return with a 12F pediatric arterial cannula (e.g., Medtronic DLP, Grand Rapids, Mich.) and percutaneously cannulating a patient's femoral vein for venous outflow with a 19F femoral artery cannula (e.g., Medtronic Bio-Medicus, Eden Prairie, Minn.). These cannulas are connected to a bypass circuit, having a centrifugal pump (e.g., Bio-Medicus), a heat exchanger (Medtronic Bio-Medicus), an oxygenator (e.g., Medtronic Cardiopulmonary, Anaheim, Calif.), and a roller pump (e.g., Sarns) incorporated therein.

This circuit is primed with crystalloids and run for a period of time (e.g., 20 minutes) before the DPF Closed Colony, α-1,3-galactosyltransferase [Gal-T] knockout pig liver is incorporated at a stabilized flow rate of 800 ml/min, maintained in a crystalloid bath occasionally supplemented with warm solution.

The aspects of the invention described above are intended to be merely exemplary; numerous variations and modifications will be apparent to those skilled in the art. All such variations and modifications are intended to be within the scope of the present invention as defined in any appended claims.

Example 5

In this example, preterm swine fetuses and neonatal piglets are derived as offspring from DPF Closed Colony, α-1,3-galactosyltransferase [Gal-T] knockout pigs, as shown and described herein in accordance with the present invention.

Such preterm swine fetuses and neonatal piglets are utilized as a source for cells, tissues and organs for xenotransplantation therapies, including, but not limited to, in regenerative or direct transplantation therapies. It will be understood that such cells, tissues and organs can be utilized as fresh or following cryopreservation in accordance with the present invention (e.g., cryopreservation in the range of −80° C.).

In one aspect, mesenchymal cells, pluripotent cells, stem cells and/or other cells that have not differentiated are harvested from such preterm swine fetuses and utilized for regenerative therapies and other therapies as described herein, whereas such undifferentiated cells can be found in high proportion in swine fetuses as well as in neonatal piglets. Since these cells are derived from fetuses earlier along the gestation period, they are less differentiated and more pliable which offers greater potential for regenerative therapies. Furthermore, since these cells may be derived from DPF Closed Colony, α-1,3-galactosyltransferase [Gal-T] knockout pigs, as shown and described herein, they do not possess aggravating immunogenic, pathogenic and/or other aggravating factors causing rejection by the human immune system, and the cells will persist and differentiate inside a human recipient offering regain of function of growth of model tissue using these genetic and cellular building blocks.

By way of example, such cells may be utilized to generate an array of organs and/or tissues, through regenerative cell-therapy methods known in the art (e.g., through utilization of biological scaffolds), for xenotransplantation including, but not limited to, skin, kidneys, liver, brain, adrenal glands, anus, bladder, blood, blood vessels, bones, brain, brain, cartilage, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, uterus, and vagina, areolar, blood, adenoid, bone, brown adipose, cancellous, cartaginous, cartilage, cavernous, chondroid, chromaffin, connective tissue, dartoic, elastic, epithelial, epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue.

Accordingly, preterm swine fetuses and neonatal piglets may be utilized as a source of tissue, cells and organs in accordance with the present invention based on their characteristics as compared to adult swine.

Example 6

Porcine skin shares fundamental properties with human skin and represents a potential alternative to human cadaver skin grafts for temporary coverage of severe burns. The impact of extended cryopreservation on porcine grafts on graft viability, graft take, and barrier function was examined in a study using a model of MHC matched and mismatched MHC class II skin transplants.

Cellular viability was assessed using formazan-MTT and the biological properties of the grafts, were assessed by grafting on swine recipients. To complement the in vivo clinical assessments, histologic, and morphologic analyses, a series of MTT-reduction assays were performed to evaluate the residual viability of porcine grafts after cryopreservation and long-term storage. Mitochondria reduce MTT into a formazan metabolite, which can be observed as purple hue. Harnessing this phenomenon, an analysis of changes in optical density values measured by a spectrophotometer, or an interpolation of the quantities of formazan produced against standard curves, can provide differential assessments of cellular viability, between experimental samples and positive and negative controls. There were 2 cohorts of 2 animals each (total, N=4) based upon the MHC match and each swine received 4 grafts: one autograft and three allografts of identical MHC-profiles. Grafts were clinically assessed for graft-take, adherence, and time to graft rejection. Rejection was also assessed histologically via the Banff grading scale.

Direct comparisons between otherwise equivalent materials yield meaningful, differential times of survival, based solely on duration of storage, holding all other factors constant. Side-by-side, in vivo evaluations are performed between equivalent grafts, preserved in identical fashion, stored for periods of 15 minutes versus 7 years. Clinical gross assessments and photographs, paired with independent histological assessments, determine whether any appreciable differences in graft survival exist relative to the length of time in the frozen state. In tandem, separate in vitro assessments of graft viability, quantified by MTT-reduction assays, characterize the metabolic activity of cells post-cryopreservation and various storage terms. Further, independent histomorphological analysis, using standard histological (H&E) staining, provides evidence as to whether these processes cause observable changes to the graft material at a structural level. This study advantageously used materials that had been stored, uninterrupted, for such a time, along with the associated surgical records and standardized institutional protocols. Further, processing methods and protocols between the comparative groups were standardized, and identically applied, with respect to cryopreservation and thawing protocols, reagents, and methods employed. Combined, this allowed for isolated, side-by-side evaluation of duration of storage, and alleviated the need to model or extrapolate findings, or otherwise use normative predictive methods. Furthermore, the use of MHC-matched and Class II mismatched donor-recipient pairs in this model of allogeneic skin transplantation served as internal controls to both confirm the identity of the tissues obtained seven years earlier, and the veracity of the surgical notes and documentation. Further, equivalent behavior exhibited by the allografts also demonstrates that the antigenicity of the grafts was not altered as a result of the duration of storage.

Figure 5A:
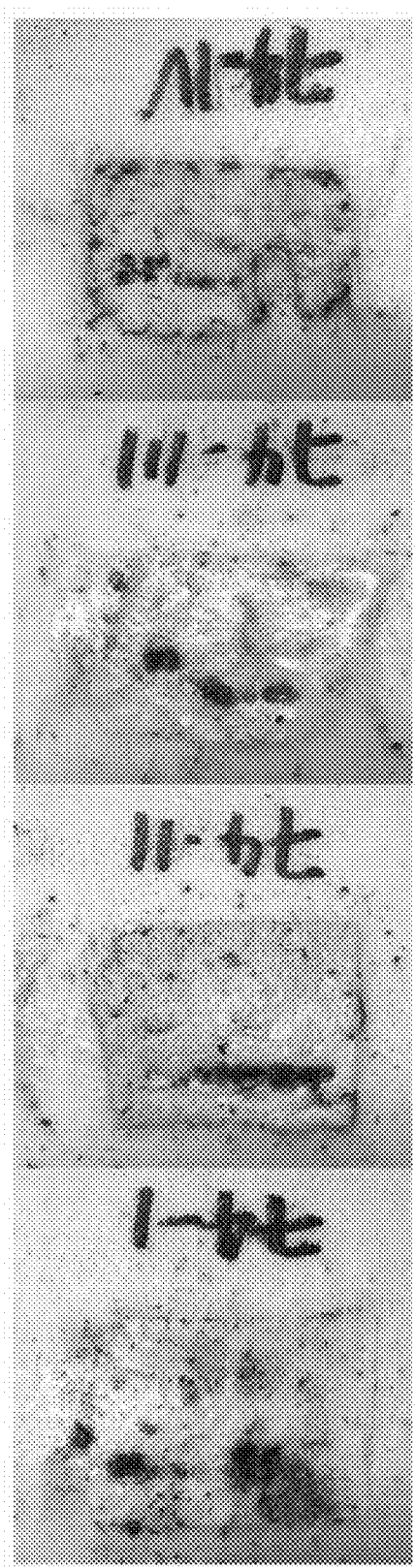
FIG. 5A depicts porcine split-thickness skin grafts at wound sites 1, 2, 3, and 4, respectively from left to right at POD-12.
Figure 5B:
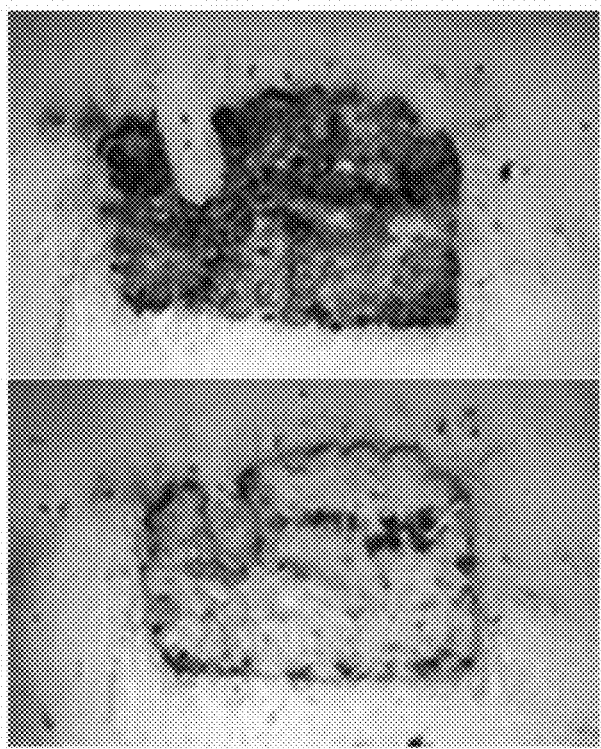
FIG. 5B depicts porcine split-thickness skin grafts at wound site 4 at POD-12 (left) and POD-14 (right).

There were no technical failures; all grafts adhered to their respective wound beds and re-vascularized. In cohort 1 (MHC-matched donor-recipient pair), all grafts remained adherent, and appeared uniformly healthy at postoperative day (POD) 12 (FIG. 5A), but at POD-14, signs of necrosis, progressive erythema and loss of adherence were observed (FIG. 5B). Clinical assessment of the 6 grafts in cohort 1 showed rejection at POD-14 to 18. In cohort 2, MHC class II mismatched, allogeneic grafts appeared comparable to autografts through POD-4. However, by POD-8, all allogeneic grafts demonstrated mild erythema, consistent with rejection and were considered fully rejected by POD-10. No statistically significant difference in the duration, quality of adherence, or cellular viability among the fresh, recently preserved, and long term preserved skin grafts were observed. The cryopreserved materials were, statistically speaking, more alive than dead, and this finding was empirically witnessed in vivo, as all 7-year grafts demonstrated adherence to the wound bed and prolonged survivability.

Such survivability would not have been exhibited by non-vital allografts. Without limiting the invention, it will be understood that the time period for cryopreservation for the present invention may, for example, include any length of time up to about 7 years.

Materials and Methods:

The study was conducted in accordance an IACUC approved protocol (2005N000279, Amendment 69) at the Center for Transplantation Sciences, and in compliance with the U.S. Department of Agriculture's (USDA) Animal Welfare Act (9 CFR Parts 1, 2 and 3), the Guide for the Care and Use of Laboratory Animals, and all state, local laws and regulations. Study protocols, surgical procedures, and animal care guidelines were independently reviewed and monitored by a standing IACUC committee.

A total of eight swine were enrolled in this experiment, and all were members of the Sachs-NIH, inbred miniature swine colony. At the time of surgery, all swine were between 10 and 20-kg in total body weight and between 2 and 4 months of age. Immunosuppression regimen(s) were not administered at any time during this experiment. Animals 24074 and 24075 were assigned to Cohort 1 and represented a MHC-matched donor-recipient pair. Animals 24043 and 24070 were assigned to Cohort 2 and represented a mismatch of MHC Class II donor-recipient pair. Separately, for the in vitro, MTT series of analyses, five, additional wild-type Göttingen miniature swine provided tissues for positive and negative controls.

Swine donors were anesthetized with I.M. 2 mg/kg telazol (tiletamine HCl and zolazepam HCl, Zoetis Inc., Kalamazoo, Mich.) and brought to the operating room for orotracheal intubation. Anesthesia was maintained using 2% isoflurane and oxygen. Skin surfaces were disinfected before surgery with chlorhexidine acetate (NolvasanR Surgical Scrub, Fort Dodge Animal Health, Fort Dodge, Iowa) and povidone-iodine, 10% (Betadine Solution, Purdue Products, L.P., Stamford, Conn.). The animals were then draped, leaving the right side of the dorsum exposed. Split-thickness skin grafts, measuring approximately 25 cm$^2$ (surface area) were harvested between the scapula and inferior margin of the lowermost rib from each animal using an air-driven Zimmer dermatome (Medfix Solution, Inc., Tucson, Ariz.) with the depth set to 0.056-cm (0.022 inches).

Following skin graft harvest, grafts intended for cryopreservation and storage for limited duration grafts underwent a standardized institutional protocol and were maintained at −80° C. for 15 minutes prior to thawing. Long-term cryopreserved grafts had been continuously stored at −80° C. for a period of more than 7 years. All grafts, previously sized to approximately 25 cm$^2$, were placed on a sterile nylon mesh backing for structural support and rolled for placement into a threaded seal cryovial under a laminar flow hood. Once all grafts were prepared, approximately 5-mL of freeze media was added to the vial and sealed. The protocol required freeze media prepared by combining 15% dimethyl sulfoxide (DMSO) cryoprotective media (Lonza BioWhittaker) with fetal porcine serum (FPS) or donor serum (if FPS is unavailable) in a 1:1 ratio, filtering (0.45 micron), and chilling to 4° C. prior to use. The vials were subsequently frozen in a controlled rate, phase freezer at a rate of 1° C. per minute to −40° C., then rapidly cooled to a temperature −80° C., at which they remained for 15 minutes for those test articles in the control group subjected to limited storage duration, or for a period of more than 7 years in the case of the those experimental grafts in the test group exposed to extended duration of cryopreservation. DMSO displaces intracellular fluid during the freezing process. Cryoprotective media, e.g., CryoStor is used in an amount of about 40-80%, or 50-70% based on maximum internal volume of the cryovial (10 ml) less the volume of the xenotransplantation product.

In order to thaw the grafts for surgical use, sealed vials were placed in 37° C. water baths for approximately 1 minute, at which point the vial was opened and the frozen graft was removed using sterile technique. Subsequently, grafts underwent 3, 1-minute serial washes in normal saline with gentle agitation, in order to dilute and systematically remove ambient, residual DMSO and prevent loss of cell viability. Grafts were then taken to the surgical field in normal saline at 25° C. for engraftment.

Two separate, but identical, surgical events were performed in succession. The entire surgical plan included a total of four (n=4) donor-recipient swine, employing two animals per each of the two experimental cohorts (Cohort 1 and Cohort 2), paired intentionally based on SLA-configurations as described previously. In total, four technical controls and twelve (n=12) experimental grafts were engrafted and subsequently observed.

Each animal received four deep-partial defects along the animal's right dorsum, in a linear (caudal to cranial) orientation, ordered from 1 to 4, respectively. Deep-partial wound defects were surgically introduced via additional passes with the dermatome after the initial split thickness graft harvest. The resulting wound beds were uniform, free of visible debris, and demonstrated independent, punctate bleeding. These defects were interrupted, and not made in a single continuous pass with the dermatome. Instead, care was given to create four, isolated but equivalent wounds with regards to overall size, depth, and anatomical location.

Following thawing, but prior to engraftment, all split-thickness skin grafts were fenestrated using a 15 (size) blade to prevent seroma or hematoma formation. Graft test articles were independently placed on the prepared wound bed and uniformly sutured in place using simple interrupted, 3-0 nylon sutures, applied in a graft-to-wound bed manner. Approximately 16 points of fixation were introduced per graft, spaced evenly around the graft, with the resulting knot located on the wound border, not the graft article. This technique ensured that minimal, but adequate, residual tension was present and uniform, which is necessary for optimal graft-to-wound adherence, minimization of hematomas, and optimal graft survivability.

At Wound Site 1 (most caudal), a split-thickness autograft was placed, serving as a technical control. This autograft test article was harvested during the wound bed creation, subsequently underwent the same freeze-thaw process concomitantly with all experimental grafts, and was held in an identical, cryopreserved state for the same duration as the control grafts identified for a limited duration (15 minutes at −80° C.). At Wound Site 2, a split-thickness allograft from its respective cohort pair-mate was sutured into place. This graft represented test articles exposed to cryopreservation for a limited duration (15 minutes at −80° C.). At Wound Site 3, a split-thickness allograft from the wild-type donor, which represented a split-thickness graft, with identical SLA matching as those at Wound Site 2 that had experienced "extended" storage in the cryopreserved state (more than 7 years at −80° C.). At Wound Site 4 (most cranial), a split-thickness allograft from a genetically engineered knockout donor, which represented a split-thickness graft, with identical SLA matching as those grafts at Wound Site 2, sourced from the genetically engineered donor animal, that had also experienced "extended" exposure in the cryopreserved state (−80° C.) for more than 7 years.

Overlying pressure dressings, consisting of Xeroform petrolatum gauze (Medtronic), Telfa™ non-adhesive dressing (Covidien, Minneapolis, Minn.), and sterile gauze were maintained in place and dry with multiple, overlapping sheets of Tegaderm™ (3M, St. Paul, Minn.). Recipients were then dressed with cotton jackets to reduce interference with the grafts. Graft dressings were removed on POD-2 and changed daily thereafter. Total postoperative follow up was 20 days. Animals were monitored for signs of pain including vocalization, tachypnea, loss of appetite, and changes in attitude, behavior, and mobility. Transdermal fentanyl patches were applied for post-operative analgesia. All sutures were removed by POD-7.

To validate the assay method and establish boundary conditions specific to test articles of split thickness skin porcine skin, two independent assay series were performed on fresh (n=5, 5) and heat denatured samples (n=5, 5). The (geometric) average formazan produced on fresh samples was 0.221±0.022-mg/mL and 0.300±0.035-mg/mL, respectively. In contrast, the (geometric) average formazan produced by heat-denatured samples was 0.094±0.020-mg/mL and 0.105±0.009-mg/mL, respectively. These differences were statistically significant in both cases ($p<0.05$).

All four porcine recipients tolerated the surgical procedure and recovered fully without incident. All sixteen (n=16) grafts re-vascularized without evidence of technical complication, and uniformly exhibited adherence to the underlying wound bed (i.e. "good take"). Over the course of the post-operative observational period, no grafts were lost due to mechanical disturbance or exhibited any clinical signs of wound infection. All four (n=4) autografts at Wound Site 1 healed permanently and were indistinguishable from surrounding tissues at the study end-point, acting as a technical control for the skin grafting, cryopreservation and thawing technique.

In Cohort 1, all six (n=6) allogeneic grafts demonstrated equivalent adherence to the underlying wound bed and uniformly exhibited clinical signs consistent with vascularization and perfusion on postoperative days (POD) 2 and 4. Notable, however, was the contrast (loss) of color exhibited by the allografts that had been cryopreserved for an extended duration. All four of these grafts appeared paler as compared to the autograft and allografts at Wound Site 2. This appearance fully resolved in all grafts, in both Animals, by POD-6. All six (n=6) allografts exhibited mild sloughing of the superficial epidermis by POD-8, but grafts remained viable, adherent, and appeared otherwise healthy at inspection on POD-12. In Animal 24074, grafts at Wound Sites 2 and 3 showed initial signs of necrosis, progressive erythema, and loss of adherence by POD-14, and presented increasing signs of immune-mediated rejection, until final rejection at POD-18. However, the allograft at Wound Site 4 (most-cranial) did not similarly persist; instead, on POD-14 this graft was significantly darker and exhibited signs of complete necrosis and was clinically assessed to be fully rejected at this time. The rapid loss of the graft 4, from viability at POD-12 to complete avulsion by POD-14, dissimilar and distinct from Wound Site 2 and Wound Site 3, was notable. For grafts on Animal 24075, all grafts were rejected on POD-14.

In Cohort 2, animals presented similarly to those in Cohort 1 through POD-4, and equivalently to each other. Overall, clinical signs were comparable in progression to the minor-mismatched grafts in Cohort 1, but at an accelerated pace. The grafts that had experienced extended cryopreservation appeared paler at POD-2 and POD-4 than the grafts that had not experienced cryopreservation, and all grafts showed increased evidence of perfusion and vascularization by POD-6. By POD-8, all three allogeneic grafts in Animal 24043, showed clear signs of rejection and were considered fully rejected. In Animal 24070, all three allogeneic grafts showed clear signs of rejection and were considered fully rejected by POD-10. However, all allogeneic grafts survived at the same rate, irrespective of the genetics or length of storage.

With respect to grafts subjected to limited or extended durations of cryopreservation, 100% of allograft comparators at Wound Sites 2 and 3 (n=4 of 4) were identical with respect to clinical assessment of duration of graft survival. Comparison of Wound Sites 2 and 4 were coincident (n=3), with the exception of the allograft at Wound Site 4, Animal 24074, which survived until POD-14 (n=1), determined to be clinically and rejected four days prior to its counterparts.

Overall, histological assessments closely mirrored the clinical assessments. Following surgery, all grafts, including autografts, exhibited early signs of acute inflammation during initial observations on POD-2 and 4, that later resolved with time. All allografts in Cohort 2, as compared to those in Cohort 1, uniformly exhibited accelerated progression towards immune-mediated rejection.

Ultimately, all six (n=6) allogeneic grafts in Cohort 1, and three allogeneic grafts (n=3) from Animal 24043 in Cohort 2, independently demonstrated histological and microscopic signs of rejection coterminous with the independent gross clinical assessments. The single exception were the three allografts engrafted on Animal 24070, where each graft received Banff scores of 4 (of 4) on POD-10, but were not deemed officially rejected until POD-12, one assessment period (2 days) later than the corresponding clinical designation assigned at POD-10.

With respect to grafts subjected to limited or extended durations of cryopreservation, 100% of allograft comparators at Wound Sites 2 and 3 (n=4 of 4) were identical with respect to histological assessment of duration of graft survival. Comparison of Wound Sites 2 and 4 were coincident (n=3), with the exception of the allograft at Wound Site 4, Animal 24074, which survived 14 days post-operatively (n=1), determined to be histologically rejected four days prior to its counterparts.

Neither the MTT nor the neutral red staining technique, as applied on either testing occasion, were deemed effective for histological and microscopic evaluation, however the standard hemotoxylin and eosin staining demonstrated observable tissue destruction of the heat denatured specimens.

Overall, using a linear, mixed effect model with random intercept, the mean survival of grafts at Wound Site 3 was 0.00 (95% CI: −1.10, 1.10 days) less than allografts at Wound Site 2. The mean survival of grafts at Wound Site 4 was 2.00 (95% CI: 1.10, 3.10 days) less than allografts at Wound Site 2. Histological assessment finds on average 0.5 days more survival than grafts assessed grossly, but this is not statistically distinguishable ($p=0.28$). Seven of the eight experimental grafts fared equivalently to their comparators. The in vivo experiments showed no statistical difference between grafts subjected to short versus long-term storage. With the exception of the graft at Wound Site 4 on Animal 24074, which was assessed as fully rejected four days earlier than its comparators, graft performance and survivability were indistinguishable between the two groups.

As noted in previous publications, cryopreserved grafts appeared notably paler during the early imbibition and vascularization periods. This contrast was starkly evident for grafts at Wound Sites 3 and 4 in all animals. Ultimately, grafts fully resolved and adhered to the underlying wound bed to an equivalent degree.

Figure 6A:
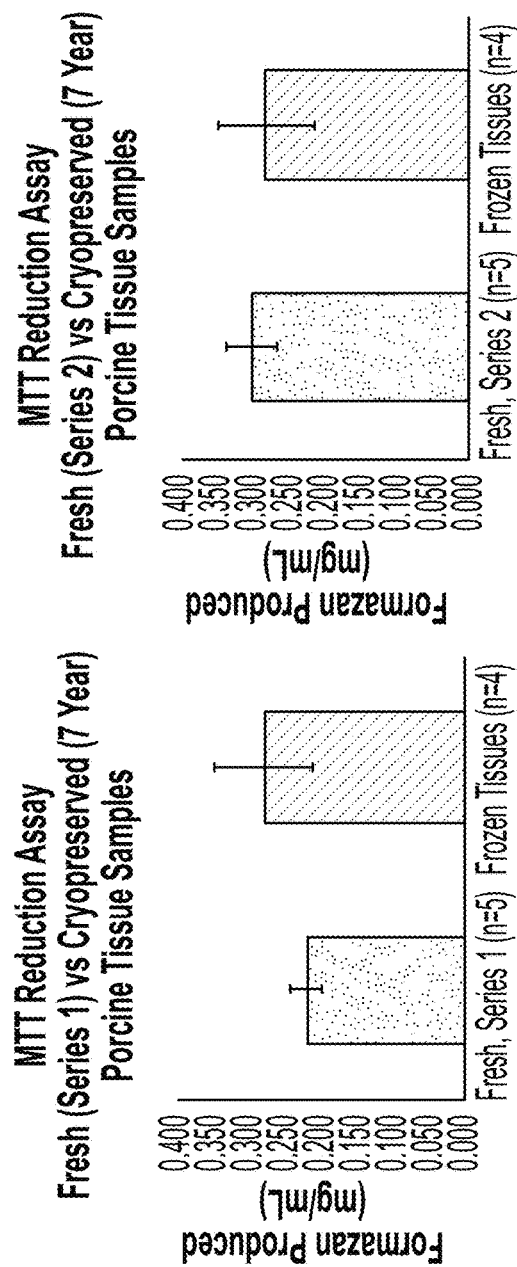
FIG. 6A graphs MTT reduction assays fresh vs. cryopreserved (7 years) in porcine tissue samples showing no statistical difference.
Figure 6B:
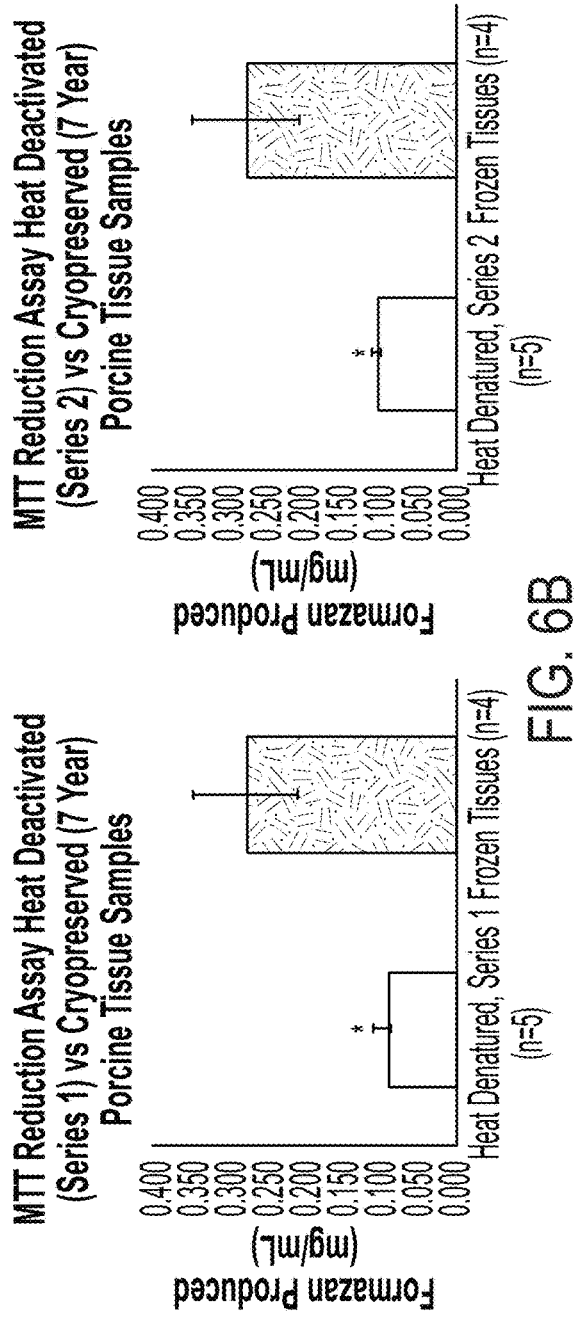
FIG. 6B graphs MTT reduction assays heat deactivated vs. cryopreserved (7 years) in porcine tissue samples showing a statistically significant different in quantity of formazan produced.
Figure 7:
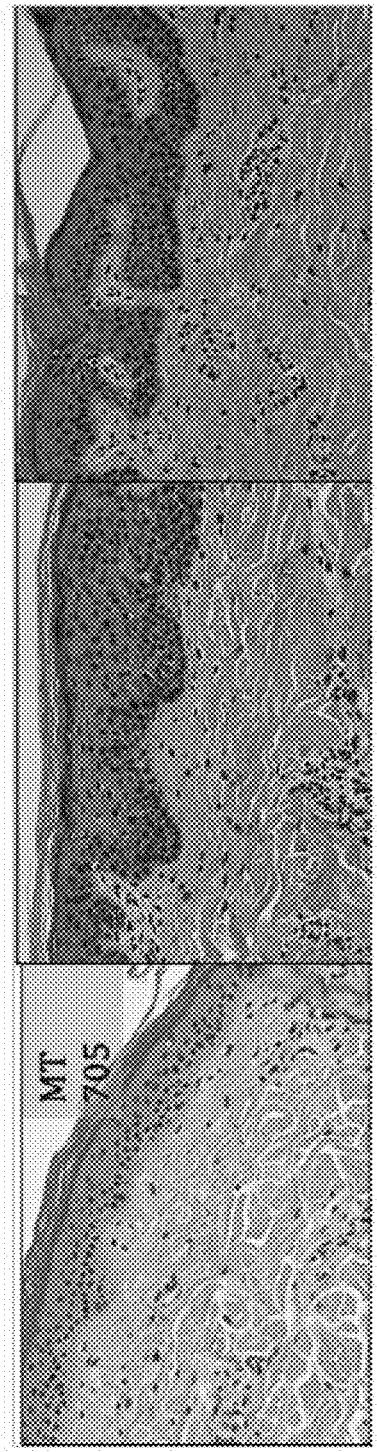
FIG. 7 shows histological images of H&E stained sections from the cryopreserved grafts and stored for 7 years show viable normal skin with intact epidermis. The blood vessels and adnexal structures were also normal. No distinguishable differences could be seen at a histological level based on duration of storage. From Left to Right (Duration of Storage): 15 minutes, 7 years, 7 years.

Demonstrated viability was evidenced uniformly across the three, independent evaluation methods. The statistical analysis of the MTT-assay shows there was no significant difference between cryopreserved and fresh specimens (FIG. 6A), but significant differences were observed between fresh and cryopreserved specimens versus heat-denatured ones (FIG. 6B). This suggests broadly that the cryopreserved materials were, statistically speaking, more alive than dead. This outcome is substantiated in the in vivo outcomes in which all 7-year grafts demonstrated adherence to the wound bed and prolonged survivability, which would not be exhibited by non-vital grafts.

Regarding the MTT-reduction assays, substantial variability existed between absolute values resulting from such assays, from specimen to specimen and from cohort-to-cohort. Indeed, absolute values of formazan production were actually higher than those obtained from non-cryopreserved samples; it is unlikely that freezing enhanced cellular activity.

Pig skin can be cryopreserved for years, e.g., 1, 3, 5, 7 or more years and retain cell viability and that the genetic modification, Gal-T-KO, did not impact metabolic stability when compared to wild type pig skin processed and stored using the same procedures.

Furthermore, the use of MHC-matched and class II mismatched donor-recipient pairs in this model of allogeneic skin transplantation served as internal controls to compare the effect of long term cryopreservation (7 years) on the survival of allogeneic skin grafts. The cell viability data after long term cryopreservation is supported by the survival of the skin in vivo. This also demonstrated that the genetic differences (wild type versus Gal-T-KO) of the grafts did not impact the survival of the grafts.

The hypothesis was that graft take, and overall survival, would be inversely proportional to the length of storage duration. In other words, it was expected that the longer the graft had been frozen, the less likely it would survive and mimic the comparator grafts preserved for shorter durations. Surprisingly, these studies revealed that the porcine tissue can be cryopreserved for significant durations, 7 years in the case of the present disclosure, and retain adequate cell viability. Moreover, the genetic modification (Gal-T-KO) did not impact metabolic activity, when compared to wild type skin processed identically. Lastly, the results confirm that the MTT-reduction assay can reliably provide an accurate, useful diagnostic method, and applicable to the assessment of porcine skin graft viability.

The promising results of this study indicate that it may be feasible to cryopreserve and store porcine skin for logistically relevant durations, and our findings are consistent with current industry practices and the multi-year "shelf life" guidance that the American Association for Tissue Banks has established for human cadaveric tissues.

Further, these data indicate that scalable, clinically useful methods of preserving and storing porcine xenotransplantation products with adequate viability are disclosed, and that vital porcine xenotransplantation products that can be effectively stored and distributed.

Example 7

It will be understood that, in the context of swine-to-human xenotransplantation, each human recipient will have a major histocompatibility complex (MHC) (Class I, Class II and/or Class III) that is unique to that individual and will not match the MHC of the donor swine. Accordingly, it will be understood that when a donor swine graft is introduced to the recipient, the swine MHC molecules themselves act as antigens, provoking an immune response from the recipient, leading to transplant rejection.

Human leukocyte antigen (HLA) genes show incredible sequence diversity in the human population. For example, there are >4,000 known alleles for the HLA-B gene alone. The genetic diversity in HLA genes in which different alleles have different efficiencies for presenting different antigens is believed to be a result of evolution conferring better population-level resistance against the wide range of different pathogens to which humans are exposed. This genetic diversity also presents problems during xenotransplantation where the recipient's immune response is the most important factor dictating the outcome of engraftment and survival after transplantation.

In accordance with one aspect the present invention, a donor swine is provided with a genome that is biologically engineered to express a specific set of known human HLA molecules. Such HLA sequences are available, e.g., in the IPD-IMGT/HLA database (available at ebi.ac.uk/ipd/imgt/hla/) and the international ImMunoGeneTics information System® (available at imgt.org). For example, HLA-A1, B8, DR17 is the most common HLA haplotype among Caucasians, with a frequency of 5%. Thus, the disclosed method can be performed using the known MHC/HLA sequence information in combination with the disclosures provided herein.

In some aspects, the recipient's human leukocyte antigen (HLA) genes and MHC (Class I, II and/or III), are identified and mapped. It will be understood that ascertaining the human recipient's HLA/MHC sequence can be done in any number of ways known in the art. For example, HLA/MHC genes are usually typed with targeted sequencing methods: either long-read sequencing or long-insert short-read sequencing. Conventionally, HLA types have been determined at 2-digit resolution (e.g., A*01), which approximates the serological antigen groupings. More recently, sequence specific oligonucleotide probes (SSOP) method has been used for HLA typing at 4-digit resolution (e.g., A*01:01), which can distinguish amino acid differences. Currently, targeted DNA sequencing for HLA typing is the most popular approach for HLA typing over other conventional methods. Since the sequence-based approach directly determines both coding and non-coding regions, it can achieve HLA typing at 6-digit (e.g., A*01:01:01) and 8-digit (e.g., A*01:01:01:01) resolution, respectively. HLA typing at the highest resolution is desirable to distinguish existing HLA alleles from new alleles or null alleles from clinical perspective. Such sequencing techniques are described in, for example, Elsner H A, Blasczyk R: (2004) Immunogenetics of HLA null alleles: implications for blood stem cell transplantation. Tissue antigens. 64 (6): 687-695; Erlich R L, et al (2011) Next-generation sequencing for HLA typing of class I loci. BMC genomics. 12: 42-10.1186/1471-2164-12-42; Szolek A, et al. (2014) OptiType: Precision HLA typing from next-generation sequencing data. Bioinformatics 30:3310-3316; Nariai N, et al. (2015) HLA-VBSeq: Accurate HLA typing at full resolution from whole-genome sequencing data. BMC Genomics 16:S7; Dilthey A T, et al. (2016) High-accuracy HLA type inference from whole-genome sequencing data using population reference graphs. PLoS Comput Biol 12:e1005151; Xie C., et al. (2017) Fast and accurate HLA typing from short-read next-generation sequence data with xHLA 114 (30) 8059-8064, each of which is incorporated herein in its entirety by reference.

The known human HLA/MHC or an individual recipient's sequenced HLA/MHC sequence(s) may be utilized as a template to modify the swine leukocyte antigen (SLA)/MHC sequence to match, e.g., to have 90%, 95%, 98%, 99%, or 100% sequence homology to a known human HLA/MHC sequence or the human recipient's HLA/MHC sequence. Upon identifying a known human recipient HLA/MHC sequence to be used or performing genetic sequencing of a human recipient to obtain HLA/MHC sequences, biological reprogramming may be performed to SLA/MHC sequences in cells of the swine based on desired HLA/MHC sequences. For example, several targeting guide RNA (gRNA) sequences are administered to the swine of the present disclosure to reprogram SLA/MHC sequences in cells of the swine with the template HLA/MHC sequences of the human recipient.

CRISPR-Cas9 is used to mediate rapid and scarless exchange of entire MHC alleles at specific native locus in swine cells. Multiplex targeting of Cas9 with two gRNAs is used to introduce single or double-stranded breaks flanking the MHC allele, enabling replacement with the template HLA/MHC sequence (provided as a single or double-stranded DNA template). In certain aspects, the CRISPR/Cas9 components are injected into swine oocytes, ova, zygotes, or blastocytes prior to transfer into foster mothers.

In certain aspects, the present disclosure includes embryogenesis and live birth of SLA-free and HLA-expressing biologically reprogrammed swine. In certain aspects, the present disclosure includes breeding SLA-free and HLA-expressing biologically reprogrammed swine to create SLA-free and HLA-expressing progeny. In certain aspects, the CRISPR/Cas9 components are injected into swine zygotes by intracytoplasmic microinjection of porcine zygotes. In certain aspects, the CRISPR/Cas9 components are injected into swine prior to selective breeding of the CRISPR/Cas9 genetically modified swine. In certain aspects, the CRISPR/Cas9 components are injected into donor swine prior to harvesting cells, tissues, zygotes, and/or organs from the swine. In certain aspects, the CRISPR/Cas9 components include all necessary components for controlled gene editing including self-inactivation utilizing governing gRNA molecules as described in U.S. Pat. No. 9,834,791 (Zhang), which is incorporated herein by reference in its entirety.

The genetic modification can be made utilizing known genome editing techniques, such as zinc-finger nucleases (ZFNs), transcription activator-like effector nucleases (TALENs), adeno-associated virus (AAV)-mediated gene editing, and clustered regular interspaced palindromic repeat Cas9 (CRISPR-Cas9). These programmable nucleases enable the targeted generation of DNA double-stranded breaks (DSB), which promote the upregulation of cellular repair mechanisms, resulting in either the error-prone process of non-homologous end joining (NHEJ) or homology-directed repair (HDR), the latter of which can be used to integrate exogenous donor DNA templates. CRISPR-Cas9 may also be used to remove viral infections in cells. For example, the genetic modification via CRISPR-Cas9 can be performed in a manner described in Kelton, W. et. al., "Reprogramming MHC specificity by CRISPR-Cas9-assisted cassette exchange," Nature, Scientific Reports, 7:45775 (2017) ("Kelton"), the entire disclosure of which is incorporated herein by reference. Accordingly, the present disclosure includes reprogramming using CRISPR-Cas9 to mediate rapid and scarless exchange of entire alleles, e.g., MHC, HLA, SLA, etc.

In one aspect, the recipient's HLA/MHC gene is sequenced and template HLA/MHC sequences are prepared based on the recipient's HLA/MHC genes. In another aspect, a known human HLA/MHC genotype from a WHO database may be used for genetic reprogramming of swine of the present disclosure. CRISPR-Cas9 plasmids are prepared, e.g., using polymerase chain reaction and the recipient's HLA/MHC sequences are cloned into the plasmids as templates. CRISPR cleavage sites at the SLA/MHC locus in the swine cells are identified and gRNA sequences targeting the cleavage sites and are cloned into one or more CRISPR-Cas9 plasmids. CRISPR-Cas9 plasmids are then administered into the swine cells and CRIPSR/Cas9 cleavage is performed at the MHC locus of the swine cells.

The SLA/MHC locus in the swine cells are replaced with one or more template HLA/MHC sequences matching the known human HLA/MHC sequences or the recipient's sequenced HLA/MHC genes. Cells of the swine are sequenced after performing the SLA/MHC reprogramming steps in order to determine if the HLA/MHC sequences in the swine cells have been successfully reprogrammed. One or more cells, tissues, and/or organs from the HLA/MHC sequence-reprogrammed swine are transplanted into a human recipient.

In certain aspects, HLA/MHC sequence-reprogrammed swine are bred for at least one generation, or at least two generations, before their use as a source for live tissues, organs and/or cells used in xenotransplantation. In certain aspects, the CRISPR/Cas9 components can also be utilized to inactivate genes responsible for PERV activity, e.g., the pol gene, thereby simultaneously completely eliminating PERV from the swine donors.

For purposes of modifying donor SLA/MHC to match recipient HLA/MHC, comparative genomic organization of the human and swine histocompatibility complex has been mapped. For example, such SLA to HLA mapping can be found in: Lunney, J., "Molecular genetics of the swine major histocompatibility complex, the SLA complex," Developmental and Comparative Immunology 33: 362-374 (2009) ("Lunney"), the entire disclosure of which is incorporated herein by reference. Accordingly, a person of ordinary skill in the art effectively and efficiently genetically reprogram swine cells in view of the present disclosure and using the mapping of Lunney et al. as a reference tool.

The modification to the donor SLA/MHC to match recipient HLA/MHC causes expression of specific MHC molecules from the swine cells that are identical, or virtually identical, to the MHC molecules of a known human genotype or the specific human recipient. In one aspect, the present disclosure involves making modifications limited to only specific portions of specific SLA regions of the swine's genome to retain an effective immune profile in the swine while biological products are hypoimmunogenic when transplanted into human recipients such that use of immunosuppressants can be reduced or avoided. In contrast to aspects of the present disclosure, xenotransplantation studies of the prior art required immunosuppressant use to resist rejection. In one aspect, the swine genome is reprogrammed to knock-out swine genes corresponding to HLA-A, HLA-B, HLA-C, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G, HLA-F, and DQ. In one aspect, the swine genome is reprogrammed to knock-out SLA-11; SLA-6,7,8; SLA-MIC2; and SLA-DQA; SLA-DQB1; SLA-DQB2, and to knock-in HLA-C; HLA-E; HLA-G; and HLA-DQ. In certain aspects, HLA-C expression is reduced in the reprogrammed swine genome. By reprogramming the swine cells to be invisible to a human's immune system, this reprogramming thereby minimizes or even eliminates an immune response that would have otherwise occurred based on swine MHC molecules otherwise expressed from the donor swine cells.

It will therefore be understood that this aspect (i.e., reprogramming the SLA/MHC to express specifically selected human MHC alleles), when applied to swine cells, tissues, and organs for purposes of xenotransplantation will decrease rejection as compared to cells, tissues, and organs derived from a wild-type swine or otherwise genetically modified swine that lacks this reprogramming, e.g., transgenic swine or swine with non-specific or different genetic modifications.

It will be further understood that causing the donor swine cells, tissues, and organs to express a known human MHC genotype or the recipient's MHC specifically as described herein, combined with the elimination in the donor swine cells of alpha-1,3-galactosytransferase, Neu5Gc, and β1,4-N-acetylgalactosaminyltransferase (B4GALNT2) (e.g., "single knockout," "double knockout," or "triple knockout"), presents a swine whose cells will have a decreased immunological rejection as compared to a triple knockout swine that lacks the specific SLA/MHC reprogramming of the present disclosure.

Example 8

Various cellular marker combinations in swine cells are made and tested to prepare biologically reprogrammed swine cells for acceptance by a human patient's body for various uses. For these tests, Porcine Aorta Endothelial Cells (PAECs) and/or a transformed porcine macrophage cell line available from ATCC® (3D4/21) are used. Cell samples to be tested include the following:

1. PAEC wild type;
2. PAEC class II SLA DQ Knock out (KO);
3. PAEC class II SLA DQ KO+HLA DQ Knock In (KI);
4. PAEC class II SL DR Knock out (KO);
5. PAEC class II SLA DR KO+HLA Dr Knock In (KI);
6. PAEC class II SLA DP Knock out (KO); and
7. PAEC class II SLA DP KO+HLA DP Knock In (KI).

Or for 3D4/21 cells:
1) Knock out surface sugar glycans (GGTA1, CMAH and B4GALNT2)
2) Knock out all MHC I
3) Trial 1
   a. Knock out DP, DQ, and $DR_\alpha$
   b. Replace $DR_\beta$ with its human equivalent
4) Trial 2
   a. Knock out DQ, DR, and $DP_\alpha$
   b. Replace $DP_\beta$ with its human equivalent
5) Trial 1
   a. Knock out DR, DP, and $DQ_\alpha$
   b. Replace $DQ_\beta$ with its human equivalent The Knockout only and knockout plus knock in cell pools are generated by designing and synthesizing a guide RNA for the target gene. Each guide RNA is composed of two components, a CRISPR RNA (crRNA) and a trans-activating RNA (tracrRNA). These components may be linked to form a continuous molecule called a single guide RNA (sgRNA) or annealed to form a two-piece guide (cr: tracrRNA).

CRISPR components (gRNA and Cas9) can be delivered to cells in DNA, RNA, or ribonucleoprotein (RNP) complex formats. The DNA format involves cloning gRNA and Cas9 sequences into a plasmid, which is then introduced into cells. If permanent expression of gRNA and/or Cas9 is desired, then the DNA can be inserted into the host cell's genome using a lentivirus. Guide RNAs can be produced either enzymatically (via in vitro transcription) or synthetically. Synthetic RNAs are typically more pure than IVT-derived RNAs and can be chemically modified to resist degradation. Cas9 can also be delivered as RNA. The ribonucleoproteins (RNP) format consists of gRNA and Cas9 protein. The RNPs are pre-complexed together and then introduced into cells. This format is easy to use and has been shown to be highly effective in many cell types.

After designing and generating the guide RNA, the CRISPR components are introduced into cells via one of several possible transfection methods, such as lipofection, electroporation, nucleofection, or microinjection. After a guide RNA and Cas9 are introduced into a cell culture, they produce a DSB at the target site within some of the cells. The NHEJ pathway then repairs the break, potentially inserting or deleting nucleotides (indels) in the process. Because NHEJ may repair the target site on each chromosome differently, each cell may have a different set of indels or a combination of indels and unedited sequences.

For knock in cells, the desired sequences are knocked into the cell genome through insertion of genomic material using, e.g., homology-directed repair (HDR). To optimize expression of class II molecules, the cells are incubated in porcine interferon gamma (IFN-γ) for 72 hours which stimulates expression. Expression is then measured by flow cytometry using target specific antibodies. Flow cytometry may include anti-HLA-C, HLA-E, HLA-G, or other HLA antibodies, or pan anti-HLA class I or class II antibodies. According to the present disclosure, cell surface HLA expression after knock-in is confirmed.

Complement Dependent Cytotoxicity (CDC) assays may be performed to determine if anti-HLA antibodies recognize the cells from the biological product of the present disclosure. Assay plates prepared by adding a specific human serum containing previously characterized anti-HLA antibodies (or control serum) can be used. IFN-γ treated donor cells are resuspended and added to the assay plates, incubated with a source of complement, e.g., rabbit serum. After at least 1 hour of incubation at room temperature, acridine orange/ethidium bromide solution is added. Percent cytotoxicity is determined by counting dead and live cells visualized on a fluorescent microscope, subtracting spontaneous lysis values obtained in the absence of anti-HLA antibodies, and scoring with a scale.

For 3D4/21 cells:
When knocking out surface sugar glycans, a cell line that does not express the sugar moieties is obtained, so there is no binding of natural preformed antibodies found in human serum. This is detected using flow cytometry and human serum and a labeled goat anti human IgG or IgM antibody; or specific antibodies directed against sugars. The result is no binding of the antibodies to the final cell line. Positive control is the original cell line (WT) without genetic modifications. In addition, a molecular analysis demonstrates changes in those genes.

In knocking out expression of SLA class I molecules using CRISPR technologies, the resulting cell line lacks the above sugar moieties as well as SLA class I expression. Analysis by flow cytometry and molecular gene are performed to demonstrate no surface expression and changes made at the gene level. Cellular reactivity is assessed using a mixed lymphocyte reaction (MLR) with human PBMCs and the irradiated cell line. In comparison to the WT line, there is a reduction in the T cell proliferation, predominantly in the CD8+ T cells.

Expression of SLA Class II molecules, DR and DQ, is performed by only knocking out the alpha gene of the heterodimer. Because there is no porcine DP, the resulting cell line lacks expression of any of the MHC molecules. Analysis is performed at the molecular level, cell surface expression, and in vitro reactivity with human PBMC. There is a significant downward modulation of reactivity against the resulting cell line.

Human class II, DR-beta gene is knocked in. Similar analysis is performed, but a human donor who would have the same DR beta would also be used. The swine DR alpha is expected to bind to the human DR beta due to the high homology of the alpha molecules and express on the cell surface, a donor with the same DR is expected to not react. In some aspects, both human alpha and beta genes of the DR are knocked in. Analogous trials are conducted with DP-beta and DQ-beta genes knocked in.

For PAECs:

To test for cellular reactivity, the PAECs are incubated with porcine IFN-γ for 72 hours then human CD4+ T cells are added to the PAECs and cultured for 7 days. The readout is a form of activation/proliferation depending on the resources available.

Potential observations are:
1. Unstimulated WT PAEC: No response
2. Stimulated PAEC: Positive response
3. Stimulated class II SLA DQ KO: No response
4. Stimulated class II SLA DQ KO+HLA DQ KI: no response or reduced response compared to #2.

To observe a specific response to DQ, human antigen presenting cells (APCs) are absent from the culture such that the cellular response is not the result of pig antigens presented by the APCs.

Upon confirmation of study results, genetically reprogrammed pigs are bred so that several populations of pigs are bred, each population having one of the desirable human cellular modifications determined from the above assays. The pigs' cellular activity after full growth is studied to determine if the pig expresses the desired traits to avoid rejection of the pigs' cells and tissues after xenotransplantation. Thereafter, further genetically reprogrammed pigs are bred having more than one of the desirable human cellular modifications to obtain pigs expressing cells and tissues that will not be rejected by the human patient's body after xenotransplantation.

Any of the above protocols or similar variants thereof can be described in various documentation associated with a medical product. This documentation can include, without limitation, protocols, statistical analysis plans, investigator brochures, clinical guidelines, medication guides, risk evaluation and mediation programs, prescribing information and other documentation that may be associated with a pharmaceutical product. It is specifically contemplated that such documentation may be physically packaged with cells, tissues, reagents, devices, and/or genetic material as a kit, as may be beneficial or as set forth by regulatory authorities.

Example 9

Product Processing

Generally

A xenotransplantation product of the present disclosure was processed according to the following procedures.

Personnel

The operator was dressed in sterile dress in accordance with institutional standards to maintain designated pathogen free conditions. The operator wore eye protection safety glasses for ultraviolet light and lasers.

Preparation of Laminar Flow Hood and Product Processing

An ultraviolet laser lamp (Model #) was set up in a laminar flow hood. Each of the four corners of the lamp was placed on two container lids that were stacked on top of each other, i.e., four pairs of lids were used to support the lamp. The distance from the lamp bulbs (2 bulb tubes total) to the floor of the hood was approximately 1.5 inches. The entire interior of the hood was sprayed with alcohol, e.g., ethanol or isopropanol. The lamp was turned on and the operator performed a calculation of time for desired exposure based on lamp specifications, number of bulbs, and distance between the bulbs and the xenotransplantation product.

The operator poured two baths (one chlorhexidine and one alcohol) into two separate bowls and placed the two bowls under the hood.

A package of new sterilized vials was placed under the hood. Vial caps were unscrewed and placed into the chlorhexidine bath. Each vial (without cap) was then turned upside down and plunged open ended into the chlorhexidine bath, for one minute each and then set upright to air dry. Thereafter, the exterior of each vial was wiped with chlorhexidine and alcohol utilizing sterile gauze. The vial caps were removed from the chlorhexidine bath and placed on sterile gauze. The open ends of each vial were plunged into alcohol bath for 1 minute each and then set aside to air dry.

A xenotransplantation product "#46 product" (5×15 cm) having a mesh backing prepared according to Example 2 was removed from its original vial and the operator placed original vial into an empty bowl. Operator placed the #46 product on the paper side of an opened sterilized instrument package. The operator unrolled the #46 product and placed it under the lamp for 2 minutes, then turned it over to the other side, removed the mesh backing, and put it under the lamp for 2 minutes on opposite side, while still on the same paper. The time period for exposing a given sample to the UV light can be varied based on the specific biological agents or the types of biological agents to be sterilized, e.g., as shown in the following Table 13:

TABLE 13

| Biological Agent | Type of Biological Agent | UV-C Dosage (uW sec/cm$^2$) for 90% sterilization | Sterilization time (sec)* |
| --- | --- | --- | --- |
| Penicillium spp. | Fungus | 224,000 | 1800 |
| Aspergillus flavus | Fungus | 34,900 | 300 |
| Aspergillus niger | Fungus | 31,500 | 250 |
| Yeast | Fungus | 4000 | 30 |
| Influenza A | Virus | 1900 | 15 |

TABLE 13-continued

| Biological Agent | Type of Biological Agent | UV-C Dosage (uW sec/cm$^2$) for 90% sterilization | Sterilization time (sec)* |
|---|---|---|---|
| HIV-1 | Virus | 28,000 | 220 |
| Vaccinia | Virus | 1500 | 10 |
| Escherichia coli | Bacteria | 2000 | 20 |
| Staphylococcus aureus | Bacteria | 6600 | 50 |
| Bacillus subtilis | Bacteria | 6800 | 50 |
| Mycoplasma spp. | Bacteria | 8400 | 70 |
| Pseudomonas aeruginosa | Bacteria | 2200 | 20 |

*Using a UV-C intensity of 125 uW/cm$^2$

Then the "#46 product was removed and cut in half. Each half was rolled by hand and placed into a new vial sterilized as explained above. Each new cap was placed on each new vial and screwed on securely. Each vial was placed under the lamp and periodically rolled for desired even exposure to light on the exterior of the vial. The vials were placed inside a glass jar that had an interior that had been previously sterilized and the exterior was sterilized by the operator with alcohol and chlorhexidine, including threads and caps.

A similar process was performed for the following xenotransplantation products, except instead of being placed on sterile paper prior to entry under the lamp, the mesh was not removed from the products and the products were placed under the lamp skin side up for 2 minutes, then the products were folded over so a first half of the bottom portion of each product faced the lamp for 2 minutes, then the second half of each product was folded over so that the other half of the bottom of each product faced the lamp for 2 minutes. Some of the products were cut into smaller sections and exposed to light, some for periods for longer than 2 minutes, but never less than 2 minutes.

Products #40 (5×15 cm), #63 (10×15 cm), #69 (10×15 cm), and #25, underwent the above processes and products #69 and #25 were rolled exclusively using instruments and the operator did not directly handle those products. As with #46, after operator securely screwed the cap on each vial, each vial was placed under the lamp and rolled for even exposure to light emitted from lamp. Vials were later removed from under the lamp and wiped down with alcohol prior to being placed into glass jars.

Four glass jars were utilized to store each of the sets of vials. Prior to being handed to the operator, the assistant drenched the exteriors of the glass jars with alcohol via a spray bottle. The assistant handed the glass jars to the operator by holding the bottom of each jar and handing to operator outside of hood. After receiving the glass jars from assistant, under the hood, the operator bathed the glass jar lids and plunged the open ends of the jars into alcohol and wiped the exterior of the jars with alcohol including threads of the jar.

The vials were wiped with alcohol utilizing gauze and placed inside each glass jar with an instrument. The lids of the glass jars were then secured and the jars were handed to the assistant. Frequently and on a periodic basis throughout these processes the assistant sprayed the operator's gloves and arms with alcohol.

Thereafter, the products were placed into the phase freezer at the conclusion of the procedures.

Example 10

A clinical trial to evaluate the safety and tolerability of xenotransplantation skin for coverage of severe and extensive, deep partial and full thickness burn wounds is conducted.

A primary endpoint includes assessing the safety and tolerability of a xenotransplantation skin product of the present disclosure after 28 days when applied as temporary coverage to severe and extensive, deep partial or full thickness burn wounds prior to autograft placement. Safety endpoints include incidence and severity of adverse events, changes in physical examination, changes in vital signs, changes in electrocardiograms, changes in hematology, serum chemistry, urinalysis, incidence of porcine endogenous retroviral (PERV) RNA present in recipient peripheral blood, as demonstrated by RT-PCR assays, and incidence and severity of local infections. PERV testing includes PCR of the subject's PBMC for PERV DNA sequence, RT-PCR of subject's PBMC for PERV RNA, and serologic analysis for PERV-specific antibodies.

Secondary endpoints include: 1) assessing the long-term safety and tolerability of a xenotransplantation skin product of the present disclosure when applied as temporary coverage to severe and extensive, deep partial or full thickness burn wounds prior to autograft placement; 2) assessing the duration of temporary barrier function afforded by the xenotransplantation skin product of the present disclosure; 3) characterizing the incidence of local wound infections at sites treated with the xenotransplantation skin product of the present disclosure; 4) assessing the ease and method of removal of the xenotransplantation skin product of the present disclosure; 5) characterizing and describing the progression and quality of the temporary barrier function provided to the subject, via the engraftment of a xenotransplantation skin product of the present disclosure from the time of initial graft placement following wound debridement to the time of loss of effective barrier function, resulting from: The time of graft rejection via graft-host immunological response (as determined by the Clinical Wound Assessment Scale); mechanical disturbance or disruption (shear forces or hematoma); or intentional removal per Investigator's direction consistent with subject's overall clinical course.

Further objectives include exploring the incidence and characterizing the quality of definitive wound closure following autograft placement at sites treated with the xenotransplantation skin product of the present disclosure as compared to similar wound sites treated with human cadaver allograft, exploring the incidence and quality of hypertrophic scarring at sites treated with the xenotransplantation skin product of the present disclosure as compared to similar wound sites treated with human cadaver allograft, and exploring the severity of scar formation at sites treated with the xenotransplanted skin product of the present disclosure as compared to similar wound sites treated with human cadaver allograft. Incidence and severity of scaring is assessed using the modified Vancouver Scar Scale (mVSS). The mVSS is shown in the following Table 14:

TABLE 14

| Characteristic | Item | Number |
|---|---|---|
| Vascularity | Normal | 0 |
| | Pink | 1 |
| | Red | 2 |
| | Purple | 3 |
| Pigmentation | Normal | 0 |
| | Hypopigmentation | 1 |
| | Mixed | 2 |
| | Hyperpigmentation | 3 |

TABLE 14-continued

| Characteristic | Item | Number |
| --- | --- | --- |
| Pliability | Normal | 0 |
|  | Finn | 1 |
|  | Ropes | 2 |
|  | Contracture | 3 |
| Height | Flat | 0 |
|  | <2 mm | 1 |
|  | > 2 < 5 mm | 2 |
|  | >5 | 3 |

Legend: 0 = best; 12 = worst

The xenotransplantation skin product of the present disclosure is packaged in a clear plastic, externally threaded, polypropylene vial with threaded seal-cap, stored on a rolled, sterile nylon mesh backing on the dermal-side of the product that serves to support and protect the product during processing and transport. Each product is individually immersed in a sterile cryoprotective medium with 5% dimethyl sulfoxide (DMSO). Source animal serum is NOT included or used in this process. The contents are cryopreserved via controlled rate, phase freezer and stored at about −80° C. until use.

The product is be placed on the burn wound and secured in place via suturing or stapling. The product remains in place until it is no longer providing effective barrier function to the wound bed, resulting from either: the time of product rejection via graft-host immunological response (as determined by the Clinical Wound Assessment Scale), mechanical disturbance or disruption (shear forces or hematoma), or intentional removal consistent with subject's overall clinical course. Subjects are monitored via a passive and active screening program using blood samples collected at time points throughout the study period, including for immunogenicity testing. Immunogenicity monitoring includes assaying serum total IgG and IgM levels, human anti-porcine antibodies, and assays to determine whether cell-mediated immune reactions are occurring.

The Clinical Wound Assessment Scale is shown in FIG. 32. Hematology tests include red blood cells (RBC), white blood cells (WBC) with differential (% and absolute), hemoglobin, hematocrit, platelets, prothrombin time (PT)/international normalized ratio (INR). Serum chemistry tests include ALT, Albumin, Alkaline phosphatase Amylase, Lipase, AST, Total bilirubin Direct bilirubin Total protein Creatinine, Blood urea nitrogen Creatine kinase, γ-glutamyl transferase (GGT), Potassium, Sodium, Glucose, Chloride, Bicarbonate, Calcium. Urinalysis tests include pH, specific gravity Protein, Glucose, Blood, Nitrite.

Based on results in non-human primates, it is expected that graft dislocation of grade 0, 1, or 2 will be observed. Based on results in non-human primates, it is expected that graft adherence of grade 3, 4, or 5 will be observed. Based on results in non-human primates, it is expected that granulation tissue having grade 3 or 4 will be observed. Based on results in non-human primates, it is expected that hypergranulation grade 0, 1, or 2 will be observed. Based on results in non-human primates, it is expected that hematoma of grade 0, 1, or 2 will be observed. Based on results in non-human primates, it is expected that fibrin deposition of grade 0, 1, or 2 will be observed. Based on results in non-human primates, it is expected that normal or pink vascularity will be observed. Based on results in non-human primates, it is expected that normal, mixed, or hypopigmentation will be observed. Based on results in non-human primates, it is expected that normal or firm pliability will be observed. Based on results in non-human primates, it is expected that flat or <2 mm scar height will be observed.

Example 11

Xenogeneic kidney derived from DPF Closed Colony, α-1,3-galactosyltransferase [Gal-T] knockout pigs produced in accordance with the present invention is transplanted into a non-human primate and a human. It is expected that survival of at least fourteen months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

Example 12

Xenogeneic lung derived from DPF Closed Colony, α-1,3-galactosyltransferase [Gal-T] knockout pigs produced in accordance with the present invention is transplanted into a non-human primate and a human. It is expected that survival of at least 30 days is observed in each of the non-human primate and the human. In some aspects, it is expected that survival of at least 3 months is observed in each of the non-human primate and the human. In some aspects, it is expected that survival of at least 6 months is observed in each of the non-human primate and the human. In some aspects, it is expected that survival of at least 12 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

Example 13

Xenogeneic liver derived from DPF Closed Colony, α-1,3-galactosyltransferase [Gal-T] knockout pigs produced in accordance with the present invention is transplanted into a non-human primate and a human. It is expected that survival of at least 60 days is observed in each of the non-human primate and the human. In some aspects, it is expected that survival of at least 3 months is observed in each of the non-human primate and the human. In some aspects, it is expected that survival of at least 6 months is observed in each of the non-human primate and the human. In some aspects, it is expected that survival of at least 12 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is

Example 14

Xenogeneic heart derived from DPF Closed Colony, α-1,3-galactosyltransferase [Gal-T] knockout pigs produced in accordance with the present invention is transplanted into a non-human primate and a human. It is expected that survival of at least 20 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

Example 15

Xenogeneic nerve tissue derived from DPF Closed Colony, α-1,3-galactosyltransferase [Gal-T] knockout pigs produced in accordance with the present invention is transplanted into a non-human primate and a human. It is expected that survival of at least 75 days is observed in each of the non-human primate and the human. In some aspects, it is expected that survival of at least 3 months is observed in each of the non-human primate and the human. In some aspects, it is expected that survival of at least 6 months is observed in each of the non-human primate and the human. In some aspects, it is expected that survival of at least 12 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

Example 16

Xenogeneic pancreas derived from DPF Closed Colony, α-1,3-galactosyltransferase [Gal-T] knockout pigs produced in accordance with the present invention is transplanted into a non-human primate and a human. It is expected that survival of at least 20 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

While the subject matter of this disclosure has been described and shown in considerable detail with reference to certain illustrative aspects, including various combinations and sub-combinations of features, those skilled in the art will readily appreciate other aspects and variations and modifications thereof as encompassed within the scope of the present disclosure. Moreover, the descriptions of such aspects, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method for xenotransplantation of a biological product into a human recipient comprising:
   (I) obtaining a biological product comprising live cells and tissue that vascularize after xenotransplantation, wherein the live cells and tissue have been obtained from a non-wild type, biologically engineered swine that:
      A) has a biologically engineered genome such that it does not express one or more extracellular surface glycan epitopes,
      B) is free of at least the following zoonotic pathogens:
         (i) *Ascaris* species, *cryptosporidium* species, *Echinococcus*, *Strongyloids sterocolis*, and *Toxoplasma gondii* in fecal matter;
         (ii) *Leptospira* species, *Mycoplasma hyopneumoniae*, porcine reproductive and respiratory syndrome virus (PRRSV), pseudorabies, transmissible gastroenteritis virus (TGE)/Porcine Respiratory Coronavirus, and *Toxoplasma Gondii* by determining antibody titers;
         (iii) Porcine Influenza;
         (iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), *Microphyton* and *Trichophyton* spp.;
         (v) Porcine cytomegalovirus; and
         (vi) *Brucella suis*;
      C) and maintained according to a bioburden-reducing procedure, said procedure comprising maintaining the swine in an isolated closed herd, wherein all other animals in the isolated closed herd are confirmed to be free of said zoonotic pathogens, wherein the swine is isolated from contact with any non-human animals and animal housing facilities outside of the isolated closed herd;
   wherein the biological product has been harvested from said swine by euthanizing the swine and aseptically removing the biological product from the swine;
   wherein the biological product has been processed using a sterilization process that does not reduce cell viability to less than 50% cell viability as determined by a 3-(4,5-dimethylthiazol-2-yl)-2,5-diphenyltetrazolium bromide (MTT)-reduction assay; and
   (II) transplanting said biological product into the human recipient.

2. The method of claim 1, wherein the biological product is free of two or more types of extracellular surface glycan epitopes as confirmed by flow cytometry.

3. The method of claim 2, wherein the biological product is free of alpha-1,3-galactosyltransferase epitopes and N-glycolylneuraminic acid epitopes as confirmed by flow cytometry.

4. The method of claim 2, wherein the biological product is free of alpha-1,3-galactosyltransferase epitopes, N-glycolylneuraminic acid epitopes, and β1,4-N-acetylgalactosaminyltransferase epitopes as confirmed by flow cytometry.

5. The method of claim 1, wherein the biological product is not terminally sterilized and is confirmed to:
   a. not promote growth of aerobic and anaerobic bacteria in a sterility assay,
   b. not promote growth of *mycoplasma* colonies in a *mycoplasma* assay,
   c. be free of endotoxins in an endotoxin assay,
   d. have at least 50% cell viability in a MTT-reduction assay,
   e. not have galactosyl-α-1,3-galactose epitopes as determined by flow cytometry, and
   f. be free of *Ascaris* species, *cryptosporidium* species, *Echinococcus, Strongyloids sterocolis, Toxoplasma gondii, Brucella suis, Leptospira* species, *mycoplasma hyopneumoniae*, porcine reproductive and respiratory syndrome, pseudorabies, *staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

6. The method of claim 1, wherein the biological product is not terminally sterilized and, and wherein the biological product has been sterilized by at least one of UV-C radiation and bathing in an anti-pathogen bath.

7. The method of claim 1, wherein said biological product is obtained from a swine produced through natural intercourse by parent swine also maintained in the isolated closed herd and also free of said zoonotic pathogens, and wherein said swine is birthed through live vaginal birth.

8. The method of claim 1, wherein the biological product has properties such that the biological product, when co-cultured with human peripheral blood mononuclear cells (PBMCs), induces a lower production of cytokine Interleukin 6 (IL-6) and a lower CD8+ T cell immune response as compared to cells from said non-genetically modified counterpart swine, as measured by an in vitro mixed lymphocyte reaction assay.

9. The method of claim 1, wherein the biological product is obtained from a non-transgenic swine.

10. The method of claim 1, wherein the biological product has at least 60% mitochondrial activity.

11. The method of claim 1, wherein said transplanting step is performed in the absence of immunosuppressant drugs or other immunosuppressant therapies.

12. The method of claim 1, wherein the biological product lacks alpha-1,3-galactosyltransferase, Neu5Gc, and β1,4-N-acetylgalactosaminyltransferase.

13. The method of claim 1, wherein the biological product is sufficiently sterile to satisfy USP<71> requirements.

14. The method of claim 1, wherein said biological product vascularizes in the region of the transplant in said patient following said transplanting step.

15. The method of claim 1, wherein upon said transplantation, said product exhibits a clinical benefit selected from forming an occlusive fibrin seal, reducing or preventing infection at the transplantation site or the healing site, increasing or retaining fluids at the transplantation site or the healing site, increasing or retaining electrolytes at the transplantation site or the healing site, increasing or retaining temperature homeostasis at the transplantation site or the healing site, reducing scarring at the transplantation site or the healing site, reducing or eliminating sepsis, reduce or eliminate protein losses, restoring bodily functions, or a combination thereof.

16. The method of claim 1, wherein the biological product has properties such that it does not transmit porcine endogenous retrovirus to the human recipient after said transplanting.

17. The method of claim 1, wherein the biological product is stored in a sterile container under storage conditions that preserve cell viability before the transplanting step.

18. The method of claim 1, further comprising obtaining a blood sample from the human recipient after the transplanting step, performing PCR analysis of peripheral blood mononuclear cells (PBMCs) in the blood sample to detect or confirm lack of migration of porcine DNA in the peripheral blood of the human recipient.

19. The method of claim 1, further comprising obtaining a blood sample from the human recipient after the transplanting step, performing PCR analysis of peripheral blood mononuclear cells (PBMCs) in the blood sample to detect or confirm lack of migration of porcine retroviral components in the peripheral blood of the human recipient.

* * * * *